United States Patent
Freier et al.

(10) Patent No.: US 9,487,780 B2
(45) Date of Patent: Nov. 8, 2016

(54) ANTISENSE COMPOUNDS TARGETING GENES ASSOCIATED WITH FIBRONECTIN

(71) Applicants: Ionis Pharmaceuticals, Inc., Carlsbad, CA (US); South West Thames Institute for Renal Research, Surrey (GB)

(72) Inventors: Susan M. Freier, San Diego, CA (US); Frank Rigo, Carlsbad, CA (US); Mark Dockrell, London (GB); Felicia Heidibrecht, London (GB)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/403,953

(22) PCT Filed: Jun. 3, 2013

(86) PCT No.: PCT/US2013/043942
§ 371 (c)(1),
(2) Date: Nov. 25, 2014

(87) PCT Pub. No.: WO2013/181666
PCT Pub. Date: Dec. 5, 2013

(65) Prior Publication Data
US 2015/0291955 A1 Oct. 15, 2015

Related U.S. Application Data

(60) Provisional application No. 61/722,030, filed on Nov. 2, 2012, provisional application No. 61/654,784, filed on Jun. 1, 2012.

(51) Int. Cl.
*A61K 48/00* (2006.01)
*C12N 15/113* (2010.01)
*A61K 31/7105* (2006.01)

(52) U.S. Cl.
CPC ......... *C12N 15/113* (2013.01); *A61K 31/7105* (2013.01); *C12N 2310/11* (2013.01); *C12N 2310/315* (2013.01); *C12N 2310/3231* (2013.01); *C12N 2310/3233* (2013.01); *C12N 2310/3341* (2013.01); *C12N 2310/343* (2013.01); *C12N 2310/346* (2013.01); *C12N 2320/33* (2013.01)

(58) Field of Classification Search
USPC .......... 435/6.1, 91.1, 9, 1.31, 455, 6.11, 1.1, 435/366, 37, 5, 375; 514/44; 536/23.1, 536/24.5, 24.3
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |

(Continued)

FOREIGN PATENT DOCUMENTS

WO    WO 99/14226       8/1999
WO    WO 2004/106356    12/2004

(Continued)

OTHER PUBLICATIONS

Sazani et al, J. Olin. Investigation, vol. 112, No. 4, pp. 481-486 (2003).*
Chauhan et al, Gene, vol. 324, pp. 55-63 (2004).*
Caputi et al, Nucleic Acids Res., vol. 22, No. 6, pp. 1018-1022 (1994).*
Roy et al, Diabetes, vol. 52, pp. 1229-1234 (2003).*

(Continued)

*Primary Examiner* — Jane Zara
(74) *Attorney, Agent, or Firm* — Knobbe, Martens, Olson & Bear, LLP

(57) ABSTRACT

Provided are compounds comprising oligonucleotides complementary to a fibronectin transcript. Certain such compounds are useful for hybridizing to a fibronectin transcript, including but not limited to a fibronectin transcript in a cell. Such hybridization results in modulation of splicing of the fibronectin transcript. Such compounds are used to treat one or more symptoms associated with fibrosis. Such compounds are used to treat one or more symptoms associated with renal fibrosis.

20 Claims, 1 Drawing Sheet

(56) References Cited

U.S. PATENT DOCUMENTS

| | | |
|---|---|---|
| 6,770,748 B2 | 8/2004 | Imanishi et al. |
| 6,794,499 B2 | 9/2004 | Wengel et al. |
| 7,034,007 B1 | 4/2006 | Nyce et al. |
| 7,034,133 B2 | 4/2006 | Wengel et al. |
| 7,064,207 B2 | 6/2006 | Du et al. |
| 7,341,835 B2 * | 3/2008 | Blume ............... C12Q 1/6876 435/287.2 |
| 7,399,845 B2 | 7/2008 | Seth et al. |
| 7,427,672 B2 | 9/2008 | Imanishi et al. |
| 7,709,630 B2 | 5/2010 | Gaarde et al. |
| 7,741,457 B2 | 6/2010 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,501,805 B2 | 8/2013 | Seth et al. |
| 8,530,640 B2 | 9/2013 | Seth et al. |
| 8,546,556 B2 | 10/2013 | Seth et al. |
| 2001/0053519 A1 | 12/2001 | Fodor et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2007/0009899 A1 * | 1/2007 | Mounts ............... C12Q 1/6883 435/6.16 |
| 2007/0031844 A1 | 2/2007 | Khvorova et al. |
| 2007/0287831 A1 | 12/2007 | Seth et al. |
| 2008/0039618 A1 | 2/2008 | Allerson et al. |
| 2009/0280118 A1 * | 11/2009 | Sheppard et al. ......... 424/133.1 |
| 2012/0115923 A1 * | 5/2012 | He et al. .................... 514/44 A |
| 2012/0172414 A1 | 7/2012 | Migawa et al. |

FOREIGN PATENT DOCUMENTS

| | | |
|---|---|---|
| WO | WO 2005/021570 | 3/2005 |
| WO | WO 2007/134181 | 11/2007 |
| WO | WO 2008/046510 | 4/2008 |
| WO | WO 2008/049085 | 4/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2013/181665 | 12/2013 |

OTHER PUBLICATIONS

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.

Braasch et al., "Locked nucleic acid (LNA): fine-tuning the recognition of DNA and RNA" Chem. Biol. (2001) 8: 1-7.

Braasch et al., "Novel Antisense and Peptide Nucleic Acid Strategies for Controlling Gene Expression" Biochemistry (2002) 41(14): 4503-4510.

Branch et al., "A good antisense molecule is hard to find," TIBS (1998) 23:45-50.

Chauhan et al., "Alternative splicing of fibronectin: a mouse model demonstrates the identiy of in vitro and in vivo systems and the processing autonomy of regulated exons in adult mice" Gene (2004) 324:55-63.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277(2): 923-937.

Elayadi et al., "Application of PNA and LNA oligomers to chemotherapy" Curr. Opinion Invest. Drugs (2001) 2: 558-561.

Englisch et al., "Chemically Modified Oligonucleotides as Probes and Inhibitors", Angewandte Chemie, International Edition, (1991) 30(6):613-722.

Freier et al., "The ups and downs of nucleic acid duplex stability: structure-stability studies on chemically-modified DNA:RNA duplexes" Nucleic Acids Research (1997) 25(22): 4429-4443.

Frieden et al., "Expanding the design horizon of antisense oligonucleotides with alpha-L-LNA" Nucleic Acids Research (2003) 31(21): 6365-6372.

GenBank Accession No. M28258.1 "Rat fibronectin gene, lb and 2a" retreived from the Internet on Apr. 2, 2013, downloaded from http://www.ncbi.nlm.nih.gov/nuccore/M28258.1.

Kabanov et al., "A new class of antivirals: antisense oligonucleotides combined with a hydrophobic substituent effectively inhibit influenza virus reproduction and synthesis of virus-specific proteins in MOCK cells" FEBS Lett., (1990) 259: 327-330.

Koller et al.,"Mechanisms of single-stranded phosphorothioate modified antisense oligonucleotide accumulation in hepatocytes" Nucleic Acids Research, (2011) 39: 4795-4807.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54: 3607-3630.

Kroschwitz, "The Concise Encyclopedia of Polymer Science and Engineering" pp. 858-859, John Wiley & Sons, 1990.

Kumar et al., "The First Analogues of LNA (Locked Nucleic Acids):Phosphorothioate-LNA and 2'-TmO-LNA" Bioorg. Med. Chem. Lett. (1998) 8: 22192222.

Letsinger et al., "Cholesteryl-conjugated oligonucleotides: Synthesis, properties, and activity as inhibitors of replication of human immunodeficiency virus in cell culture" PNAS (1989) 86: 6553-6556.

Leumann, "DNA Analogues: From Supramolecular Principles to Biological Properties" Bioorg. Med. Chem. (2002) 10: 841-854.

Manoharan et al., "Chemical Modifications to Improve Uptake and Bioavailability of Antisense Oligonucleotides" Ann. N.Y. Acad. Sci. (1992) 660: 306-309.

Manoharan et al., "Cholic Acid-Oligonucleotide Conjugates for Antisense Applications" Bioorg. Med. Chem. Let. (1994) 4(8): 1053-1060.

Manoharan et al., "Inoduction of a lipophilic thioether tether in the minor groove of nucleic acids for antisense applications" Bioorg. Med. Chem. Let. (1993) 3(12): 2765-2770.

Manoharan et al., "Lipidic Nucleic Acids" Tetrahedron Lett. (1995) 36(21): 3651-3654.

Manoharan et al., "Oligonucleotide Conjugates: Alteration of the Pharmacokinetic Properties of Antisense Agents" Nucleosides & Nucleotides (1995) 14(3-5): 969-973.

Mishra et al., "Improved leishmanicidal effect of phosphorotioate antisense oligonucleotides by LDL-mediated delivery" Biochim. Biophys. Acta (1995) 1264: 229-237.

Muro et al., "An Essential Role for Fibronectin Extra Type III Domain A in Pulmonary Fibrosis" American Journal of Respitory and Critical Care Medicine (2008) 177:638-45.

Muro et al., "Regulation of the fibronectin EDA exon alternative splicing. Cooperative role of the exonic enhancer element and the 5' splicing site" FEBS Letters (1998) 437:137-141.

New England Biolabs 1998/99 Catalog (cover page and pp. 121 and 284).

Oberhauser et al., "Effective incorporation of 2'-O-methyl-oligoribonucleotides into liposomes and enhanced cell association through modification with thiocholesterol" Nucl. Acids Res. (1992) 20(3): 533-538.

Orum et al., "Locked nucleic acids: A promising molecular family for gene-function analysis and antisense drug development" Curr. Opinion Mol. Ther. (2001) 3: 239-243.

Phanish et al., "The differential role of Smad2 and Smad3 in the regulation of pro-fibrotic TGF[beta]l responses in human proximal-tubule epithelial cells" Biochemical Journal (2006) 393(2):601-607.

Reynolds et al., "Rational siRNA design for RNA interference" Nature Biotechnology (2004) 22(3):326-330.

(56) References Cited

OTHER PUBLICATIONS

Roy et al, "Downregulation of Fibronectin Overxpression Reduces Basement Membrane Thickening and Vascular Lesions in Retinas of Galactose-Fed Rats" Diabetes (2003) 52:1229-1234.

Saison-Behmoaras et al., "Short modified antisense oligonucleotides directed against Ha-ras point mutation induce selective cleavage of the mRNA and inhibit T24 cells proliferation" EMBO J. (1991) 10:1111-1118.

Sanghvi et al., "Heterocyclic Base Modifications in Nucleic Acids and Their Applications in Antisense Oligonucleotides" Antisense Research and Applications (1993) pp. 273-288.

Sazani et al., "Therapeutic potential of antisense oligonucleotides as modulators of alternative splicing" The Journal of Clinical Investigation (2003) 112(4):481-486.

Shea et al., "Synthesis, hybridization properties and antiviral activity of lipid-oligodeoxynucleotide conjugates" Nucl. Acids Res. (1990) 18: 3777-3783.

Singh et al., "LNA (locked nucleic acids): synthesis and high-affinity nucleic acid recognition" Chem. Commun. (1998) 4: 455-456.

Singh et al., "Synthesis of 2'-Amino-LNA: A Novel Conformationally Restricted High-Affinity Oligonucleotide Analogue with a Handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.

Svinarchuk et al., "Inhibition of HIV proliferation in MT-4 cells by antisense oligonucleotide conjugated to lipophilic groups" Biochimie (1993) 75: 49-54.

Wahlestedt et al., "Potent and nontoxic antisense oligonucleotides containing locked nucleic acids" PNAS (2000) 97: 5633-5638.

Woolf et al., "Specificity of antisense oligonucleotide in vivo" PNAS (1992) 89:7305-7309.

White et al., "Fibronectin Splice Variants: Understanding Their Multiple Roles in Health and Disease Using Engineered Mouse Models" Life (2011) 63(7):538-546.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for application PCT/US2013/043935 dated Nov. 5, 2013.

International Search Report for application PCT/US2013/043942 dated Jan. 10, 2014.

\* cited by examiner

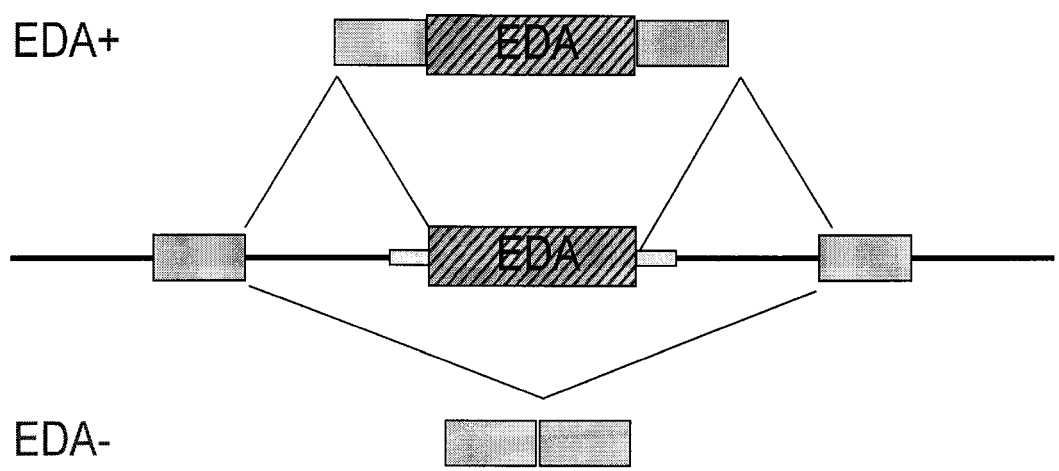

ANTISENSE COMPOUNDS TARGETING GENES ASSOCIATED WITH FIBRONECTIN

CROSS REFERENCED TO RELATED APPLICATIONS

This application is a U.S. National Phase filing under 35 U.S.C. §371 claiming priority to International Serial No. PCT/US2013/043942 filed Jun. 3, 2013, which claims priority to U.S. Provisional Application 61/722,030, filed Nov. 2, 2012, and U.S. Provisional Application 61/654,784, filed Jun. 1, 2012 each of which is incorporated herein by reference in its entirety.

SEQUENCE LISTING

The present application is being filed along with a Sequence Listing in electronic format. The Sequence Listing is provided as a file entitled BIOL0203USASEQ_ST23.txt, created Nov. 25, 2014, which is 280 Kb in size. The information in the electronic format of the sequence listing is incorporated herein by reference in its entirety.

BACKGROUND OF THE INVENTION

Fibronectin is a high-molecular weight glycoprotein of the extracellular matrix that binds to membrane-spanning receptor integrin proteins. Fibronectin has been implicated in a number of fibrotic disorders, including renal fibrosis. Alternative splicing of fibronectin pre-mRNA leads to the creation of fibronectin mRNA having a different combination of exons, which in turn leads to the creation of several isoforms of fibronectin protein. In certain instances, alternative splicing of the fibronectin gene results in a fibronectin protein isoform containing the extra type III domain A (EDA). Fibronectin containing extra type III domain A (EDA) is implicated in the formation of fibrosis. See, e.g., Muro et al., *An Essential Role for Fibronectin Extra Type III Domain A in Pulmonary Fibrosis*, American Journal of Respiratory and Critical Care Medicine, Vol. 177, 638 (2008).

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Certain antisense compounds have been described previously. See for example U.S. Pat. No. 7,399,845 and published International Patent Application No. WO 2008/049085, which are hereby incorporated by reference herein in their entirety.

SUMMARY OF THE INVENTION

In certain embodiments, the present invention provides compounds comprising oligonucleotides. In certain embodiments, such oligonucleotides are complementary to a fibronectin transcript. In certain such embodiments, oligonucleotides are complementary to a target region of the fibronectin transcript comprising the EDA exon. In certain such embodiments, oligonucleotides are complementary to a target region of the fibronectin transcript comprising an intron adjacent to the EDA exon. In certain such embodiments, oligonucleotides are complementary to a target region of the fibronectin transcript comprising an intron adjacent to the EDA exon and downstream of the EDA exon. In certain such embodiments, oligonucleotides are complementary to a target region of the fibronectin transcript comprising an intron adjacent to the EDA exon and upstream of the EDA exon. In certain embodiments, the fibronectin transcript comprises an exonic splice enhancer for the EDA exon. In certain embodiments, the fibronectin transcript comprises an exonic splice silencer for the EDA exon. In certain embodiments, oligonucleotides inhibit inclusion of the EDA exon. In certain embodiments, oligonucleotides promote skipping of the of the EDA exon. In certain such embodiments, fibronectin mRNA without EDA mRNA is increased. In certain such embodiments, fibronectin protein without EDA is increased.

The present disclosure provides the following non-limiting numbered embodiments:

Embodiment 1

A compound comprising a modified oligonucleotide consisting of 8 to 30 linked nucleosides and having a nucleobase sequence comprising a complementary region comprising at least 8 contiguous nucleobases complementary to a target region of equal length of a fibronectin transcript.

Embodiment 2

The compound of embodiment 1, wherein the complementary region of the modified oligonucleotide is 100% complementary to the target region.

Embodiment 3

The compound of embodiment 1 or 2, wherein the complementary region of the modified oligonucleotide comprises at least 10 contiguous nucleobases.

Embodiment 4

The compound of embodiment 1 or 2, wherein the complementary region of the modified oligonucleotide comprises at least 12 contiguous nucleobases.

Embodiment 5

The compound of embodiment 1 or 2, wherein the complementary region of the modified oligonucleotide comprises at least 15 contiguous nucleobases.

Embodiment 6

The compound of embodiment 1 or 2, wherein the complementary region of the modified oligonucleotide comprises at least 18 contiguous nucleobases.

Embodiment 7

The compound of embodiment 1 or 2, wherein the complementary region of the modified oligonucleotide comprises at least 20 contiguous nucleobases.

Embodiment 8

The compound of any of embodiments 1-5, wherein the nucleobase sequence of the oligonucleotide is at least 80% complementary to an equal-length region of the fibronectin transcript, as measured over the entire length of the oligonucleotide.

Embodiment 9

The compound of any of embodiments 1-5, wherein the nucleobase sequence of the oligonucleotide is at least 90% complementary to an equal-length region of the fibronectin transcript, as measured over the entire length of the oligonucleotide.

Embodiment 10

The compound of any of embodiments 1-5, wherein the nucleobase sequence of the oligonucleotide is 100% complementary to an equal-length region of the fibronectin transcript, as measured over the entire length of the oligonucleotide.

Embodiment 11

The compound of any of embodiments 1-10, wherein the target region is within nucleobase 55469 and nucleobase 55790 of SEQ ID NO.: 1.

Embodiment 12

The compound of any of embodiments 1-10, wherein the target region is within nucleobase 55469 and nucleobase 55511 of SEQ ID NO.: 1.

Embodiment 13

The compound of any of embodiments 1-10, wherein the target region is within nucleobase 55511 and nucleobase 55732 of SEQ ID NO.: 1.

Embodiment 14

The compound of any of embodiments 1-10, wherein the target region is within nucleobase 55732 and nucleobase 55790 of SEQ ID NO.: 1.

Embodiment 15

The compound of any of embodiments 1-10, wherein the target region is within nucleobase 55491 and nucleobase 55511 of SEQ ID NO.: 1.

Embodiment 16

The compound of any of embodiments 1-10, wherein the target region is within nucleobase 55490 and nucleobase 55510 of SEQ ID NO.: 1.

Embodiment 17

The compound of any of embodiments 1-10, wherein the target region is within nucleobase 55491 and nucleobase 55513 of SEQ ID NO.: 1.

Embodiment 18

The compound of any of embodiments 1-10, wherein the target region is within nucleobase 55536 and nucleobase 55555 of SEQ ID NO.: 1.

Embodiment 19

The compound of any of embodiments 1-10, wherein the target region is within nucleobase 55576 and nucleobase 55600 of SEQ ID NO.: 1.

Embodiment 20

The compound of any of embodiments 1-10, wherein the target region is within nucleobase 55604 and nucleobase 55623 of SEQ ID NO.: 1.

Embodiment 21

The compound of any of embodiments 1-10, wherein the target region is within nucleobase 55610 and nucleobase 55697 of SEQ ID NO.: 1.

Embodiment 22

The compound of any of embodiments 1-10, wherein the target region is within nucleobase 55701 and nucleobase 55737 of SEQ ID NO.: 1.

Embodiment 23

The compound of any of embodiments 1-10, wherein the target region is within nucleobase 55738 and nucleobase 55757 of SEQ ID NO.: 1.

Embodiment 24

The compound of any of embodiments 1-10, wherein the target region is within nucleobase 55753 and nucleobase 55781 of SEQ ID NO.: 1.

Embodiment 25

The compound of any of embodiments 1-24, wherein the antisense oligonucleotide comprises SEQ ID NO: 5.

Embodiment 26

The compound of any of embodiments 1-24, wherein the antisense oligonucleotide comprises SEQ ID NO: 9.

Embodiment 27

The compound of any of embodiments 1-24, wherein the antisense oligonucleotide comprises SEQ ID NO: 13.

Embodiment 28

The compound of any of embodiments 1-24, wherein the antisense oligonucleotide comprises SEQ ID NO: 14.

Embodiment 29

The compound of any of embodiments 1-24, wherein the antisense oligonucleotide comprises SEQ ID NO: 15.

Embodiment 30

The compound of any of embodiments 1-24, wherein the antisense oligonucleotide comprises SEQ ID NO: 18.

Embodiment 31

The compound of any of embodiments 1-24, wherein the antisense oligonucleotide comprises SEQ ID NO: 22.

Embodiment 32

The compound of any of embodiments 1-24, wherein the antisense oligonucleotide comprises SEQ ID NO: 66.

Embodiment 33

The compound of any of embodiments 1-24, wherein the antisense oligonucleotide comprises SEQ ID NO: 67.

Embodiment 34

The compound of any of embodiments 1-24, wherein the antisense oligonucleotide comprises any of SEQ ID NOs: 5 to 24.

Embodiment 35

The compound of any of embodiments 1-24, wherein the antisense oligonucleotide comprises any of SEQ ID NOs: 30 to 90.

Embodiment 36

The compound of any of embodiments 1-24, wherein the antisense oligonucleotide comprises SEQ ID NO: 413.

Embodiment 37

The compound of any of embodiments 1-24, wherein the antisense oligonucleotide comprises SEQ ID NO: 346.

Embodiment 38

The compound of any of embodiments 1-24, wherein the antisense oligonucleotide comprises any of SEQ ID NOs: 104 to 176.

Embodiment 39

The compound of any of embodiments 1-24, wherein the antisense oligonucleotide comprises any of SEQ ID NOs: 177 to 329.

Embodiment 40

The compound of any of embodiments 1-24, wherein the antisense oligonucleotide comprises any of SEQ ID NOs: 403 to 435.

Embodiment 41

The compound of any of embodiments 1-24, wherein the antisense oligonucleotide comprises any of SEQ ID NOs: 105, 87, 126, 133, 134, 140, 141, 147, 149, 157, 159, 190, 223, 238, 244, 268, 285, 300, 302, 303, 308, 319, 327, 381, 382, 339, 346, 348, 364, 365, 367, 368, 369, 370, 268, 276, 280, 406, 407, 412, 413, and 324.

Embodiment 42

The compound of any of embodiments 1-24, wherein the antisense oligonucleotide has a nucleobase sequence comprising CTTCTTCT.

Embodiment 43

The compound of any of embodiments 1-24, wherein the antisense oligonucleotide has a nucleobase sequence comprising GTTCC.

Embodiment 44

The compound of any of embodiments 1-24, wherein the antisense oligonucleotide has a nucleobase sequence comprising GTCCC.

Embodiment 45

The compound of any of embodiments 1-24, wherein the antisense oligonucleotide comprises a sugar motif described by Formula I as follows:

$$[(A)-(B)_2-(A)]_n$$

wherein:
each A is independently a bicyclic nucleoside;
each B is independently a 2'-substituted nucleoside or a 2'-deoxynucleoside; and
n is an integer from 3-6.

Embodiment 46

The compound of any of embodiments 1-24, wherein the antisense oligonucleotide comprises a sugar motif described by Formula II as follows:

$$(A)_2-[(B)_2-(A)]_n-(A)$$

wherein:
each A is independently a bicyclic nucleoside;
each B is independently a 2'-substituted nucleoside or a 2'-deoxynucleoside; and
n is an integer from 3-6.

Embodiment 47

The compound of any of embodiments 1-24, wherein the antisense oligonucleotide comprises a sugar motif described by Formula III as follows:

$$(A)_2-[(B)_2-(A)]_n$$

wherein:
each A is independently a bicyclic nucleoside;
each B is independently a 2'-substituted nucleoside or a 2'-deoxynucleoside; and
n is an integer from 3-6.

Embodiment 48

The compound of any of embodiments 45 to 47, wherein each A comprises a bicyclic nucleoside selected from among LNA and cEt.

Embodiment 49

The compound of any of embodiments 45 to 47, wherein each A comprises a cEt modification.

Embodiment 50

The compound of any of embodiments 45 to 47, wherein each A comprises an LNA modification.

Embodiment 51

The compound of any of embodiments 45 to 50, wherein each B comprises a 2'-substituted nucleoside having a 2'-modification selected from among 2'-OMe, 2'-F, and 2'-MOE.

Embodiment 52

The compound embodiment 51, wherein the 2'-modification is a 2'-MOE modification.

Embodiment 53

The compound of any of embodiments 45 to 50, wherein each B comprises a 2'-deoxynucleoside.

Embodiment 54

The compound of any of embodiments 1-44, wherein the modified oligonucleotide comprises at least one modified nucleoside.

Embodiment 55

The compound of embodiment 54, wherein at least one modified nucleoside comprises a modified sugar moiety.

Embodiment 56

The compound of embodiment 55, wherein at least one modified sugar moiety is a 2'-substituted sugar moiety.

Embodiment 57

The compound of embodiment 56, wherein the 2'-substitutent of at least one 2'-substituted sugar moiety is selected from among: 2'-OMe, 2'-F, and 2'-MOE.

Embodiment 58

The compound of embodiment 57, wherein the 2'-substituent of at least one 2'-substituted sugar moiety is a 2'-MOE.

Embodiment 59

The compound of any of embodiments 54-56, wherein at least one modified sugar moiety is a bicyclic sugar moiety.

Embodiment 60

The compound of embodiment 59, wherein at least one bicyclic sugar moiety is LNA or cEt.

Embodiment 61

The compound of any of embodiments 54-60, wherein at least one sugar moiety is a sugar surrogate.

Embodiment 62

The compound of embodiment 61, wherein at least one sugar surrogate is a morpholino.

Embodiment 63

The compound of embodiment 61, wherein at least one sugar surrogate is a modified morpholino.

Embodiment 64

The compound of any of embodiment 1-63, wherein the modified oligonucleotide comprises at least 5 modified nucleosides, each independently comprising a modified sugar moiety.

Embodiment 65

The compound of embodiment 64, wherein the modified oligonucleotide comprises at least 10 modified nucleosides, each independently comprising a modified sugar moiety.

Embodiment 66

The compound of embodiment 64, wherein the modified oligonucleotide comprises at least 15 modified nucleosides, each independently comprising a modified sugar moiety.

Embodiment 67

The compound of any of embodiments 1 to 44 or 54 to 66, wherein each nucleoside of the modified oligonucleotide is a modified nucleoside, each independently comprising a modified sugar moiety Embodiment 68

The compound of any of embodiments 1-67, wherein the modified oligonucleotide comprises at least two modified nucleosides comprising modified sugar moieties that are the same as one another.

Embodiment 69

The compound of any of embodiments 1-68, wherein the modified oligonucleotide comprises at least two modified nucleosides comprising modified sugar moieties that are different from one another.

Embodiment 70

The compound of any of embodiments 1-69, wherein the modified oligonucleotide comprises a modified region of at least 5 contiguous modified nucleosides.

Embodiment 71

The compound of any of embodiments 1 to 44 or 54 to 70, wherein the modified oligonucleotide comprises a modified region of at least 10 contiguous modified nucleosides.

Embodiment 72

The compound of any of embodiments 1 to 44 or 54 to 70, wherein the modified oligonucleotide comprises a modified region of at least 15 contiguous modified nucleosides.

Embodiment 73

The compound of any of embodiments 1 to 44 or 54 to 70, wherein the modified oligonucleotide comprises a modified region of at least 20 contiguous modified nucleosides.

Embodiment 74

The compound of any of embodiments 70-73, wherein each modified nucleoside of the modified region has a modified sugar moiety independently selected from among: 2'-F, 2'-OMe, 2'-MOE, cEt, LNA, morpholino, and modified morpholino.

Embodiment 75

The compound of any of embodiments 70-73, wherein the modified nucleosides of the modified region each comprise the same modification as one another.

Embodiment 76

The compound of embodiment 75, wherein the modified nucleosides of the modified region each comprise the same 2'-substituted sugar moiety.

Embodiment 77

The compound of embodiment 75, wherein the 2'-substituted sugar moiety of the modified nucleosides of the region of modified nucleosides is selected from 2'-F, 2'-OMe, and 2'-MOE.

Embodiment 78

The compound of embodiment 77, wherein the 2'-substituted sugar moiety of the modified nucleosides of the region of modified nucleosides is 2'-MOE.

Embodiment 79

The compound of embodiment 75, wherein the modified nucleosides of the region of modified nucleosides each comprise the same bicyclic sugar moiety.

Embodiment 80

The compound of embodiment 79, wherein the bicyclic sugar moiety of the modified nucleosides of the region of modified nucleosides is selected from LNA and cEt.

Embodiment 81

The compound of embodiment 75, wherein the modified nucleosides of the region of modified nucleosides each comprises a sugar surrogate.

Embodiment 82

The compound of embodiment 81, wherein the sugar surrogate of the modified nucleosides of the region of modified nucleosides is a morpholino.

Embodiment 83

The compound of embodiment 81, wherein the sugar surrogate of the modified nucleosides of the region of modified nucleosides is a modified morpholino.

Embodiment 84

The compound of any of embodiments 1-83, wherein the modified nucleotide comprises no more than 4 contiguous naturally occurring nucleosides.

Embodiment 85

The compound of any of embodiments 1 to 44 or 54 to 85, wherein each nucleoside of the modified oligonucleotide is a modified nucleoside.

Embodiment 86

The compound of embodiment 85 wherein each modified nucleoside comprises a modified sugar moiety.

Embodiment 87

The compound of embodiment 86, wherein the modified nucleosides of the modified oligonucleotide comprise the same modification as one another.

Embodiment 88

The compound of embodiment 87, wherein the modified nucleosides of the modified oligonucleotide each comprise the same 2'-substituted sugar moiety.

Embodiment 89

The compound of embodiment 88, wherein the 2'-substituted sugar moiety of the modified oligonucleotide is selected from 2'-F, 2'-OMe, and 2'-MOE.

Embodiment 90

The compound of embodiment 89, wherein the 2'-substituted sugar moiety of the modified oligonucleotide is 2'-MOE.

Embodiment 91

The compound of embodiment 87, wherein the modified nucleosides of the modified oligonucleotide each comprise the same bicyclic sugar moiety.

Embodiment 92

The compound of embodiment 91, wherein the bicyclic sugar moiety of the modified oligonucleotide is selected from LNA and cEt.

Embodiment 93

The compound of embodiment 87, wherein the modified nucleosides of the modified oligonucleotide each comprises a sugar surrogate.

Embodiment 94

The compound of embodiment 93, wherein the sugar surrogate of the modified oligonucleotide is a morpholino.

Embodiment 95

The compound of embodiment 93, wherein the sugar surrogate of the modified oligonucleotide is a modified morpholino.

Embodiment 96

The compound of any of embodiments 1-95, wherein the modified oligonucleotide comprises at least one modified internucleoside linkage.

Embodiment 97

The compound of embodiment 96, wherein each internucleoside linkage is a modified internucleoside linkage.

Embodiment 98

The compound of embodiment 96 or 97, comprising at least one phosphorothioate internucleoside linkage.

Embodiment 99

The compound of embodiment 77, wherein each internucleoside linkage is a modified internucleoside linkage and wherein each internucleoside linkage comprises the same modification.

Embodiment 100

The compound of embodiment 99, wherein each internucleoside linkage is a phosphorothioate internucleoside linkage.

Embodiment 101

The compound of any of embodiments 1-100 comprising at least one conjugate.

Embodiment 102

The compound of any of embodiments 1-101 consisting of the modified oligonucleotide.

Embodiment 103

The compound of any of embodiments 1-102, wherein the compound modulates splicing of the fibronectin transcript.

Embodiment 104

The compound of any of embodiments 1-103, having a nucleobase sequence comprising any of the sequences as set forth in SEQ ID NOs. 5 to 25 or 30 to 90.

Embodiment 105

The compound of any of embodiments 1-103, having a nucleobase sequence comprising the sequence as set forth in SEQ ID NO: 5.

Embodiment 106

The compound of any of embodiments 1-103, having a nucleobase sequence comprising the sequence as set forth in SEQ ID NO: 9.

Embodiment 107

The compound of any of embodiments 1-103, having a nucleobase sequence comprising the sequence as set forth in SEQ ID NO: 13.

Embodiment 108

The compound of any of embodiments 1-103, having a nucleobase sequence comprising the sequence as set forth in SEQ ID NO: 14.

Embodiment 109

The compound of any of embodiments 1-103, having a nucleobase sequence comprising the sequence as set forth in SEQ ID NO: 15.

Embodiment 110

The compound of any of embodiments 1-103, having a nucleobase sequence comprising the sequence as set forth in SEQ ID NO: 18.

Embodiment 111

The compound of any of embodiments 1-103, having a nucleobase sequence comprising the sequence as set forth in SEQ ID NO: 22.

Embodiment 112

The compound of any of embodiments 1-103, having a nucleobase sequence comprising the sequence as set forth in SEQ ID NO: 66.

Embodiment 113

The compound of any of embodiments 1-103, having a nucleobase sequence comprising the sequence as set forth in SEQ ID NO: 67.

Embodiment 114

The compound of any of embodiments 1-103, wherein the antisense oligonucleotide has a nucleobase sequence comprising CTTCTTCT.

Embodiment 115

The compound of any of embodiments 1-103, wherein the antisense oligonucleotide has a nucleobase sequence comprising GTTCC.

Embodiment 116

The compound of any of embodiments 1-103, wherein the antisense oligonucleotide has a nucleobase sequence comprising GTCCC.

Embodiment 117

A pharmaceutical composition comprising a compound according to any of embodiments 1-116 and a pharmaceutically acceptable carrier or diluent.

Embodiment 118

The pharmaceutical composition of embodiment 117, wherein the pharmaceutically acceptable carrier or diluent is sterile saline.

Embodiment 119

A method of decreasing the amount of EDA+ fibronectin protein in a cell, comprising contacting the cell with a compound according to any of embodiments 1-117.

Embodiment 120

A method of increasing the amount of EDA− fibronectin protein in a cell, comprising contacting the cell with a compound according to any of embodiments 1-117.

Embodiment 121

A method of reducing fibrosis, comprising contacting the cell with a compound according to any of embodiments 1-117.

Embodiment 122

A method of reversing fibrosis, comprising contacting the cell with a compound according to any of embodiments 1-117.

Embodiment 123

A method of reducing changes in cell phenotype due to fibrosis, comprising contacting the cell with a compound according to any of embodiments 1-117.

Embodiment 124

A method of reversing changes in cell phenotype due to fibrosis, comprising contacting the cell with a compound according to any of embodiments 1-117.

Embodiment 125

The method of embodiments 123-124, wherein the change in cell phenotype due to fibrosis is the modulation of cadherin expression.

Embodiment 126

The method of embodiments 123-124, wherein the change in cell phenotype due to fibrosis is the induction of a Smooth Muscle Actin (αSMA).

Embodiment 127

The method of embodiments 123-124, wherein the change in cell phenotype due to fibrosis is the alteration of cortical f-actin localization.

Embodiment 128

The method of embodiments 123-124, wherein the change in cell phenotype due to fibrosis is the induction of connexin 43 (Cx 43) expression.

Embodiment 129

The method of embodiments 123-124, wherein the change in cell phenotype due to fibrosis is the increased secretion of MMP2 & MMP9.

Embodiment 130

The method of embodiments 123-124, wherein the change in cell phenotype due to fibrosis is the alteration of the amount vimentin or the arrangement of vimentin within a cell.

Embodiment 131

The method of embodiments 123-124, wherein the change in cell phenotype due to fibrosis is the alteration of the amount tight junction protein ZO-1 or the arrangement of tight junction protein ZO-1 within a cell.

Embodiment 132

A method of reducing loss of cell phenotype due to fibrosis, comprising contacting the cell with a compound according to any of embodiments 1-117.

Embodiment 133

A method of reversing the loss of cell phenotype due to fibrosis, comprising contacting the cell with a compound according to any of embodiments 1-117.

Embodiment 134

A method of increasing the ratio of EDA+/EDA− fibronectin in a cell, comprising contacting the cell with a compound according to any of embodiments 1-117.

Embodiment 135

A method of decreasing the ratio of EDA+/EDA− fibronectin in a cell, comprising contacting the cell with a compound according to any of embodiments 1-117.

Embodiment 136

A method of increasing the ratio of EDA−/EDA+ fibronectin in a cell, comprising contacting the cell with a compound according to any of embodiments 1-117.

Embodiment 137

A method of decreasing the ratio of EDA−/EDA+ fibronectin in a cell, comprising contacting the cell with a compound according to any of embodiments 1-117.

Embodiment 138

A method of increasing the ratio of EDA+/EDA− fibronectin protein in a cell, comprising contacting the cell with a compound according to any of embodiments 1-117.

Embodiment 139

A method of decreasing the ratio of EDA+/EDA− fibronectin protein in a cell, comprising contacting the cell with a compound according to any of embodiments 1-117.

Embodiment 140

A method of increasing the ratio of EDA−/EDA+ fibronectin protein in a cell, comprising contacting the cell with a compound according to any of embodiments 1-117.

Embodiment 141

A method of decreasing the ratio of EDA−/EDA+ fibronectin protein in a cell, comprising contacting the cell with a compound according to any of embodiments 1-117.

Embodiment 142

The method of any of embodiments 119-142, wherein the cell is in vitro.

Embodiment 143

The method of embodiments 119-142, wherein the cell is in an animal.

Embodiment 144

The method of embodiments 119-142, wherein the animal is a mouse.

Embodiment 145

The method of embodiments 119-142, wherein the animal is a human.

Embodiment 146

The method of any of embodiments 119-145, wherein TGFβ1 is present in the cell.

Embodiment 147

The method of any of embodiments 119-146, wherein the healing and/or restoration functions of the cell are not substantially affected.

Embodiment 148

A pharmaceutical composition comprising a compound according to any of embodiments 1-117 and a pharmaceutically acceptable carrier or diluent.

Embodiment 149

The pharmaceutical composition of embodiment 148, wherein the pharmaceutically acceptable carrier or diluent is sterile saline.

Embodiment 150

A method comprising administering the pharmaceutical composition of embodiments 148 or 149 to an animal.

Embodiment 151

The method of embodiment 150, wherein the animal is a mouse.

Embodiment 152

The method of embodiment 150, wherein the animal is a human.

Embodiment 153

The method of embodiment 150, wherein the administration is by injection.

Embodiment 154

The method of embodiment 150, wherein the administration is systemic.

Embodiment 155

The method of embodiment 150 wherein the administration is local.

Embodiment 156

The method of any of embodiments 150-155, wherein the animal has one or more symptom associated with fibrosis.

Embodiment 157

The method of embodiment 156, wherein the administration results in amelioration of at least one symptom associated with fibrosis.

Embodiment 158

The method of embodiment 156-157, wherein the fibrosis is renal fibrosis.

Embodiment 159

The method of embodiment 156-157, wherein the fibrosis is lung fibrosis.

Embodiment 160

The method of embodiment 156-157, wherein the fibrosis is liver fibrosis.

Embodiment 161

The method of embodiment 156-157, wherein the fibrosis is brain fibrosis.

Embodiment 162

The method of embodiment 156-157, wherein the fibrosis is muscular fibrosis.

Embodiment 163

The method of embodiment 156-157, wherein the fibrosis is cardiovascular fibrosis.

Embodiment 164

The method of embodiment 156-157, wherein the fibrosis is in the bone or the bone marrow.

Embodiment 165

The method of embodiment 156-157, wherein the fibrosis is intestinal fibrosis.

Embodiment 166

The method of embodiment 156-157, wherein the fibrosis is epidural fibrosis.

Embodiment 167

The method of any of embodiments 156-167, wherein the animal is a mouse.

Embodiment 168

The method of any of embodiments 156-167, wherein the animal is a human.

Embodiment 169

Use of the compound of any of embodiments 1 to 117 or the composition of embodiments 148-149 for the preparation of a medicament for use in the treatment of at least one symptom associated with fibrosis.

Embodiment 170

Use of the compound of any of embodiments 1 to 117 or the composition of embodiments 148-149 for the preparation of a medicament for use in the amelioration of one or more symptoms associated with fibrosis.

Embodiment 171

The use of any of embodiment 169-170, wherein the fibrosis is selected from among renal, lung, liver, brain, muscular, cardiovascular, bone or bone marrow, intestinal, and/or epidural fibrosis.

Embodiment 172

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a sugar motif described by Formula I as follows:

$$[(A)\text{-}(B)_2\text{-}(A)]_n$$

wherein:
each A is independently a bicyclic nucleoside;
each B is independently a 2'-substituted nucleoside or a 2'-deoxynucleoside; and
n is an integer from 3-6.

Embodiment 173

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a sugar motif described by Formula II as follows:

$$(A)_2\text{-}[(B)_2\text{-}(A)]_n\text{-}(A)$$

wherein:
each A is independently a bicyclic nucleoside;
each B is independently a 2'-substituted nucleoside or a 2'-deoxynucleoside; and
n is an integer from 3-6.

Embodiment 174

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a sugar motif described by Formula III as follows:

$$(A)_2\text{-}[(B)_2\text{-}(A)]_n$$

wherein:
each A is independently a bicyclic nucleoside;
each B is independently a 2'-substituted nucleoside or a 2'-deoxynucleoside; and
n is an integer from 3-6.

Embodiment 175

The compound of any of embodiments 172 to 174, wherein each A comprises a bicyclic nucleoside selected from among LNA and cEt.

Embodiment 176

The compound of any of embodiments 172 to 174, wherein each A comprises a cEt modification.

Embodiment 177

The compound of any of embodiments 172 to 174, wherein each A comprises an LNA modification.

Embodiment 178

The compound of any of embodiments 172 to 177, wherein each B comprises a 2'-substituted nucleoside having a 2'-modification selected from among 2'-OMe, 2'-F, and 2'-MOE.

Embodiment 179

The compound embodiments 178, wherein the 2'-modification is a 2'-MOE modification.

Embodiment 180

The compound of any of embodiments 172 to 179, wherein each B comprises a 2'-deoxynucleoside.

Embodiment 181

A compound comprising a modified oligonucleotide consisting of 8 to 30 linked nucleosides and having a nucleobase sequence comprising a complementary region comprising at least 8 contiguous nucleobases complementary

Embodiment 182

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkddkddkddkddkk motif, wherein each k comprises a cEt modification and each d comprises a 2'-deoxynucleoside.

Embodiment 183

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkeekeekeekeekeeke motif, wherein each k comprises a cEt modification and each e comprises a 2'-MOE modification.

Embodiment 184

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kddkddkddkddkddk motif wherein each k comprises a cEt modification and each d comprises a 2'-deoxynucleoside.

Embodiment 185

A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a keekeekeekeekeek motif, wherein each k comprises a cEt modification and each e comprises a 2'-MOE modification.

In certain embodiments, including, but not limited to any of the above numbered embodiments, the fibronectin transcript is in a human. In certain embodiments, including, but not limited to any of the above numbered embodiments, the fibronectin transcript is in a mouse.

BRIEF DESCRIPTION OF THE FIGURES

FIG. 1 shows a schematic of fibronectin splicing. Exons are represented as boxes and introns are represented as lines. Diagonal lines indicate splicing pathways. As illustrated by the schematic, alternative splicing produces two different mRNA products. Inclusion of the EDA exon results in mRNA containing the EDA exon (EDA+) which results in fibronectin protein having EDA. Alternatively, exclusion of the EDA exon results in mRNA without the EDA exon (EDA−) and results in fibronectin protein without EDA.

DETAILED DESCRIPTION OF THE INVENTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero.

Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "fibronectin transcript" means a transcript transcribed from a fibronectin gene. In certain embodiments, a fibronectin transcript comprises SEQ ID NO: 1: the complement of GENBANK Accession No. NT_005403.14 truncated from nucleotides 66434501 to 66510708.

As used herein, "fibronectin gene" means a gene that encodes a fibronectin protein and any fibronectin protein isoforms. In certain embodiments, a fibronectin gene is represented by GENBANK Accession No. NT_005403.14 truncated from nucleotides 66434501 to 66510708, or a variant thereof. In certain embodiments, a fibronectin gene is at least 95% identical to GENBANK Accession No. NT_005403.14 truncated from nucleotides 66434501 to 66510708. In certain embodiments, a fibronectin gene is at least 90% identical to GENBANK Accession No. NT_005403.14 truncated from nucleotides 66434501 to 66510708.

As used herein, "EDA− fibronectin protein" means a fibronectin protein isoform that does not contain extra type III domain A.

As used herein, "EDA+ fibronectin protein" means a fibronectin protein isoform that contains extra type III domain A.

As used herein, "EDA− fibronectin mRNA" means a fibronectin transcript that does not contain the extra type III domain A exon.

As used herein, "EDA+ fibronectin mRNA" means a fibronectin transcript that contains the extra type III domain A exon.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C$_1$-C$_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, O($CH_2$)$_3$$NH_2$, $CH_2$—CH=$CH_2$, O—$CH_2$—CH=$CH_2$, $OCH_2CH_2OCH_3$, O($CH_2$)$_2$$SCH_3$, O—($CH_2$)$_2$—O—N($R_m$)($R_n$), O($CH_2$)$_2$O($CH_2$)$_2$N($CH_3$)$_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, O($CH_2$)$_2$$SCH_3$, O—($CH_2$)$_2$—O—N($CH_3$)$_2$, —O($CH_2$)$_2$O($CH_2$)$_2$N($CH_3$)$_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_a$$R_b$)—N(R)—O— or, —C($R_a$$R_b$)—O—N(R)—; 4'-$CH_2$-2', 4'-($CH_2$)$_2$-2', 4'-($CH_2$)$_3$-2'; 4'-($CH_2$)—O-2' (LNA); 4'-($CH_2$)—S-2; 4'-($CH_2$)$_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., J. Org. Chem., 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=$NR_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

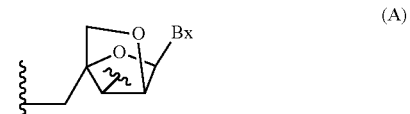
(A)

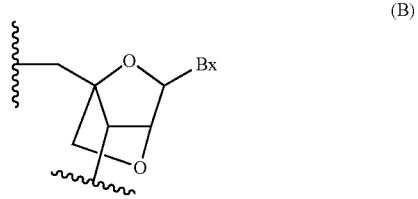
(B)

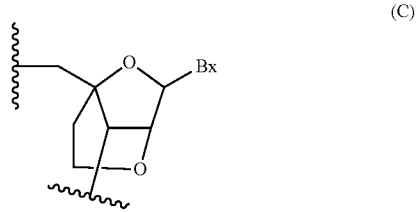
(C)

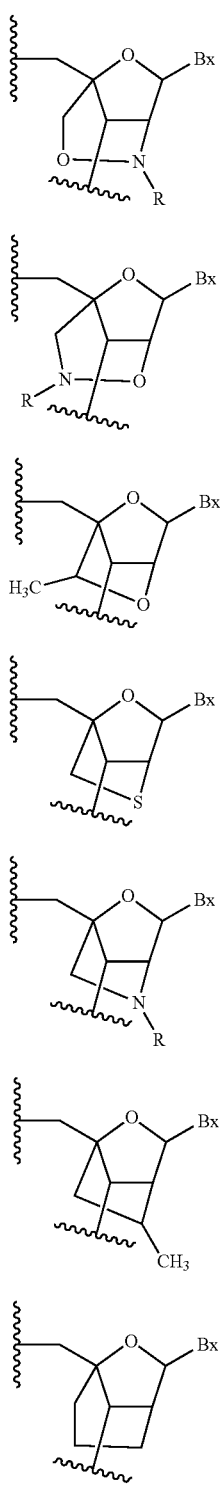

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

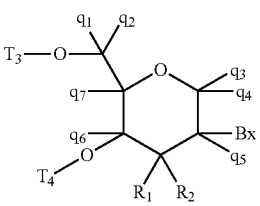

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

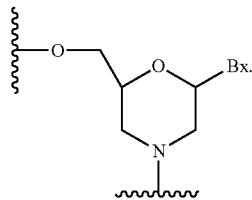

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH₂—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Splicing Motifs

In certain embodiments, oligonucleotides have a certain modification pattern and/or motif designed to alter the splicing of certain nucleic acid transcripts. In certain embodiments, oligonucleotides have a certain modification pattern and/or motif designed to alter the splicing of certain pre-mRNA transcripts. In certain embodiments, oligonucleotides have a certain modification pattern and/or motif designed in such a fashion that the oligonucleotide will not recruit RNase H once bound to a target nucleic acid transcript. For example, in certain such embodiments, an oligonucleotide may have one or more sugar modifications placed throughout the oligonucleotide so as to have no segment comprising more than 4 contiguous 2'-deoxynucleosides. In certain such embodiments, an oligonucleotide may have one or more sugar modifications placed throughout the oligonucleotide so as to have no segment comprising more than 3 contiguous 2'-deoxynucleosides. In certain such embodiments, an oligonucleotide may have one or more sugar modifications placed throughout the oligonucleotide so as to have no segment comprising more than 2 contiguous 2'-deoxynucleosides.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a $Ad_2Ad_2Ad_2Ad_2Ad_2A$ motif, wherein each A independently comprises a bicyclic modification selected from among LNA and cEt and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a AAddAddAddAddAddAA motif, wherein each A independently comprises a bicyclic modification selected from among LNA and cEt and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a AABBABBABBABBABBAB motif, wherein each A independently comprises a bicyclic modification selected from among LNA and cEt and each B independently comprises a 2'-modification selected from among a 2'-OMe, 2'-F, or 2'-MOE modification.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a AddAddAddAddAddA motif wherein each A independently comprises a bicyclic modification selected from among LNA and cEt and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a keekeekeekeekeek motif, wherein each k comprises a cEt modification and each e comprises a 2'-MOE modification.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a $kd_2kd_2kd_2kd_2kd_2k$ motif, wherein each k comprises a cEt modification and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkddkddkddkddkddkk motif, wherein each k comprises a cEt modification and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkeekeekeekeekeeke motif, wherein each k comprises a cEt modification and each e comprises a 2'-MOE modification.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kddkddkddkddkddk motif wherein each k comprises a cEt modification and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a keekeekeekeekeek motif, wherein each k comprises a cEt modification and each e comprises a 2'-MOE modification.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleosides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths. In certain embodiments, an antisense oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Pathways and Mechanisms Associated with Fibrosis

TGFβ1 and its associated pathways contribute to many processes associated with wound healing and tissue repair. After an injury, TGFβ1 contributes to the healing and restoration of normal tissue by, among other things, stimulating the production of certain extracellular matrix proteins and inhibiting the degradation of certain matrix proteins. In certain embodiments, TGFβ1 stimulates the production of fibronectin. In certain embodiments, TGFβ1 stimulates the production of both the EDA+ and EDA− isoforms of fibronectin. In certain embodiments, excessive amounts of the EDA+ fibronectin isoform causes tissue fibrosis. In certain embodiments, excessive tissue fibrosis induced by TGFβ1/EDA+ impairs normal organ function, impairs cellular function, and/or causes cells to change or lose their phenotype. In certain embodiments, the release and/or activation of TGFβ1 causes the formation of fibrosis and consequent changes in cell phenotype. In certain embodiments, changes in cell phenotype due to fibrosis include, but are not limited to, modulation of cadherin expression, induction of α Smooth Muscle Actin (αSMA), alteration of cortical f-actin localization, induction of connexin 43 (Cx 43) expression, alteration of vimentin, alteration of tight junction protein ZO-1, and/or increased secretion of MMP2 & MMP9. In certain embodiments, the release and/or activation of TGFβ1 causes a loss of cell phenotype. In certain embodiments, the loss of cell phenotype due to fibrosis impairs the structure or function of a cell. In certain embodiments, the loss of cell phenotype due to fibrosis destroys the function of a cell.

In certain embodiments, it is therefore desirable to reduce fibrosis without affecting the healing and/or restoration process. In certain embodiments, it is therefore desirable to reduce the formation of fibrosis in a cell without reducing or altering the amount and/or activity of TGFβ1 in the cell. In certain embodiments, it is therefore desirable to reduce the amount of EDA+ fibronectin in a cell without reducing or altering the amount of EDA− fibronectin in the cell. In certain embodiments, the reduction of the amount of EDA+ fibronectin in a cell in response to TGFβ1 will result in wound healing and tissue repair without incurring excessive fibrosis. In certain embodiments, the selective reduction of the amount of EDA+ fibronectin in a cell, relative to the amount of EDA− fibronectin in the cell in the response to TGFβ1 will stimulate wound healing and tissue repair without incurring changes in cell phenotype associated with fibrosis. In certain embodiments, the reduction of the amount of EDA+ fibronectin in a cell, relative to the amount of EDA− fibronectin in the cell in response to TGFβ1 will stimulate wound healing and tissue repair without incurring the loss of cell phenotype due to fibrosis.

In certain embodiments, it is desirable to reverse the formation of fibrosis in a cell without reducing or altering the wound healing function of TGFβ1 in the cell. In certain embodiments, it is therefore desirable to reverse the changes caused by fibrosis in the phenotype of a cell without reducing or altering the wound healing function of TGFβ1 in the cell. In certain embodiments, it is therefore desirable to reverse the loss of phenotype in a cell caused by fibrosis without reducing or altering the wound healing function of TGFβ1 in the cell.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is a fibronectin transcript. In certain embodiments, the target RNA is a fibronectin pre-mRNA.

In certain embodiments, an antisense compound is complementary to a region of fibronectin pre-mRNA. In certain embodiments, an antisense compound is complementary within a region of fibronectin pre-mRNA comprising an exon encoding EDA. In certain embodiments, an antisense compound is complementary to a region of fibronectin pre-mRNA comprising an intron-exon splice junction. In certain embodiments, an antisense compound is complementary to a region of fibronectin pre-mRNA comprising the intron-exon splice junction adjacent to the EDA exon. In certain embodiments, an antisense compound is complementary within a region of fibronectin pre-mRNA consisting of an exon encoding EDA. In certain embodiments, an antisense compound is complementary within a region of fibronectin pre-mRNA comprising an exonic splicing silencer within an exon encoding EDA. In certain embodiments, an antisense compound is complementary within a region of fibronectin pre-mRNA comprising an exonic splicing enhancer within an exon encoding EDA.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equal length of a fibronectin transcript. In certain embodiments, the target region is within nucleobase 55469 and nucleobase 55790 of SEQ ID NO.: 1. In certain embodiments, the target region is within nucleobase 55469 and nucleobase 55511 of SEQ ID NO.: 1. In certain embodiments, the target region is within nucleobase 55511 and nucleobase 55732 of SEQ ID NO.: 1. In certain embodiments, the target region is within nucleobase 55732 and nucleobase 55790 of SEQ ID NO.: 1.

In certain embodiments, an antisense oligonucleotide modulates splicing of a pre-mRNA. In certain embodiments, an antisense oligonucleotide modulates splicing a fibronectin pre-mRNA. In certain embodiments, an antisense oligonucleotide increases the amount of fibronectin mRNA. In certain embodiments, an antisense oligonucleotide increases the amount of EDA− fibronectin mRNA. In certain embodiments, an antisense oligonucleotide decreases the amount of EDA+ fibronectin mRNA. In certain embodiments, an antisense oligonucleotide decreases the amount of EDA+ fibronectin mRNA in the presence of TGFβ1. In certain embodiments, an antisense oligonucleotide decreases the amount of EDA+ fibronectin mRNA in a cell without substantially affecting the healing and/or restoration functions of the cell.

In certain embodiments, an antisense oligonucleotide alters the ratio of EDA+/EDA− fibronectin. In certain embodiments, an antisense oligonucleotide increases the ratio of EDA+/EDA− fibronectin. In certain embodiments, it is desirable to increase the ratio of EDA+/EDA− fibronectin to create a fibrosis model. In certain embodiments, it is desirable to increase the ratio of EDA+/EDA− fibronectin to create a fibrosis phenotype. In certain embodiments, it is desirable to increase the ratio of EDA+/EDA− fibronectin in the presence of TGFβ1 to create a fibrosis model. In certain embodiments, it is desirable to increase the ratio of EDA+/EDA− fibronectin in the presence of TGFβ1 to create a fibrosis phenotype. In certain embodiments, it is desirable to increase the ratio of EDA+/EDA− fibronectin to create a fibrosis mouse model. In certain embodiments, it is desirable to increase the ratio of EDA+/EDA− fibronectin to create a fibrosis mouse phenotype. In certain embodiments, it is desirable to increase the ratio of EDA+/EDA− fibronectin in the presence of TGFβ1 to create a fibrosis mouse model. In certain embodiments, it is desirable to increase the ratio of EDA+/EDA− fibronectin in the presence of TGFβ1 to create a fibrosis mouse phenotype.

In certain embodiments, an antisense oligonucleotide alters the ratio of EDA+/EDA− fibronectin. In certain embodiments, an antisense oligonucleotide decreases the ratio of EDA+/EDA− fibronectin. In certain embodiments, it is desirable to decrease the ratio of EDA+/EDA− fibronectin to create a fibrosis model. In certain embodiments, it is desirable to decrease the ratio of EDA+/EDA− fibronectin to create a fibrosis phenotype. In certain embodiments, it is desirable to decrease the ratio of EDA+/EDA− fibronectin in the presence of TGFβ1 to create a fibrosis model. In certain embodiments, it is desirable to decrease the ratio of EDA+/EDA− fibronectin in the presence of TGFβ1 to create a fibrosis phenotype. In certain embodiments, it is desirable to decrease the ratio of EDA+/EDA− fibronectin to create a fibrosis mouse model. In certain embodiments, it is desirable to decrease the ratio of EDA+/EDA− fibronectin to create a fibrosis mouse phenotype. In certain embodiments, it is desirable to decrease the ratio of EDA+/EDA− fibronectin in the presence of TGFβ1 to create a fibrosis mouse model. In certain embodiments, it is desirable to decrease the ratio of EDA+/EDA− fibronectin in the presence of TGFβ1 to create a fibrosis mouse phenotype.

In certain embodiments, an antisense oligonucleotide alters the ratio of EDA−/EDA+ fibronectin. In certain embodiments, an antisense oligonucleotide increases the ratio of EDA−/EDA+ fibronectin. In certain embodiments, it is desirable to increase the ratio of EDA−/EDA+ fibronectin to create a fibrosis model. In certain embodiments, it is desirable to increase the ratio of EDA−/EDA+ fibronectin to create a fibrosis phenotype. In certain embodiments, it is desirable to increase the ratio of EDA−/EDA+ fibronectin in the presence of TGFβ1 to create a fibrosis model. In certain embodiments, it is desirable to increase the ratio of EDA−/EDA+ fibronectin in the presence of TGFβ1 to create a fibrosis phenotype. In certain embodiments, it is desirable to increase the ratio of EDA−/EDA+ fibronectin to create a fibrosis mouse model. In certain embodiments, it is desirable to increase the ratio of EDA−/EDA+ fibronectin to create a fibrosis mouse phenotype. In certain embodiments, it is desirable to increase the ratio of EDA−/EDA+ fibronectin in the presence of TGFβ1 to create a fibrosis mouse model. In certain embodiments, it is desirable to increase the ratio of EDA−/EDA+ fibronectin in the presence of TGFβ1 to create a fibrosis mouse phenotype.

In certain embodiments, an antisense oligonucleotide alters the ratio of EDA−/EDA+ fibronectin. In certain embodiments, an antisense oligonucleotide decreases the ratio of EDA−/EDA+ fibronectin. In certain embodiments, it is desirable to decrease the ratio of EDA−/EDA+ fibronectin to create a fibrosis model. In certain embodiments, it is desirable to decrease the ratio of EDA−/EDA+ fibronectin to create a fibrosis phenotype. In certain embodiments, it is desirable to decrease the ratio of EDA−/EDA+ fibronectin in the presence of TGFβ1 to create a fibrosis model. In certain embodiments, it is desirable to decrease the ratio of EDA−/EDA+ fibronectin in the presence of TGFβ1 to create a fibrosis phenotype. In certain embodiments, it is desirable to decrease the ratio of EDA−/EDA+ fibronectin to create a fibrosis mouse model. In certain embodiments, it is desirable to decrease the ratio of EDA−/EDA+ fibronectin to create a fibrosis mouse phenotype. In certain embodiments, it is desirable to decrease the ratio of EDA−/EDA+ fibronectin in the presence of TGFβ1 to create a fibrosis mouse model. In certain embodiments, it is desirable to decrease the ratio of EDA−/EDA+ fibronectin in the presence of TGFβ1 to create a fibrosis mouse phenotype.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one symptom associated with fibrosis. In certain embodiments, such administration results in amelioration of at least one symptom. In certain embodiments, administration of a pharmaceutical composition to an animal results in a decrease of EDA+ fibronectin mRNA in a cell of the animal. In certain embodiments, such administration results in an increase in EDA− fibronectin mRNA. In certain embodiments, such administration results in a decrease in EDA+ fibronectin protein and an increase EDA− fibronectin protein. In certain embodiments, a fibronectin protein lacking EDA amino acids is preferred over a fibronectin protein having EDA amino acids. In certain embodiments, the administration of certain antisense oligonucleotides delays the onset of fibrosis. In certain embodiments, the administration of certain antisense oligonucleotides slows the progression of fibrosis. In certain embodiments, the administration of certain antisense oligonucleotides prevents the formation of fibrosis. In certain embodiments, the administration of certain antisense oligonucleotides reverses fibrosis. In certain embodiments, the administration of certain antisense oligonucleotides rescues cellular phenotype. In certain embodiments, the administration of certain antisense oligonucleotides rescues cellular morphology.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "Ar$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

In Vitro Screening of Human Fibronectin Splicing with Antisense Oligonucleotides in HKC-8 Cells Antisense oligonucleotides were designed targeting a fibronectin nucleic acid and were tested for their effects on the alternative splicing of the fibronectin gene sequence in vitro. The newly designed antisense oligonucleotides in Table 1 were designed as uniform MOE oligonucleotides. Each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. "Start site" indicates the 5'-most nucleoside to which the oligonucleotide is targeted in the human gene sequence. "Stop site" indicates the 3'-most nucleoside to which the oligonucleotide is targeted human gene sequence. Each oligonucleotide listed in Table 1 is targeted to SEQ ID NO: 1 (the complement of GENBANK Accession No. NT_005403.14 truncated from nucleotides 66434501 to 66510708). ISIS 141923 (CCTTCCCTGAAGGTTCCTCC (SEQ ID NO: 25), no known human target) was used as a negative control.

Cultured HKC-8 cells, which are SV40-transformed human proximal tubular cells, were transfected using 3 µL LipofectAMINE2000®/mL OptiMEM with 200 nM antisense oligonucleotide. After a treatment period of approximately 4 hours, the medium was removed and new medium was added, left in culture overnight. RNA was isolated from the cells and the ratio of Extra Domain A positive fibronectin (EDA⁺FN) to EDA negative fibronectin (EDA⁻FN) was measured by conventional PCR. Human primers with forward sequence GGAGAGAGTCAGCCTCTGGTTCAG, designated herein as SEQ ID NO: 2; reverse sequence TGTCAACTGGGCGCTCAGGCTTGTG, designated herein as SEQ ID NO: 3) was used to measure mRNA levels. To compare the efficacy of antisense treatments performed in different experiments and allow for inter-assay variability, ratios were indexed on the corresponding negative control. Results are presented in Table 1 and demonstrate that treatment with antisense oligonucleotides targeted to the EDA region of fibronectin resulted in decreased expression of the EDA⁺FN isoform compared to the negative control. 'null' indicates that the EDA⁺ band was undetectable for that sample.

TABLE 1

Ratio of EDA⁺FN to EDA⁻FN in HKC-8 cells after treatment with antisense oligonucleotides targeted to SEQ ID NO: 1

| ISIS NO | SEQ ID NO: 1 Start Site | SEQ ID NO: 1 Stop Site | Sequence | EDA⁺FN/ EDA⁻FN | SEQ ID NO |
|---|---|---|---|---|---|
| 511399 | 55469 | 55483 | GCAAATTAATGGTAA | 0.07 | 5 |
| 511400 | 55473 | 55487 | TTAGGCAAATTAATG | 0.07 | 6 |
| 511401 | 55477 | 55491 | TCTGTTAGGCAAATT | 0.05 | 7 |
| 511402 | 55480 | 55494 | ATGTCTGTTAGGCAA | 0.09 | 8 |
| 511403 | 55483 | 55497 | TCAATGTCTGTTAGG | 0.04 | 9 |
| 511404 | 55486 | 55500 | CGATCAATGTCTGTT | 0.04 | 10 |
| 511405 | 55489 | 55503 | GGGCGATCAATGTCT | 0.03 | 11 |
| 511406 | 55493 | 55507 | TTTAGGGCGATCAAT | 0.03 | 12 |
| 511407 | 55497 | 55511 | GTCCTTTAGGGCGAT | 0.4 | 13 |
| 511408 | 55732 | 55746 | CCAATCAGGGGCTGG | 0.02 | 14 |
| 511409 | 55736 | 55750 | GGTTCCAATCAGGGG | null | 15 |
| 511410 | 55740 | 55754 | ACTGGGTTCCAATCA | 0.01 | 16 |
| 511411 | 55743 | 55757 | TGGACTGGGTTCCAA | 0.02 | 17 |
| 511412 | 55746 | 55760 | CTGTGGACTGGGTTC | null | 18 |
| 511413 | 55749 | 55763 | TACCTGTGGACTGGG | 0.06 | 19 |
| 511414 | 55752 | 55766 | ATATACCTGTGGACT | 0.04 | 20 |
| 511415 | 55756 | 55770 | AACCATATACCTGTG | 0.05 | 21 |
| 511416 | 55760 | 55774 | AATTAACCATATACC | 0.15 | 22 |
| 511417 | 55482 | 55499 | GATCAATGTCTGTTAGGC | 0.12 | 23 |
| 511418 | 55744 | 55761 | CCTGTGGACTGGGTTCCA | null | 24 |
| 141923 | n/a | n/a | CCTTCCCTGAAGGTTCCTCC | 1.00 | 25 |

Example 2

In Vitro Screening of Human Fibronectin Splicing with Antisense Oligonucleotides in Primary Human Proximal Tubular Cells The antisense oligonucleotides described in Example 1 were also tested for their effects on the alternative splicing of the fibronectin gene sequence in primary human proximal tubular cells (PTEC). Cultured PTEC cells were transfected using 2 µL LipofectAMINE2000®/mL OptiMEM with 100 nM antisense oligonucleotide for 4 hours, the medium was removed and new medium added, left in culture overnight, and then treated with 0.1% BSA (vehicle) or 2.5 ng/mL TGFβ1 in 0.1% BSA for 24 hrs. RNA was isolated from the cells and levels were measured by conventional PCR. The ratio of EDA⁺FN to EDA⁻FN for the given oligonucleotide-treated cells to the ratio for the negative control-treated cells was calculated. Results are presented in Table 2 and indicate that treatment with antisense oligonucleotides targeted to the EDA region of fibronectin resulted in decreased expression of the EDA⁺FN isoform compared to the negative control, even after induction with TGFβ1. 'null' indicates that the EDA⁺ band was undetectable for that sample.

TABLE 2

Ratio of EDA⁺FN to EDA⁻FN in PTEC cells after treatment with antisense oligonucleotides

| ISIS NO | EDA⁺FN/ EDA⁻FN (without TGFβ1) | EDA⁺FN/ EDA⁻FN (with TGFβ1) | SEQ ID NO |
|---|---|---|---|
| 511399 | 0.13 | 0.17 | 5 |
| 511400 | 0.23 | 0.26 | 6 |
| 511401 | 0.14 | 0.26 | 7 |

TABLE 2-continued

Ratio of EDA⁺FN to EDA⁻FN in PTEC cells after treatment with antisense oligonucleotides

| ISIS NO | EDA⁺FN/ EDA⁻FN (without TGFβ1) | EDA⁺FN/ EDA⁻FN (with TGFβ1) | SEQ ID NO |
|---|---|---|---|
| 511402 | 0.20 | 0.27 | 8 |
| 511403 | 0.13 | 0.23 | 9 |
| 511404 | 0.09 | 0.11 | 10 |
| 511405 | 0.06 | 0.08 | 11 |
| 511406 | 0.03 | 0.04 | 12 |
| 511407 | 0.41 | 0.66 | 13 |
| 511408 | null | null | 14 |
| 511409 | null | null | 15 |
| 511410 | null | null | 16 |
| 511411 | 0.10 | 0.09 | 17 |
| 511412 | null | null | 18 |
| 511413 | 0.08 | 0.09 | 19 |
| 511414 | 0.15 | 0.13 | 20 |
| 511415 | 0.34 | 0.42 | 21 |
| 511416 | 0.62 | 0.97 | 22 |
| 511417 | 0.17 | 0.20 | 23 |
| 511418 | null | null | 24 |
| 141923 | 1.00 | 1.61 | 25 |

Example 3

Effect of Antisense Oligonucleotides Targeting the EDA Region of Fibronectin on TGFβ1 Induction of EDA⁺FN mRNA Expression in Primary Human Proximal Tubular Cells Antisense oligonucleotides selected from the studies described above were tested for their effects on the alternative splicing of the fibronectin gene sequence in primary human proximal tubular cells (PTEC) treated with TGFβ1. One set of cultured PTEC cells were transfected using 2 μL LipofectAMINE2000®/mL OptiMEM with 100 nM antisense oligonucleotide. These cells were treated for 4 hours with antisense oligonucleotide; the medium was removed and new medium added; left in culture overnight; and then treated with 0.1% BSA (vehicle) or 2.5 ng/mL TGFβ1 in 0.1% BSA for 24 hrs. These cells were designated as pre-TGFβ1. Another set of cells were first treated with 0.1% BSA (vehicle) or 2.5 ng/mL TGFβ1 in 01% BSA for 24 hrs; then transfected using 2 μL LipofectAMINE2000®/mL OptiMEM with 100 nM antisense oligonucleotide for 4 h; the medium was removed and new medium added; and then left in culture overnight. These cells were designated as post-TGFβ1. RNA was isolated from the cells and levels were measured by conventional PCR. The ratio of EDA⁺FN to EDA⁻FN for the given oligonucleotide-treated cells to the ratio for the negative control-treated cells was calculated. Results are presented in Tables 3 and 4, and indicate that treatment with antisense oligonucleotides targeted to the EDA region of fibronectin resulted in decreased expression of the EDA⁺FN isoform compared to the negative control, irrespective of whether the treatment with antisense oligonucleotides took place before or after induction with TGFβ1 'null' indicates that the EDA⁺ band was undetectable for that sample.

TABLE 3

Ratio of EDA⁺FN to EDA⁻FN in pre-TGFβ1 PTEC cells after treatment with antisense oligonucleotides

| ISIS NO | EDA⁺FN/ EDA⁻FN (without TGFβ1) | EDA⁺FN/ EDA⁻FN (with TGFβ1) | SEQ ID NO |
|---|---|---|---|
| 511399 | 0.13 | 0.17 | 5 |
| 511403 | 0.13 | 0.23 | 9 |
| 511407 | 0.41 | 0.66 | 13 |
| 511408 | null | null | 14 |
| 511412 | null | null | 18 |
| 511416 | 0.62 | 0.97 | 22 |
| 141923 | 1.00 | 1.61 | 25 |

TABLE 4

Ratio of EDA⁺FN to EDA⁻FN in post-TGFβ1 PTEC cells after treatment with antisense oligonucleotides

| ISIS NO | EDA⁺FN/ EDA⁻FN (without TGFβ1) | EDA⁺FN/ EDA⁻FN (with TGFβ1) | SEQ ID NO |
|---|---|---|---|
| 511399 | 0.68 | 0.75 | 5 |
| 511403 | 0.48 | 0.30 | 9 |
| 511407 | 0.68 | 0.68 | 13 |
| 511408 | 0.22 | 0.16 | 14 |
| 511412 | null | null | 18 |
| 511416 | 0.79 | 0.69 | 22 |
| 141923 | 1.00 | 1.57 | 25 |

Example 4

Effect of Antisense Oligonucleotides Targeting the EDA Region of Fibronectin on TGFβ1 Induction of EDA⁺FN Protein Expression in Primary Human Proximal Tubular Cells The antisense oligonucleotides described above were tested for their effects on the alternative splicing of the fibronectin gene sequence in primary human proximal tubular cells (PTEC) treated with TGFβ1. Cultured PTEC cells were transfected using 2 μL LipofectAMINE2000®/mL OptiMEM with 100 nM antisense oligonucleotide. The cells were treated for 4 hours with antisense oligonucleotide; the medium was removed and new medium added; left in culture overnight; and then treated with 0.1% BSA (vehicle) or 2.5 ng/mL TGFβ1 in 01% BSA for 48 hrs. The cells were lysed in lysis buffer (20 mM Tris-HCl, 150 mM NaCl, 1 mM EDTA, 1% Triton X, 0.5% sodium deoxycholate, 0.1% SDS; pH 7.2) and protein was extracted as described in Phanish M K et al., Biochem J. 2006 Jan. 15; 393(Pt 2):601-7. The protein samples were run on an SDS-PAGE and analyzed via western analysis using the anti-Fibronectin antibody [IST-9] (Abcam, ab6328) that reacts with an epitope located in the ED-A sequence of cellular fibronectin. Results are presented in Table 5, and indicate that treatment with antisense oligonucleotides targeted to the EDA region of fibronectin resulted in decreased protein expression of the EDA⁺FN isoform compared to the negative control.

TABLE 5

EDA+FN expression in PTEC cells after treatment with antisense oligonucleotides (densitometric analysis on one Western blot)

| ISIS NO | EDA+FN (without TGFβ1) | EDA+FN (with TGFβ1) | SEQ ID NO |
|---|---|---|---|
| 511399 | 0.07 | 0.03 | 5 |
| 511403 | 0.02 | 0.04 | 9 |
| 511407 | 0.13 | 0.75 | 13 |
| 511408 | 0.08 | 0.77 | 14 |
| 511412 | 0.25 | 0.30 | 18 |
| 511416 | 0.61 | 0.58 | 22 |
| 141923 | 0.31 | 0.74 | 25 |

Example 5

Effect of ISIS 511403 on TGFβ1 Induction of Fibrosis in Primary Human Proximal Tubular Cells ISIS 511403 was tested for its effect on the alternative splicing of the fibronectin gene sequence in primary human proximal tubular cells (PTEC) treated with TGFβ1. Cultured PTEC cells were treated with 0.1% BSA (vehicle) or with 2.5 ng/mL TGFβ1 in 01% BSA for 24 hrs and then transfected using 2 μL LipofectAMINE2000®/mL OptiMEM with 100 nM ISIS 511403 or 100 nM ISIS 141923 for 24 h. After a recovery period of 24 h in normal growth medium, RNA was isolated and the ratio of EDA+FN to EDA−□FN was measured by conventional PCR. In addition, the individual expressions of EDA+FN and EDA−□FN normalized to 18s RNA were also measured (human primer probe set for 18S: forward sequence: GTAACCCGTTGAACCCCATT (SEQ ID NO: 26), reverse sequence: CCATCCAATCGG-TAGTAGCG (SEQ ID NO: 27)). In addition, the expression of total fibronectin was also measured by quantitative real-time PCR (probe set Hs01549940_m1, Applied Biosystems). The results are presented in Table 6 and indicate that treatment with ISIS 511403 decreased the ratio of EDA+FN to EDA−FN, decreased expression of EDA+FN, increased expression of EDA−FN, and had no effect on total fibronectin expression compared to that of the negative control cells.

TABLE 6

Effect of ISIS 511403 in PTEC cells treated with TGFβ1

| | | without TGFβ1 | with TGFβ1 |
|---|---|---|---|
| EDA+FN/ | ISIS 141923 | 0.90 | 1.54 |
| EDA−□FN | ISIS 511403 | 0.21 | 0.12 |
| EDA+FN/18S | ISIS 141923 | 0.21 | 0.21 |
| | ISIS 511403 | 0.07 | 0.68 |
| EDA−□FN/18S | ISIS 141923 | 0.23 | 0.11 |
| | ISIS 511403 | 0.32 | 0.86 |
| Total Fibronectin (range) | ISIS 141923 | 1.00 (0.82-1.23) | 3.98 (3.60-4.40) |
| | ISIS 511403 | 1.37 (1.17-1.60) | 4.14 (4.05-4.23) |

The effect of treatment with ISIS 511403 on lactate dehydrogenase (LDH) release by the cells was also measured using the CytoTox 96® Non-Radioactive Cytotoxicity Assay (Promega, G1780). The results are presented in Table 7 and indicate the decrease in LDH release in cells treated with ISIS 511403 compared to the cells treated with the negative control. This demonstrates that ISIS 511403 can rescue certain pronounced changes in cell phenotype caused by TGFβ1 induction, e.g. the release of LDH.

TABLE 7

Effect of ISIS 511403 on LDH release in PTEC cells treated with TGFβ1

| | | Absorbance at 490 nm |
|---|---|---|
| ISIS 141923 | without TGFβ1 | 0.14 |
| | with TGFβ1 | 0.12 |
| ISIS 511403 | without TGFβ1 | 0.33 |
| | with TGFβ1 | 0.16 |

The effect of treatment with ISIS 511403 on αSMA mRNA expression by the cells was also measured by quantitative real-time PCR, using primer probe set Hs00909449_m1 (Applied Biosystems). The results are presented in Table 8 and indicate the decrease in αSMA in cells treated with ISIS 511403 compared to the cells treated with the negative control. The numbers in parentheses indicate the range. This demonstrates that ISIS 511403 can rescue certain pronounced changes in cell phenotype caused by TGFβ1 induction, e.g. the induction of αSMA.

TABLE 8

Effect of ISIS 511403 on αSMA expression in PTEC cells treated with TGFβ1

| | | Fold increase over basal levels |
|---|---|---|
| ISIS 141923 | without TGFβ1 | 1.00 |
| | | (0.79-1.26) |
| | with TGFβ1 | 1.96 |
| | | (1.70-2.25) |
| ISIS 511403 | without TGFβ1 | 0.70 |
| | | (0.59-0.83) |
| | with TGFβ1 | 0.79 |
| | | (0.68-0.91) |

The data presented in Tables 7 and 8 indicate that treatment with antisense oligonucleotides inhibiting the splicing and inclusion of the EDA region of fibronectin resulted in decreased fibrosis in primary human PTEC and therefore have therapeutic benefit in the prevention, treatment, or amelioration of fibrosis.

Additionally, by staining it was observed that prevention of EDA inclusion by treatment with ISIS 511403 resulted in a significant reduction in αSMA compared to treatment with a control (ISIS 141923). By western blot analysis, it was also observed that prevention of EDA inclusion by treatment with ISIS 511403 resulted in reduction in secretion of MMP2 & MMP9. The fold-change in the cell motility marker, S100A4 was measured and is presented in Table 9. Treatment with ISIS 511403 resulted in significant reduction in S100A4 in TGF-β-treated cells.

TABLE 9

Effect of ISIS 511403 on S100A4 expression in PTEC cells treated with TGFβ1

| | | Fold increase over basal levels |
|---|---|---|
| ISIS 141923 | without TGFβ1 | 1.00 |
| | with TGFβ1 | 1.45 |

TABLE 9-continued

Effect of ISIS 511403 on S100A4 expression in PTEC cells treated with TGFβ1

| | | Fold increase over basal levels |
|---|---|---|
| ISIS 511403 | without TGFβ1 | 0.62 |
| | with TGFβ1 | 0.74 |

By staining and by western blot analysis, it was also observed that prevention of EDA inclusion by treatment with ISIS 511403 resulted in near complete inhibition of Connexin 43. By staining, it was also observed that prevention of EDA inclusion by treatment with ISIS 511403 resulted in a moderate increase in f-actin localization.

Example 6

Design of Antisense Oligonucleotides Targeting Human and Murine Fibronectin

Antisense oligonucleotides were designed targeting a fibronectin nucleic acid. The newly designed chimeric antisense oligonucleotides in Table 10 were designed as uniform MOE oligonucleotides. Each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in Table 10 is targeted to the human fibronectin genomic sequence, SEQ ID NO: 1 (the complement of GENBANK Accession No. NT_005403.14 truncated from nucleotides 66434501 to 66510708) or to murine fibronectin genomic sequence, SEQ ID NO: 29 (the complement of Accession No. NT_039170.2 truncated from nucleotides 20696091 to 20764741), or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the number of nucleotides in the oligonucleotide that are mismatched with the gene sequence. 'n/a.' indicates that the oligonucleotide contains more than 2 mismatches with the particular gene sequence.

TABLE 10

Antisense oligonucleotides targeted to SEQ ID NO: 1 and SEQ ID NO: 29

| Human target Start Site (SEQ ID NO: 1) | Mismatches with SEQ ID NO: 1 | Sequence | ISIS No | Mouse Target Start Site (SEQ ID NO: 29) | Mismatches with SEQ ID NO: 29 | SEQ ID NO of oligo |
|---|---|---|---|---|---|---|
| 55458 | 0 | GTAAGAGGTTATGTG | 594692 | 49712 | 0 | 30 |
| 55464 | 0 | TTAATGGTAAGAGGT | 594693 | 49718 | 0 | 31 |
| 55478 | 0 | AATGTCTGTTAGGCAAAT | 594685 | 49732 | 0 | 32 |
| 55479 | 0 | CAATGTCTGTTAGGCAAA | 594686 | 49733 | 0 | 33 |
| 55480 | 0 | TCAATGTCTGTTAGGCAA | 594687 | 49734 | 0 | 34 |
| 55481 | 0 | AATGTCTGTTAGGCA | 594681 | 49735 | 0 | 35 |
| 55481 | 0 | ATCAATGTCTGTTAGGCA | 594688 | 49735 | 0 | 36 |
| 55482 | 0 | CAATGTCTGTTAGGC | 594682 | 49736 | 0 | 37 |
| 55483 | 0 | CGATCAATGTCTGTTAGG | 594689 | 49737 | 0 | 38 |
| 55484 | 0 | ATCAATGTCTGTTAG | 594683 | 49738 | 0 | 39 |
| 55484 | 0 | GCGATCAATGTCTGTTAG | 594690 | 49738 | 0 | 40 |
| 55485 | 0 | GATCAATGTCTGTTA | 594684 | 49739 | 0 | 41 |
| 55485 | 0 | GGCGATCAATGTCTGTTA | 594691 | 49739 | 0 | 42 |
| 55501 | 0 | GCCAGTCCTTTAGGG | 594694 | 49755 | 0 | 43 |
| 55507 | 0 | GTGAATGCCAGTCCT | 594695 | 49761 | 0 | 44 |
| 55513 | 0 | ACATCAGTGAATGCC | 594696 | 49767 | 0 | 45 |
| 55519 | 0 | ACATCCACATCAGTG | 594697 | 49773 | 0 | 46 |
| 55525 | 0 | GAATCGACATCCACA | 594698 | 49779 | 0 | 47 |
| 55531 | 0 | TTGATGGAATCGACA | 594699 | 49785 | 0 | 48 |
| 55537 | 0 | GCAATTTTGATGGAA | 594700 | 49791 | 0 | 49 |

TABLE 10-continued

Antisense oligonucleotides targeted to SEQ ID NO: 1 and SEQ ID NO: 29

| Human target Start Site (SEQ ID NO: 1) | Mismatches with SEQ ID NO: 1 | Sequence | ISIS No | Mouse Target Start Site (SEQ ID NO: 29) | Mismatches with SEQ ID NO: 29 | SEQ ID NO of oligo |
|---|---|---|---|---|---|---|
| 55543 | 0 | TCCCAAGCAATTTTG | 594701 | 49797 | 0 | 50 |
| 55549 | 0 | GGGCTTTCCCAAGCA | 594702 | 49803 | 0 | 51 |
| 55555 | 0 | CCCTGTGGGCTTTCC | 594703 | 49809 | 0 | 52 |
| 55561 | 0 | ACTTGCCCCTGTGGG | 594704 | 49815 | 0 | 53 |
| 55567 | 0 | CTGGAAACTTGCCCC | 594705 | 49821 | 0 | 54 |
| 55573 | 0 | CTGTACCTGGAAACT | 594706 | 49827 | 0 | 55 |
| 55579 | 0 | GTCACCCTGTACCTG | 594707 | 49833 | 0 | 56 |
| 55585 | 0 | GAGTAGGTCACCCTG | 594708 | 49839 | 0 | 57 |
| 55591 | 0 | GGGCTCGAGTAGGTC | 594709 | 49845 | 0 | 58 |
| 55597 | 0 | TCCTCAGGGCTCGAG | 594710 | 49851 | 0 | 59 |
| 55603 | 0 | ATTCCATCCTCAGGG | 594711 | 49857 | 0 | 60 |
| 55609 | 0 | TCATGGATTCCATCC | 594712 | 49863 | 2 | 61 |
| 55615 | 0 | AATAGCTCATGGATT | 594713 | n/a | n/a | 62 |
| 55621 | 0 | GCAGGGAATAGCTCA | 594714 | 49875 | 2 | 63 |
| 55627 | 0 | TCAGGTGCAGGGAAT | 594715 | 49881 | 1 | 64 |
| 55633 | 0 | TCACCATCAGGTGCA | 594716 | 49887 | 0 | 65 |
| 55639 | 0 | TCTTCTTCACCATCA | 594717 | 49893 | 1 | 66 |
| 55645 | 0 | GCAGTGTCTTCTTCA | 594718 | 49899 | 1 | 67 |
| 55651 | 0 | AGCTCTGCAGTGTCT | 594719 | 49905 | 1 | 68 |
| 55657 | 0 | CCTTGCAGCTCTGCA | 594720 | 49911 | 1 | 69 |
| 55663 | 0 | CTGAGGCCTTGCAGC | 594721 | 49917 | 1 | 70 |
| 55669 | 0 | CCCGGTCTGAGGCCT | 594722 | 49923 | 2 | 71 |
| 55675 | 0 | TCAGAACCCGGTCTG | 594723 | 49929 | 2 | 72 |
| 55681 | 0 | GTGTACTCAGAACCC | 594724 | 49935 | 1 | 73 |
| 55687 | 0 | CTGACTGTGTACTCA | 594725 | 49941 | 0 | 74 |
| 55693 | 0 | ACCACACTGACTGTG | 594726 | 49947 | 0 | 75 |
| 55699 | 0 | AAGGCAACCACACTG | 594727 | 49953 | 0 | 76 |
| 55705 | 0 | TCGTGCAAGGCAACC | 594728 | 49959 | 0 | 77 |
| 55711 | 0 | ATATCATCGTGCAAG | 594729 | 49965 | 0 | 78 |
| 55717 | 0 | CTCTCCATATCATCG | 594730 | 49971 | 0 | 79 |
| 55723 | 0 | GGCTGGCTCTCCATA | 594731 | 49977 | 0 | 80 |
| 55736 | 1 | GATTCCAATCAGGGG | 594670 | 49990 | 0 | 81 |
| 55740 | 1 | ACTGGATTCCAATCA | 594671 | 49994 | 0 | 82 |
| 55743 | 1 | TGGACTGGATTCCAA | 594672 | 49997 | 0 | 83 |
| 55744 | 1 | CCTGTGGACTGGATTCCA | 594677 | 49998 | 0 | 84 |
| 55746 | 1 | CTGTGGACTGGATTC | 594673 | 50000 | 0 | 85 |

TABLE 10-continued

Antisense oligonucleotides targeted to SEQ ID NO: 1 and SEQ ID NO: 29

| Human target Start Site (SEQ ID NO: 1) | Mismatches with SEQ ID NO: 1 | Sequence | ISIS No | Mouse Target Start Site (SEQ ID NO: 29) | Mismatches with SEQ ID NO: 29 | SEQ ID NO of oligo |
|---|---|---|---|---|---|---|
| 55749 | 1 | TACCTGTGGACTGGA | 594674 | 50003 | 0 | 86 |
| 55756 | 1 | AACGATATACCTGTG | 594675 | 50010 | 0 | 87 |
| 55760 | 2 | AATTAATCATAAACC | 594676 | 39337 | 0 | 88 |
| 55765 | 0 | GGTGCAATTAACCAT | 594732 | n/a | n/a | 89 |
| 55771 | 0 | CCTGGTGGTGCAATT | 594733 | n/a | n/a | 90 |

Example 7

In Vitro Screening of Uniform MOE Antisense Oligonucleotides Targeting Human and/or Mouse Fibronectin in MHT Cells Some of the antisense oligonucleotides presented in Example 6 were tested for potency in cultured primary PTEC cells. ISIS 511403 was also included in the study.

Cultured PTEC cells were transfected using 2 µL LipofectAMINE2000®/mL OptiMEM with 100 nM antisense oligonucleotide for 4 hours, the medium was removed and new medium added, left in culture overnight, and then treated with 0.1% BSA (vehicle) or 2.5 ng/mL TGFβ1 in 0.1% BSA for 24 hrs. RNA was isolated from the cells and levels of EDA⁺FN mRNA were measured by RT-PCR using primer probe sets RTS3963_MGB (forward sequence GCCTTGCACGATGATATGGA, designated herein as SEQ ID NO: 91; reverse sequence TGTGGGTGTGACCTGAGTGAA, designated herein as SEQ ID NO: 92; probe sequence ATTGGAACCCAGTCCAC, designated herein as SEQ ID NO: 93), as well as with primer probe set RTS3964 (forward sequence GAATCCAAGCGGAGAGAGTCA, designated herein as SEQ ID NO: 94; reverse sequence ACATCAGTGAATGCCAGTCCTTT, designated herein as SEQ ID NO: 95; probe sequence TTCAGACTGCAGTAACCAACATTGATCGCC, designated herein as SEQ ID NO: 96), both of which are designed to the EDA+ variant of the FN mRNA transcript (NM_212478.1, designated herein as SEQ ID NO: 97) and which target different regions of the transcript. For data analysis, the levels of EDA⁺FN mRNA were normalized to the levels of the house-keeping gene, the large ribosomal protein transcript (Human RPLPO, Applied Biosystems, cat#4333761F). For each antisense oligonucleotide, the ratio of EDA⁺FN to RPLPO in antisense oligonucleotide-treated cells was then normalized to the ratio of EDA⁺FN mRNA to RPLPO in untreated cells. The results are presented in Table 11. The results indicate that treatment with antisense oligonucleotides reduced expression of the EDA+ transcript compared to untreated cells, both in the presence or absence of TGFβ1.

TABLE 11

EDA⁺FN mRNA levels compared to untreated cells (designated 1.00) in primary PTEC cells

| ISIS No | PPset Used | without TGFβ1 | with TGFβ1 |
|---|---|---|---|
| 511403 | RTS3963_MGB | 0.21 | 0.21 |
| 594692 | RTS3963_MGB | 0.17 | 0.29 |
| 594693 | RTS3963_MGB | 0.21 | 0.32 |
| 594694 | RTS3963_MGB | 0.02 | 0.03 |
| 594695 | RTS3963_MGB | 0.15 | 0.24 |
| 594696 | RTS3963_MGB | 0.23 | 0.41 |
| 594697 | RTS3963_MGB | 0.40 | 0.70 |
| 594698 | RTS3963_MGB | 0.50 | 0.81 |
| 594699 | RTS3963_MGB | 0.51 | 0.76 |
| 594700 | RTS3963_MGB | 0.13 | 0.18 |
| 594701 | RTS3963_MGB | 0.33 | 0.47 |
| 594702 | RTS3963_MGB | 0.30 | 0.49 |
| 594703 | RTS3963_MGB | 0.16 | 0.32 |
| 594704 | RTS3963_MGB | 0.56 | 0.73 |
| 594705 | RTS3963_MGB | 0.40 | 0.68 |
| 594706 | RTS3963_MGB | 0.40 | 0.81 |
| 594707 | RTS3963_MGB | 0.29 | 0.40 |
| 594708 | RTS3963_MGB | 0.06 | 0.05 |
| 594709 | RTS3963_MGB | 0.03 | 0.02 |
| 594710 | RTS3963_MGB | 0.18 | 0.16 |
| 594711 | RTS3963_MGB | 0.43 | 0.27 |
| 594712 | RTS3963_MGB | 0.36 | 0.31 |
| 594713 | RTS3963_MGB | 0.14 | 0.15 |
| 594714 | RTS3963_MGB | 0.06 | 0.08 |
| 594715 | RTS3963_MGB | 0.05 | 0.07 |
| 594716 | RTS3963_MGB | 0.18 | 0.16 |
| 594717 | RTS3963_MGB | 0.71 | 0.68 |
| 594718 | RTS3963_MGB | 0.22 | 0.33 |
| 594719 | RTS3963_MGB | 0.46 | 0.44 |
| 594720 | RTS3963_MGB | 0.13 | 0.14 |
| 594721 | RTS3963_MGB | 0.14 | 0.13 |
| 594722 | RTS3963_MGB | 0.07 | 0.15 |
| 594723 | RTS3963_MGB | 0.05 | 0.05 |
| 594724 | RTS3963_MGB | 0.11 | 0.17 |
| 594725 | RTS3963_MGB | 0.06 | 0.07 |
| 594726 | RTS3963_MGB | 0.12 | 0.17 |
| 594727 | RTS3964 | 0.06 | 0.10 |
| 594728 | RTS3964 | 0.03 | 0.02 |
| 594729 | RTS3964 | 0.08 | 0.06 |
| 594730 | RTS3964 | 0.39 | 0.38 |
| 594731 | RTS3964 | 0.10 | 0.07 |
| 594732 | RTS3963_MGB | 0.92 | 0.79 |
| 594733 | RTS3963_MGB | 0.37 | 0.38 |

Example 8

In Vitro Screening of Uniform MOE Antisense Oligonucleotides Targeting Human and/or Mouse Fibronectin in MHT Cells Antisense oligonucleotides were designed targeting a fibronectin nucleic acid and were tested for their effects on blocking of splicing in vitro. The newly designed chimeric antisense oligonucleotides in Table 12 were designed as uniform MOE oligonucleotides. Each oligonucleotide is 15 nucleosides long and each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in Table 12 is targeted to the human fibronectin genomic sequence, SEQ ID NO: 1 or to murine fibronectin genomic sequence, SEQ ID NO: 22, or both. Several of the oligonucleotides are cross-reactive with human and mouse gene sequences. The greater the complementary between the oligonucleotide and the gene sequence, the more likely the oligonucleotide can target the gene sequence. 'Mismatches' indicates the least number of nucleotides in the oligonucleotide that are mismatched with the gene sequence; the antisense oligonucleotide may target the gene sequence with more mismatches. 'n/a.' indicates that the antisense oligonucleotide has more than 3 mismatches with the particular gene sequence.

Cultured MHT cells, a mouse hepatocellular carcinoma cell line (Koller, E. et al., Nucleic Acids Research, 2011, 1-13), were transfected using 5 µL LipofectAMINE2000®/mL OptiMEM with 50 nM antisense oligonucleotide. After a treatment period of approximately 4 hours, the medium was removed and new medium was added, and the cells were left in culture overnight RNA was isolated from the cells and measured by RT-PCR. EDA$^+$FN mRNA expression was measured with mouse primer probe set LTS01050 (forward sequence AAACTGCAGTGACCAACATTGATC, designated herein as SEQ ID NO: 98; reverse sequence CTTGCCCCTGTGGGCTTT, designated herein as SEQ ID NO: 99; probe sequence CTGATGTGGATGTCGATT, designated herein as SEQ ID NO: 100), as well as with LTS01052 (forward sequence GCCAGCCCCTGATTGGA, designated herein as SEQ ID NO: 101; reverse sequence CCGGTAGCCAGTGAGCTGAA, designated herein as SEQ ID NO: 102; probe sequence CACCAATCTGAAGTTC, designated herein as SEQ ID NO: 103). The primer probe sets target different regions of the mouse sequence.

Results are presented in Table 12 and are the average of the values measured in three separate experiments. The results demonstrate blocking of splicing, as represented by EDA$^+$FN expression. The expression value of untreated cells was taken as 1.00. 'n.d.' indicates that the mRNA expression level values were not considered because the oligonucleotide targeted an amplicon region of the specific primer probe set.

TABLE 12

EDA$^+$FN mRNA levels compared to untreated cells (designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 55469 | 0 | GCAAATTAATGGTAA | 49723 | 511399 | 0.43 | 0.44 | 104 |
| 55486 | 0 | CGATCAATGTCTGTT | 49740 | 511404 | n.d. | 0.27 | 105 |
| 55746 | 1 | CTGTGGACTGGATTC | 50000 | 594673 | 0.61 | n.d. | 85 |
| 55756 | 1 | AACGATATACCTGTG | 50010 | 594675 | 0.28 | n.d. | 87 |
| 55481 | 0 | AATGTCTGTTAGGCA | 49735 | 594681 | n.d. | 0.37 | 35 |
| 55501 | 0 | GCCAGTCCTTTAGGG | 49755 | 594694 | n.d. | 0.46 | 43 |
| 55531 | 0 | TTGATGGAATCGACA | 49785 | 594699 | n.d. | 0.93 | 48 |
| 55561 | 0 | ACTTGCCCCTGTGGG | 49815 | 594704 | n.d. | 0.94 | 53 |
| 55591 | 0 | GGGCTCGAGTAGGTC | 49845 | 594709 | 0.18 | 0.37 | 58 |
| 55711 | 0 | ATATCATCGTGCAAG | 49965 | 594729 | 0.50 | 0.33 | 78 |
| 55418 | 3 | TCCATACCATGCAAA | 49670 | 598110 | 1.11 | 1.04 | 106 |
| 20288 | 3 | ATATTTCCATACCAT | 49675 | 598111 | 1.11 | 1.02 | 107 |
| 51489 | 3 | | | | | | |
| 17531 | 3 | | | | | | |
| 19804 | 3 | CAAGCATATTTCCAT | 49680 | 598112 | 0.93 | 1.03 | 108 |
| 23642 | 3 | | | | | | |
| 42202 | 3 | | | | | | |
| 43710 | 2 | TGAAACAAGCATATT | 49685 | 598113 | 1.04 | 1.15 | 109 |
| 55431 | 2 | | | | | | |

TABLE 12-continued

EDA+FN mRNA levels compared to untreated cells
(designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 55436 | 1 | AGTTGTGAAACAAGC | 49690 | 598114 | 0.42 | 0.58 | 110 |
| 55441 | 0 | AAGCAAGTTGTGAAA | 49695 | 598115 | 0.08 | 0.35 | 111 |
| 55446 | 0 | GTGAAAAGCAAGTTG | 49700 | 598116 | 0.85 | 0.94 | 112 |
| 55451 | 0 | GTTATGTGAAAAGCA | 49705 | 598117 | 0.63 | 0.68 | 113 |
| 55456 | 0 | AAGAGGTTATGTGAA | 49710 | 598118 | 0.58 | 0.54 | 114 |
| 55461 | 0 | ATGGTAAGAGGTTAT | 49715 | 598119 | 0.47 | 0.43 | 115 |
| 55466 | 0 | AATTAATGGTAAGAG | 49720 | 598120 | 0.49 | 0.53 | 116 |
| 55471 | 0 | AGGCAAATTAATGGT | 49725 | 598121 | 0.27 | 0.29 | 117 |
| 55476 | 0 | CTGTTAGGCAAATTA | 49730 | 598122 | 0.23 | 0.34 | 118 |
| 55491 | 0 | TAGGGCGATCAATGT | 49745 | 598123 | n.d. | 0.29 | 119 |
| 55496 | 0 | TCCTTTAGGGCGATC | 49750 | 598124 | n.d. | 0.39 | 120 |
| 55506 | 0 | TGAATGCCAGTCCTT | 49760 | 598125 | n.d. | 0.70 | 121 |
| 55511 | 0 | ATCAGTGAATGCCAG | 49765 | 598126 | n.d. | 0.54 | 122 |
| 55516 | 0 | TCCACATCAGTGAAT | 49770 | 598127 | n.d. | 0.53 | 123 |
| 55521 | 0 | CGACATCCACATCAG | 49775 | 598128 | n.d. | 0.47 | 124 |
| 55526 | 0 | GGAATCGACATCCAC | 49780 | 598129 | n.d. | 0.32 | 125 |
| 55536 | 0 | CAATTTTGATGGAAT | 49790 | 598130 | n.d. | 0.26 | 126 |
| 55541 | 0 | CCAAGCAATTTTGAT | 49795 | 598131 | n.d. | 0.45 | 127 |
| 55546 | 0 | CTTTCCCAAGCAATT | 49800 | 598132 | n.d. | 0.51 | 128 |
| 55551 | 0 | GTGGGCTTTCCCAAG | 49805 | 598133 | n.d. | 0.92 | 129 |
| 55556 | 0 | CCCCTGTGGGCTTTC | 49810 | 598134 | n.d. | 0.59 | 130 |
| 55566 | 0 | TGGAAACTTGCCCCT | 49820 | 598135 | n.d. | 0.70 | 131 |
| 55571 | 0 | GTACCTGGAAACTTG | 49825 | 598136 | n.d. | 0.50 | 132 |
| 55576 | 0 | ACCCTGTACCTGGAA | 49830 | 598137 | 78 | 0.27 | 133 |
| 55581 | 0 | AGGTCACCCTGTACC | 49835 | 598138 | 78 | 0.27 | 134 |
| 55586 | 0 | CGAGTAGGTCACCCT | 49840 | 598139 | 71 | 0.41 | 135 |
| 55596 | 0 | CCTCAGGGCTCGAGT | 49850 | 598140 | 73 | 0.42 | 136 |
| 55601 | 0 | TCCATCCTCAGGGCT | 49855 | 598141 | 63 | 0.42 | 137 |
| 55606 | 1 | CGGATTCCATCCTCA | 49860 | 598142 | 52 | 0.35 | 138 |
| 55611 | 2 | GCTCCCGGATTCCAT | 49865 | 598143 | 78 | 0.31 | 139 |
| 48384 55616 | 3 3 | GAAAAGCTCCCGGAT | 49870 | 598144 | 0.20 | 0.28 | 140 |
| 55621 | 2 | GCAGGGAAAAGCTCC | 49875 | 598145 | 0.19 | 0.21 | 141 |
| 55626 | 1 | CAGGTGCAGGGAAAA | 49880 | 598146 | 0.32 | 0.33 | 142 |
| 55631 | 0 | ACCATCAGGTGCAGG | 49885 | 598147 | 0.31 | 0.30 | 143 |
| 55636 | 0 | TCTTCACCATCAGGT | 49890 | 598148 | 0.47 | 0.38 | 144 |

TABLE 12-continued

EDA+FN mRNA levels compared to untreated cells (designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 55641 | 1 | TGTCGTCTTCACCAT | 49895 | 598149 | 0.39 | 0.37 | 145 |
| 55646 | 1 | TGCAGTGTCGTCTTC | 49900 | 598150 | 0.66 | 0.41 | 146 |
| 55651 | 1 | AGCTCTGCAGTGTCG | 49905 | 598151 | 0.29 | 0.24 | 147 |
| 55656 | 1 | CCTGCAGCTCTGCAG | 49910 | 598152 | 0.40 | 0.42 | 148 |
| 55661 | 1 | GAGGCCCTGCAGCTC | 49915 | 598153 | 0.25 | 0.21 | 149 |
| 55666 | 2 | GGCCTGAGGCCCTGC | 49920 | 598154 | 0.79 | 0.80 | 150 |
| 55671 | 2 | ACCCCGGCCTGAGGC | 49925 | 598155 | 0.48 | 0.54 | 151 |
| 55676 | 2 | CTCAGACCCCGGCCT | 49930 | 598156 | 0.68 | 0.76 | 152 |
| 55681 | 1 | GTGTACTCAGACCCC | 49935 | 598157 | 0.57 | 0.41 | 153 |
| 55686 | 0 | TGACTGTGTACTCAG | 49940 | 598158 | 0.56 | 0.54 | 154 |
| 55691 | 0 | CACACTGACTGTGTA | 49945 | 598159 | 0.59 | 0.51 | 155 |
| 55696 | 0 | GCAACCACACTGACT | 49950 | 598160 | 0.54 | 0.49 | 156 |
| 55701 | 0 | GCAAGGCAACCACAC | 49955 | 598161 | 0.27 | 0.27 | 157 |
| 55706 | 0 | ATCGTGCAAGGCAAC | 49960 | 598162 | 0.56 | 0.49 | 158 |
| 55716 | 0 | TCTCCATATCATCGT | 49970 | 598163 | 0.31 | 0.22 | 159 |
| 55721 | 0 | CTGGCTCTCCATATC | 49975 | 598164 | 0.66 | n.d. | 160 |
| 55741 | 1 | GACTGGATTCCAATC | 49995 | 598165 | 0.56 | n.d. | 161 |
| 55751 | 0 | TATACCTGTGGACTG | 50005 | 598166 | 0.39 | n.d. | 162 |
| 55761 | 3 | CGGTTAACGATATAC | 50015 | 598167 | 0.30 | 0.25 | 163 |
| n/a | n/a | GGGTGCGGTTAACGA | 50020 | 598168 | 0.91 | 0.95 | 164 |
| n/a | n/a | GTGGTGGGTGCGGTT | 50025 | 598169 | 0.95 | 0.51 | 165 |
| 7620 | 3 | CCCGGGTGGTGGGTG | 50030 | 598170 | 0.81 | 0.79 | 166 |
| n/a | n/a | AAGCACCCGGGTGGT | 50035 | 598171 | 0.92 | 1.00 | 167 |
| n/a | n/a | CCCAGAAGCACCCGG | 50040 | 598172 | 1.36 | 1.32 | 168 |
| 50882 | 3 | CTGTTCCCAGAAGCA | 50045 | 598173 | 1.44 | 1.41 | 169 |
| 23948 47171 | 1 1 | AGCCACTGTTCCCAG | 50050 | 598174 | 1.11 | 1.14 | 170 |
| 55796 64745 | 2 2 | CATAAAGCCACTGTT | 50055 | 598175 | 0.94 | 0.91 | 171 |
| 55801 | 3 | CAAGGCATAAAGCCA | 50060 | 598176 | 1.13 | 0.97 | 172 |
| n/a | n/a | GCCAGCAAGGCATAA | 50065 | 598177 | 0.78 | 0.95 | 173 |
| 61226 | 3 | ATAACGCCAGCAAGG | 50070 | 598178 | 1.08 | 1.10 | 174 |
| n/a | n/a | AAAGTATAACGCCAG | 50075 | 598179 | 1.13 | 1.08 | 175 |
| 3323 55824 60705 | 3 3 3 | CCAGTAAAGTATAAC | 50080 | 598180 | 1.09 | 1.20 | 176 |

Example 9

Antisense Inhibition of Fibronectin mRNA in MHT Cells by Uniform MOE Oligonucleotides Designed by Microwalk Additional antisense oligonucleotides were designed based on the ISIS oligonucleotides that demonstrated significant effect on fibronectin splicing in the studies described above. These oligonucleotides were designed by creating oligonucleotides shifted slightly upstream and downstream (i.e. "microwalk") of ISIS 511417, ISIS 594685, ISIS 594686, ISIS 594686, ISIS 594687, ISIS 594688, ISIS 594689, ISIS 594690, ISIS 594691, and ISIS 598145. The newly designed antisense oligonucleotides in Tables 13 and 14 were designed as uniform MOE oligonucleotides. Each oligonucleotide is 18 nucleosides long and each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. The oligonucleotides are presented in the tables below. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in the tables is targeted to the human fibronectin genomic sequence, SEQ ID NO: 1 or to murine fibronectin genomic sequence, SEQ ID NO: 29, or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the least number of nucleotides in the oligonucleotide that are mismatched with the gene sequence; the antisense oligonucleotide may target the gene sequence with more mismatches. 'n/a.' indicates that the antisense oligonucleotide has more than 3 mismatches with the particular gene sequence.

Cultured MHT cells were transfected using 5 µl LipofectAMINE2000®/mL OptiMEM with 10 nM antisense oligonucleotide. After a treatment period of approximately 4 hours, the medium was removed and new medium was added, left in culture overnight. RNA was isolated from the cells and measured by RT-PCR. EDA$^+$FN mRNA expression was measured with mouse primer probe set LTS01050, as well as with LTS01052.

Results are presented in Tables 13 and 14, and are the average of the values measured in three separate experiments. The results demonstrate blocking of splicing, as represented by EDA$^+$FN expression. The expression value of untreated cells was taken as 1.00. 'n.d.' indicates that the mRNA expression level values were not considered because the oligonucleotide targeted an amplicon region of the specific primer probe set.

TABLE 13

EDA$^+$FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55471 | 0 | GTTAGGCAAATTAATGGT | 606663 | 49725 | n.d. | 0.77 | 177 |
| 55472 | 0 | TGTTAGGCAAATTAATGG | 606664 | 49726 | n.d. | 0.80 | 178 |
| 55473 | 0 | CTGTTAGGCAAATTAATG | 606665 | 49727 | n.d. | 0.78 | 179 |
| 55474 | 0 | TCTGTTAGGCAAATTAAT | 606666 | 49728 | n.d. | 0.73 | 180 |
| 55475 | 0 | GTCTGTTAGGCAAATTAA | 606667 | 49729 | n.d. | 0.70 | 181 |
| 55476 | 0 | TGTCTGTTAGGCAAATTA | 606668 | 49730 | n.d. | 0.62 | 182 |
| 55477 | 0 | ATGTCTGTTAGGCAAATT | 606669 | 49731 | n.d. | 0.66 | 183 |
| 55478 | 0 | AATGTCTGTTAGGCAAAT | 594685 | 49732 | n.d. | 0.79 | 32 |
| 55479 | 0 | CAATGTCTGTTAGGCAAA | 594686 | 49733 | 0.57 | 0.50 | 33 |
| 55480 | 0 | TCAATGTCTGTTAGGCAA | 594687 | 49734 | 1.21 | 0.99 | 34 |
| 55481 | 0 | ATCAATGTCTGTTAGGCA | 594688 | 49735 | 1.04 | 0.83 | 36 |
| 55482 | 0 | GATCAATGTCTGTTAGGC | 511417 | 49736 | 0.70 | 0.63 | 184 |
| 55483 | 0 | CGATCAATGTCTGTTAGG | 594689 | 49737 | n.d. | 0.66 | 38 |
| 55484 | 0 | GCGATCAATGTCTGTTAG | 594690 | 49738 | n.d. | 0.64 | 40 |
| 55485 | 0 | GGCGATCAATGTCTGTTA | 594691 | 49739 | n.d. | 0.85 | 42 |
| 55486 | 0 | GGGCGATCAATGTCTGTT | 606670 | 49740 | n.d. | 0.83 | 185 |
| 55487 | 0 | AGGGCGATCAATGTCTGT | 606671 | 49741 | n.d. | 0.82 | 186 |
| 55488 | 0 | TAGGGCGATCAATGTCTG | 606672 | 49742 | n.d. | 0.80 | 187 |
| 55489 | 0 | TTAGGGCGATCAATGTCT | 606673 | 49743 | n.d. | 0.56 | 188 |

TABLE 13-continued

EDA⁺FN mRNA levels compared to untreated cells
(designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55490 | 0 | TTTAGGGCGATCAATGTC | 606674 | 49744 | n.d. | 0.56 | 189 |
| 55491 | 0 | CTTTAGGGCGATCAATGT | 606675 | 49745 | n.d. | 0.55 | 190 |
| 55492 | 0 | CCTTTAGGGCGATCAATG | 606676 | 49746 | n.d. | 0.47 | 191 |
| 55493 | 0 | TCCTTTAGGGCGATCAAT | 606677 | 49747 | n.d. | 0.57 | 192 |
| 55494 | 0 | GTCCTTTAGGGCGATCAA | 606678 | 49748 | n.d. | 0.62 | 193 |
| 55495 | 0 | AGTCCTTTAGGGCGATCA | 606679 | 49749 | n.d. | 0.94 | 194 |
| 55496 | 0 | CAGTCCTTTAGGGCGATC | 606680 | 49750 | n.d. | 0.92 | 195 |
| 55523 | 0 | GGAATCGACATCCACATC | 606681 | 49777 | n.d. | 0.68 | 196 |
| 55524 | 0 | TGGAATCGACATCCACAT | 606682 | 49778 | n.d. | 0.70 | 197 |
| 55525 | 0 | ATGGAATCGACATCCACA | 606683 | 49779 | n.d. | 0.66 | 198 |
| 55526 | 0 | GATGGAATCGACATCCAC | 606684 | 49780 | n.d. | 0.63 | 199 |
| 55527 | 0 | TGATGGAATCGACATCCA | 606685 | 49781 | n.d. | 0.63 | 200 |
| 55528 | 0 | TTGATGGAATCGACATCC | 606686 | 49782 | n.d. | 0.88 | 201 |
| 55529 | 0 | TTTGATGGAATCGACATC | 606687 | 49783 | n.d. | 0.93 | 202 |
| 55533 | 0 | CAATTTGATGGAATCGA | 606688 | 49787 | n.d. | 1.05 | 203 |
| 55534 | 0 | GCAATTTTGATGGAATCG | 606689 | 49788 | n.d. | 0.81 | 204 |
| 55535 | 0 | AGCAATTTTGATGGAATC | 606690 | 49789 | n.d. | 0.60 | 205 |
| 55536 | 0 | AAGCAATTTTGATGGAAT | 606691 | 49790 | n.d. | 0.66 | 206 |
| 55537 | 0 | CAAGCAATTTTGATGGAA | 606692 | 49791 | n.d. | 0.56 | 207 |
| 55538 | 0 | CCAAGCAATTTTGATGGA | 606693 | 49792 | n.d. | 0.61 | 208 |
| 55539 | 0 | CCCAAGCAATTTTGATGG | 606694 | 49793 | n.d. | 0.84 | 209 |
| 55576 | 0 | GTCACCCTGTACCTGGAA | 606695 | 49830 | n.d. | 0.88 | 210 |
| 55577 | 0 | GGTCACCCTGTACCTGGA | 606696 | 49831 | 1.32 | 1.07 | 211 |
| 55578 | 0 | AGGTCACCCTGTACCTGG | 606697 | 49832 | 0.74 | 0.81 | 212 |
| 55579 | 0 | TAGGTCACCCTGTACCTG | 606698 | 49833 | 0.61 | 0.69 | 213 |
| 55580 | 0 | GTAGGTCACCCTGTACCT | 606699 | 49834 | 0.52 | 0.49 | 214 |
| 55581 | 0 | AGTAGGTCACCCTGTACC | 606700 | 49835 | 0.48 | 0.57 | 215 |
| 55582 | 0 | GAGTAGGTCACCCTGTAC | 606701 | 49836 | 0.45 | 0.59 | 216 |
| 55583 | 0 | CGAGTAGGTCACCCTGTA | 606702 | 49837 | 0.60 | 0.80 | 217 |
| 55584 | 0 | TCGAGTAGGTCACCCTGT | 606703 | 49838 | 0.60 | 0.91 | 218 |
| 55585 | 0 | CTCGAGTAGGTCACCCTG | 606704 | 49839 | 0.60 | 0.78 | 219 |
| 55586 | 0 | GCTCGAGTAGGTCACCCT | 606705 | 49840 | 0.59 | 0.69 | 220 |
| 55587 | 0 | GGCTCGAGTAGGTCACCC | 606706 | 49841 | 0.57 | 0.57 | 221 |
| 55588 | 0 | GGGCTCGAGTAGGTCACC | 606707 | 49842 | 0.53 | 0.58 | 222 |
| 55589 | 0 | AGGGCTCGAGTAGGTCAC | 606708 | 49843 | 0.62 | 0.63 | 223 |
| 55590 | 0 | CAGGGCTCGAGTAGGTCA | 606709 | 49844 | 0.45 | 0.50 | 224 |

TABLE 13-continued

EDA⁺FN mRNA levels compared to untreated cells
(designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55591 | 0 | TCAGGGCTCGAGTAGGTC | 606710 | 49845 | 0.60 | 0.60 | 225 |
| 55592 | 0 | CTCAGGGCTCGAGTAGGT | 606711 | 49846 | 0.83 | 0.86 | 226 |
| 55593 | 0 | CCTCAGGGCTCGAGTAGG | 606712 | 49847 | 0.95 | 0.99 | 227 |
| 55594 | 0 | TCCTCAGGGCTCGAGTAG | 606713 | 49848 | 0.95 | 0.83 | 228 |
| 55595 | 0 | ATCCTCAGGGCTCGAGTA | 606714 | 49849 | 0.67 | 0.61 | 229 |
| 55596 | 0 | CATCCTCAGGGCTCGAGT | 606715 | 49850 | 0.58 | 0.59 | 230 |
| 55597 | 0 | CCATCCTCAGGGCTCGAG | 606716 | 49851 | 0.65 | 0.58 | 231 |
| 55598 | 0 | TCCATCCTCAGGGCTCGA | 606717 | 49852 | 0.64 | 0.54 | 232 |
| 55599 | 0 | TTCCATCCTCAGGGCTCG | 606718 | 49853 | 0.65 | 0.62 | 233 |
| 55600 | 0 | ATTCCATCCTCAGGGCTC | 606719 | 49854 | 0.87 | 0.88 | 234 |
| 55601 | 0 | GATTCCATCCTCAGGGCT | 606720 | 49855 | 0.87 | 0.82 | 235 |
| 55602 | 0 | GGATTCCATCCTCAGGGC | 606721 | 49856 | 0.53 | 0.66 | 236 |
| 55603 | 1 | CGGATTCCATCCTCAGGG | 606722 | 49857 | 0.48 | 0.51 | 237 |
| 55604 | 2 | CCGGATTCCATCCTCAGG | 606723 | 49858 | 0.58 | 0.50 | 238 |
| 55605 | 2 | CCCGGATTCCATCCTCAG | 606724 | 49859 | 0.53 | 0.49 | 239 |
| 55606 | 2 | TCCCGGATTCCATCCTCA | 606725 | 49860 | 0.51 | 0.53 | 240 |
| 55607 | 2 | CTCCCGGATTCCATCCTC | 606726 | 49861 | 0.61 | 0.62 | 241 |
| 55608 | 2 | GCTCCCGGATTCCATCCT | 606727 | 49862 | 0.68 | 0.75 | 242 |
| 55609 | 2 | AGCTCCCGGATTCCATCC | 606728 | 49863 | 0.83 | 0.90 | 243 |
| 55610 | 3 | AAGCTCCCGGATTCCATC | 606729 | 49864 | 0.48 | 0.68 | 244 |
| 55611 | 3 | AAAGCTCCCGGATTCCAT | 606730 | 49865 | 0.26 | 0.53 | 245 |
| 55612 | 3 | AAAAGCTCCCGGATTCCA | 606731 | 49866 | 0.32 | 0.52 | 246 |
| 55613 | 3 | GAAAAGCTCCCGGATTCC | 606732 | 49867 | 0.37 | 0.52 | 247 |
| 55614 | 3 | GGAAAAGCTCCCGGATTC | 606733 | 49868 | 0.49 | 0.59 | 248 |
| 55615 | 3 | GGGAAAAGCTCCCGGATT | 606734 | 49869 | 0.61 | 0.57 | 249 |
| 55621 | 2 | GCAGGGAAAAGCTCC | 598145 | 49875 | 0.78 | 0.92 | 141 |

TABLE 14

EDA⁺FN mRNA levels compared to untreated cells
(designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 48384 | 3 | AGGGAAAAGCTCCCGGAT | 606735 | 49870 | 0.95 | 0.77 | 250 |
| 55617 | 3 | CAGGGAAAAGCTCCCGGA | 606736 | 49871 | 1.04 | 0.83 | 251 |
| 55618 | 3 | GCAGGGAAAAGCTCCCGG | 606737 | 49872 | 0.85 | 0.82 | 252 |
| 55619 | 3 | TGCAGGGAAAAGCTCCCG | 606738 | 49873 | 0.71 | 0.76 | 253 |
| 55620 | 3 | GTGCAGGGAAAAGCTCCC | 606739 | 49874 | 0.65 | 0.68 | 254 |

TABLE 14-continued

EDA⁺FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55621 | 2 | GCAGGGAAAAGCTCC | 598145 | 49875 | 0.79 | 0.55 | 141 |
| 55621 | 2 | GGTGCAGGGAAAAGCTCC | 606740 | 49875 | 0.79 | 0.76 | 255 |
| 55622 | 1 | AGGTGCAGGGAAAAGCTC | 606741 | 49876 | 0.88 | 0.83 | 256 |
| 55623 | 1 | CAGGTGCAGGGAAAAGCT | 606742 | 49877 | 0.77 | 0.88 | 257 |
| 55624 | 1 | TCAGGTGCAGGGAAAAGC | 606743 | 49878 | 1.11 | 0.98 | 258 |
| 55625 | 1 | ATCAGGTGCAGGGAAAAG | 606744 | 49879 | 1.05 | 0.97 | 259 |
| 55626 | 1 | CATCAGGTGCAGGGAAAA | 606745 | 49880 | 0.76 | 0.79 | 260 |
| 55627 | 1 | CCATCAGGTGCAGGGAAA | 606746 | 49881 | 0.50 | 0.63 | 261 |
| 55628 | 0 | ACCATCAGGTGCAGGGAA | 606747 | 49882 | 0.53 | 0.73 | 262 |
| 55629 | 0 | CACCATCAGGTGCAGGGA | 606748 | 49883 | 0.70 | 0.77 | 263 |
| 55630 | 0 | TCACCATCAGGTGCAGGG | 606749 | 49884 | 0.83 | 0.85 | 264 |
| 55631 | 0 | TTCACCATCAGGTGCAGG | 606750 | 49885 | 1.11 | 0.94 | 265 |
| 55632 | 0 | CTTCACCATCAGGTGCAG | 606751 | 49886 | 0.88 | 0.82 | 266 |
| 55633 | 0 | TCTTCACCATCAGGTGCA | 606752 | 49887 | 0.68 | 0.71 | 267 |
| 55634 | 1 | GTCTTCACCATCAGGTGC | 606753 | 49888 | 0.49 | 0.55 | 268 |
| 55635 | 1 | CGTCTTCACCATCAGGTG | 606754 | 49889 | 0.90 | 0.53 | 269 |
| 55636 | 1 | TCGTCTTCACCATCAGGT | 606755 | 49890 | 1.17 | 0.49 | 270 |
| 55637 | 1 | GTCGTCTTCACCATCAGG | 606756 | 49891 | 1.58 | 0.57 | 271 |
| 55638 | 1 | TGTCGTCTTCACCATCAG | 606757 | 49892 | 1.48 | 0.64 | 272 |
| 55639 | 1 | GTGTCGTCTTCACCATCA | 606758 | 49893 | 1.27 | 0.96 | 273 |
| 55640 | 1 | AGTGTCGTCTTCACCATC | 606759 | 49894 | 0.78 | 0.75 | 274 |
| 55641 | 1 | CAGTGTCGTCTTCACCAT | 606760 | 49895 | 0.52 | 0.54 | 275 |
| 55642 | 1 | GCAGTGTCGTCTTCACCA | 606761 | 49896 | 0.47 | 0.53 | 276 |
| 55643 | 1 | TGCAGTGTCGTCTTCACC | 606762 | 49897 | 0.49 | 0.55 | 277 |
| 55644 | 1 | CTGCAGTGTCGTCTTCAC | 606763 | 49898 | 0.61 | 0.54 | 278 |
| 55645 | 1 | TCTGCAGTGTCGTCTTCA | 606764 | 49899 | 0.93 | 0.57 | 279 |
| 55646 | 1 | CTCTGCAGTGTCGTCTTC | 606765 | 49900 | 0.98 | 0.67 | 280 |
| 55647 | 1 | GCTCTGCAGTGTCGTCTT | 606766 | 49901 | 0.72 | 0.83 | 281 |
| 55648 | 1 | AGCTCTGCAGTGTCGTCT | 606767 | 49902 | 0.71 | 0.65 | 282 |
| 55649 | 1 | CAGCTCTGCAGTGTCGTC | 606768 | 49903 | 0.71 | 0.62 | 283 |
| 55650 | 1 | GCAGCTCTGCAGTGTCGT | 606769 | 49904 | 0.64 | 0.60 | 284 |
| 55651 | 1 | TGCAGCTCTGCAGTGTCG | 606770 | 49905 | 0.40 | 0.47 | 285 |
| 55652 | 1 | CTGCAGCTCTGCAGTGTC | 606771 | 49906 | 0.35 | 0.53 | 286 |
| 55653 | 1 | CCTGCAGCTCTGCAGTGT | 606772 | 49907 | 0.47 | 0.56 | 287 |
| 55654 | 1 | CCCTGCAGCTCTGCAGTG | 606773 | 49908 | 0.71 | 0.97 | 288 |
| 55655 | 1 | GCCCTGCAGCTCTGCAGT | 606774 | 49909 | 0.83 | 0.97 | 289 |

TABLE 14-continued

EDA+FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55656 | 1 | GGCCCTGCAGCTCTGCAG | 606775 | 49910 | 0.91 | 0.73 | 290 |
| 55657 | 1 | AGGCCCTGCAGCTCTGCA | 606776 | 49911 | 0.74 | 0.64 | 291 |
| 55658 | 1 | GAGGCCCTGCAGCTCTGC | 606777 | 49912 | 0.60 | 0.66 | 292 |
| 55659 | 1 | TGAGGCCCTGCAGCTCTG | 606778 | 49913 | 0.49 | 0.50 | 293 |
| 55660 | 1 | CTGAGGCCCTGCAGCTCT | 606779 | 49914 | 0.47 | 0.57 | 294 |
| 55661 | 2 | CCTGAGGCCCTGCAGCTC | 606780 | 49915 | 0.54 | 0.65 | 295 |
| 55698 | 0 | GCAAGGCAACCACACTGA | 606781 | 49952 | 0.60 | 0.71 | 296 |
| 55699 | 0 | TGCAAGGCAACCACACTG | 606782 | 49953 | 0.75 | 0.79 | 297 |
| 55700 | 0 | GTGCAAGGCAACCACACT | 606783 | 49954 | 0.75 | 0.63 | 298 |
| 55701 | 0 | CGTGCAAGGCAACCACAC | 606784 | 49955 | 0.53 | 0.59 | 299 |
| 55702 | 0 | TCGTGCAAGGCAACCACA | 606785 | 49956 | 0.46 | 0.46 | 300 |
| 55703 | 0 | ATCGTGCAAGGCAACCAC | 606786 | 49957 | 0.48 | 0.55 | 301 |
| 55704 | 0 | CATCGTGCAAGGCAACCA | 606787 | 49958 | 0.46 | 0.45 | 302 |
| 55708 | 0 | ATATCATCGTGCAAGGCA | 606788 | 49962 | 0.36 | 0.45 | 303 |
| 55709 | 0 | CATATCATCGTGCAAGGC | 606789 | 49963 | 0.59 | 0.49 | 304 |
| 55710 | 0 | CCATATCATCGTGCAAGG | 606790 | 49964 | 1.00 | 0.72 | 305 |
| 55711 | 0 | TCCATATCATCGTGCAAG | 606791 | 49965 | 1.00 | 0.58 | 306 |
| 55712 | 0 | CTCCATATCATCGTGCAA | 606792 | 49966 | 0.78 | 0.54 | 307 |
| 55713 | 0 | TCTCCATATCATCGTGCA | 606793 | 49967 | 0.61 | 0.46 | 308 |
| 55714 | 0 | CTCTCCATATCATCGTGC | 606794 | 49968 | 0.52 | n.d. | 309 |
| 55715 | 0 | GCTCTCCATATCATCGTG | 606795 | 49969 | 0.69 | n.d. | 310 |
| 55716 | 0 | GGCTCTCCATATCATCGT | 606796 | 49970 | 0.70 | n.d. | 311 |
| 55717 | 0 | TGGCTCTCCATATCATCG | 606797 | 49971 | 0.71 | n.d. | 312 |
| 55718 | 0 | CTGGCTCTCCATATCATC | 606798 | 49972 | 1.37 | n.d. | 313 |
| 55719 | 0 | GCTGGCTCTCCATATCAT | 606799 | 49973 | 1.82 | n.d. | 314 |
| 55749 | 1 | ATATACCTGTGGACTGGA | 606800 | 50003 | 0.77 | n.d. | 315 |
| 55750 | 1 | GATATACCTGTGGACTGG | 606801 | 50004 | 0.56 | n.d. | 316 |
| 55751 | 1 | CGATATACCTGTGGACTG | 606802 | 50005 | 0.40 | n.d. | 317 |
| 55752 | 1 | ACGATATACCTGTGGACT | 606803 | 50006 | 0.34 | n.d. | 318 |
| 55753 | 1 | AACGATATACCTGTGGAC | 606804 | 50007 | 0.33 | n.d. | 319 |
| 55754 | 1 | TAACGATATACCTGTGGA | 606805 | 50008 | 0.47 | n.d. | 320 |
| 55755 | 1 | TTAACGATATACCTGTGG | 606806 | 50009 | 0.57 | n.d. | 321 |
| 55756 | 2 | GTTAACGATATACCTGTG | 606807 | 50010 | 0.73 | n.d. | 322 |
| 55757 | 3 | GGTTAACGATATACCTGT | 606808 | 50011 | 0.59 | n.d. | 323 |
| 55758 | 3 | CGGTTAACGATATACCTG | 606809 | 50012 | 0.40 | n.d. | 324 |
| 55759 | 3 | GCGGTTAACGATATACCT | 606810 | 50013 | 0.40 | n.d. | 325 |
| 55760 | 3 | TGCGGTTAACGATATACC | 606811 | 50014 | 0.40 | n.d. | 326 |

TABLE 14-continued

EDA⁺FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55761 | 3 | GTGCGGTTAACGATATAC | 606812 | 50015 | 0.43 | 0.46 | 327 |
| 55762 | 3 | GGTGCGGTTAACGATATA | 606813 | 50016 | 0.48 | 0.59 | 328 |
| n/a | n/a | GGGTGCGGTTAACGATAT | 606814 | 50017 | 0.77 | 0.83 | 329 |

Example 10

In Vitro Screening of Antisense Oligonucleotides with (S)-cEt Modifications Targeting Human and/or Mouse Fibronectin in b.END Cells Antisense oligonucleotides were designed targeting a fibronectin nucleic acid and were tested for their effects on blocking of fibronectin splicing in vitro. ISIS 606793 was also included in the study. The newly designed antisense oligonucleotides in Tables 15-22 were designed as deoxy and (S)-cEt oligonucleotides. Each nucleoside in the oligonucleotide has a 2'-MOE, deoxy, or (S)-cEt modification, as presented in the Chemistry column of the tables. 'e' indicates MOE; 'k' indicates (S)-cEt; 'd' indicates deoxy modifications. The internucleoside linkages throughout each oligonucleotide are phosphorothioate (P=S) linkages. All cytosine residues throughout each oligonucleotide are 5-methylcytosines. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in Tables 15-22 is targeted to the human fibronectin genomic sequence, SEQ ID NO: 1 or to murine fibronectin genomic sequence, SEQ ID NO: 29, or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the least number of nucleotides in the oligonucleotide that are mismatched with the gene sequence; the antisense oligonucleotide may target the gene sequence with more mismatches. 'n/a.' indicates that the antisense oligonucleotide has more than 3 mismatches with the particular gene sequence.

Cultured b.END cells were transfected using 2 µl Cytofectin/mL with 3 nM antisense oligonucleotide. After a treatment period of approximately 4 hours, the medium was removed and new medium was added, left in culture overnight RNA was isolated from the cells and measured by RT-PCR. EDA⁺FN mRNA expression was measured with mouse primer probe set LTS01050, as well as with LTS01052.

Results are presented in Tables 15-22, and are the average of the values measured in three separate experiments. The results demonstrate blocking of splicing, as represented by EDA⁺FN expression. The expression value of untreated cells was taken as 1.00. 'n.d.' indicates that the mRNA expression level values were not considered because the oligonucleotide targeted an amplicon region of the specific primer probe set.

TABLE 15

EDA⁺FN mRNA levels compared to untreated cells (designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 48386 | 3 | 49872 | AGGGAAAAGCTCCCGG | 607180 | kddkddkddkddkddk | 0.80 | 330 |
| 55578 | 0 | 49832 | GTCACCCTGTACCTGG | 607170 | kddkddkddkddkddk | 0.86 | 331 |
| 55582 | 0 | 49836 | GTAGGTCACCCTGTAC | 607171 | kddkddkddkddkddk | 0.71 | 332 |
| 55586 | 0 | 49840 | TCGAGTAGGTCACCCT | 607172 | kddkddkddkddkddk | 0.56 | 333 |
| 55590 | 0 | 49844 | GGGCTCGAGTAGGTCA | 607173 | kddkddkddkddkddk | 0.41 | 334 |
| 55594 | 0 | 49848 | CTCAGGGCTCGAGTAG | 607174 | kddkddkddkddkddk | 0.50 | 335 |
| 55598 | 0 | 49852 | CATCCTCAGGGCTCGA | 607175 | kddkddkddkddkddk | 0.44 | 336 |
| 55602 | 0 | 49856 | ATTCCATCCTCAGGGC | 607176 | kddkddkddkddkddk | 0.42 | 337 |
| 55606 | 2 | 49860 | CCGGATTCCATCCTCA | 607177 | kddkddkddkddkddk | 0.47 | 338 |
| 55610 | 2 | 49864 | GCTCCCGGATTCCATC | 607178 | kddkddkddkddkddk | 0.18 | 339 |

TABLE 15-continued

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55614 | 3 | 49868 | AAAAGCTCCCGGATTC | 607179 | kddkddkddkddkddk | 0.31 | 340 |
| 55622 | 1 | 49876 | GTGCAGGGAAAAGCTC | 607181 | kddkddkddkddkddk | 0.73 | 341 |
| 55626 | 1 | 49880 | TCAGGTGCAGGGAAAA | 607182 | kddkddkddkddkddk | 0.72 | 342 |
| 55630 | 0 | 49884 | ACCATCAGGTGCAGGG | 607183 | kddkddkddkddkddk | 0.36 | 343 |
| 55634 | 0 | 49888 | CTTCACCATCAGGTGC | 607184 | kddkddkddkddkddk | 0.49 | 344 |
| 55638 | 1 | 49892 | TCGTCTTCACCATCAG | 607185 | kddkddkddkddkddk | 0.34 | 345 |
| 55642 | 1 | 49896 | AGTGTCGTCTTCACCA | 607186 | kddkddkddkddkddk | 0.22 | 346 |
| 55646 | 1 | 49900 | CTGCAGTGTCGTCTTC | 607187 | kddkddkddkddkddk | 0.36 | 347 |
| 55650 | 1 | 49904 | AGCTCTGCAGTGTCGT | 607188 | kddkddkddkddkddk | 0.19 | 348 |
| 55654 | 1 | 49908 | CTGCAGCTCTGCAGTG | 607189 | kddkddkddkddkddk | 0.71 | 349 |
| 55658 | 1 | 49912 | GGCCCTGCAGCTCTGC | 607190 | kddkddkddkddkddk | 0.29 | 350 |
| 55662 | 1 | 49916 | CTGAGGCCCTGCAGCT | 607191 | kddkddkddkddkddk | 0.32 | 351 |
| 55666 | 2 | 49920 | CGGCCTGAGGCCCTGC | 607192 | kddkddkddkddkddk | 0.48 | 352 |
| 55670 | 2 | 49924 | ACCCCGGCCTGAGGCC | 607193 | kddkddkddkddkddk | 0.33 | 353 |
| 55674 | 2 | 49928 | TCAGACCCCGGCCTGA | 607194 | kddkddkddkddkddk | 0.34 | 354 |
| 55678 | 2 | 49932 | GTACTCAGACCCCGGC | 607195 | kddkddkddkddkddk | 0.27 | 355 |
| 55682 | 1 | 49936 | CTGTGTACTCAGACCC | 607196 | kddkddkddkddkddk | 0.63 | 356 |
| 55686 | 0 | 49940 | CTGACTGTGTACTCAG | 607197 | kddkddkddkddkddk | 0.61 | 357 |
| 55690 | 0 | 49944 | CACACTGACTGTGTAC | 607198 | kddkddkddkddkddk | 0.57 | 358 |
| 55694 | 0 | 49948 | CAACCACACTGACTGT | 607199 | kddkddkddkddkddk | 0.51 | 359 |
| 55698 | 0 | 49952 | AAGGCAACCACACTGA | 607200 | kddkddkddkddkddk | 0.47 | 360 |
| 55702 | 0 | 49956 | GTGCAAGGCAACCACA | 607201 | kddkddkddkddkddk | 0.28 | 361 |
| 55706 | 0 | 49960 | CATCGTGCAAGGCAAC | 607202 | kddkddkddkddkddk | 0.27 | 362 |
| 55710 | 0 | 49964 | ATATCATCGTGCAAGG | 607203 | kddkddkddkddkddk | 0.44 | 363 |
| 55713 | 0 | 49967 | TCTCCATATCATCGTGCA | 606793 | eeeeeeeeeeeeeeeee | 0.13 | 308 |
| 55714 | 0 | 49968 | CTCCATATCATCGTGC | 607204 | kddkddkddkddkddk | 0.18 | 364 |
| 55718 | 0 | 49972 | GGCTCTCCATATCATC | 607205 | kddkddkddkddkddk | 0.22 | 365 |
| 55722 | 0 | 49976 | GGCTGGCTCTCCATAT | 607206 | kddkddkddkddkddk | 0.53 | 366 |
| 55738 | 1 | 49992 | CTGGATTCCAATCAGG | 607207 | kddkddkddkddkddk | 0.17 | 367 |
| 55742 | 1 | 49996 | TGGACTGGATTCCAAT | 607208 | kddkddkddkddkddk | 0.17 | 368 |
| 55746 | 1 | 50000 | CCTGTGGACTGGATTC | 607209 | kddkddkddkddkddk | 0.23 | 369 |
| 55750 | 0 | 50004 | TATACCTGTGGACTGG | 607210 | kddkddkddkddkddk | 0.24 | 370 |
| 55754 | 1 | 50008 | ACGATATACCTGTGGA | 607211 | kddkddkddkddkddk | 0.51 | 371 |
| 55758 | 2 | 50012 | GTTAACGATATACCTG | 607212 | kddkddkddkddkddk | 0.40 | 372 |
| 55762 | 3 | 50016 | TGCGGTTAACGATATA | 607213 | kddkddkddkddkddk | 0.18 | 373 |
| n/a | n/a | 50020 | TGGGTGCGGTTAACGA | 607214 | kddkddkddkddkddk | 1.39 | 374 |

TABLE 16

EDA+FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55466 | 0 | 49720 | AAATTAATGGTAAGAG | 607142 | kddkddkddkddkddk | 0.19 | 375 |
| 55470 | 0 | 49724 | AGGCAAATTAATGGTA | 607143 | kddkddkddkddkddk | 0.20 | 376 |
| 55474 | 0 | 49728 | TGTTAGGCAAATTAAT | 607144 | kddkddkddkddkddk | 0.53 | 377 |
| 55478 | 0 | 49732 | TGTCTGTTAGGCAAAT | 607145 | kddkddkddkddkddk | 0.59 | 378 |
| 55482 | 0 | 49736 | TCAATGTCTGTTAGGC | 607146 | kddkddkddkddkddk | 0.59 | 379 |
| 55486 | 0 | 49740 | GCGATCAATGTCTGTT | 607147 | kddkddkddkddkddk | 0.65 | 380 |
| 55490 | 0 | 49744 | TAGGGCGATCAATGTC | 607148 | kddkddkddkddkddk | 0.67 | 381 |
| 55494 | 0 | 49748 | CCTTTAGGGCGATCAA | 607149 | kddkddkddkddkddk | 0.68 | 382 |
| 55498 | 0 | 49752 | CAGTCCTTTAGGGCGA | 607150 | kddkddkddkddkddk | 0.68 | 383 |
| 55502 | 0 | 49756 | ATGCCAGTCCTTTAGG | 607151 | kddkddkddkddkddk | 0.71 | 384 |
| 55506 | 0 | 49760 | GTGAATGCCAGTCCTT | 607152 | kddkddkddkddkddk | 0.75 | 385 |
| 55510 | 0 | 49764 | ATCAGTGAATGCCAGT | 607153 | kddkddkddkddkddk | 0.75 | 386 |
| 55514 | 0 | 49768 | CCACATCAGTGAATGC | 607154 | kddkddkddkddkddk | 0.83 | 387 |
| 55518 | 0 | 49772 | ACATCCACATCAGTGA | 607155 | kddkddkddkddkddk | 0.84 | 388 |
| 55522 | 0 | 49776 | ATCGACATCCACATCA | 607156 | kddkddkddkddkddk | 0.88 | 389 |
| 55526 | 0 | 49780 | TGGAATCGACATCCAC | 607157 | kddkddkddkddkddk | 0.90 | 390 |
| 55530 | 0 | 49784 | TTGATGGAATCGACAT | 607158 | kddkddkddkddkddk | 0.91 | 391 |
| 55534 | 0 | 49788 | AATTTTGATGGAATCG | 607159 | kddkddkddkddkddk | 0.91 | 392 |
| 55538 | 0 | 49792 | AAGCAATTTTGATGGA | 607160 | kddkddkddkddkddk | 0.91 | 393 |
| 55542 | 0 | 49796 | TCCCAAGCAATTTTGA | 607161 | kddkddkddkddkddk | 0.95 | 394 |
| 55546 | 0 | 49800 | GCTTTCCCAAGCAATT | 607162 | kddkddkddkddkddk | 0.96 | 395 |
| 55550 | 0 | 49804 | GTGGGCTTTCCCAAGC | 607163 | kddkddkddkddkddk | 0.97 | 396 |
| 55554 | 0 | 49808 | CCCTGTGGGCTTTCCC | 607164 | kddkddkddkddkddk | 0.97 | 397 |
| 55558 | 0 | 49812 | TTGCCCCTGTGGGCTT | 607165 | kddkddkddkddkddk | 1.00 | 398 |
| 55562 | 0 | 49816 | AAACTTGCCCCTGTGG | 607166 | kddkddkddkddkddk | 1.06 | 399 |
| 55566 | 0 | 49820 | CTGGAAACTTGCCCCT | 607167 | kddkddkddkddkddk | 1.09 | 400 |
| 55570 | 0 | 49824 | GTACCTGGAAACTTGC | 607168 | kddkddkddkddkddk | 1.16 | 401 |
| 55574 | 0 | 49828 | CCCTGTACCTGGAAAC | 607169 | kddkddkddkddkddk | 1.17 | 402 |
| 55713 | 0 | 49967 | TCTCCATATCATCGTGCA | 606793 | eeeeeeeeeeeeeeee | 0.16 | 308 |

TABLE 17

EDA+FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55713 | 0 | 49967 | TCTCCATATCATCGTGCA | 606793 | eeeeeeeeeeeeeeee | 0.16 | 308 |
| 55578 | 0 | 49832 | GTCACCCTGTACCTGG | 607243 | keekeekeekeekeek | 0.83 | 331 |
| 55582 | 0 | 49836 | GTAGGTCACCCTGTAC | 607244 | keekeekeekeekeek | 0.97 | 332 |
| 55586 | 0 | 49840 | TCGAGTAGGTCACCCT | 607245 | keekeekeekeekeek | 0.27 | 333 |
| 55590 | 0 | 49844 | GGGCTCGAGTAGGTCA | 607246 | keekeekeekeekeek | 0.65 | 334 |
| 55594 | 0 | 49848 | CTCAGGGCTCGAGTAG | 607247 | keekeekeekeekeek | 0.71 | 335 |
| 55598 | 0 | 49852 | CATCCTCAGGGCTCGA | 607248 | keekeekeekeekeek | 0.85 | 336 |
| 55602 | 0 | 49856 | ATTCCATCCTCAGGGC | 607249 | keekeekeekeekeek | 0.59 | 337 |
| 55606 | 2 | 49860 | CCGGATTCCATCCTCA | 607250 | keekeekeekeekeek | 0.72 | 338 |
| 55610 | 2 | 49864 | GCTCCCGGATTCCATC | 607251 | keekeekeekeekeek | 0.52 | 339 |
| 55614 | 3 | 49868 | AAAGCTCCCGGATTC | 607252 | keekeekeekeekeek | 0.38 | 340 |
| 48386 | 3 | 49872 | AGGGAAAAGCTCCCGG | 607253 | keekeekeekeekeek | 0.64 | 330 |
| 55622 | 1 | 49876 | GTGCAGGGAAAAGCTC | 607254 | keekeekeekeekeek | 0.61 | 341 |
| 55626 | 1 | 49880 | TCAGGTGCAGGGAAAA | 607255 | keekeekeekeekeek | 0.80 | 342 |
| 55630 | 0 | 49884 | ACCATCAGGTGCAGGG | 607256 | keekeekeekeekeek | 0.47 | 343 |
| 55634 | 0 | 49888 | CTTCACCATCAGGTGC | 607257 | keekeekeekeekeek | 0.83 | 344 |
| 55638 | 1 | 49892 | TCGTCTTCACCATCAG | 607258 | keekeekeekeekeek | 0.53 | 345 |
| 55642 | 1 | 49896 | AGTGTCGTCTTCACCA | 607259 | keekeekeekeekeek | 0.40 | 346 |
| 55646 | 1 | 49900 | CTGCAGTGTCGTCTTC | 607260 | keekeekeekeekeek | 0.84 | 347 |
| 55650 | 1 | 49904 | AGCTCTGCAGTGTCGT | 607261 | keekeekeekeekeek | 0.55 | 348 |
| 55654 | 1 | 49908 | CTGCAGCTCTGCAGTG | 607262 | keekeekeekeekeek | 0.93 | 349 |
| 55658 | 1 | 49912 | GGCCCTGCAGCTCTGC | 607263 | keekeekeekeekeek | 0.88 | 350 |
| 55662 | 1 | 49916 | CTGAGGCCCTGCAGCT | 607264 | keekeekeekeekeek | 0.87 | 351 |
| 55666 | 2 | 49920 | CGGCCTGAGGCCCTGC | 607265 | keekeekeekeekeek | 0.82 | 352 |
| 55670 | 2 | 49924 | ACCCCGGCCTGAGGCC | 607266 | keekeekeekeekeek | 0.46 | 353 |
| 55674 | 2 | 49928 | TCAGACCCCGGCCTGA | 607267 | keekeekeekeekeek | 0.84 | 354 |
| 55678 | 2 | 49932 | GTACTCAGACCCCGGC | 607268 | keekeekeekeekeek | 0.67 | 355 |
| 55682 | 1 | 49936 | CTGTGTACTCAGACCC | 607269 | keekeekeekeekeek | 0.78 | 356 |
| 55686 | 0 | 49940 | CTGACTGTGTACTCAG | 607270 | keekeekeekeekeek | 0.75 | 357 |
| 55690 | 0 | 49944 | CACACTGACTGTGTAC | 607271 | keekeekeekeekeek | 0.90 | 358 |
| 55694 | 0 | 49948 | CAACCACACTGACTGT | 607272 | keekeekeekeekeek | 0.41 | 359 |
| 55698 | 0 | 49952 | AAGGCAACCACACTGA | 607273 | keekeekeekeekeek | 0.30 | 360 |
| 55702 | 0 | 49956 | GTGCAAGGCAACCACA | 607274 | keekeekeekeekeek | 0.35 | 361 |
| 55706 | 0 | 49960 | CATCGTGCAAGGCAAC | 607275 | keekeekeekeekeek | 0.24 | 362 |
| 55710 | 0 | 49964 | ATATCATCGTGCAAGG | 607276 | keekeekeekeekeek | 0.24 | 363 |
| 55714 | 0 | 49968 | CTCCATATCATCGTGC | 607277 | keekeekeekeekeek | 0.20 | 364 |

TABLE 17-continued

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55718 | 0 | 49972 | GGCTCTCCATATCATC | 607278 | keekeekeekeekeek | 0.35 | 365 |
| 55722 | 0 | 49976 | GGCTGGCTCTCCATAT | 607279 | keekeekeekeekeek | 0.84 | 366 |
| 55738 | 1 | 49992 | CTGGATTCCAATCAGG | 607280 | keekeekeekeekeek | 0.28 | 367 |
| 55742 | 1 | 49996 | TGGACTGGATTCCAAT | 607281 | keekeekeekeekeek | 0.54 | 368 |
| 55746 | 1 | 50000 | CCTGTGGACTGGATTC | 607282 | keekeekeekeekeek | 0.42 | 369 |
| 55750 | 0 | 50004 | TATACCTGTGGACTGG | 607283 | keekeekeekeekeek | 0.50 | 370 |
| 55754 | 1 | 50008 | ACGATATACCTGTGGA | 607284 | keekeekeekeekeek | 0.16 | 371 |
| 55758 | 2 | 50012 | GTTAACGATATACCTG | 607285 | keekeekeekeekeek | 0.18 | 372 |
| 55762 | 3 | 50016 | TGCGGTTAACGATATA | 607286 | keekeekeekeekeek | 0.20 | 373 |
| n/a | n/a | 50020 | TGGGTGCGGTTAACGA | 607287 | keekeekeekeekeek | 1.28 | 374 |

TABLE 18

EDA⁺FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55713 | 0 | 49967 | TCTCCATATCATCGTGCA | 606793 | eeeeeeeeeeeeeeee | 0.19 | 308 |
| 55466 | 0 | 49720 | AAATTAATGGTAAGAG | 607215 | keekeekeekeekeek | 0.55 | 375 |
| 55470 | 0 | 49724 | AGGCAAATTAATGGTA | 607216 | keekeekeekeekeek | 0.39 | 376 |
| 55474 | 0 | 49728 | TGTTAGGCAAATTAAT | 607217 | keekeekeekeekeek | 0.67 | 377 |
| 55478 | 0 | 49732 | TGTCTGTTAGGCAAAT | 607218 | keekeekeekeekeek | 0.87 | 378 |
| 55482 | 0 | 49736 | TCAATGTCTGTTAGGC | 607219 | keekeekeekeekeek | 0.74 | 379 |
| 55486 | 0 | 49740 | GCGATCAATGTCTGTT | 607220 | keekeekeekeekeek | 0.60 | 380 |
| 55490 | 0 | 49744 | TAGGGCGATCAATGTC | 607221 | keekeekeekeekeek | 0.59 | 381 |
| 55494 | 0 | 49748 | CCTTTAGGGCGATCAA | 607222 | keekeekeekeekeek | 0.71 | 382 |
| 55498 | 0 | 49752 | CAGTCCTTTAGGGCGA | 607223 | keekeekeekeekeek | 0.97 | 383 |
| 55502 | 0 | 49756 | ATGCCAGTCCTTTAGG | 607224 | keekeekeekeekeek | 0.83 | 384 |
| 55506 | 0 | 49760 | GTGAATGCCAGTCCTT | 607225 | keekeekeekeekeek | 1.00 | 385 |
| 55510 | 0 | 49764 | ATCAGTGAATGCCAGT | 607226 | keekeekeekeekeek | 1.09 | 386 |
| 55514 | 0 | 49768 | CCACATCAGTGAATGC | 607227 | keekeekeekeekeek | 0.84 | 387 |
| 55518 | 0 | 49772 | ACATCCACATCAGTGA | 607228 | keekeekeekeekeek | 0.96 | 388 |
| 55522 | 0 | 49776 | ATCGACATCCACATCA | 607229 | keekeekeekeekeek | 0.84 | 389 |
| 55526 | 0 | 49780 | TGGAATCGACATCCAC | 607230 | keekeekeekeekeek | 0.95 | 390 |
| 55530 | 0 | 49784 | TTGATGGAATCGACAT | 607231 | keekeekeekeekeek | 0.96 | 391 |
| 55534 | 0 | 49788 | AATTTTGATGGAATCG | 607232 | keekeekeekeekeek | 0.83 | 392 |
| 55538 | 0 | 49792 | AAGCAATTTTGATGGA | 607233 | keekeekeekeekeek | 0.65 | 393 |

TABLE 18-continued

EDA⁺FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55542 | 0 | 49796 | TCCCAAGCAATTTTGA | 607234 | keekeekeekeekeek | 0.73 | 394 |
| 55546 | 0 | 49800 | GCTTTCCCAAGCAATT | 607235 | keekeekeekeekeek | 0.96 | 395 |
| 55550 | 0 | 49804 | GTGGGCTTTCCCAAGC | 607236 | keekeekeekeekeek | 0.93 | 396 |
| 55554 | 0 | 49808 | CCCTGTGGGCTTTCCC | 607237 | keekeekeekeekeek | 0.99 | 397 |
| 55558 | 0 | 49812 | TTGCCCCTGTGGGCTT | 607238 | keekeekeekeekeek | 0.92 | 398 |
| 55562 | 0 | 49816 | AAACTTGCCCCTGTGG | 607239 | keekeekeekeekeek | 0.95 | 399 |
| 55566 | 0 | 49820 | CTGGAAACTTGCCCCT | 607240 | keekeekeekeekeek | 0.79 | 400 |
| 55570 | 0 | 49824 | GTACCTGGAAACTTGC | 607241 | keekeekeekeekeek | 0.68 | 401 |
| 55574 | 0 | 49828 | CCCTGTACCTGGAAAC | 607242 | keekeekeekeekeek | 0.84 | 402 |

TABLE 19

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55713 | 0 | 49967 | TCTCCATATCATCGTGCA | 606793 | eeeeeeeeeeeeeeeee | 0.20 | 308 |
| 55578 | 0 | 49832 | AGGTCACCCTGTACCTGG | 607388 | kkeekeekeekeekeeke | 0.76 | 212 |
| 55582 | 0 | 49836 | GAGTAGGTCACCCTGTAC | 607389 | kkeekeekeekeekeeke | 0.76 | 216 |
| 55586 | 0 | 49840 | GCTCGAGTAGGTCACCCT | 607390 | kkeekeekeekeekeeke | 0.83 | 220 |
| 55590 | 0 | 49844 | CAGGGCTCGAGTAGGTCA | 607391 | kkeekeekeekeekeeke | 1.03 | 224 |
| 55594 | 0 | 49848 | TCCTCAGGGCTCGAGTAG | 607392 | kkeekeekeekeekeeke | 0.88 | 228 |
| 55598 | 0 | 49852 | TCCATCCTCAGGGCTCGA | 607393 | kkeekeekeekeekeeke | 0.74 | 232 |
| 55602 | 0 | 49856 | GGATTCCATCCTCAGGGC | 607394 | kkeekeekeekeekeeke | 1.16 | 236 |
| 55606 | 2 | 49860 | TCCCGGATTCCATCCTCA | 607395 | kkeekeekeekeekeeke | 0.81 | 240 |
| 55610 | 3 | 49864 | AAGCTCCCGGATTCCATC | 607396 | kkeekeekeekeekeeke | 0.71 | 244 |
| 55614 | 3 | 49868 | GGAAAAGCTCCCGGATTC | 607397 | kkeekeekeekeekeeke | 0.74 | 248 |
| 55618 | 3 | 49872 | GCAGGGAAAAGCTCCCGG | 607398 | kkeekeekeekeekeeke | 0.69 | 252 |
| 55622 | 1 | 49876 | AGGTGCAGGGAAAAGCTC | 607399 | kkeekeekeekeekeeke | 0.57 | 256 |
| 55626 | 1 | 49880 | CATCAGGTGCAGGGAAAA | 607400 | kkeekeekeekeekeeke | 0.80 | 260 |
| 55630 | 0 | 49884 | TCACCATCAGGTGCAGGG | 607401 | kkeekeekeekeekeeke | 0.64 | 264 |
| 55634 | 1 | 49888 | GTCTTCACCATCAGGTGC | 607402 | kkeekeekeekeekeeke | 0.65 | 268 |
| 55638 | 1 | 49892 | TGTCGTCTTCACCATCAG | 607403 | kkeekeekeekeekeeke | 0.46 | 272 |
| 55642 | 1 | 49896 | GCAGTGTCGTCTTCACCA | 607404 | kkeekeekeekeekeeke | 0.51 | 276 |
| 55646 | 1 | 49900 | CTCTGCAGTGTCGTCTTC | 607405 | kkeekeekeekeekeeke | 0.39 | 280 |
| 55650 | 1 | 49904 | GCAGCTCTGCAGTGTCGT | 607406 | kkeekeekeekeekeeke | 0.75 | 284 |

TABLE 19-continued

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55654 | 1 | 49908 | CCCTGCAGCTCTGCAGTG | 607407 | kkeekeekeekeekeekeeke | 0.40 | 288 |
| 55658 | 1 | 49912 | GAGGCCCTGCAGCTCTGC | 607408 | kkeekeekeekeekeekeeke | 1.00 | 292 |
| 55662 | 2 | 49916 | GCCTGAGGCCCTGCAGCT | 607409 | kkeekeekeekeekeekeeke | 0.64 | 403 |
| 55666 | 2 | 49920 | CCCGGCCTGAGGCCCTGC | 607410 | kkeekeekeekeekeekeeke | 0.24 | 404 |
| 55670 | 2 | 49924 | AGACCCCGGCCTGAGGCC | 607411 | kkeekeekeekeekeekeeke | 0.47 | 405 |
| 55674 | 2 | 49928 | ACTCAGACCCCGGCCTGA | 607412 | kkeekeekeekeekeekeeke | 0.62 | 406 |
| 55678 | 2 | 49932 | GTGTACTCAGACCCCGGC | 607413 | kkeekeekeekeekeekeeke | 0.74 | 407 |
| 55682 | 1 | 49936 | GACTGTGTACTCAGACCC | 607414 | kkeekeekeekeekeekeeke | 0.53 | 408 |
| 55686 | 0 | 49940 | CACTGACTGTGTACTCAG | 607415 | kkeekeekeekeekeekeeke | 1.03 | 409 |
| 55690 | 0 | 49944 | ACCACACTGACTGTGTAC | 607416 | kkeekeekeekeekeekeeke | 0.95 | 410 |
| 55694 | 0 | 49948 | GGCAACCACACTGACTGT | 607417 | kkeekeekeekeekeekeeke | 0.83 | 411 |
| 55698 | 0 | 49952 | GCAAGGCAACCACACTGA | 607418 | kkeekeekeekeekeekeeke | 0.80 | 296 |
| 55702 | 0 | 49956 | TCGTGCAAGGCAACCACA | 607419 | kkeekeekeekeekeekeeke | 0.78 | 300 |
| 55706 | 0 | 49960 | ATCATCGTGCAAGGCAAC | 607420 | kkeekeekeekeekeekeeke | 0.88 | 412 |
| 55710 | 0 | 49964 | CCATATCATCGTGCAAGG | 607421 | kkeekeekeekeekeekeeke | 0.71 | 305 |
| 55714 | 0 | 49968 | CTCTCCATATCATCGTGC | 607422 | kkeekeekeekeekeekeeke | 0.84 | 309 |
| 55718 | 0 | 49972 | CTGGCTCTCCATATCATC | 607423 | kkeekeekeekeekeekeeke | 0.42 | 313 |
| 55738 | 1 | 49992 | GACTGGATTCCAATCAGG | 607424 | kkeekeekeekeekeekeeke | 0.47 | 413 |
| 55742 | 1 | 49996 | TGTGGACTGGATTCCAAT | 607425 | kkeekeekeekeekeekeeke | 0.49 | 414 |
| 55746 | 1 | 50000 | TACCTGTGGACTGGATTC | 607426 | kkeekeekeekeekeekeeke | 0.48 | 415 |
| 55750 | 1 | 50004 | GATATACCTGTGGACTGG | 607427 | kkeekeekeekeekeekeeke | 0.30 | 316 |
| 55754 | 1 | 50008 | TAACGATATACCTGTGGA | 607428 | kkeekeekeekeekeekeeke | 0.19 | 320 |
| 55758 | 3 | 50012 | CGGTTAACGATATACCTG | 607429 | kkeekeekeekeekeekeeke | 0.19 | 324 |
| 55762 | 3 | 50016 | GGTGCGGTTAACGATATA | 607430 | kkeekeekeekeekeekeeke | 0.41 | 328 |
| n/a | n/a | 50020 | GGTGGGTGCGGTTAACGA | 607431 | kkeekeekeekeekeekeeke | 0.44 | 416 |

TABLE 20

EDA⁺FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55713 | 0 | 49967 | TCTCCATATCATCGTGCA | 606793 | eeeeeeeeeeeeeeeeee | 0.19 | 308 |
| 55466 | 0 | 49720 | GCAAATTAATGGTAAGAG | 607360 | kkeekeekeekeekeekeeke | 0.51 | 417 |
| 55470 | 0 | 49724 | TTAGGCAAATTAATGGTA | 607361 | kkeekeekeekeekeekeeke | 0.53 | 418 |
| 55474 | 0 | 49728 | TCTGTTAGGCAAATTAAT | 607362 | kkeekeekeekeekeekeeke | 0.64 | 180 |
| 55478 | 0 | 49732 | AATGTCTGTTAGGCAAAT | 607363 | kkeekeekeekeekeekeeke | 1.06 | 32 |

TABLE 20-continued

EDA⁺FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55482 | 0 | 49736 | GATCAATGTCTGTTAGGC | 607364 | kkeekeekeekeekeekee | 0.85 | 184 |
| 55486 | 0 | 49740 | GGGCGATCAATGTCTGTT | 607365 | kkeekeekeekeekeekee | 1.12 | 185 |
| 55490 | 0 | 49744 | TTTAGGGCGATCAATGTC | 607366 | kkeekeekeekeekeekee | 0.44 | 189 |
| 55494 | 0 | 49748 | GTCCTTTAGGGCGATCAA | 607367 | kkeekeekeekeekeekee | 0.88 | 193 |
| 55498 | 0 | 49752 | GCCAGTCCTTTAGGGCGA | 607368 | kkeekeekeekeekeekee | 1.09 | 419 |
| 55502 | 0 | 49756 | GAATGCCAGTCCTTTAGG | 607369 | kkeekeekeekeekeekee | 1.04 | 420 |
| 55506 | 0 | 49760 | CAGTGAATGCCAGTCCTT | 607370 | kkeekeekeekeekeekee | 0.97 | 421 |
| 55510 | 0 | 49764 | ACATCAGTGAATGCCAGT | 607371 | kkeekeekeekeekeekee | 0.95 | 422 |
| 55514 | 0 | 49768 | ATCCACATCAGTGAATGC | 607372 | kkeekeekeekeekeekee | 1.05 | 423 |
| 55518 | 0 | 49772 | CGACATCCACATCAGTGA | 607373 | kkeekeekeekeekeekee | 1.04 | 424 |
| 55522 | 0 | 49776 | GAATCGACATCCACATCA | 607374 | kkeekeekeekeekeekee | 0.94 | 425 |
| 55526 | 0 | 49780 | GATGGAATCGACATCCAC | 607375 | kkeekeekeekeekeekee | 1.07 | 199 |
| 55530 | 0 | 49784 | TTTTGATGGAATCGACAT | 607376 | kkeekeekeekeekeekee | 1.05 | 426 |
| 55534 | 0 | 49788 | GCAATTTTGATGGAATCG | 607377 | kkeekeekeekeekeekee | 0.89 | 204 |
| 55538 | 0 | 49792 | CCAAGCAATTTTGATGGA | 607378 | kkeekeekeekeekeekee | 0.88 | 208 |
| 55542 | 0 | 49796 | TTTCCCAAGCAATTTTGA | 607379 | kkeekeekeekeekeekee | 0.97 | 427 |
| 55546 | 0 | 49800 | GGGCTTTCCCAAGCAATT | 607380 | kkeekeekeekeekeekee | 1.09 | 428 |
| 55550 | 0 | 49804 | CTGTGGGCTTTCCCAAGC | 607381 | kkeekeekeekeekeekee | 1.05 | 429 |
| 55554 | 0 | 49808 | GCCCTGTGGGCTTTCCC | 607382 | kkeekeekeekeekeekee | 1.26 | 430 |
| 55558 | 0 | 49812 | ACTTGCCCCTGTGGGCTT | 607383 | kkeekeekeekeekeekee | 1.26 | 431 |
| 55562 | 0 | 49816 | GGAAACTTGCCCCTGTGG | 607384 | kkeekeekeekeekeekee | 1.07 | 432 |
| 55566 | 0 | 49820 | ACCTGGAAACTTGCCCCT | 607385 | kkeekeekeekeekeekee | 0.91 | 433 |
| 55570 | 0 | 49824 | CTGTACCTGGAAACTTGC | 607386 | kkeekeekeekeekeekee | 0.85 | 434 |
| 55574 | 0 | 49828 | CACCCTGTACCTGGAAAC | 607387 | kkeekeekeekeekeekee | 1.03 | 435 |

TABLE 21

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55713 | 0 | 49967 | TCTCCATATCATCGTGCA | 606793 | eeeeeeeeeeeeeeeeee | 0.15 | 308 |
| 55578 | 0 | 49832 | AGGTCACCCTGTACCTGG | 607316 | kkddkddkddkddkddkk | 0.47 | 212 |
| 55582 | 0 | 49836 | GAGTAGGTCACCCTGTAC | 607317 | kkddkddkddkddkddkk | 0.66 | 216 |
| 55586 | 0 | 49840 | GCTCGAGTAGGTCACCCT | 607318 | kkddkddkddkddkddkk | 0.78 | 220 |
| 55590 | 0 | 49844 | CAGGGCTCGAGTAGGTCA | 607319 | kkddkddkddkddkddkk | 0.78 | 224 |

TABLE 21-continued

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55594 | 0 | 49848 | TCCTCAGGGCTCGAGTAG | 607320 | kkddkddkddkddkddkk | 0.60 | 228 |
| 55598 | 0 | 49852 | TCCATCCTCAGGGCTCGA | 607321 | kkddkddkddkddkddkk | 0.72 | 232 |
| 55602 | 0 | 49856 | GGATTCCATCCTCAGGGC | 607322 | kkddkddkddkddkddkk | 0.68 | 236 |
| 55606 | 2 | 49860 | TCCCGGATTCCATCCTCA | 607323 | kkddkddkddkddkddkk | 0.69 | 240 |
| 55610 | 3 | 49864 | AAGCTCCCGGATTCCATC | 607324 | kkddkddkddkddkddkk | 0.31 | 244 |
| 55614 | 3 | 49868 | GGAAAAGCTCCCGGATTC | 607325 | kkddkddkddkddkddkk | 0.58 | 248 |
| 55618 | 3 | 49872 | GCAGGGAAAAGCTCCCGG | 607326 | kkddkddkddkddkddkk | 0.52 | 252 |
| 55622 | 1 | 49876 | AGGTGCAGGGAAAAGCTC | 607327 | kkddkddkddkddkddkk | 0.28 | 256 |
| 55626 | 1 | 49880 | CATCAGGTGCAGGGAAAA | 607328 | kkddkddkddkddkddkk | 0.45 | 260 |
| 55630 | 0 | 49884 | TCACCATCAGGTGCAGGG | 607329 | kkddkddkddkddkddkk | 0.34 | 264 |
| 55634 | 1 | 49888 | GTCTTCACCATCAGGTGC | 607330 | kkddkddkddkddkddkk | 0.16 | 268 |
| 55638 | 1 | 49892 | TGTCGTCTTCACCATCAG | 607331 | kkddkddkddkddkddkk | 0.23 | 272 |
| 55642 | 1 | 49896 | GCAGTGTCGTCTTCACCA | 607332 | kkddkddkddkddkddkk | 0.18 | 276 |
| 55646 | 1 | 49900 | CTCTGCAGTGTCGTCTTC | 607333 | kkddkddkddkddkddkk | 0.17 | 280 |
| 55650 | 1 | 49904 | GCAGCTCTGCAGTGTCGT | 607334 | kkddkddkddkddkddkk | 0.41 | 284 |
| 55654 | 1 | 49908 | CCCTGCAGCTCTGCAGTG | 607335 | kkddkddkddkddkddkk | 0.44 | 288 |
| 55658 | 1 | 49912 | GAGGCCCTGCAGCTCTGC | 607336 | kkddkddkddkddkddkk | 0.42 | 292 |
| 55662 | 2 | 49916 | GCCTGAGGCCCTGCAGCT | 607337 | kkddkddkddkddkddkk | 0.23 | 403 |
| 55666 | 2 | 49920 | CCCGGCCTGAGGCCCTGC | 607338 | kkddkddkddkddkddkk | 0.14 | 404 |
| 55670 | 2 | 49924 | AGACCCCGGCCTGAGGCC | 607339 | kkddkddkddkddkddkk | 0.15 | 405 |
| 55674 | 2 | 49928 | ACTCAGACCCCGGCCTGA | 607340 | kkddkddkddkddkddkk | 0.15 | 406 |
| 55678 | 2 | 49932 | GTGTACTCAGACCCCGGC | 607341 | kkddkddkddkddkddkk | 0.22 | 407 |
| 55682 | 1 | 49936 | GACTGTGTACTCAGACCC | 607342 | kkddkddkddkddkddkk | 0.17 | 408 |
| 55686 | 0 | 49940 | CACTGACTGTGTACTCAG | 607343 | kkddkddkddkddkddkk | 0.39 | 409 |
| 55690 | 0 | 49944 | ACCACACTGACTGTGTAC | 607344 | kkddkddkddkddkddkk | 0.58 | 410 |
| 55694 | 0 | 49948 | GGCAACCACACTGACTGT | 607345 | kkddkddkddkddkddkk | 0.38 | 411 |
| 55698 | 0 | 49952 | GCAAGGCAACCACACTGA | 607346 | kkddkddkddkddkddkk | 0.43 | 296 |
| 55702 | 0 | 49956 | TCGTGCAAGGCAACCACA | 607347 | kkddkddkddkddkddkk | 0.56 | 300 |
| 55706 | 0 | 49960 | ATCATCGTGCAAGGCAAC | 607348 | kkddkddkddkddkddkk | 0.20 | 412 |
| 55710 | 0 | 49964 | CCATATCATCGTGCAAGG | 607349 | kkddkddkddkddkddkk | 0.22 | 305 |
| 55714 | 0 | 49968 | CTCTCCATATCATCGTGC | 607350 | kkddkddkddkddkddkk | 0.44 | 309 |
| 55718 | 0 | 49972 | CTGGCTCTCCATATCATC | 607351 | kkddkddkddkddkddkk | 0.29 | 313 |
| 55738 | 1 | 49992 | GACTGGATTCCAATCAGG | 607352 | kkddkddkddkddkddkk | 0.15 | 413 |
| 55742 | 1 | 49996 | TGTGGACTGGATTCCAAT | 607353 | kkddkddkddkddkddkk | 0.51 | 414 |
| 55746 | 1 | 50000 | TACCTGTGGACTGGATTC | 607354 | kkddkddkddkddkddkk | 0.23 | 415 |
| 55750 | 1 | 50004 | GATATACCTGTGGACTGG | 607355 | kkddkddkddkddkddkk | 0.24 | 316 |

TABLE 21-continued

EDA⁺FN mRNA levels compared to untreated cells
(designated 1.00) in b.END cells measured with LTS01050

| Human Start Site | Mismatches to the human sequence | Murine Start Site | Sequence | ISIS No | Chemistry | EDA + FN | SEQ ID NO |
|---|---|---|---|---|---|---|---|
| 55754 | 1 | 50008 | TAACGATATACCTGTGGA | 607356 | kkddkddkddkddkddkk | 0.21 | 320 |
| 55758 | 3 | 50012 | CGGTTAACGATATACCTG | 607357 | kkddkddkddkddkddkk | 0.14 | 324 |
| 55762 | 3 | 50016 | GGTGCGGTTAACGATATA | 607358 | kkddkddkddkddkddkk | 0.23 | 328 |
| n/a | n/a | 50020 | GGTGGGTGCGGTTAACGA | 607359 | kkddkddkddkddkddkk | 0.25 | 416 |

TABLE 22

EDA⁺FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55713 | 0 | 49967 | TCTCCATATCATCGTGCA | 606793 | eeeeeeeeeeeeeeeeee | 0.14 | 308 |
| 55466 | 0 | 49720 | GCAAATTAATGGTAAGAG | 607288 | kkddkddkddkddkddkk | 0.75 | 417 |
| 55470 | 0 | 49724 | TTAGGCAAATTAATGGTA | 607289 | kkddkddkddkddkddkk | 0.62 | 418 |
| 55474 | 0 | 49728 | TCTGTTAGGCAAATTAAT | 607290 | kkddkddkddkddkddkk | 0.47 | 180 |
| 55478 | 0 | 49732 | AATGTCTGTTAGGCAAAT | 607291 | kkddkddkddkddkddkk | 0.88 | 32 |
| 55482 | 0 | 49736 | GATCAATGTCTGTTAGGC | 607292 | kkddkddkddkddkddkk | 0.4 | 184 |
| 55486 | 0 | 49740 | GGGCGATCAATGTCTGTT | 607293 | kkddkddkddkddkddkk | 0.49 | 185 |
| 55490 | 0 | 49744 | TTTAGGGCGATCAATGTC | 607294 | kkddkddkddkddkddkk | 0.35 | 189 |
| 55494 | 0 | 49748 | GTCCTTTAGGGCGATCAA | 607295 | kkddkddkddkddkddkk | 0.53 | 193 |
| 55498 | 0 | 49752 | GCCAGTCCTTTAGGGCGA | 607296 | kkddkddkddkddkddkk | 0.66 | 419 |
| 55502 | 0 | 49756 | GAATGCCAGTCCTTTAGG | 607297 | kkddkddkddkddkddkk | 0.58 | 420 |
| 55506 | 0 | 49760 | CAGTGAATGCCAGTCCTT | 607298 | kkddkddkddkddkddkk | 0.67 | 421 |
| 55510 | 0 | 49764 | ACATCAGTGAATGCCAGT | 607299 | kkddkddkddkddkddkk | 0.67 | 422 |
| 55514 | 0 | 49768 | ATCCACATCAGTGAATGC | 607300 | kkddkddkddkddkddkk | 0.78 | 423 |
| 55518 | 0 | 49772 | CGACATCCACATCAGTGA | 607301 | kkddkddkddkddkddkk | 0.72 | 424 |
| 55522 | 0 | 49776 | GAATCGACATCCACATCA | 607302 | kkddkddkddkddkddkk | 0.65 | 425 |
| 55526 | 0 | 49780 | GATGGAATCGACATCCAC | 607303 | kkddkddkddkddkddkk | 0.84 | 199 |
| 55530 | 0 | 49784 | TTTTGATGGAATCGACAT | 607304 | kkddkddkddkddkddkk | 0.88 | 426 |
| 55534 | 0 | 49788 | GCAATTTGATGGAATCG | 607305 | kkddkddkddkddkddkk | 0.62 | 204 |
| 55538 | 0 | 49792 | CCAAGCAATTTGATGGA | 607306 | kkddkddkddkddkddkk | 0.78 | 208 |
| 55542 | 0 | 49796 | TTTCCCAAGCAATTTGA | 607307 | kkddkddkddkddkddkk | 0.59 | 427 |
| 55546 | 0 | 49800 | GGGCTTTCCCAAGCAATT | 607308 | kkddkddkddkddkddkk | 0.61 | 428 |
| 55550 | 0 | 49804 | CTGTGGGCTTTCCCAAGC | 607309 | kkddkddkddkddkddkk | 1.08 | 428 |
| 55554 | 0 | 49808 | GCCCCTGTGGGCTTTCCC | 607310 | kkddkddkddkddkddkk | 1.13 | 430 |
| 55558 | 0 | 49812 | ACTTGCCCCTGTGGGCTT | 607311 | kkddkddkddkddkddkk | 1.14 | 431 |
| 55562 | 0 | 49816 | GGAAACTTGCCCCTGTGG | 607312 | kkddkddkddkddkddkk | 0.94 | 432 |

TABLE 22-continued

EDA+FN mRNA levels compared to untreated cells
(designated 1.00) in b.END cells measured with LTS01052

| Human Start Site | Mismatches to the human sequence | Murine Start Site | Sequence | ISIS No | Chemistry | EDA + FN | SEQ ID NO |
|---|---|---|---|---|---|---|---|
| 55566 | 0 | 49820 | ACCTGGAAACTTGCCCCT | 607313 | kkddkddkddkddkddkk | 0.65 | 433 |
| 55570 | 0 | 49824 | CTGTACCTGGAAACTTGC | 607314 | kkddkddkddkddkddkk | 0.68 | 434 |
| 55574 | 0 | 49828 | CACCCTGTACCTGGAAAC | 607315 | kkddkddkddkddkddkk | 0.77 | 435 |

Example 11

Dose-Dependent Antisense Inhibition of Fibronectin with Deoxy, MOE and (S)-cEt Antisense Oligonucleotides in b.END Cells Antisense oligonucleotides from the studies described above exhibiting significant in vitro inhibition of EDA+FN mRNA were selected and tested at various doses in b.END cells. Cells were transfected using Cytofectin reagent with 0.19 nM, 0.39 nM, 0.78 nM, 1.56 nM, 3.125 nM, or 6.25 nM concentrations of antisense oligonucleotide, as specified in Tables 23-27. After a treatment period of approximately 16 hours, RNA was isolated from the cells and EDA+FN mRNA levels were measured by quantitative real-time PCR. Primer probe sets LTS01050 and LTS01052 were used to measure mRNA levels. EDA+FN mRNA levels were adjusted according to total RNA content, as measured by RIBOGREEN®. The results demonstrate blocking of splicing, as represented by EDA+FN expression. The expression value of untreated cells was taken as 1.00. Different primer probe sets were used for different antisense oligonucleotide-treated cells to avoid the amplicon effect. Each table represents a separate experiment.

The half maximal inhibitory concentration (IC$_{50}$) of each oligonucleotide is also presented in Tables 23-27. As illustrated in the tables, EDA+FN mRNA levels were significantly reduced in a dose-dependent manner in antisense oligonucleotide treated cells.

TABLE 23

EDA+FN mRNA levels compared to untreated cells (designated 1.00) by 16-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607178 | 0.7 | 0.6 | 0.5 | 0.3 | 0.2 | 0.1 | 0.59 |
| 607186 | 0.6 | 0.5 | 0.4 | 0.2 | 0.2 | 0.1 | 0.39 |
| 607188 | 0.8 | 0.6 | 0.4 | 0.3 | 0.2 | 0.1 | 0.67 |
| 607204 | 0.6 | 0.4 | 0.3 | 0.2 | 0.1 | 0.1 | 0.27 |
| 607205 | 0.6 | 0.5 | 0.4 | 0.3 | 0.2 | 0.1 | 0.34 |
| 607207 | 0.5 | 0.4 | 0.3 | 0.2 | 0.1 | 0.1 | 0.21 |
| 607208 | 0.9 | 0.5 | 0.4 | 0.3 | 0.2 | 0.2 | 0.62 |
| 607209 | 0.7 | 0.6 | 0.5 | 0.3 | 0.3 | 0.2 | 0.68 |
| 607210 | 0.8 | 0.6 | 0.5 | 0.3 | 0.3 | 0.2 | 0.77 |

TABLE 24

EDA+FN mRNA levels compared to untreated cells (designated 1.00) by 16-mer MOE, deoxy and (S)-cEt antisense oligonucleotides in b.END cells measured with LTS01052

| ISIS No | 0.19 nM | 0.39 nM | 0.78 nM | 1.56 nM | 3.125 nM | 6.25 nM | IC$_{50}$ |
|---|---|---|---|---|---|---|---|
| 607148 | 0.6 | 0.5 | 0.6 | 0.4 | 0.2 | 0.1 | 0.60 |
| 607149 | 0.7 | 0.5 | 0.3 | 0.3 | 0.1 | 0.1 | 0.44 |

TABLE 25

EDA+FN mRNA levels compared to untreated cells (designated 1.00) by 18-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607330 | 0.6 | 0.4 | 0.3 | 0.2 | 0.2 | 0.1 | 0.28 |
| 607332 | 0.6 | 0.5 | 0.3 | 0.2 | 0.1 | 0.1 | 0.35 |
| 607333 | 0.6 | 0.6 | 0.5 | 0.3 | 0.2 | 0.2 | 0.59 |
| 607338 | 0.8 | 0.9 | 0.8 | 0.7 | 0.5 | 0.4 | 3.64 |
| 607339 | 0.8 | 0.8 | 0.7 | 0.6 | 0.6 | 0.5 | 5.89 |
| 607340 | 0.7 | 0.6 | 0.5 | 0.3 | 0.3 | 0.2 | 0.63 |
| 607341 | 0.6 | 0.5 | 0.4 | 0.3 | 0.2 | 0.1 | 0.44 |
| 607342 | 0.9 | 0.7 | 0.5 | 0.5 | 0.4 | 0.4 | 1.54 |
| 607348 | 0.9 | 0.7 | 0.5 | 0.3 | 0.2 | 0.2 | 0.96 |
| 607352 | 0.4 | 0.4 | 0.2 | 0.1 | 0.1 | 0.1 | 0.16 |
| 607357 | 0.7 | 0.5 | 0.4 | 0.2 | 0.2 | 0.1 | 0.48 |

TABLE 26

EDA+FN mRNA levels compared to untreated cells (designated 1.00) by 16-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607245 | 0.9 | 0.9 | 0.5 | 0.5 | 0.4 | 0.4 | 2.04 |
| 607275 | 0.8 | 0.8 | 0.5 | 0.5 | 0.2 | 0.2 | 1.09 |
| 607276 | 0.8 | 0.6 | 0.4 | 0.3 | 0.2 | 0.2 | 0.57 |
| 607277 | 0.7 | 0.6 | 0.4 | 0.2 | 0.2 | 0.1 | 0.48 |
| 607284 | 0.6 | 0.6 | 0.3 | 0.1 | 0.1 | 0.1 | 0.37 |
| 607285 | 0.4 | 0.4 | 0.2 | 0.1 | 0.1 | 0.1 | 0.12 |
| 607286 | 0.7 | 0.4 | 0.3 | 0.2 | 0.1 | 0.1 | 0.36 |

TABLE 27

EDA+FN mRNA levels compared to untreated cells (designated
1.00) by MOE, deoxy and (S)-cEt antisense oligonucleotides
in b.END cells measured with LTS01050

| ISIS No | Length (nt) | 0.19 nM | 0.39 nM | 0.78 nM | 1.56 nM | 3.125 nM | 6.25 nM | $IC_{50}$ |
|---|---|---|---|---|---|---|---|---|
| 607428 | 18 | 0.5 | 0.3 | 0.1 | 0.1 | 0.1 | 0.1 | 0.16 |
| 607429 | 18 | 0.6 | 0.7 | 0.5 | 0.3 | 0.2 | 0.1 | 0.58 |
| 607213 | 16 | 0.9 | 0.8 | 0.5 | 0.3 | 0.2 | 0.2 | 0.95 |

Example 12

Dose-Dependent Antisense Inhibition of Fibronectin with Uniform MOE Antisense Oligonucleotides in b.END Cells Antisense oligonucleotides from the studies described above exhibiting significant in vitro inhibition of EDA+FN mRNA were selected and tested at various doses in b.END cells. Cells were transfected using Cytofectin reagent with 0.39 nM, 0.78 nM, 1.56 nM, 3.125 nM, 6.25 nM or 12.5 nM concentrations of antisense oligonucleotide, as specified in Tables 28-31. After a treatment period of approximately 16 hours, RNA was isolated from the cells and EDA+FN mRNA levels were measured by quantitative real-time PCR. Primer probe sets LTS01050 and LTS01052 were used to measure mRNA levels. EDA+FN mRNA levels were adjusted according to total RNA content, as measured by RIBOGREEN®. The results demonstrate blocking of splicing, as represented by EDA+FN expression. The expression value of untreated cells was taken as 1.00. Different primer probe sets were used for different antisense oligonucleotide-treated cells to avoid the amplicon effect. Each table represents a separate experiment.

The half maximal inhibitory concentration ($IC_{50}$) of each oligonucleotide is also presented in Tables 28-31. As illustrated in the tables, EDA+FN mRNA levels were significantly reduced in a dose-dependent manner in antisense oligonucleotide treated cells.

TABLE 28

EDA+FN mRNA levels compared to untreated cells
(designated 1.00) by 18-mer uniform MOE oligonucleotides
in b.END cells measured with LTS01050

| ISIS No | 0.39 nM | 0.78 nM | 1.56 nM | 3.125 nM | 6.25 nM | 12.5 nM | $IC_{50}$ |
|---|---|---|---|---|---|---|---|
| 606708 | 1.1 | 0.8 | 0.6 | 0.4 | 0.3 | 0.2 | 2.79 |
| 606723 | 0.8 | 0.8 | 0.6 | 0.4 | 0.2 | 0.1 | 2.39 |
| 606729 | 0.8 | 0.6 | 0.3 | 0.2 | 0.1 | 0.1 | 1.10 |
| 606753 | 0.8 | 0.5 | 0.4 | 0.3 | 0.2 | 0.1 | 1.09 |
| 606770 | 0.7 | 0.5 | 0.4 | 0.2 | 0.1 | 0.1 | 0.87 |
| 606785 | 0.5 | 0.3 | 0.2 | 0.1 | 0.1 | 0.1 | 0.37 |
| 606787 | 0.5 | 0.3 | 0.3 | 0.1 | 0.1 | 0.1 | 0.30 |
| 606788 | 0.4 | 0.2 | 0.2 | 0.1 | 0.1 | 0.1 | 0.21 |
| 606793 | 0.3 | 0.3 | 0.2 | 0.1 | 0.1 | 0.1 | 0.09 |
| 606804 | 0.5 | 0.3 | 0.3 | 0.1 | 0.1 | 0.1 | 0.40 |
| 606812 | 0.4 | 0.3 | 0.2 | 0.1 | 0.1 | 0.1 | 0.23 |

TABLE 29

EDA+FN mRNA levels compared to untreated cells
(designated 1.00) by ISIS 606675 in b.END cells
measured with LTS01052

| 0.39 nM | 0.8 |
| 0.78 nM | 0.6 |
| 1.56 nM | 0.5 |
| 3.125 nM | 0.3 |
| 6.25 nM | 0.1 |
| 12.5 nM | 0.1 |
| $IC_{50}$ | 1.38 |

TABLE 30

EDA+FN mRNA levels compared to untreated cells
(designated 1.00) by 15-mer uniform MOE oligonucleotides
in b.END cells measured with LTS01050

| ISIS No | 0.39 nM | 0.78 nM | 1.56 nM | 3.125 nM | 6.25 nM | 12.5 nM | $IC_{50}$ |
|---|---|---|---|---|---|---|---|
| 598137 | 1.0 | 0.8 | 0.7 | 0.5 | 0.4 | 0.2 | 4.08 |
| 598138 | 0.8 | 0.9 | 0.6 | 0.6 | 0.4 | 0.2 | 4.11 |
| 598144 | 0.9 | 0.7 | 0.4 | 0.4 | 0.2 | 0.1 | 1.75 |
| 598151 | 0.7 | 0.5 | 0.3 | 0.2 | 0.1 | 0.1 | 0.79 |
| 598153 | 0.9 | 0.6 | 0.5 | 0.3 | 0.2 | 0.1 | 1.54 |
| 598161 | 0.9 | 0.5 | 0.5 | 0.3 | 0.2 | 0.2 | 1.50 |
| 598163 | 0.6 | 0.5 | 0.4 | 0.3 | 0.1 | 0.1 | 0.60 |
| 594675 | 0.8 | 0.6 | 0.4 | 0.3 | 0.1 | 0.1 | 1.18 |
| 598145 | 0.9 | 0.7 | 0.5 | 0.3 | 0.2 | 0.1 | 1.58 |

TABLE 31

EDA+FN mRNA levels compared to untreated cells
(designated 1.00) by 15-mer uniform MOE oligonucleotides
in b.END cells measured with LTS01052

| ISIS No | 0.39 nM | 0.78 nM | 1.56 nM | 3.125 nM | 6.25 nM | 12.5 nM | $IC_{50}$ |
|---|---|---|---|---|---|---|---|
| 511404 | 0.9 | 0.8 | 0.7 | 0.4 | 0.3 | 0.2 | 2.81 |
| 598130 | 0.9 | 1.0 | 0.9 | 0.9 | 0.7 | 0.5 | 13.18 |

Example 13

Efficacy and Tolerability of Antisense Oligonucleotides Targeting Fibronectin in C57BL/6 Mice C57BL/6 mice are a multipurpose mice model, frequently utilized for safety and efficacy testing. The mice were treated with ISIS antisense oligonucleotides selected from studies described above and evaluated for efficacy, as well as changes in the levels of various plasma chemistry markers.
Study with Uniform MOE Oligonucleotides
Treatment Groups of eight-week old C57BL/6 mice were injected subcutaneously twice a week for 3 weeks with 100 mg/kg of ISIS 594675, ISIS 598145, ISIS 598151, ISIS 598153, ISIS 598163, ISIS 606770, ISIS 606785, ISIS 606787, ISIS 606788, ISIS 606793, ISIS 606804, or ISIS 606812. One group of eight-week old C57BL/6 mice was injected subcutaneously twice a week for 3 weeks with PBS. Mice were euthanized 48 hours after the last dose, and organs and plasma were harvested for further analysis.
RNA Analysis To evaluate the effect of ISIS oligonucleotides on blocking fibronectin splicing, mRNA levels of EDA+FN were measured by RT-PCR using mouse primer probe set LTS01050 and LTS01052. The results are presented in Table 32, normalized to total fibronectin. The results demonstrate blocking of splicing, as represented by EDA⁺FN expression. The expression value in untreated mice was taken as 1.00. 'n.d.' indicates that the mRNA expression level values were not considered because the oligonucleotide targeted an amplicon region of the specific primer probe set.

TABLE 32

EDA⁺FN expression after antisense oligonucleotide treatment in C57BL/6 mice

| ISIS No | Lungs | | Kidneys | |
|---|---|---|---|---|
| | EDA⁺FN/ total FN (LTS01050) | EDA⁺FN/ total FN (LTS01052) | EDA⁺FN/ total FN (LTS01050) | EDA⁺FN/ total FN (LTS01052) |
| 594675 | 0.43 | 0.43 | 0.52 | 0.57 |
| 598145 | 0.65 | 0.61 | 0.61 | 0.64 |
| 598151 | 0.40 | 0.33 | 0.43 | 0.36 |
| 598153 | 0.75 | 0.57 | 1.07 | 0.69 |
| 598163 | 0.24 | 0.23 | 0.15 | 0.17 |
| 606770 | 0.50 | 0.38 | 0.54 | 0.52 |
| 606785 | 0.31 | 0.33 | 0.22 | 0.29 |
| 606787 | 0.36 | 0.32 | 0.26 | 0.32 |
| 606788 | 0.40 | 0.36 | 0.19 | 0.22 |
| 606793 | 0.28 | 0.23 | 0.12 | 0.14 |
| 606804 | 0.32 | n.d. | 0.27 | n.d. |
| 606812 | 0.39 | n.d. | 0.42 | n.d. |

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 33. ISIS oligonucleotides did not cause any changes in the levels of any of the liver or kidney function markers outside the expected range for antisense oligonucleotides.

TABLE 33

Plasma chemistry markers in C57BL/6 mice plasma

| | ALT (IU/L) | AST (IU/L) | Bilirubin (mg/dL) | BUN (mg/dL) |
|---|---|---|---|---|
| PBS | 26 | 46 | 0.19 | 35 |
| ISIS 594675 | 19 | 42 | 0.20 | 31 |
| ISIS 598145 | 25 | 49 | 0.20 | 29 |
| ISIS 598151 | 30 | 67 | 0.18 | 35 |
| ISIS 598153 | 26 | 71 | 0.17 | 34 |
| ISIS 598163 | 64 | 102 | 0.19 | 38 |
| ISIS 606770 | 22 | 54 | 0.18 | 29 |
| ISIS 606785 | 48 | 94 | 0.17 | 32 |
| ISIS 606787 | 30 | 71 | 0.15 | 30 |
| ISIS 606788 | 82 | 116 | 0.15 | 33 |
| ISIS 606793 | 50 | 83 | 0.15 | 32 |
| ISIS 606804 | 31 | 56 | 0.16 | 28 |
| ISIS 606812 | 29 | 49 | 0.15 | 27 |

Organ Weights

Liver, spleen and kidney weights were measured at the end of the study, and are presented in Table 34. ISIS oligonucleotides did not cause any changes in organ weights outside the expected range for antisense oligonucleotides.

TABLE 34

Organ weights (% of the PBS control) of C57BL/6 mice

| ISIS No | Liver | Kidneys | Spleen |
|---|---|---|---|
| 594675 | 102 | 102 | 99 |
| 598145 | 98 | 105 | 117 |
| 598151 | 108 | 103 | 90 |
| 598153 | 106 | 100 | 88 |
| 598163 | 102 | 102 | 94 |
| 606770 | 106 | 104 | 93 |
| 606785 | 101 | 102 | 98 |
| 606787 | 108 | 99 | 93 |
| 606788 | 98 | 97 | 99 |
| 606793 | 103 | 94 | 99 |
| 606804 | 95 | 98 | 89 |
| 606812 | 105 | 101 | 86 |

Study with Deoxy, (S)-cEt and MOE Oligonucleotides Treatment

Groups of eight-week old C57BL/6 mice were injected subcutaneously twice a week for 3 weeks with 100 mg/kg of ISIS 607149, ISIS 607186, ISIS 607204, ISIS 607205, ISIS 607207, ISIS 607277, ISIS 607285, ISIS 607286, ISIS 607330, ISIS 607332, ISIS 607341, ISIS 607352, ISIS 607428, or ISIS 607429. One group of eight-week old C57BL/6 mice was injected subcutaneously twice a week for 3 weeks with PBS. Mice were euthanized 48 hours after the last dose, and organs and plasma were harvested for further analysis.

RNA Analysis

To evaluate the effect of ISIS oligonucleotides on blocking fibronectin splicing, mRNA levels of EDA⁺FN were measured by RT-PCR using mouse primer probe set LTS01050 and LTS01052. The results are presented in Table 35, normalized to total fibronectin. The results demonstrate blocking of splicing, as represented by EDA⁺FN expression. The expression value in untreated mice was taken as 1.00. 'n.d.' indicates that the mRNA expression level values were not considered because the oligonucleotide targeted an amplicon region of the specific primer probe set.

TABLE 35

EDA⁺FN expression after antisense oligonucleotide treatment in C57BL/6 mice

| ISIS No | Lungs | | Kidneys | |
|---|---|---|---|---|
| | EDA⁺FN/ total FN (LTS01050) | EDA⁺FN/ total FN (LTS01052) | EDA⁺FN/ total FN (LTS01050) | EDA⁺FN/ total FN (LTS01052) |
| 607149 | n.d. | 0.32 | n.d. | 0.07 |
| 607186 | 0.26 | 0.14 | 0.02 | 0.02 |
| 607204 | 0.15 | 0.13 | 0.02 | 0.03 |
| 607205 | 0.30 | n.d. | 0.03 | n.d. |
| 607207 | 0.42 | n.d. | 0.04 | n.d. |
| 607277 | 0.33 | 0.27 | 0.05 | 0.08 |
| 607285 | 0.21 | n.d. | 0.29 | n.d. |
| 607286 | 0.13 | n.d. | 0.02 | n.d. |
| 607330 | 0.29 | 0.27 | 0.02 | 0.06 |
| 607332 | 0.08 | 0.13 | 0.01 | 0.05 |
| 607341 | 0.15 | 0.24 | 0.10 | 0.16 |
| 607352 | 0.11 | n.d. | 0.01 | n.d. |
| 607357 | 0.12 | n.d. | 0.09 | n.d. |
| 607428 | 0.12 | n.d. | 0.07 | n.d. |
| 607429 | 0.33 | n.d. | 0.20 | n.d. |

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 36. ISIS oligonucleotides that caused any changes in organ weights outside the expected range for antisense oligonucleotides were excluded from further studies.

TABLE 36

Plasma chemistry markers in C57BL/6 mice plasma

|  | ALT (IU/L) | AST (IU/L) | Bilirubin (mg/dL) | BUN (mg/dL) |
|---|---|---|---|---|
| PBS | 38 | 96 | 0.18 | 36 |
| ISIS 607149 | 35 | 170 | 0.29 | 31 |
| ISIS 607186 | 22 | 73 | 0.21 | 26 |
| ISIS 607204 | 41 | 75 | 0.15 | 29 |
| ISIS 607205 | 38 | 83 | 0.15 | 32 |
| ISIS 607207 | 70 | 92 | 0.19 | 32 |
| ISIS 607277 | 54 | 108 | 0.16 | 30 |
| ISIS 607285 | 78 | 139 | 0.32 | 28 |
| ISIS 607286 | 40 | 94 | 0.38 | 27 |
| ISIS 607330 | 23 | 40 | 0.16 | 30 |
| ISIS 607332 | 41 | 66 | 0.20 | 28 |
| ISIS 607341 | 70 | 102 | 0.24 | 28 |
| ISIS 607352 | 20 | 75 | 0.13 | 27 |
| ISIS 607357 | 85 | 100 | 0.15 | 26 |
| ISIS 607428 | 21 | 82 | 0.24 | 25 |
| ISIS 607429 | 21 | 50 | 0.17 | 26 |

Organ Weights

Liver, spleen and kidney weights were measured at the end of the study, and are presented in Table 37. ISIS oligonucleotides that caused any changes in organ weights outside the expected range for antisense oligonucleotides were excluded from further studies.

TABLE 37

Organ weights (% of the PBS control) of C57BL/6 mice

| ISIS No. | Liver | Kidneys | Spleen |
|---|---|---|---|
| 607149 | 103 | 103 | 99 |
| 607186 | 91 | 106 | 101 |
| 607204 | 93 | 97 | 116 |
| 607205 | 112 | 114 | 276 |
| 607207 | 98 | 99 | 96 |
| 607277 | 98 | 100 | 108 |
| 607285 | 99 | 97 | 105 |
| 607286 | 96 | 103 | 98 |
| 607330 | 97 | 101 | 85 |
| 607332 | 102 | 98 | 97 |
| 607341 | 93 | 98 | 92 |
| 607352 | 98 | 101 | 84 |
| 607357 | 88 | 101 | 113 |
| 607428 | 96 | 101 | 90 |
| 607429 | 91 | 101 | 99 |

We claim:

1. A method of modulating splicing of a fibronectin transcript in a cell, comprising contacting a cell with a compound comprising a modified oligonucleotide consisting of 12 to 30 linked nucleosides and having a nucleobase sequence comprising a complementary region comprising at least 12 contiguous nucleobases complementary to a target region of equal length of a fibronectin transcript, wherein the target region is within nucleobase 55469 and nucleobase 55790 of SEQ ID NO.: 1.

2. The method of claim 1, wherein the modulation of the fibronectin transcript in a cell decreases the amount of EDA+ fibronectin mRNA in a cell.

3. The method of claim 1, wherein the complementary region of the modified oligonucleotide comprises at least 15 contiguous nucleobases.

4. The method of claim 1, wherein the complementary region of the modified oligonucleotide comprises at least 18 contiguous nucleobases.

5. The method of claim 1, wherein the complementary region of the modified oligonucleotide comprises at least 20 contiguous nucleobases.

6. The method of claim 1, wherein the complementary region of the modified oligonucleotide is 100% complementary to the target region.

7. The method of claim 3, wherein the complementary region of the modified oligonucleotide is 100% complementary to the target region.

8. The method of claim 4, wherein the nucleobase sequence of the oligonucleotide is at least 90% complementary to an equal-length region of the fibronectin transcript, as measured over the entire length of the oligonucleotide.

9. The method of claim 1, wherein the modified oligonucleotide comprises at least one modified nucleoside comprising a modified sugar moiety.

10. The method of claim 9, wherein the modified sugar moiety is a 2'-substituted sugar moiety, wherein the 2'-substituent is selected from among: 2'-OMe, 2'-F, and 2'-MOE.

11. The method of claim 9, wherein the modified sugar moiety is a bicyclic sugar moiety.

12. The method of claim 11, wherein the bicyclic sugar moiety is LNA or cEt.

13. The method of claim 9, wherein the modified sugar moiety is a sugar surrogate, wherein the sugar surrogate is a morpholino or a modified morpholino.

14. The method of claim 9, wherein the modified oligonucleotide comprises at least two modified nucleosides comprising modified sugar moieties that are different from one another.

15. The method of claim 9, wherein the modified oligonucleotide comprises at least two modified nucleosides that have the same 2'-substituted sugar moiety.

16. The method of claim 15, wherein the 2'-substituent of the 2'-substituted sugar moiety is 2'-MOE.

17. The method of claims 1, wherein the modified oligonucleotide comprises at least one modified internucleoside linkage.

18. The method of claim 17, comprising at least one phosphorothioate internucleoside linkage.

19. The method of claim 1, wherein the cell is in a human.

20. The method of claim 19, wherein fibrosis in the human is reduced.

* * * * *

SEQUENCE LISTING

<160> NUMBER OF SEQ ID NOS: 435

<210> SEQ ID NO 1
<211> LENGTH: 76208
<212> TYPE: DNA
<213> ORGANISM: Homo sapiens

<400> SEQUENCE: 1

```
tattttatgg gttttcttcc tcacaaaata cactcctata agcagagatt ccccccctcc      60
accccgaaga gaggtgacgc aatgtcctca aacactacca ccaccccaa taaaaagaa      120 aagggaaggg ggagcgtctt gcaacccctt cgcttcacac aagtccagcc actcccttc      180 ctcccagccg cttcccatcc cttccccat cccctaaaaa gtttgatgac cgcaaaggaa      240
accgaaaaaa agttgtcttg ccccagtcct ggcgggccat cagcatctct tttgttcgct      300
gcgaacccac agtccccgt gacgtcaccc ggagcccggg ccaatcggcg cgcggtcggc      360
tgcggcggcc ggcgggcggg cgggcgggtg gggtggggcg gggcggggac agcccggcgg      420
gtctctcctc ccccgcgccc cgggcctcca gaggggcggg aggggaccgt cccatataag      480
ccccggctcc cggcgctcgg acgcccgcgc cggctgtgct gcacaggggg aggagaggga      540
accccaggcg cgagcgggaa gaggggacct gcagccacaa cttctctggt cctctgcatc      600
ccttctgtcc ctccacccgt ccccttcccc accctctggc cccaccttc ttggaggcga      660 caaccccgg gaggcattag aagggatttt tcccgcaggt tgcgaaggga agcaaacttg      720
gtggcaactt gcctcccggt gcgggcgtct ctcccccacc gtctcaacat gcttaggggt      780
ccggggcccg ggctgctgct gctggccgtc cagtgcctgg ggacagcggt gccctccacg      840
ggagcctcga agagcaagag gcaggctcag caaatggttc agcccccagtc cccggtggct      900 gtcagtcaaa gcaagcgtga gtactgaccg cgggctgaaa caggctgcct cagggatggg      960
accctaaagc cgaccaaagt tgggggctgaa gttttgtgcg cgcgcgtgtg tgcgagtgtg      1020
tgcgcgcttt actgagagaa accagctgtg cacacaaaag gaccgagttt tgagcacgct      1080
```

```
ggttctgagg gcctgggatg ataagaccgt gcattggagg acgaggactc tgcgactttc    1140
ccgtgttcta ataaattctg cacgttcaga ttgtccttct aggaattaac caaaacttgc    1200 cttttaaagag aaaaatgatg catgtctata aattttccgt ctgggattag tgtggtcctt    1260
actgctactt atttccttct gttaaataat tggtcaaata ttttcaacat gggggtggaa    1320
agggggtatt gaaatagctg tcttgtttct aactaacttg gaagagatgt aattggttca    1380
gacctcttta gggccgctca ggatacttca ccaagaacag aggttggaat tcttccgtt    1440 tttcaaagac acaccctcct tttgctttga gaaagctgct taaagttgtc cttttgact     1500 attactccaa aagaatattt aagttccttg catgttttaa aaatgtgact tcaattgtct    1560
gccttccaaa atgttccaa ctttttatg tagacccctg gccagatgga aatgacatca      1620
ttgtatataa cttttagcaa agttaaaagg aaaaaaatat gtacgtcaat attcacatga    1680
agaaaattcc ataattttgg gaaaggaga aatgcaaatg taacgttttc cttcaattat     1740
ttgcagccgg ttgttatgac aatggaaaac actatcagat aaatcaacag tgggagcgga    1800
cctacctagg caatgcgttg gtttgtactt gttatggagg aagccgaggt tttaactgcg    1860
agagtaaacc tgaaggtaag tgacaacaag ccccatagtt agtatctttt aatacatgaa    1920
gtggtaattg ttaaactttg cattagtaag taaaaataca tacaccattt ttctaataga    1980
attacctgtc atttcctctt aagtttaaaa actgcttata tttgcttttc acatgctttt    2040
acctttaaaa caaagaaacg aatctttccc aaattagttc ctagagtctt ctttttgctt    2100
tactctccca aagttttga tgagaaaat gaaagatttt gtgtgtcctc cgacaaaaaa      2160
aattgcttat aaaattttaa tttattagaa agcagtctca aatcttaaac tgttagttta    2220
tgagccagaa aacactttgg ggacttacat cgtaaaatga tttgtcagcg gcagttaaca    2280
caaaaccatt agccacttca aagttctcat tcctttagga ccaatgatat ttttctcata    2340
aattatagca actctgtcag agaagcactg atcaggggaa aatggaaatc ataggattaa    2400
caactgtcaa ggccttgtgg gaggtgggga tcttcgaatt gtttgtttgt tttgttttg     2460 ttttgttttt gagacagagt cttgctctgt caccaggctg gagtgcagta gcactatctc    2520
agctcactgc aacctctgcc tccagggttc aagcaattct cctgcctcag cctcctgagt    2580
agctgggact acaggcacat gccaccacac ccagctaatt ttcatatttt tagtagagac    2640
ggggtttcac cgtattggtc agggtggtct cgaattcctg acctcaggtg atccacccgc    2700
ctcagcctcc caaagtgctg ggattacagg cgtgagccac tgtgcccggc caatcgtttg    2760 cttttatgt gaaccttgct ttgacttct gagtcagaga ttggaatgtg aaacccttca      2820
caaatctagc tctgtcataa gttagtactt tatatggcct tttcctaaga gcctgagatt    2880
tttctacaat atgaataatt tacagaaaat ttgacaatat gtcaaggtca aaaaccatgg    2940
ccttattaga gcttaggata aaaatctgta tctctcactt cattttattc tttgaggtgt    3000
accatgttac ttgtgaata gagaagtggg ttttcctta gagggatta gtgaactaga      3060 aaagcttgta cctaagtgag gctcacatgg actttccttt tcccctcagc tgaagagact    3120
tgctttgaca agtacactgg gaacacttac cgagtgggtg acacttatga gcgtcctaaa    3180
gactccatga tctgggactg tacctgcatc ggggctgggc gagggagaat aagctgtacc    3240
atcgcaagta aggaagagat tgtgtaaaat gatgccaaaa tatcaaatat gaatttctct    3300
gttaccatca ctgtcatttt ctgttatcca tgactggata ttccgaactt tgaggttgc     3360 ccctggtgac caggtactct taagtggtca cccaactggt tcctgtgttt cttaaagacg    3420
```

```
ggtatgagca cagatggaat cagtgtttga tgtgtgtgcg tttatgagtg tgtgtgcatt    3480
tatgagtgtg tgtgtttctg tacatagtag aaccaagaga cctcttgggt tccatttcag    3540
taagacatgc ttaggggagt tgcccatttt aaatcacctg atatcttca agctagacaa    3600
atcatgagac ttttctgcag tgactgggaa ggtgttcatg aagagtgaac cagccatgtg    3660
ttgtctggtc ttcatgtttg caatgcagag acctcttgca cctcacagaa acagtctggt    3720
ttcttggtga ccagtaggtt atacccagga agcagatgtc actattccta gggataatac    3780
aaaattatta acccaataga gtttgctaag gaactttggg aaccgggctg attctcaact    3840
ctagtttagc taaggcactc tttccagtat gattcactgg gttaccaata gattctatta    3900
agatagtatt taagttttt  aatccattct ttaaatataa gtcgtcttaa agacttctat    3960
tcaaaagaac aagtcccgtg tgaataggcc aatcaactt  tccccatatt tcatgttagg    4020
gtttatccaa gttcacaggc aaatcgcaag aggcaagggt ccatagtgtt tacaatctag    4080
ttcagcattt gaatgtgcca ttgggcttaa caacttagaa aactaccagg atttccacac    4140
tttatatgca tatgtctgtt tgcttccac  caaaatgaca tttctatcct agggtaaaat    4200
acaggctctc catgctccca aaagctggag tgctgtgcct gatgtggcct tttcactgaa    4260
ttagtctcag tcttagcctg ctgtgtatga gtgaagacca agcctcccag cctttctttt    4320
ctgcttagga cccaatttcc tgtgatctct ctgggaaagc aggattcatg acctcttcct    4380
tgccatccag atttctctgt ggttttccat tgtgttctaa gcaagacact taactgaatt    4440
gactccaagt gaccagacct gttaacgttt ccctgtctc  tgatgggaaa gctgttgtct    4500
gtgtctctac tttagccaac ctaagtacct accatgggtg aatatgaga ccaaaaaaaa    4560
aaatctgttc tgccctctcc taacattttc gttgtatctt caacagaccg ctgccatgaa    4620
gggggtcagt cctacaagat tggtgacacc tggaggagac cacatgagac tggtggttac    4680
atgttagagt gtgtgtgtct tggtaatgga aaaggagaat ggacctgcaa gcccataggt    4740
gtgtgagtct tagggctgag caagagctgg gatgcttagt tctaatgtgg ggttggacca    4800
gaatcacatc tacataggtc atagacctga attccagtga aaaccaataa agaaatggga    4860
atttgtttg  aaataatgaa ttattatata atccatagtc ttcttacagg agttagatca    4920
aaaagtactg actacacata gaagtcttaa ctttgcttca aaagcataag gtagaattga    4980
aagatttaga atggagtcat ttcttttacc taatagctga tctcagattc ctccttcgtc    5040
aagatataat ttatttaaaa gaaaaaaaaa tgacactttg gacacatttc tatatggaat    5100
gtcctggacc gaaacatgaa atagtgtgtg cttgtcacac tctgctcatt tcttttcaaa    5160
ttaaaagttg ttgagcttct ttggatctca atcctcagtt gaattttgta agtacaagcc    5220
tgaaagtttc tggctataaa ttttactctg tttacttgtc ttctaattta gaggtttttg    5280
tcttgttttg tattgttttg ctttccaata tttaaaaata gctttctttg tcattgtatt    5340
taggccactc aaaattcata attggtcatt tataattaag attggaattt tgcatatgta    5400
gtctcccaca gactagatac atacatagat ccttgctact ggaaatgctg ctgggaagtt    5460
tggggctcgc tgaaaatatg tagtccatgt acttattagg agaatggaat ttctgcctgc    5520
caactcagct tgagctttct tttgccttgg ctacttactg tgtgcttaga tgctgggtgt    5580
gtcattcttt ctgaacagag tgccacttaa aaaaaatgtg gctgaatttt tgcttacaca    5640
ctacacttta aattacaggg agcttgcaca attcaaaata accttttttt cctgttttc     5700
ttccaaattt ccctacagct gagaagtgtt ttgatcatgc tgctgggact tcctatgtgg    5760
tcggagaaac gtgggagaag ccctaccaag gctggatgat ggtagattgt acttgcctgg    5820
```

-continued

| | |
|---|---|
| gagaaggcag cggacgcatc acttgcactt ctagaagtat gttttacatc tttatgttaa | 5880 |
| agattaagcc aggtattgtt ttctggattc ctagagagaa gggtaatact atgttactca | 5940 |
| gaacacatcc agtatatcag catgctttgg taacttctgg aagtcaagaa aactttcata | 6000 |
| accaacttat tccgcatctt cagagaagac tacataaata gaaaaacata tcactttgat | 6060 |
| aaggttcaat ctcagctcac tgccactgac atagagttga acaaaaggtt taggtttcct | 6120 |
| tctatgtttg aaatttaaat agggcacatt cacaggctaa attgataaaa ttaaaaagaa | 6180 |
| tttatcccat aaattaaaat gatttatcta ctctggagtt agggatagtg tctctgacct | 6240 |
| aacgcatttg attagtgctg taaagaagct ggcctctggt gtctttactg ctccttctaa | 6300 |
| gattgtcttg gggtcttaat tgttgccttt gggtttgaag gctccttttt tgatattgta | 6360 |
| aactaataac agctagagag tttgttgaag taaaacagcc attaactact ggtgttgtaa | 6420 |
| ataagtttaa aatcaaatcc aaataatttg aacctgtttt atttatctag ctgaacccat | 6480 |
| ttaactacct ttaacatagc catcatccaa attcaaattc tttgctaaca aaaataggtc | 6540 |
| tctcatgaaa agtggtaacc attttgacca aagctttccc agaaacttgc tggtttatta | 6600 |
| gatattttgc atttaaaatg ttactgtgat catcagactt ccaagatctt tgtggcaata | 6660 |
| ttttagctta agacaaatta gatgtctgat tcaaaccttg tctgttattt agaactcttt | 6720 |
| aaatagcaag ttgggaaaag tttctcaaag agaagtcatt tattccagaa aattttataa | 6780 |
| ggacttactt tgttcaaggt attatagggg tgcagatatg aaatgaacat tagcccagcc | 6840 |
| ttcaaagagt acttagggggg tcagggagat gagaaagtct tatacatatt tatcatctgc | 6900 |
| aaaacacagt attaaagatt tcaacagaaa tactgaaagt agtgctatgg aggttcaggg | 6960 |
| gatgataata ctttcgctg gggatttggg aaaaagctct aatcagtaat tataccttca | 7020 |
| tgcaaacttc tattcttgtg gtagatggat gtgggtgtgt atttgtttga acctacatca | 7080 |
| actattaatt ttttttctct aacccaggag ttgcaacaat atccaattca caaagacatc | 7140 |
| agatcctcta tactcacatc gtggcacaga gcaaatttgg attataattt aaataatcta | 7200 |
| tttaccagat aaatgcacgc atagactaat ggtcatttag ttacaaatta tcattttatg | 7260 |
| ttgatcccac tcttccagtg gagggctaac actgaataat ttggggctat tttgctagtg | 7320 |
| atttttaaat actgtagatg tttgggtata ggggaaggga aaataatatt ttagtcaaag | 7380 |
| aaattgtgca tcctctacat ttttttacata acaaatgaag aaagagatac taccaccttc | 7440 |
| ttatagcttc tttgtagcca ttggtgaaga ccctttgata cctgcttgcc tccccattgt | 7500 |
| tataagcttt tttttgtttg cttgtttttt ttgttttgtt ttgttttgtt ttgttttga | 7560 |
| gacagtctca ccctgtcgcc caggctggag tgcaatggtg tgatctcagc tcattgcaac | 7620 |
| ctccacctcc cgggttcaag cgattctctt gcctcagctt cccgagtagc ttggattaca | 7680 |
| ggcgcccgcc accacagccg gctaattttt tttggtattt ttagtagaga cggggggttc | 7740 |
| accatgttgc ccaggctggt cttgaactcc tgactgcagg tgatccaccc tcctaaagta | 7800 |
| ctaggattac aggcgtgagc caccgcgctt agcctgtttt tagttttcta aagcaaggtc | 7860 |
| cctattgaaa ggcaggccat aaacagtgat gactaagaaa atcctggaa gagcctgaga | 7920 |
| aggaaaaaga tgaaatataa tgccagaaa tgaagttagt caaggaaca gtgtgaaaac | 7980 |
| aataaataaa tagataaatg aaatgttat ttgacagaga gatgaaacta gactaaacca | 8040 |
| ttcagctgcc tttccactgt aacaaatgta atttcatctt tcagaagtgt aatacccttgc | 8100 |
| agcaccagag ctgaatatga acatattacc aaaaatagat taccaggcat agatagcatt | 8160 |

```
ccttttttaa gtttgaattg accacttgcg actctcgacc tgatgtatgt atgtgcttcc    8220
tttgtgacac agatagatgc aacgatcagg acacaaggac atcctataga attggagaca    8280
cctggagcaa gaaggataat cgaggaaacc tgctccagtg catctgcaca ggcaacggcc    8340
gaggagagtg gaagtgtgag aggcacacct ctgtgcagac cacatcgagc ggtgaggcac    8400
aggacgagca ggggcgggaa atggggaagc aggtcaagaa atatttccgc aaatccatct    8460
ttcctttgac atgccatttg aggataattt gcagtgtttc agctaataac ctaagataat    8520
ttacacatta ttggttgtta aaactttttt taatgtcaag tttttaaattt ttcagaaaaa    8580 aagaaaaatg acatacaaat aaaccttagg gggaaaaaag ccagatttat ctccaaaaga    8640
taaaactgag tttttaaagaa tgctagcatc ataaaactta ccatggatag atcacgcaca    8700
cacgcacaca cacacgtatt ttgaatatcc aaagttcatt tgaaaggaaa tgagagttat    8760
aattaattat atgactacct ggttcttctg ctaggaaagg acaaaaaaag tgcatttgga    8820
ttttttgttt gtttgttttt gaatgaaata tacttccctg tcccgacatt gaactctttt    8880
tgtagtggaa accatccttt tatgtggtt tctatgctct ggcaaacttt gttacattct    8940
ataaagtaac acacaattat ttccttcatg tattggcatt cgaattttta gaaattcaga    9000
gaggacttag agatggccat gaaagacatg atatctaagc attcttttta aaaacaagt    9060 tttaatcatt tttggcatga gaaaagatt tttacgtcat aaatgtttca taaaaatctg    9120
aagagagaaa tatggccaac aaggacgtgc actcctctca ttattttaa tatgttttga    9180 ttaactttt actatatgat gtgccaacat cattacgtag tgtctcagcc atccttcaat    9240 taaaatatt aattgttcta attttcttc ttttgatgag ttttgtctt gctttgagca    9300 cttatgaagg tgaacaagat tagatttgat aatatctttg agttatttta ttatcattaa    9360
taaaattgct actggccaaa aaaaattata acatcggcc acgcgcggtg gctcacgcct    9420
gtaatcccag cactttggga ggccgaggca ggcggatcac gaggtcagga gatcaagacc    9480
atcctggcta acacggtgaa accccatctc tactaaaaat acaaaaaatt aaccaggcgt    9540
tgtggcgggc gcctgtagtc ccagctactc gggaggctga ggcaggagaa tggcatgaac    9600
ccgggaggtg gagtttgcag tgaccccgaga tcgcaccact gcactccagc ctgggtgata    9660
cagcgagacc ccatctcaaa aaataaaat aaaataaaaa ataaaaaaaa ttataaatgt    9720
cagtctacca aaatagatta aaagtgtagg tgggaattaa atggggataa acactcaata    9780
aatgttagct atatatgaat attgccaata ctgaaaagat tccattgttc aaaaaagttt    9840
gagaagcaat gggttaaaca aaatggaacc tgctctgcag aatctgtgtg ttcctttaca    9900
tcatactctc catggtagag tgtaggggat gggcgccatg tctccctagt acgtttgacc    9960
ttgggattct ttgtctgtga acatctttgg gttctagtgt tcagcagcac ttagggaggc   10020
actgaattca gtgtacccttt ggtctagcct cagccctgat tctgttctgc ggtgggccct   10080
ggccttcaag agaacagata tctaaaagtt gaaagaaaag atcggccggg cgcggtggct   10140
cacgcctgta atcccagcac tttgggaggc caaggcgggt ggatcacaag gtcaggagat   10200
cgagaccatc ctggctaaca cggtgaaacc ccgtctctac taaaaataca aaaaattagc   10260
cgggcgtggt ggcgggtgcc tgtagtccca gctactcggg aggctgaggc aggagaatgg   10320
cgtgaacccg ggaggcagag cttgcagtga gccgagattg cgccactgca ctccagcctg   10380
ggtgacagag tgagactccg tctcaaaaaa aaaaaaaaa aaaaaagaa aaagaaaag   10440 atcaacacat cctgttgtgt tattctgaaa ggaaagctgt cttaagagga tcaattggtt   10500
ttagaaaaaa cacaatagaa tcacaaataa tccagaggag aaataaaatg tggaaggtgg   10560
```

-continued

```
aggtgacctc cagaaaatcc aggacagctg ctgaaggcac cctctgatga gctcggttac   10620
tcagaagagt gaggatgtgt tgaaggtatc tgctgtatgg agtggcagga tgatgtctgt   10680
gattgagaaa tataatcccg gccaggcgag gtggctcatg cctgtaatcc cagcactttg   10740
ggaggccgaa gcgggtggat ccctgaggt caggagtttg agacaggagt ttgaggtcag    10800
gagtttgcca acatggcaaa accccgtctc tactaaaaaa tacaaaaaaa atcagctggg   10860
catggtggtg cgtgcctgta attgcagcta cttgggaggt tgaggcagga gaatagcttg   10920
aacccaggag gcagaggttg cagtgagccg agaccgcgcc actgcactcc agcctgggca   10980
acagagtgag accccatctc aaaaacaacc caaaaaacca aaaacaaac aaacaaaaag    11040 aaatataatc ccagtagccc cagctgagct ggaggatgga gaccacttgg tagacacttg   11100
tggattattt cctaggctaa atgcaaaagc tactgctgaa taggggacat ttttttccag   11160
tcccaggcca gtagcgacat agatttcaga gtgatctctg tgagatcctg aagatcctga   11220
ctgcagaaag tagtgaattg tcttctctca cccagttttg tgacattccc ttttcatgcc   11280
attaggatct ggccccttca ccgatgttcg tgcagctgtt taccaaccgc agcctcaccc   11340
ccagcctcct ccctatggcc actgtgtcac agacagtggt gtggtctact ctgtggggat   11400
gcagtggctg aagacacaag gaaataagca aatgctttgc acgtgcctgg gcaacggagt   11460
cagctgccaa gagacaggta tgcattatct ttttgaagaa taggactgat gactttatta   11520
tttagttttt gaaggacaat acattttcaa tgtgaaacaa taaaacaaac aagaagcctg   11580
taatcttacc accctgtgat aacaattagg gttggcattt gaaatagttt cttccaatct   11640
ttttaattta tgtatttct ttctggtcat ggatatcatg ggtaaaaatt ttattgtatt    11700
tatctgtcta aagtgttgtt acaagagagc tactttctga ataatcatca atgttttata   11760
ttctaaatct caaatttcag cagctttgtg atgtaaacat cttccaataa cctaatatat   11820
gtattctgca ctacaaacat ggtagtcact atggcaataa caattgctac acaattctcc   11880
cccagaatag tctcatatat taattttatg gcatagatat agtcataaat attatcccaa   11940
catccttaag cagcatcctt aattgacctg tataaatata gctttacaaa tagagaaact   12000
gaggcatggc agcagaagtg gtcatgaagg acatcagcag aagaactcag gtgtcgttct   12060
atccacagta gacatggatt cctgagtaat gcattttgac tgaaattaac gagatgatca   12120
tctatactca tagcttcttc ctttgagggc acaagctcag tatctcattg aagccataaa   12180
taagcagctg ctggtgggag ataaagcatc tctgtttact gacactcttt tgattatgat   12240
tgtagctgta acccagactt acggtggcaa ctcaaatgga gagccatgtg tcttaccatt   12300
cacctacaat ggcaggacgt tctactcctg caccacagaa gggcgacagg acggacatct   12360
ttggtgcagc acaacttcga attatgagca ggaccagaaa tactctttct gcacagacca   12420
cactggtgag tgtcccaagg gggagccaca gaagtgagaa aaactcactt tcatgccta   12480 gttttatttg ccagcattct agccatttat tttgaacccg cccaagaagc atcgcttttg   12540
ttcagtttgg actcaagaga tcgcagcgct cacgtaacag ctgaggattc ttccatcttc   12600
cccagtactg ttgggaaatg acaccaaggg agtagccttc cagttcattt gatttaacac   12660
attgggatta tgatgtgatt aaagatactt gtatttggga atcagtagat gatcccacag   12720
ggctgaggaa tacaaaggat gaatgtttta gtgccttagc ttattttcca gttaaaacaa   12780
tgttttattc aaagctatca tttaatcttt tgtgggggg gtgctgggga aatgacagtg    12840
aaagtgggat ttaaacctgt tttgaaggtg tgaaggtaaa tatgctaaga agcttagaac   12900
```

```
tatattatca gacattttt attctgagat agactgtctg tgaatgagct gcagaaacct    12960
ggctctctca gaccagtaat tctgtgtaca ttggaaagct cagcggtaat cttttccttc    13020
tttgttgtgt attgttcctg gcagttttgg ttcagactcg aggaggaaat tccaatggtg    13080
ccttgtgcca cttcccette ctatacaaca accacaatta cactgattgc acttctgagg    13140
gcagaagaga caacatgaag tggtgtggga ccacacagaa ctatgatgcc gaccagaagt    13200
ttgggttctg ccccatggct ggtaagatga agcccttgtg ggttgtcttg tttgacaaca    13260
atttagggag tagagactaa agactagtgt ccagtttact cccatttcat tcattaacac    13320
aattttgaga caacagaaaa cttcatgtga agtgtgtttg tgtgtgtgtg tgtgtgtgtg    13380
tgtgtgtgtg atgttacatc atatacataa ggattgggaa gaataattag ataattattt    13440
atataatttt taaacctcat tgacatgatt taatgtcaaa aatataatta cttatttgta    13500
agtctggaaa tatgaatttg cacaggtttg tctttgtaaa gagcacacaa ctgagtagct    13560
tacaacattt aatatatgta tgacggcttt agtcacagag ctacaatatt gacacatggt    13620
tgtggtttga tgggcataag ctctatcact tattaataag tgccaaagtg actaaaactc    13680
aatgttttct aacaggtagg gaatctcact cttttttaa aggtccccag tttgtataga    13740
tggcgaacaa atgaaacga ataccttta cttgttttca gatttcaaga accccataga    13800
ttccctttaa ttttccagtt gtagaaacaa gagcctgggc ggtaggcact gtcaagtgtg    13860
actatgagac aaagaaattg cttatacttt tatttctttc aacaaaagaa gatgctgagt    13920
ttagaagaaa aaacccactt ttgcttgtaa ttctatatcc aaacccatag ttttttattg    13980
atccagaata aactggaact gggaaaagtt atgaagctgt agttaaatcc aggcttctag    14040
aacagcaaga acccttgtg tggatgtgta gatattatct tagtttaaca tcccctaacc    14100
cttcctgtaa ctattttcta tgacacgttt ggactacgtt ttctgcctcc agggctcaaa    14160
aattctaccc cttcacctga cagcacttag atgtctttga tgcacacaaa gcttcttccc    14220
aagtgagaat tcttaggatg accaaactga actgatcctt ttgcacacat acatgtttag    14280
acctggtgat catttatcaa gtgcatttct tatccatttc caaacagccc acgaggaaat    14340
ctgcacaacc aatgaagggg tcatgtaccg cattggagat cagtgggata agcagcatga    14400
catgggtcac atgatgaggt gcacgtgtgt tgggaatggt cgtggggaat ggacatgcat    14460
tgcctactcg cagcttcgag gtatgctggc tgattaacaa aaatatttga gatggcaaaa    14520
ggtacagaaa gggacacttt tttttatgaa aacttgcact atgccaaaag caggggaaga    14580
aatatggaat gccacgtcat tcattagtct actgtgcatg gtaagataag cctgaaaggc    14640
ttagcaggca gcctgctaag acaagcggca tagcaatgct aatgttctga aacactccta    14700
gcatgtaagt acttaggctg agccaaaaag atggcttcaa aagtaagaat gaaacatttg    14760
atccattcag ctttaggcta tgccactgga ttcatgtcta gaaaagatag gataatttct    14820
gtaaagaaat gaagaccttg ctattctaaa atcagatcct tacagatcca gatttcagga    14880
aacaaataca tagggactaa acttccttg ttcagattag tttttctcct ttgcacccag    14940
ctatataata tgaggaagta ttgactttt aaaagtgttt tagtttccaa tttctttgat    15000
atgaaaagta atatttcggg agaacccctga gctattaata atctatgtgg ctagtgcgta    15060
gatattggtc tgaatttgtt ctccttttgt ggtgtccagt gggtaacacc atccgggagt    15120
aataattaca tgtggtgttg cagaactgaa agagacctta ataacacata gagacctcac    15180
tctatataga tcaaggagct gagacccaaa aaggaaaaag taattttctc aggatctctc    15240
aaagagtgag caacagagtt ggcctaattt attttagcgt tgtgaatact gttgacattt    15300
```

```
tatttcccaa atctaagtat ctcctcccct tccccctatt ccagagacca gaccaccaca   15360
tcatgctggg tgttagataa atatgtttaa tcttcttctt atttatccta acaagcagat   15420
atttaaagga aattatcaac taagcaagaa attttcagaa agtaagacat gtatttgttc   15480
aaatactggc ttctcacagg aaagtgtatt ttaccacatt ctttacttga gcatactgta   15540
acctctgcaa aagttacaca ttttgggaag aaaaaatttt ttttggcaaa aattgtatta   15600
ctgaccaaac tttgaaaaaa atgttattct atgcttgtag aaaagttatt ttagtggaag   15660
gtgttgataa ttaagtggaa gtagttgtat gctttgagaa gcatacctttt tttctttcat  15720 caatggaact ttaaaaagtt tctcactcac ccacctgttt cctaaacaga tcagtgcatt   15780
gttgatgaca tcacttacaa tgtgaacgac acattccaca agcgtcatga agaggggcac   15840
atgctgaact gtacatgctt cggtcagggt cggggcaggt ggaagtgtga tcccgtcggt   15900
gagtagccct atttccctag atgagtttgc acaggggaa tggttagcaa gtttcagata    15960
agaaaagcta tgtgaaatca catgactgaa gttggctcca gactttgatc agttgcttgc   16020
aaagaacttt gcaaagtctt ctctctaata ctggaccaaa atatctcgat attggtagtc   16080
gtctggtttt tgctgaattt ggtgacaaat ttaggcttat tttaattgaa tggaattat    16140 tcttgggttt agaatcataa agataatcca tgctattaaa agtattcttt ccttttttt   16200 ttgtttgttt ttgtttttgt ttttgttttt ttgagagaga gtttcgctct tgttgcccag   16260
gctggagtgt atggcacaat ctcggctcac tgcaacctct gcttcctggg ttcaagcaat   16320
tctgctgcct cagcctcctg agtagctggg attacaggca tgcgccacca ggcccagcta   16380
attttgtatc tttagtagag atggggtttc tccatgtggg tcaggctggt ctcaaactca   16440
cttccttacc agctgtgtaa cagcatgagc aaagggtgta aatatcaccc accaaaacac   16500
tctaggtttt ttttttggccg cccttcaaaa tagaactaag caaatagtga aggctgagcc   16560 ttaaagagc tgtgttacca gcactacaaa gtttaaggtg atccattact atttctttac     16620
caaaagagac aggttgctca ctgagaaaac aaactgataa catccgtttg tttgacgtga   16680
gattaccaga actgagagag aagcctgaga ggttttctta gaagctgctc agcaggtata   16740
ctcgtaaagt ctagttcatt catttaaatg tcaaacagtt tctttaaatt ttgaagaagt   16800
aaggaaaatg aaattattgc agattttttt cttgctattt aaatgttaag ccagttatat   16860
taatatgggt aaaaataata actaatattt aaaattaatg tgtagattat caatatacac   16920
tgaaatctaa atcttacat ttttatttag aaatattacc ttttagaaaa ctaaatattc     16980
ctcctaatag gtactttggt ttttttttta ctacaaactg tcctgtaagg taagaatgt    17040 gaacaaaata ttttttaac tgcatatatt tgtaagaaca attgcaaatt tctatttaag    17100
ctaaatgtat gctctagcac cctgaaatta aattcgtagt tataagtctt caaggctgtt   17160
tatcttttcc ttccatgtat tttagaccaa tgccaggatt cagagactgg gacgttttat   17220
caaattggag attcatggga gaagtatgtg catggtgtca gataccagtg ctactgctat   17280
ggccgtggca ttggggagtg gcattgccaa ccttttacaga cctatccaag taagtagctc   17340
tattactgca agttgagaac tgccaattgg gttataacaa cagggcagtg attattaatg   17400
ctctcatgcc taagttgggg gtctcccctc tttcccaccc ttttctcttg ttattatcta   17460
ataatcaatt gaattttga ttaaaataat ttttctctct tcctctatca agtaaaaggt    17520
agagaaggct atgaaaatgt gcctgtttat aatttttactt cttaactctg taaaatattc  17580
tgttaggtta agacactctg gctaatttca tcttatatcc atacatggaa ataaaaacca   17640
```

```
ccaagtgagt tatgctggga gtaaaggttt ggggctttat attatgattc ttaacagaga   17700
agctgcatag agagatggca tgaaatgcag cataaggtac gtgttcattc aacatgtcat   17760
ctaagctccc tttgcatcaa acttttcatt tgtttgatca gttgccacca ggaacacagt   17820
atgttgggcc aagggttgag taacttggtc aactctctgc ccacacagtt caaacactct   17880
caaatgttta ttgctgggtt tttccaggtc acaaagacat catgcctagc tgtaggtgta   17940
attagttcat ttgggggggaa aattgcattt aaatattcac tgagtgatta taataaaaca   18000
tgttaataaa acatgaaagg ctaattaaaa ggcatcagtt atttgagcaa ctgctgaggt   18060
gcaaagtctc caaagtcttc actaacgttt gactgaaaat atggcctaca ttcagaaaca   18120
aaagagtttc agggtgtcag aatctgcatg cgacagaaat taagattaac tctgtgataa   18180
aagattcact gtgacagaga acaagctatg gaacaactt ggccaaaggt agtgttagcc   18240
aagcctcatt cctccatttc ctcatctgta atatgggaag attgtagctg attacctta   18300
atgttccatc ctaaatacta aacacccaga tgcacctttt ctaggaactt ggaagattct   18360
gcttttccca acctcagac actgtcagtg ctggggaagg tgacttcact tttgaaggct   18420
tatagcacag attgaccaac ctcctaaatt gtatttcttg gaggatttag gtgtaggaat   18480
cacttaattt tttgtaactt aatatatatt taaatctgat tgtggaagta ctataagtat   18540
atgaatggtt tgtttgttta tatgatgcaa atgatactta aatggtagaa acttctaaaa   18600
aaatgctctg tggtttctat atttatgatt gttattggtg ttgcaatttg ctgaaaatga   18660
tttccttctg aatgattgag agagatcttc gtctctctca acataaggct gtccacatag   18720
ctgcttgctg gaagcattta ggtggacatg ttggagataa aatctggaaa ggaaggaatc   18780
cttgagtatt ggagtattac atgttgacct tactcctact ctttaaaaag gagaacagca   18840
agatcccact gagcatagag gtgatttcgg agggaagaga ttggaatttg acctcagata   18900
tgctctttgg tgcttatctg tatgtctggt ttgctccgtg gcctagcacg tagggcttta   18960
agagtgtggt gagaataagg gaacagcaga ttaccaacag attgtctctg agtcctgcct   19020
tgtttgttcc tcctacagag aacttggtag agttgttcaa actagcaaaa gataagaggc   19080
atttggtttg tcaataagca actagaaaag cacagatctc agcaaaataa atagagaaaa   19140
aaaggactga gtcaaaaaat cataaatgtt taacttctcc aaggacacta ctattggaaa   19200
ttattcattt agactttatt tgaaactaat tttaaaagtg tagacattgt actatctcct   19260
ttttttggta tcatctcaac tatttttattg ttagtttatt catattgaat aagagaggga   19320
gtaaagattt cacaatggcg atagctagta tatgccaatt aagttaattt aaaaagttat   19380
accaactacc agtagcgaaa aaggactgtc aaaagtttaa atctaaataa tgtaaaagat   19440
gtcataattt ttaactttc tgtctttaaa ggatacatag tataagctag agtaattata   19500
cgtagtataa gctagaatat aggaatttaa ttgatctaag aaataactga cacaaagtct   19560
ctttacttcc tgaacaaaaa catgctaaat tccatgctgt tcagtccatt tcctttaaag   19620
gtgggctatg ccacagggct agattttaaa acgtggaatt tcacaccagt gctcgaaatc   19680
ttatgaaagc aaaagggacc tctgtagttg tactccactt tggcttgagt aaaaaccact   19740
gctgtaccct ttttctttcc tttccctgcc cattttttatc ctcctccttg tgtccttgtg   19800
gacatagaaa tatgattagg cttagaggtg aacagtaaag gtcatttatg ttatctttc   19860
aaaacttaat agacatttat ccatcataag cttgtccccc ctcaaaatca tgattgacaa   19920
gactaaataa agtgtatatc aggtgtctct ttatggagga aattgtagta ggattttttt   19980
aaaggatcaa tatttaaata gccctatgcc aattatcata aataattaag gacatgatat   20040
```

```
tcctagcttt cctgatttac atggaagtac gttaaatagt cacatctcca aaattttcct   20100
tgaatagttg tctttaaaaa tgtgtttaca tttgtaagga tcttcataaa cagaaggggt   20160
aattcaaaga taggcatgga attgacttat gccaattgat taaaacaaac atcctgtgtg   20220
ttctgtgaaa tacatacaac tttaaaatga aaaactcata attttatgca tgaattttgg   20280
tgttcatgtg gcttggaaat atgtgcatta aatggaatta agattcaaag tatttgctaa   20340
tcttcaacca actttgaatt gttactggtg tggaagtgag catattgttt tagaatttct   20400
gaatctacat ggatatccaa gttatatatt ttttctgcta cagaaagctt tgttttccaa   20460
gagaatttaa tggcttagat aataaagttt gaaaatcaat gtattttttt tcctagaagc   20520
tttcagaaaa cttaaatctg ttaataatct ggtgaagtgc tttattacac atacaaaatt   20580
ttgctctgtt tgacagagtg tcagttagaa attcttgaaa aggttactat aagacacaat   20640
ttttatttct agtaatttaa acattgactg acatcataaa gatagtgttt taagaaaaga   20700
tagttttctg ttctgcaagc ataaattttc tagctatttc attattatct taaatggagt   20760
taacactact tagaaattga tgctacttcc cttatttttcc ttttatttta aacaaaagaa   20820
ccaaaaccat actttaaatt ttgttgataa cagtgatata catcaaggtg tagaaatact   20880
gaatttagta tacacttcat aaagtcattt ctgttgacaa ctgattttgg aaaaaaaata   20940
aatttaatca cttaataatt tgatggatca atggtgtgat ttgggagtaa acttcttgaa   21000
taaaaataaa acttgatgtt ttttccaaac tgatagactg cttagactga tgagaaataa   21060
aactaggtct ttaattatta cctttgctat ttgtctaaga ttctacccccc atttagaaat   21120 gtgtttgttt tacatcatct catatggcct ttggaatgtt gtttccttct taggtagtag   21180
attcattctt gatgaaaacc ttccaaaatt agaatttgct ttaaaagagg ctcaatacaa   21240
taagtaaatg aagtctgtgt tctgtattac attattttttg taggatcgtt tcacaatttt   21300
ctcacaattc ttactttgat agtagagaaa ataaaagcaa gccaagagac ttttttttaa   21360
aaatatattt tatttgctat aaacaactat gatttgcatt tctcatgtga agaataataa   21420
ttatcggcta aaaatggatt tgctgcattg attttcaacg taaatattta aaagattaat   21480
gccagataat tttattatac tcacatttaa cgacaagcaa agctgtttat aatgatgact   21540
gtccatgtac acagttttaa gttgaagtga gtgaatattc aagataatta aatgctacat   21600
tttcattttc aggctcaagt ggtcctgtcg aagtatttat cactgagact ccagtcagc   21660 ccaactccca ccccatccag tggaatgcac acagccatc tcacatttcc aagtacattc   21720
tcaggtggag acctgtgagt atcccaccca gaaaccttgg atactgagtc tcctaatctt   21780
atcaattctg atggtttctt tttttcccag cttttgagcc aacaactctg attaactatt   21840
cctatagcat ttactatatt tgtttagtga acaaacaata tgtggtcaat taaattgact   21900
tgtagactga ggggattttg gtttttggttt tgggttttgt ttttttgcgg tgggggggct   21960
ggtatttgga agaatttagc tctttatgtt acagaaatct tttttgcaag gacttagaaa   22020
tgataatgct taagattgtt cttgcccaat gtgggaagag aatctaaggt ttttatatgt   22080
cttgcaacct catcaaagga aaattactgg catcattttc ataatttgaa aaaaaaagcc   22140
aaattaatat atttctttttt tgattcactt tttaagtgat catttttaaa actttacttt   22200
tgacccactg aatttattta gatagaagga aaagagatga tgggagggaa gtttagataa   22260
aggatggaag ttggttttat ttaaacaata gccctgtgat ttcctaatga gaagtgacta   22320
gaaattgaag aaaccaaata aggaggatat tggtcaattt agctttagtt tctcttactc   22380
```

```
tctcaagcct gccctgttta actccaaagt tcatggctca taatttgaga aacactgttt   22440
taaacacagg agaaaaaaat gtccatttta aatcatagct attgaattct acaattacaa   22500
agaaacaaac aaacaaaatt tgaccaaccc aggcggttaa atttaaactc ttcaggaaaa   22560
atttaagctg ttaaaattat tcttttcta aatttctaaa gtggagggac agaattttc    22620 agatttaaaa gggcctccta ggtgcccaga aaattagtgg aaagaaccac gtctagacgc   22680
atctttgatg tgtcagagtt ccaaggataa aagaaactt ttaaagtctt ctatactcag    22740
ccaggttatc aatcaaatat gagggcaaaa taatatttc agacagattt taggcagttt    22800
atcttccata tatccttttc tttaagggta tttgtagata cactccagaa aaacaagagt   22860
gaaatatgaa ggaagttgtg gggtccagca aacagtgctt ccaaatcaga cccctgatag   22920
aggtggaaaa ctttgcaatg caacaactgc gtagctggct tagaggacag ccaatacaga   22980
tggaacagaa agatgaggat gggattgagg gatcagggat tgaggtctcc aagaataaaa   23040
agggacttca tggaaaaagt aggcttgtgg ataattaatc acaggggcaa ataatgcagt   23100
taaaataaca acatgacaat caggtggagg aatgtataat aaacccaaat gtggctgggt   23160
agagtggctc acacctgtaa tcccagcact ttgggaggcc aagccgggca gattacctga   23220
ggtcaggagt tcgagaccag cttggccaac atggcgaaac cccgtctcta ctaaaaatac   23280
aaaaattagc caggcttggg ggcgcacgcc tgtagtccca gctcctcagg agctgaggta   23340
ggagaatcac ttgaacccag gaggcaaagg ttgcaggag ttgagccaag atcgcgccat    23400
tgcaccctag cctgggcaac agagcgagat tctgtttcaa aaaccccca agtgtattat    23460 aaggcaataa ttcctatacg aagcaaacta aaatgcagca atattaaggt ataaaaacaa   23520
agaggaataa ttccattgaa ccttgattct ggaaactttg atccacccag cagtcatgat   23580
gttagactca ttgaaaagaa tgtatttcta atgcatgatg cgatcggtct atagatgtgt   23640
catggaaact tggttgcaac ttcaagacaa aataaaaagt aaacatttac atgaaaaatg   23700
gtggatatgg aagtggagag agagaggaga taacagcttt atctttcaaa atagagaatt   23760
gagagatggt accaaaagct gatgaagtaa aaaaaaaaaa aaaaaaaaaa gatacttaat   23820
ataatacttt aaattacaaa tataaacaca agaagaacaa atataatgat acaaatgtca   23880
gacactggga atgtccaaga ttctggaagg aaagggtggt attattgagc taaatcctca   23940
actttgtctg ggcacagtgg ctaaaaatta gccgggcatg gtagcatgca cctgtagtcc   24000
cagctacttg ggaggctgag gcggaaggat cgcttgagct tgagaggcgg aagttgcagt   24060
gagccaagat ggcactactg cactccagcc tgggagacag agaaagaccc tgtgtcaaca   24120
taaataaata tataaataaa tcatcaagtc tcatattaaa gactctgtaa atatgactta   24180
ttgttgacaa atgaaacaaa tagaggtgta agcatgttgt ctacatggag gcaagaccag   24240
aataatagaa aatggaaaca gattcccta aagagggaa tcgtgtctt ctcattggct      24300 caatgtagtc tccgtagagt ctagaatgct tcagcacctg gcacactgct taacaaatgg   24360
tgaatgaaaa aaaaaaaag aaaagtcatt cttttttcttc tttcaccta tgtccataat    24420 ctggccattt gcagaacttg atgtccagtg atcgaaatca acagcatcag tgcatccaat   24480
atcttctagt ctctcatctt cttattacat cattaatttt atttacttta aattaaggga   24540
tatccaaagt attatgtgag accattgcaa tgggagactt aaaagtggta taaaatgtac   24600
tttgggccag gcgcagtggc tcacgcctgt aatcccagca ctttgggagg ccaaggtggg   24660
cggatcacga ggtcaagaga tcgagagcat cctggccaac atggtgaaac cccgtctcta   24720
ttaaaaatac aaaaaaatta gctgggcatg gtggcgcata cctgtaatcc cagctactcg   24780
```

```
ggaagctgag gcaggagaat cgcttgaaac cagaaggcgg aggttgcagt gagccaggat   24840
cacgccactg cactccagcc tgggcaacaa gagcgaaact ccatctcaaa aaaaaaaaaa   24900
aaaaagtaca ttgaattgga aagtcttcaa aaagcagcag tgatgaattt tttgagattt   24960
ttaacaatta caaaaattca gggttttttc taatggatgc cacctgagac tttattttct   25020
gttattttct tgtaataact aaccaaacaa gctcatgttg aaaaatgatt actaaatttg   25080
agctaattgc aatgactggt ttcaaaattt tccacagtgt atttgagtta aaatttcact   25140
gtgaagagta ctacgatcac tctcgcttat tccaaaaata taaatggaca cttgagtatt   25200
tgaattattg aggaaatggt tgactgggta atttttaaaa atcactgggc acaaaaaata   25260
tattttgact tatattagtt tagagtattt acacttgaaa gagtctcatc ttttctgaag   25320
ggtgtttctt tcatacacat tttattgcac tgagttttgt gacccatggc atattaatga   25380
agctgaacag gatgtgaaat ataaactgga agcaaaagat taaataaacc aaaattgcat   25440
tttttctgta gtcttgtcca aaattgggta accacttctg atggggtagc tcatatccaa   25500
gaatgagtca caaaaccaga ctcgttgaac ctggtatatg atgagtcaca aagcaacatt   25560
ctgcctttgt tttttcagga caagaaactt gaattgtatc ccactgagtt aaaagataaa   25620
atatatggca ttggcatttc tgtacttcag agaggaatat atctgtttgt ggtaggaata   25680
aaaaataagt gagagaggca aagcttaggt tcatcatatt atgttactga tataacacaa   25740
ttaacttggt aaaagtgaag gtgtgggtgg gcgtggtggc tcacgcttgt aatcccagca   25800
ctttgggagt ccgaggcggg tggatcacct gaggtcggga gttcgagacc agcctgacca   25860
acatggagaa accccatctc tactaaaaat ataaaattag ccaggcatgg tggcacacgc   25920
ctctaatccc agctactcgg gaggctgagg caggagaagc gcttaaacct gggaggtgga   25980
gtttgcagtg agctgagatt gagccactgc actctagcct gggcaacaag agcaaaactc   26040
tgtctcaaaa aaaaaaaaaa aaagtgaagg tgcccagtgt ctgcaactat gtcaccccgg   26100
gcatatcaca tatcactctg tttttccgtc tgtaaaacgg gagcaacaat gccattgcct   26160
tatcatcaga aggatatgga gactaaatgg gagaatgtag gtaaacagca cagagtatgg   26220
gtatcagtaa gtaaactgca gcagtttgtt gatgttaaca atagttagca ttatatctaa   26280
ctatatctaa cgatataacc attgggaatc cagttttcca tgattttcct ctagaatgga   26340
gctgcctaag tcctgcttaa gtcatttttc tttgaagatt actgaacatc atcttcaaat   26400
gttcatcctt gtaaacacgt gtgtgtgtgt gtgtgtgtgt taatttaaat tttcagaaaa   26460
attctgtagg ccgttggaag gaagctacca taccaggcca cttaaactcc tacaccatca   26520
aaggcctgaa gctggtgtg gtatacgagg ccagctcat cagcatccag cagtacggcc   26580
accaagaagt gactcgcttt gacttccacc ccaccagcac cagcacacct gtgaccgta   26640 tgtacacaac caccctcatg cctcctaccc ccgaggttcc tagagctagg ctctcctgag   26700
gcaatgcttt ccttctcaat tcatattctt ccaggagggg caccaacgtt ttttaaaatg   26760
atgttggcga cgaggacggt aaattttcta gatgactgaa ggctgacttt cccctttctg   26820
tgactctcta gcaacaccg tgacaggaga gacgactccc ttttctcctc ttgtggccac   26880
ttctgaatct gtgaccgaaa tcacagccag tagcttgtg gtctcctggg tctcagcttc   26940
cgacaccgtg tcgggattcc gggtggaata tgagctgagt gaggagggag atgagccaca   27000
gtacctgggt aagctcaata tgtcgctcaa gacaggttca gggcagctgc tggaaaactc   27060
tccttgtggg ggtgggtggc tctaggcag gtggtatctg tggtttggaa ctggttgaca   27120
```

```
gctcagactg aacaaaccac cctctggcat gaggaaggga aggactgact ctttctaaga   27180
agtggccggg ttttcccaa gccactgtca catgttcctg gtccctgatg ccagctgcat    27240
catgcgccta cctgtgcaca agttcctaca gcaaaagctg tgttcttggt ggaagtaatt   27300
accaggactg cagctgacaa tgtgagcaca gtacggtcac tcatactttt caaattgtta   27360
tggtgagggg cctttaaaaa acttcattgg cgcactgaag tgtgtgccat cgtaagcact   27420
gagttcagtg aatttgaatt cttataaagt gaacacacca caagaccagc acccagatca   27480
aggaaaagaa tatctctcta ccctcacccc atcatcttcc gccaataatc actaccctga   27540
ctcttactgc agagagctat ttttaaaaat ttggcattcg attacaaaaa ttatacgtct   27600
ttagaaaaaa agttggaaaa atgaaaggaa gaggaggag gaggagaaag gagaaagaca    27660
agaagtggtg ttttcccata gtacattaat aatcacagat taggtgggtg cggtggctaa   27720
ctcctataat ctcagcactt cgggaagctg aggctggtgg atcacttgag gccaggagtt   27780
cgagatcagc ctggccaaca tgtgaacct ccatctctaa taaaaatgca aaaaaaatag    27840
ccgggtgtgg tggtgtgcac ctgtaatccc agctactcgg gaggccgagg cagaagaatt   27900
gcttgaaccg gaaaggtaga ggatgcagtg agctgaaatt gtgccactgc actccagcct   27960
gggcaacaca gcaagactct gtgtaaaaat aataataata atcactgatt agctattagc   28020
acattacctt ctagtcgctt ttccctatga atatataatt cttaaaatat ccttcttata   28080
agctgtagag tcatttgagg gactagtttg ctctgattag ttaccttttc ttttcatttc   28140
aaagatcttc caagcacagc cacttctgtg aacatccctg acctgcttcc tggccgaaaa   28200
tacattgtaa atgtctatca gatatctgag gatggggagc agagtttgat cctgtctact   28260
tcacaaacaa caggtacatg tgtgctacat agtgttaaaa gaatcttttt ctgtaaaaca   28320
caggcctgta gtagcacttc ctgactgttt gccccacttt cttcttttct tagcgcctga   28380
tgcccctcct gacacgactg tggaccaagt tgatgacacc tcaattgttg ttcgctggag   28440
cagaccccag gctcccatca caggtcagct aagcgtcccc ctctttggct gctatgttaa   28500
tcttaatgac atcagcaggg agggcgcaga ttctgactgc ggacctgcat atcactttaa   28560
atctccaata taatttatgg gagaggggtt tgtgtgtgtg tgtgtgtgtg tgtgtggcgg   28620
gggtggggga gttattttct atggcacatt tccccttgaa accattcac caactccctt    28680 atacacacac accacaacat acacacaacc tgtaaagcca gctcattggc ttattaaagc   28740
aagtgttccc agggttgaag aggtgtaatt tcctgaaaac gttgctctaa gatttatcct   28800
taaggagaaa gctgagctgt cgtcttagct cattaggtga ttcaactgcc tcatcactga   28860
agttccaaaa agacacacac agtgctagac aactctgctt aggctggttc attaattgct   28920
tccctcgtct ggagctcaaa gaggaaaaat cagcttaaca tgaatatttt cacctaatgg   28980
catctctaat tgacatttat taaggatgtc aggtcttcaa ggatgacatt tattattaaa   29040
aaggttcgca tgactgttct tattttatct tcgtgctgaa tagtcattat tagaagaagt   29100
ggcaatattc aaagagtcaa aaagtatcac tggctcttca ctaatcaagc aagatgctaa   29160
gggatattag aaaagggagg atttatggtg tttctaagcc tctgtctcaa agaaaacagt   29220
gcatcttact tttgctcatg aatctgcagg gtacagaata gtctattcgc catcagtaga   29280
aggtagcagc acagaactca accttcctga aactgcaaac tccgtcaccc tcagtgactt   29340
gcaacctggt gttcagtata acatcactat ctatgctgtg gaagaaaatc aagaaagtac   29400
acctgttgtc attcaacaag aaaccactgg caccccacgc tcaggtaact ttttaagaa    29460 gacacttcct atgttatctt atcaggattg ttcctgaagg agggttgttt tgtctctgtc   29520
```

```
aacagtcctc tcattcaaga aatcttatat attagttttt ccctaaactt ctgatattta    29580
gctgaaatgt cataagtaac ttatcaaagc tggctactgg cctttctgat taaaaactga    29640
caccataacg tccatctaca aattttcccc tagaagctta agggtcattt cattttTgat    29700
tcttaagtat tataaaatga ttcagtaaaa caaaaactgt tacattattt tctgcagtta    29760
tttcaaaggc ttttTctaaa aaatttttta gtatcttttc ttataaccct ctcccccccac   29820 caccatatga cacttcatat gctggtaact cacttattac ctattttaga taaaaggttc    29880
aaatgtcata atttaagcac tatgactgga ccatgaaaat gtgatctgat taagagacaa    29940
aacttagcaa aactctcgaa tgagaggctc aatgaactgc ctaacatatc caagaaactg    30000
gcttcttaaa agtaatcttc agcagagaat gtgaatgacc agttgactct tgtctgtcag    30060
atacagtgcc ctctcccagg gacctgcagt ttgtggaagt gacagacgtg aaggtcacca    30120
tcatgtggac accgcctgag agtgcagtga ccggctaccg tgtggatgtg atccccgtca    30180
acctgcctgg cgagcacggg cagaggctgc ccatcagcag gaacaccttt gcagaagtca    30240
ccgggctgtc ccctgggggtc acctattact tcaaagtctt tgcagtgagc catgggaggg    30300
agagcaagcc tctgactgct caacagacaa ccagtatgtc ttctcctatc tctatctccc    30360
ctccaaattc tccacccctca cttgcagcct gtgagaaagt gcagtaaacc attcactcag    30420
aggtgtatgg cttagagaga gggaaatacc cagccggcaa gggaatgcat agtgaacaca    30480
aagcacatta aacttgaaaa caaaactcag acaagctcca tggatgctaa gtggtaaccc    30540
atttctaaaa tacatgtacc agctgaaggg tactaagagg ggagaactga agagaatcta    30600
atttgagtgc atttttcgtg taactaaata tatctagatc aaagttaaaa tgcaggatca    30660
taacacttag agtagaattc atttaacaat agcaattgtc aagtgtctag tattactagc    30720
caccagctta tctgctcagt ttttacaagc attattctca tatttactct ttgttttgac    30780
cttaggaagg aaggtcttat tattattatt ttatttattt attttTtttga gatggagtct    30840 cgctctgtcg ccagggctgg agtacagtgg caccatctca gctcactgga acctctacca    30900
cctgggttca agcaattctc ctgcctcagc ctcccgagta gctgggacta caggcgtgtg    30960
ccaccatgcc ctgctaattt ttgtgttttt agtagaaatg ggtttcgctg tgttggccaa    31020
gctggtctga aactcctgac ctcaagtgat ccaccactt tggcctccca aagtgctggg    31080
attacaggcg tgagccatcg tgcccagccg gaaggtctta ctagtatccg tattgaatac    31140
ttaaagaaac tgaggcttta aaaaagttct gcaacttgta gggtcacaga gataggaagg    31200
gatagagctg gctctataac ctatgtccga agcccatgct ctcaattatt atactcgact    31260
gcctcttaaa gatttcctct atttgaaagg taatttaaat ttcggtggga aaactgctgg    31320
ttattattct caagaataaa ctccacaact tatgtgattc tgatagtgca aactcaccag    31380
tatcctacca tgaatctgag gatacgttat cattactgta attactgtct aatctgaacc    31440
atgtgaaaat aactttTtatt tctctagcaa agggctattc acagaatatt gcttttgacc    31500
catagagagc ttcttcttgc tgtcattttTa ggaggcatat ccctttttTcc ttaatctgtt    31560 tggctcagag ctaactgtga acttcagaag tgtttgttTTT gccttttTtaa aaataccatt    31620 gctttaatgt aactataatt tctgagactg atgcgaaagt cttgctggaa aattagactt    31680
cccaaaggat cacagtcaag caaaatggtt ccacaatttc tcatgactgg cagagttttg    31740
gcaaagtttt gtgtagcact caatctctta ctggctcagt ttttccaggg ttttgacttt    31800
cacatagtta caaccttgag gagagaaaac ttagacattc aatcaagttt caggacttga    31860
```

```
gttatgatca ttactgatct aaatatttct tggcatgttt catcttttt  cctagaactg   31920 gatgctccca ctaacctcca gtttgtcaat gaaactgatt ctactgtcct ggtgagatgg   31980
actccacctc gggcccagat aacaggatac cgactgaccg tgggccttac ccgaagagga   32040
cagcccaggc agtacaatgt gggtccctct gtctccaagt acccactgag gaatctgcag   32100
cctgcatctg agtacaccgt atccctcgtg gccataaagg gcaaccaaga gagccccaaa   32160
gccactggag tctttaccac acgtaagctg aaaattaagt gccttttctt aactatattt   32220
acattctcta ttcttcatgc tttaaaacaa aacaaaacaa aacaaaaaaa acattaaaaa   32280
attagtacat aatttaaatc agtgatacta aaaatgtgct ccatagactg gctgctggcc   32340
cgttaattgt ttgctgctag tctgcaacaa gaaaaacggt tgtgccagaa cgtaaatcac   32400
aaagcacact gcttagtaca gctgagaatt tttctgaagc cagattttct tgatgaagga   32460
agcagtgtgt taatttgcac acattgccaa gctcgctctt tcctctaggg ccagcacttt   32520
gagtaacatg ggtttaaagc agtctgttat tagaaaaatt aaattcgatt acattaaatg   32580
aatttaccaa acactagtta acgcaagaaa aaattagcac ctatgtctac attctattac   32640
tttgggcatt gaatagtaac tataaatgca gaataaaaat atctatggat tgaatgggaa   32700
ccaactaatt gaacatgaag ccaaggaaat gatttcttta tgagtgttgg ctgcagaaga   32760
ttaaagtact tttgcagacg gaatcgctct tttcttaaat tactcttgaa attcctcaga   32820
ggagaaaaat actaacaata atttttggtc atgtctatcc ttttgctcaa catttttaaag   32880 gaagtggtct taaatctccc acatatctac atcacaataa caacctctat tcacaaaccg   32940
attcctatta aatacatttc catttacatt acagagaatt atgagactcc ttatttctag   33000
ctgaacatca tttgttattt tcaactcgac attttgaatt atagaagcac ctaacataag   33060 tacttttca  gcatatattc taaccatgga ctagtttgca attttctaag agctttcaac   33120
aaatgttact cttcgactaa tttaaaagta tggatgttaa aaagcattca aaaagtccat   33180
acaagcctag tttgtaaata actatggaat tgatttccca aagaaaatac aaactttttcc  33240 ccataagaat tcatacttta agaaaaactt acttccattt aaatttactg tatgaagttt   33300
ggctcatgaa ggcttttcc taaataatag ttaatcgtaa gcaagtaaaa ttcactttta   33360
atttgcaaat aagcttactt gaaaatttgg ctaaaatttt acacggttct aagatagtct   33420
aagatctact ctcatgaaat taatgtcttt atatttcttg taaatattca tttcttataa   33480
atgtccttca gtgaattaga atggagattt cagtgaatgc gcccttcag  tagatgtcgt   33540 cttttactaa aatgtagaat tctatagttg tcttgttcat tccttaacat gagacatatt   33600
ttatgtagtt tcttttgttg aacacagtgc ttataaaaga aaaagcattt ttaatgatgc   33660
taacaataat taagggaagg tggtgggcca agatatttca agtacttctg aagactgata   33720
tattggatat attattttat gctttgcata atacattcat ataaaatata atgattttaa   33780
ctgaagtact gatagccaaa actaatttta ttagataaag gttaacatag tgtctggaac   33840
attgtatgct ttcaaaaact atttggtgaa tagataattg agaaggaat  aataataaaa   33900 acagctaaat gaagcttata tttaaataaa ctaatgtaag cagggtattc tacaactcca   33960
tttgaacttt aagcactccc taaggctgta aacatccaca aggcttgcat gttttttgaaa  34020 ttactaaatt tctgtagttt tttactatct tactaagctg aattctggga gtaacttttc   34080
tgagttttat aacttgtgct aaattcttaa gagcaaatgt gagaaagtt  aggggaaaaa   34140 gctgtttctg gggaaaattc agcttagtct tatattgata gggcaattt  tatttcttta   34200 acagctgggc tgttcttccc taacaagacc tgccagaacc catagctcac acttagaatc   34260
```

```
acatcctttg tttgacatcg tttgtgggtt tgtggtttgg tgattttccc ataatggcct   34320
tcccaggcag agagcatcat cttaaacttg ggaagactct aggtggctgg ctcaagcaat   34380
agaaaatacc tagtcttaaa gcccaggaca gttgaggcga atataatttg taaaaaaagt   34440
tgtggttttc acagatgttc agtgaaagaa actgactgtt ctctgaattg ttttttgtgg   34500
gccattaaaa atggtcacac agggctggcc atggcatttt ggcacagtca ccagcagtca   34560
agtggtgtat aatttcagag gtactaaaag gcatcgggtc acccatccca gtcatgtccc   34620
cccacccccc accaaacacc atcaaaataa taacatacat agatgaaaca gcccactaaa   34680
ccagtagtac ctcaattcag ccattagagc tatcattatg aagtggccca cacatatatt   34740
tggcttttc tcacacaata ttttaaaat aaaataaaa aatggctcct tagaatccag   34800
actgaaaaaa aaatgcgaga attgcgatgt tgattctaaa ttcccacatg gcaaagaaaa   34860
aaaaattgac tggagttgag ttgagactgg agtctgaaca cttttaatc cctgtttgta   34920
taactctgga gactaattct ttgtcttgcc agccattcat aatttagtat aaatgcattc   34980
agaggttttt tcccaatggg aacaaaattt gattgagatg taaagagagg aagaattgtg   35040
gagatgtcaa acatgtgacc agagctatga acacacttga tacccttgaa cttaaactta   35100
cccaactcaa aatatctggc cttctgcgat cttacctttc tacatttata ataagatttg   35160
caaggttgtt ggaaatctct atcttaactt tatatataca tgcctctttc tttcttttc   35220
tttcctttcc tttcccttc tttctttctc tttccttcct tccttccttt ctctctctct   35280
cttttcttcc tttcctttcc tttccttcct ttctttcttc ctttctttct ttctttcttt   35340
ctttctttct ttctttcttt ctttctttct tttctttctt tctctctcac tctctctctc   35400
tttctttctt tcttatttt ggtgctaaaa cccaaaacaa atcttttatt taaaaataag   35460
attttttttt ttttggcca ggtgtgatgg ctcatgcctg taattccagc actttgggag   35520
gccgaggtgg gtagatcacc taaggtcagg agttcgagac tggcctggcc aacatagtga   35580
aaccccatct ttactaaaaa tacaaaaatt agctggatgt ggtggtgggc aactgtagtc   35640
ccagctactt gggagtctga ggcaggagaa tcacttgaac ccaggaggct gaggttacag   35700
tgagatgaga ttgcgccact gcactccagc ctgggtgaca gagcaagagt ccatctcaaa   35760
aaaaaaattg tttaagtaaa attttatttt ctttctttt ttttttttt tttttttttg   35820
agatggagcc ttgctctctc accctggctg gagtgcagtg gtgtgatctt ggctcactga   35880
aacctccatc tcccaggttc aggtgattct cctgcctcag cttcccaagc agctaggatt   35940
acaggcatcc accatcacac ctggctaatt tttatttt tagcagagac aaggtttcac   36000
catgttggcc aggttggtct tgaactcctg gcctcaagtg attcacctac atcagcctcc   36060
caaagtgctg ggattacagg catgagccac tgcgcctggc caaagtaata ttttcaataa   36120
gaaaaataac agtgatgtca ggatgctaga aaatgcaaaa taaatttgtt ataattcctg   36180
attctggtga taaatacta attttttgca gtattattct gaaagaataa tcacgtattt   36240
aaagtacaaa tctttagact tcaaagtgca tccatggtgg cagattttgt ttaacttta   36300
tatagcatct tttattgcaa ccaaaaatag ctgaccatta ttgtggaata attcagcgta   36360
aagcttttt ttttctttt tttgagacgg agtctcattc tgtcacccag gctggagtgc   36420
aatggcatga tctcggctca ctgcaacttc tatctccagg gttcaagcga ttcttgtgtc   36480
tcagcctccc aagaagctgg gactacaggc atgagccacc atgacagtta attttcata   36540
tttttaatag agacagggtt tcaccatgtt tgccagcctg gtctcgaact cctgacctca   36600
```

```
agtgatccac ccacctcggc ttcccaaagt gctgggatta cagtcatgag ccaccgatcc    36660
ccgcccagca taaagctgtt tttagatcac cttctataat ttaccattgt tcttaaatta    36720
atggttaaga aacaatatga taatcagttt gtggtggcca gttttacatt ttataaggga    36780
ttttacactg acgatatagg gaaatttatt gtcatcaaag tcaaatccca acaatcataa    36840
aaagacatga attagattat ataatttcaa tgaaaggacc accttagcaa acatctaacc    36900
ccttgttact caggtatcat tcacgggcca gcagaattgg tattatctgt gtttgtcaga    36960
aatgcaaact ccctagtttt ttgttggacc tccagaaaca gaatctgcat tttagccaga    37020
ccccagatga tgtgtgtggc acattaaaga ttgagaagcc tgatcctctc ccaattctca    37080
cccaatgaaa aaatatgtta catcctctat ccactgcttg gttaaactga ggttctccat    37140
aaaaatactt gttatctata tgctatgcaa tcatctgtga gtttgagttt tgaatatgtg    37200
cattgattct ctctcacagt gcagcctggg agctctattc caccttacaa caccgaggtg    37260
actgagacca ccattgtgat cacatggacg cctgctccaa gaattggttt taaggtaaac    37320
tgcagatgtt cctaatctct gtgatacagc cctgagctgt ccttgtggtt cccatgtagt    37380
ggaaacaggg tgctcaggag tcaggagacc tgggttttgt cacctgcttc tgtccataca    37440
tctttgacta cattgtcagg gcctaacagt ccttccctgc ctacctcact gaattgttgg    37500
aagggtagat ggaggctgcg aaagtgtttt gcaaaggata aaacattagc acgaagctgc    37560
tgcttattgt tatcttattt tctctatcct ttcctgcagg gaattacatt tcaaaaaaac    37620
atgggaaaac tttatttgat gtgttgttct aaatgagtgt gaacaagttc acaaaagcca    37680
gtttagggag accagttaaa ctcagagtca cttaaaaatc gcattttcat ccaatcagtt    37740
tcatctccaa ctgttcaaag cactgagggt gaatctctta atagaagtta agattaaggt    37800
ttccctgtgg atatctggat tcatcttctt taaagtaatg atattaggga agcggtgaat    37860
acaaatgaat atgtttaaaa gaattccatt ctttggcatt tagtgtgaag agagaaatat    37920
ttgttatcgc tggaaatcat gactcaatcc ccttgatcgt ttaaaaaaat acaccaaaga    37980
taaagtttgt aaatggccat atttatgatt atgctactca aatatagaag aactttctga    38040
agagtgccag tataccttt aattccctta ataatgtcat gctgactttc agaagcctta    38100
tgatgtgtga aggatctctc tagagttgaa cactattgga taacagtgtt acctaagttt    38160
ttgaaataga atcttaaaag gattttaaat tatgggcata gttattctaa ttcttctctt    38220
gtaatgtatc atcctgcagt tgaagctatg tacatatctc ttcaaaaggt gtgttttgc    38280 aatacagttg ctacagggc tggtgccttt aaatggcaac taaaaggtta attgaatgtg    38340
aataactcgt taagggaga gctcagacat tccttctagc acacacacag aaaaatagaa    38400
atgaactacc atgtgaccca cagtccctgt atacgtctgg tttgtaacaa gagattctttt    38460 atcaagcaaa acagtatgta atgacatttc tctggaacct tccattacaa gccaccttaa    38520
tgcagtttgg aagataccctc ccccacctgg gggaatttcc agctaaagta tataaaagag    38580
tccccaaatc atttcccaat aaaagtacac tgtgcagttt ctgaagagtt tacactattt    38640
aaagcataat catagcctca cagcagtaac agtcctctgg aaatatttgt ccttggtgtt    38700
tactttgcat tccttcctct agctgggtgt acgaccaagc cagggaggag aggcaccacg    38760
agaagtgact tcagactcag gaagcatcgt tgtgtccggc ttgactccag gagtagaata    38820 cgtctcacc atccaagtcc tgagagatgg acaggaaaga gatgcgccaa ttgtaaacaa    38880
agtggtgaca cgtaagaaga attttttccc ttttctatta gttttttaaaa ctgttctact    38940 tttcgaaaaa agctagtgtc aatatcactt tttacttatg agaatggcac aggggagata    39000
```

```
tcttatcctt acttatatta ttaatgctat tcctgaattt ggagtagcag gttcaattca   39060
tgctttatat tttatggcat cagaaatgtt ctttccatgt caagaatatt tatgaactgg   39120
caagatgaaa ataatttcaa tagtattgca aaatcattaa tcataaagaa gtctttgtca   39180
gagaattact gctgtccatc atattttcat aatgtaacct atattttat gggagggagg    39240
gagggaggga agaagcatgg aagagaggga ggtagggaag gaggaaagat tacacaggtc   39300
aagagctttg tgtcagcttt gactttaaa atgttctttc tgcatagcat tgtctccacc    39360
aacaaacttg catctggagg caaaccctga cactggagtg ctcacagtct cctgggagag   39420
gagcaccacc ccaggtaagt ttgggatgga tcagagggca agtatacacc ataccttccc   39480
aagacaaaga ttttagaaac tgtgtttctt tcagagaaag aagggattca aattacaaat   39540
gcttagctct ccataaaaac tatagcagta catgatgtac atcatggagc agcctgcagg   39600
atgctttaat gcacgttgac ttcaatcaca ggaagcagaa caaccttaca ctagtctagg   39660
gggacaagac agatcctcac acagctgtag ggctgaagaa aagcactgtg gaaggtggct   39720
tttgctgagt gcattaaaaa ttgccaaaca aatggttgaa gtcatattac gtaatttccc   39780
ttttgtgagt tgttacagag cctaagttta ttattccctg aagttttatg aatgttttgt   39840
catgggttgc accacaaata tttaagggtg atgaaaggca gaaatacctt cattttacag   39900
aataagaaaa ctgagactta gaaaaaattg gcctactcat agtcacacat tttaaatgtt   39960
acaaaactgg gattgtaact taagtttgta gactccttct cacacccaat gtcacatatt   40020
tggaatgtaa tttttttta attatattct atgcaaactg aaaattctga ttaagggtt    40080
tcctgaccat ttttagagct ttaaatgaag catttgtcta aattccttgt tcacatatat   40140
ttgaaaatta tttataaaat gctaaaatgt ataaagatag ttgttaacaa tattcaaaca   40200
gcatgacgta ctatagcaat aacaggaaat tttagatacc cattactttt gccaaaacca   40260
catggaagtc tcaacaaacc tatggagaaa atcttaaac aaaataaaa gttccaatta    40320
atgttgattg cattcttacc tcatatactt gttaatttaa gggatatgtt taggttatta   40380
tttagctatt tctaatttta ctgtaaaatt cttgtgaaat ttttgtttaa aaaaagtat    40440
tatatagttc ttatctttgc cggggcacag agctaaggct atcatctcta aatctgatta   40500
atgtatgcaa acacacagaa tgaaactagc tcagaatatc tcttttaatc tccctctgaa   40560
gtagagtgat tttggtaaag ttttcattat ctgcggaaac attgtttaag ccaaagctat   40620
acaatttcca gctgagttgc tctgaatttg aaactttaag ttgacaatct tcgtgcttgt   40680
tagcagcagg atcattaata tctcgtctca atggcccagc ccacacatat ggatgaccac   40740
tagcaagtgt aatgatctca atatttattt ctcattcagt tgggtttcct tgtatttgcc   40800
acattagtgt ttaccctgtt cctaatggca aaatattctg tcatctcctt gccttttata   40860
aagtttaata tactttctca ttttaatctg tccccacaga tctctagtca tcactgtttt   40920
tatttgaatg tctctcatcc ctctcaactc ttttactgcc caatttctgt gattcctgaa   40980
gacttcaaca atcaatactc tcttttttg tttgttttgt ttttttttt tgagacagag    41040
tctcactctg tcacccaggc ttggagtgca gtggcgccat ctcaactcac tgcaacctcc   41100
gtctcctggg ctcaagcgat tctcgtgcct cagcctcccc aagtagctgg gactacgac    41160
atgcgccacc aagcccagct atttttaga tttttagtag agacagggtt ttaccgtgtt   41220
ggccaggctg gtctcgaact cccaacctca ggtgatctgc ctgcctcaac ctcccaatca   41280
atactctttc tagaataagt atcagcactt ttgtttctca cctttctcc tttcttggtt    41340
```

```
ctcttcctat aaatcccata gtttcagacc ttttaaatta ggagagctct ctggggaatg    41400
tgcttaaggt ggagagcgat tctatactag gcaggtagaa aggaatattc ctcagctgtc    41460
ttcaaatgat tcattaagga aaagcagggt acagtgatag gaccatgaga tttggaaaca    41520
aagaaagctt tggggaatca ctcccctggt tcaagatttc ctttaaagtg aggatcttgg    41580
cggaggttga agtgagccaa gatcacaccg ctgcactcca gcctgggtga tagagggaga    41640
ctgtctcaaa aaataaaaat aaaaaaataa agtgaggatc ttagtactgc ctgaaaggat    41700
tgttgcaagc attgaataac agtgacagtg gagtcctcag taaatgccaa gtcctgcatt    41760
ccgccctgtg aatccatcat tggagtctag ttaaatatgc tctggctcac agatcctctg    41820
tgcaataact tcccttttct tttttctcca gacattactg gttatagaat taccacaacc    41880
cctacaaacg gccagcaggg aaattctttg gaagaagtgg tccatgctga tcagagctcc    41940
tgcacttttg ataacctgag tcccggcctg gagtacaatg tcagtgttta cactgtcaag    42000
gatgacaagg aaagtgtccc tatctctgat accatcatcc caggtaatag aaaaataagc    42060
tgctatcctg agagtgacac ttccaataag agtggggatt agcatcttaa tccccagatg    42120
cttaagggtg tcaactatat ttgggattta attccgatct cccagctgca ctttccaaaa    42180
ccaagaagtc aaagcagcga tttggacaaa tgcttgctgt taacactgct ttactgtctg    42240
tgcttcactg ggatgctgtg tgttgcagcg agtatgtaat ggagtggcag ccatggcttt    42300
aactctgtat tgtctgctca catggaagta tgactaaaac actgtcacgt gtctgtactc    42360
agtactgata ggctcaaagt aatatggtaa atgcatccca tcagtacatt tctgcccgat    42420
tttacaatcc atatcaattt ccaacagctg cctataaaat agttttgtcc ctgtatgtga    42480
gcactgaaac agcatttggt tgacacatct agttttcat  cttgcagttt caaatccttc    42540
tttttgaaaa ttggatttta aaaaaagaa gtaaaagtca caccttcagg gtgttctttc    42600
ttgtggcttg aaagacaaca ttgcaaaggc ctgtctaagg ataggcttgt tgtccattg    42660 ggttataaca taatgaaagc attggacaga tcgtgtcccc cttttggactc ttcagtagaa    42720 tgcttttact aacgctaatt acatgttttg attatgaatg aactaaaata gtggcaatgg    42780
ccttaacctt aggcctgtct ttcctcagcc tgaatgtgct tttgaatggc acatttcaca    42840
ccatacattc ataatgcatt agcgttatgg ccatgatgtt gtcatgagtt ttgtatggga    42900 gaaaaaaat caatttatca cccatttatt attttttaac cttcttcatg caagcttatt    42960
ttctactaaa acagttttgg aattattaaa agcattgctg atacttactt cagatattat    43020
gtctaggctc taagaatggt tttgacatcc taaacagcca tatgattttt aggaatctga    43080
acagttcaaa ttgtacccct taaggatgtt ttcaaaatgt aaaaaatata tatatata    43140 tattccctaa aagaatattc ctgtttattc ttctagggaa gcaaactgtt catgatgctt    43200
aggaagtctt ttcagagaat ttaaaacaga ttgcatatta ccatcattgc tttaacattc    43260
caccaatttt actactagta acctgatata cactgcttta tttttcctc ttttttccc     43320 tctatttcc ttttgcctcc ccctcccttt gctttgtaac tcaatagagg tgccccaact    43380
cactgaccta agctttgttg atataaccga ttcaagcatc ggcctgaggt ggaccccgct    43440
aaactcttcc accattattg ggtaccgcat cacagtagtt gcggcaggag aaggtatccc    43500 tattttgaa gattttgtgg actcctcagt aggatactac acagtcacag ggctggagcc    43560
gggcattgac tatgatatca gcgttatcac tctcattaat ggcggcgaga gtgcccctac    43620
tacactgaca caacaaacgg gtgaattttg aaaacttctg cgtttgagac atagatggtg    43680
ttgcatgctg ccaccagtta ctccggttaa atatggatgt ttcatggggg aagtcagcaa    43740
```

```
ttggccaaag attcagatag ggtggattgg ggggataagg aatcaaatgc atctgctaaa    43800
ctgattggag aaaaacacat gcaagtattc ttcagtacac tctcatttaa accacaagta    43860
gatataaagc tagagaaata cagatgtctg ctctgttaaa tataaaatag caaatgttca    43920
ttcaatttga agacctagaa ttttcgtct taaataccaa acacgaatac caaattgcgt     43980
aagtaccaat taattataag aaatatatca ccaaaatgta ccatcatgat cttccttcta    44040 cccttgata aactctacca tgctccttct ttgtagctaa aaacccatca aaatttaggg     44100
tagagtggat gggcattgtt ttgaggtagg agaaaagtaa acttgggagc attctaggtt    44160
ttgttgctgt cactaggtaa agaaacacct ctttaaccac agtctgggga caagcatgca    44220
acatttaaaa ggttctctgc tgtgcatggg aaaagaaaca tgctgagaac caatttgcat    44280
gaacatgttc acttgtaagt agaattcact gaatggaact gtagctctag atatctcaca    44340 tgggggaag tttaggaccc tcttgtcttt ttgtctgtgt gcatgtattt ctttgtaaag     44400
tactgctatg tttctctttg ctgtgtggca acttaagcct cttcggcctg ggataaaata    44460
atctgcagtg gtattaataa tgtacataaa gtcaacatat ttgaaagtag attaaaattt    44520
tttttaaata tatcaatgat ggcaaaaagg ttaaagggg cctaacagta ctgtgtgtag     44580
tgttttattt ttaacagtag tacactataa cttaaaatag acttagatta gactgtttgc    44640
atgattatga ttctgtttcc tttatgcatg aaatattgat tttacctttc cagctacttc    44700
gttagcttta atttaaaat tacattaact gagtcttcct tcttgttcga aaccagctgt     44760
tcctcctccc actgacctgc gattcaccaa cattggtcca gacaccatgc gtgtcacctg    44820
ggctccaccc ccatccattg atttaaccaa cttcctggtg cgttactcac ctgtgaaaaa    44880
tgaggaagat gttgcagagt tgtcaattc tccttcagac aatgcagtgg tcttaacaag    44940
taagcagttg aatgtatctg ttccataaat attaacctag agcatagcaa atgaattcta    45000
aattctcaag taggaggagc taagagcaag agagctgcaa ccaagctaca aactaaactc    45060
tgaattcaat gcacagctcc attaattttg aaagatgtaa tgtttgttgc tatcttaata    45120 tactttgat atctcacagct ttaaaaaaat catagtggaa aaacacctgc aggaaagttc    45180
catgacttca aacaaattct gcttctaaat aagcacgtaa aaataagtga atatcaagag    45240
aaattatatg actaaatcta aatctttaga gaaaaaatg agaactgaaa atagtgtcac      45300
catatgtgct ttattctcat ttttataaaa aaagtgtcag cagttgattg atttaggatt    45360
tgaatactta gaaaagtgac tgattgtttg gtctagatta gaatgttgtt gtgaagagag    45420
tcagaagttt aatttgtact tcaaaaagaa tctgttagaa ggatttctca gaagactgag    45480
agcttagaaa aaaactgac attaaataaa taacaacaat ttatggaaat tgtctctttc     45540
tagtcccaac cattatagaa tagacatctt ttgttaaaga ataaaacagt aggctgcaag    45600
atggtgctgt gtttcacata aacagtgctt tttattattt tcactgtaat agtcaaatat    45660
ataacaacag caaagattc tacataaggg aaaaatagct tacatttagg tacattacca     45720
agtattagtc tgaaaacatc tacctttcaa acataattta gataatgaaa cacaaagaag    45780
agcagctcag cgtgaccata atcttggttt cttactttgt ggctgagggc aagaatatct    45840
ttatattggc atatccacca ccccagggct gttgcttctg ttctagagca ccctggaatc    45900
actaattaca gcatcaccca gtatacaagc ccctgcatca caatgtctgt cccttagccg    45960
tagacctgtc acatgctaat catgtgttct aagaccttat tataatccta atgctacaga    46020
tgacctcagg gtagcccctc tccctcctag caaagtcatt attatcctct tttaaagatg    46080
```

```
aagcaaacca gtgcagtggc tctcgcctgt ataatcccag cactttggga ggctgaggtg   46140
ggccaattgc ttgagcccag gagttcgaga ccagcctggg caacacagtg agaccaagtc   46200
tctacaaaaa atacaaaaat tagccgggca tggtggtgca cacctgtggt ctcagctatg   46260
taggaagttg aggtaggagg atcacctgag cctggggagg ttgaggctgc agcaagccat   46320
gatcgtgcca ctgcactcca gcctgggtga cagagtgaga ccctgtctca aaaaaataaa   46380
caaacaaata aacatgaagc cgtcgaggtc cccagcagtt aagtaaattg ccactggcca   46440
gctagtatgg tggaaatgga atccaggcat ctggtcctcc attctggcac ttttccaaac   46500
ttttgtaggg ggctttatag aaacgctgaa gggcaaatgg tgtgcagggg aatgaggggtt  46560 tagtgagtag gagttccaaa tttagaaacc tcactctctg tatcttttag atatacaaat   46620
atttaccata tattacagtt gcctctagtg ttcagtacag taacatgctg cacaggctca   46680
tagcctagga gcaataggct agaccacata gcttatagct taggtgtgtc aaaggctcta   46740
ccatctaggt tttttgtttt gttttgtttt gttttgtttt tgagacggag tctccctctg   46800
ttgcccagga tggagtgcag tggcacgatc tgggctcact gcaacctcca ccaccaaggc   46860
tcaagtgatt ctcctgcctc agcctcccga gtagctggga ttacaggcgt gagccaccac   46920
gcccagctaa tttttttgta tttttagtag acgaggggtt tcaccatgtt ggccaggctg   46980
gtttcaaact cctgacctca gtgatccac cctcctcggc ctcccaaagt gctgggatta   47040
caagcccatc taggtttgtg taggtacact ctatgatgct tacacaataa aatcaccaaa   47100
tcacacactt atcaaaatgt atctccacca ttaagctatg cctgactgtg tatcaaaatg   47160
gaagaagaag ctgggcacag tggctcacgc ctgtaatccc agcactttga gaggccaagg   47220
cgggtggatc acaaggtcag gatttccagt ccaagcctgg ttaacacggt gaagccccgt   47280
ctctattaaa aatacaaaaa ttagccaggc atggtggcag gcacctgtaa tcccagctac   47340
tcaggagtct gaggcaggag aatcacttga acccaggagg cagaggtttc agtgagccaa   47400
gatcacacca ctgcactccg gcctgggcaa cagagtaaaa cctcgtcaaa agaaaaaat   47460 aataaaaata aaaaaaaatg gaacaagata ctcagggatg tatatttaat ttttttaaaaa  47520 atattctgct ctcatttttaa tatggcagaa ccgattgctt tctaagtgtg cttttttcc   47580 agtaaaggtt aattattaag accactagtc ctggcctggg tcaatcccag tatgatcctg   47640
ggcaagtaaa ttaaagaaga taacttctct gtgcctcagt ttttttttgt tttgttttt   47700 gttttttcat ttacaaaatg gagataattg tagtaaatca aattttttaga ggtgataggt  47760 ttgttcattt cttgaatgcg gtgatggtct cccaagtcac acatatgtaa aaacccatca   47820
ctttaaagat atgcagtacg ttgtatgaca agaaattgct tttaaaagga gcaaactacc   47880
ttccagggtt gttgtgaggc ataaatggca atccacagca ccacagcaag gattatcatg   47940
tgccctccag agacatactc tcaggtggat gcgagaaata tccagctgtt gcagcaactt   48000
catcccactc gaaatccagc tgagtcacac tcacaggtgg aatggagggc ttcgagaggc   48060 catgggcaa ggtgaccctt ccttatcatc taattacaga ccttctcaag gtctgttcac    48120
tgaacacttc gctgtagtgt tcacttaggt gtaagtaggc tataggactg gacatttgga   48180
tatttcatca gttcaaatag tcctgggcgt gctttagttt ctcatgcttt tgagcagagt   48240
tttaaaataa gccccatttg cccctacaga tctcctgcct ggtacagaat atgtagtgag   48300
tgtctccagt gtctacgaac aacatgagag cacacctctt agaggaagac agaaaacagg   48360
tgagtggtgt tggcagtatg actatccagt agcttttgcc tatcaattct gtataacaaa   48420
tgaaatgcta cttctaaaaa tacatctcca ttttttgttg tcatggtgtg tgtacctttg   48480
```

```
tcatcacagt atgattttat cgctggtctc aaaaactaaa agatacctta ctcaacaatc   48540
acctagactt tcagtcacta acaaattaag aaatttgttg tctgtccttt taaaaaacat   48600
tttctaagaa gatctttgtt atttagattt agcagacatt cctttcatt aggcagctct    48660
gtctaatggc tgacccaaca ctcattgtca tctatttgtc ttcctttact aagccagcaa   48720
gtttacattt tctttttact taataaaata tgcatttact agaaggaagt tgaattgaat   48780
ctcataaata ttacatactt aaatatgaat gcttttaatt ttttctttca aaaggtacac   48840
tttagtgtat tcattaattt atttatagtc cacttgcttc caaaaaggac ttatgatatc   48900
ttagtttggt ttcttattga aaagaactag taaatgctgt aactgaaaca gaaatttgct   48960
ggaagtccca gagactaagt gatttgaatt tgcaacaaac tctgaatttt tgtgcatttt   49020
tgaaaaatgc attttcaaa actgtcaatt cacgaggaat tatcagcatt gtaatttgtc    49080
tgggataatg tctttagttt cagaaagttt tgtgtttggc atcattacca ctctgttgac   49140
atataaattt cctcttgagc ttaggaggct tctctgagag tcaaacattt actttgagag   49200
tgggcagatc ttgctttact tggaaggata cacttacagg atagaaacac agaatacttg   49260
aacactgaag aatttgaaaa tgtcaattct cagaagatct tgaacactta tctccaaatg   49320
tgacacagaa acttactgta ataaccccta aaatctgctt gaattactta gcacaagaaa   49380
aaaatgaatg cttgagctgg ctattttgaa ttgagtcaat ttaagatttt aaaattcata   49440
tgtagcttag aatcagtaca tcttactctt tggtttatgg caaatcatgg tattgatgag   49500
acaggaacga aatgttggat gtacgttaat ttcccctaca ccttcctcac ttcctaaact   49560
ggtggtgtct tttctttttt ttttctcttc ctcccccggg tgggaaaaac aggtcttgat   49620
tccccaactg gcattgactt ttctgatatt actgccaact cttttactgt gcactggatt   49680
gctcctcgag ccaccatcac tggctacagg atccgccatc atcccgagca cttcagtggg   49740
agacctcgag aagatcgggt gccccactct cggaattcca tcaccctcac caacctcact   49800
ccaggcacag agtatgtggt cagcatcgtt gctcttaatg gcagagagga aagtccctta   49860
ttgattggcc aacaatcaac aggtaacttt tcttgtctgc aaagaaactc agaagacttt   49920
cctacccagt tggtagattc tgtaaagtag cttgctgttg tctgtcatca gctctcaaaa   49980
aaaaaaaaaa aaaaaaaaaa aatagatcat tgtcatggta catggagagg gaagtgagaa   50040
aatgtggaga aacatcttcc ttagaatatg gtaaagaagc ccgggcgtgg tggcagtaaa   50100
gaagataatt ttttcctct caagaaattt ctcacctgat ttgggtattt atgcatttct    50160
aataacacaa gttttgttga aaatgtagaa aattggccgg acggggtggc tcacgtcagt   50220
aatctcagca ctttgggagg ccgaaatggg cagatcactt gaggtcagaa gttcaagacc   50280
agcctggcca acatagtgaa accccatctc tactaaatat acaaaaatta gcaaggtgtg   50340
gtggcatgca cctgtaatcc cagctactgg ggaggctgag gcaggagaat ctttgaacct   50400
gggaggcgaa ggttgcagtg agctgagatc aggccattgc actccaacct gggtgacaga   50460
gcaagaccct gtctcaaaaa aaaaaaaaaa aaagggcca ggcgcaatgg ctcacgcttg    50520
taatcccagc actttgggag gccaaggcgg gtggatcacg aggtcaagag atcgagacca   50580
tcctggccaa catgatgaaa cctcgtctct actaaaaata caaaaattag ctgggcgtgg   50640
tggcatgcac ctgtagtccc agctactcag gaggctgagg caggagaatt gcttgaaccc   50700
aggaggcgga ggttgcagta agccaagatt gtgtcactgc actccagcct ggtgacagag   50760
ggagactctg tctcaaaaaa aaaaaaaaaa aaggtggaaa actgaacact gtttcaaagt   50820
```

```
acctttaaaa atataatttt agggtaatag tgtcattgtt cttagcagat agaggctgaa    50880
gtacttacgg gaacagtagc atcatgttat ctgtatttta gtctcaagtc gtcaagccag    50940
agacaaatac ctaagggaag ggtatatagg tgttcattgt attacttttt tttttttttt    51000
tttcttcctg aaatggagtc ttgctctgtc gcccaggctg gagtgcaatg gtgggatctt    51060
ggctcactgc aacctctgcc tcccaggctc gagcaattct cttgcctcag cctcccaagt    51120
agctgggact acaggtgccc gccaccacgc ccggctaatt tttgtatttt tagtagagat    51180
gggattttac catgttggcc aggctggttt tgaactcctg acctcaaatg atccacccgc    51240
ctcggcctcc caaagtgctg ggattacagg cgtgagccac cacgcccggc cttgtatcac    51300
tttttttttt ttttttttttt ttaacttttc tgtagttttg aaattttttcc aaataaaatg    51360
ttgagggaaa aaaactcttc cccaaatttg aaataatcat tttatcacaa tttgaatggg    51420
ctctgtaacc ccttatcttg aattcgtcat aatataaaat tctgctaatt acacgtagta    51480
tttacatgat tgtatggaag aatcattaag acaattatct ggaaaatgaa caaacagtaa    51540
atctgaatat tgtttgaaaa ttcggatgt gaaaagtttc cctttttttt ctagtttctg    51600
atgttccgag ggacctggaa gttgttgctg cgaccccccac cagcctactg atcagctggg    51660
atgctcctgc tgtcacagtg agatattaca ggatcactta cggagagaca ggtacagcag    51720
taaaatgcta ttttacactc tgattaaatc agattctgtt gtggataacc tgaaagccca    51780
acagtgaaca aagaattaaa gaaactttgg caagtccatt caacggagcc cttgtttttt    51840
ccaagaaaat acgtaagata tagatgatat aatttgttct aaaacccaaa taaaagttg    51900
tttatatact acaactagag ggggaacggc agagctgagg aaataaaagg attgtaaatt    51960
cacaaacata ttatcagtgg tggaaataag tgatttttat ttttttcttct ctttactttt    52020
ctgtatttc caaattttat ttaaaaggaa tgtattctgt taaagttttt aaaaaggaca    52080
caatgcatgc aatcctgggt tgagggctta ccttctccca cttctaatgc tactctacta    52140
ctcagtgaca tttaaagct gaaatgttaa aacagcgcta actgtaattt tctctcaatg    52200
tttatacact taccaaggtt tgctacatgc ataaataccc cttctgttc aagatagcgc    52260
tcttttaaaag ggaataagca agaagatgtg atttacatgc tgctataaat gtggtaattc    52320
aattaatcag taatacccaa gtagctctaa acccctcaca ctctgaacta accctttttc    52380
atacaggagg aaatagccct gtccaggagt tcactgtgcc tgggagcaag tctacagcta    52440
ccatcagcgg ccttaaacct ggagttgatt ataccatcac tgtgtatgct gtcactggcc    52500
gtggagacag ccccgcaagc agcaagccaa tttccattaa ttaccgaaca ggtacaaact    52560
tctactctgg ggtgacacca gcttttactt attcagatac tgttttgcaa tgttctccca    52620
aggtattttt ctaattgtag aatagatttt cctttttaat gagcaacaac ctgcagctag    52680
cacctgcagc gaacagagtt ttgagccaga taaagaagga agcaccccaa gggcaggaag    52740
ttcagtcagt tttgtcgata tattccgcat gtctgcaata cgacaggcat agagagtgtt    52800
cagtaagtat ttgtgggaaa agaatggatg agttgataaa gtaggaagag acacctgctt    52860
gtggaatgta gcttctttgt gaatgaagca accatctcaa aaataggaaa tggtattgag    52920
atgcctgccc catccctcta aaagctctct ctgtattctt tcgagaagaa atacctttct    52980
catgtaagcg atcattcgaa tatgtaccag acctagagag gaggacttgt ccaatcttgt    53040
ctccaaggac tgggggcttca ctggtttctc cctgctttta tttgtagaaa ttgacaaacc    53100
atcccagatg caagtgaccg atgttcagga caacagcatt agtgtcaagt ggctgccttc    53160
aagttcccct gttactggtt acagagtaac caccactccc aaaaatggac caggaccaac    53220
```

```
aaaaactaaa actgcaggtc caggtaagaa tcatctgcat ctcggccagg tgcggtggct    53280
cactcctata atcccagaac tttgggaggc tgatgcgggc agatcacttg aggttaggag    53340
ttcgagacca gcctggccaa tatggcgaaa ccccgtctgt actaaaaaat acaaaaaaat    53400
tagctgggca tggtggcttg tgcctgtaat cccagctact caggaggctg aggcaggaga    53460
atggcttgaa gtctggaggc agaggttgca gtgagccaag atagccccac tgcactccag    53520
cctgggtgac agagtgagag actccatctc agggaaaaaa aaaaaaaaag agtaatctgc    53580
atctcatata caacaggata gatggggtag gaccacctaa tattctttttt tatataaatg    53640 gctaccttgt tgtgagtact atgtatttttt ttgtcctatg tcatcattgt ccccattcat    53700
gagttcaggg ctcaagatca ttatcaaccc ttttcacagt agaagtctta agtgcatttc    53760 tgttttaca tggatagttc tatttagtga tatggacatc ttaaattact agattcaccc     53820
ttctggtttt gtttatcatt cacactaaga agagataaat ggcctaactg acttttttcag   53880 ctcttttttag ctatgttgtc tttgtttttta aatagaatac ttgtgaaatt aggatcttaa  53940
ggcaatttat tagagtcaag ttaattttca ttttttctga gagcagtatc actaattgtt   54000
gggggcatca tattaagttt tagatcttat ccttgagtgt gacttcactc ccatatggta    54060
atttgtatta gcaatgaaca ggtttgtcca agaggaaatc aaagtctgac tctccatatt   54120
tttgttacaa ttctgcaaat aaaaattcta ggccaccata tgtttactac caaactctag   54180
acgccacttg aggactttat agtggatgac gtggatgttg catttgcttt tcactcccttt  54240 tgcagatcaa acagaaatga ctattgaagg cttgcagccc acagtggagt atgtggttag   54300
tgtctatgct cagaatccaa gcggagagag tcagcctctg gttcagactg cagtaaccag   54360
tacgtaacca ctgcttggtt tccatttca aagtcaaatt ttgttcttgg gtgtctgaat    54420
gcccacgaca tgtcttttgc aattacacat agggaaagtg aacttgttgg ttagtttatg   54480
tcttgagctg agccctttac gaacatcttt ttttccttctc agtgccaagc gaggaattta  54540
cagagaaaga agttgtgaaa ccaccatagt tagttgctgt gctttgaatt tcttttgctc   54600
aaatggcctc agcgaaatct tatttgccta tagcaaatct acaaaaaatt ttcctagacc   54660
gtcttttcta caactggatg gtaaagttga ttgaagtgtg cctcatgtag ctttatgttt   54720
ggggcatttg aagggctatg gctggaccag agtgtaatat aaatgcttaa tagagagggg   54780
aaaagaagag tgtaagaacc attatagggc tgggctcacg cctgtaatcc cagcatttg    54840 ggaggctgag gcaggcggat cacgaggtca ggagttcgag accagcctga ccaacatggt   54900 gaaacccat ctctactaaa aatacaaaaa ttagccagtc gcggtggcac gtgcctgtaa    54960
tcccagctac tcaggaggct gaggcagaag aatcacttgg acccaggagg cagaagttgc   55020
agtgagccaa gatcatgcct ctgcacccca gcctaggtga tagagtgaga ctccatctca   55080
aaaaaaaaca aaacaaaaca attataacaa tttgaatctg acattgcaaa tcagctttac   55140
cacttccaag gtatagaaaa tccaggtcta tgagactaac atcacattgt aaaaatcaaa   55200
tcgtggtaga atatctttaa attaatataa atacatcccc attgtgggga catttttgcag  55260 ggtatctgct tatctcacat acacctatgt tttaataagt gatgcaacat tgcatatttt   55320
ctaaaccaag aaaaattaag caagtgttta agtgattttt ccttttgata gtgggttaat   55380
tggacttcat caaagaaaat ggtatctgca aaactgcttt gcatgttata aaaatgctta   55440
tttcacaact tgcttttcac ataacctctt accattaatt tgcctaacag acattgatcg   55500
ccctaaagga ctggcattca ctgatgtgga tgtcgattcc atcaaaattg cttgggaaag   55560
```

```
cccacagggg caagtttcca ggtacagggt gacctactcg agccctgagg atggaatcca    55620
tgagctattc cctgcacctg atggtgaaga agacactgca gagctgcaag gcctcagacc    55680
gggttctgag tacacagtca gtgtggttgc cttgcacgat gatatggaga gccagcccct    55740
gattggaacc cagtccacag gtatatggtt aattgcacca ccaggtgccc atgggagcag    55800
cggctttatg ccctactgaa tgaattatgc ttcactgggc tattgattcc cgtgtaaggg    55860
tgaaaaagaa ttattaggaa agatcctctt taaagaggaa tggtaagaaa caataaaact    55920
taggtgatat ttaaggaaac aagtctgatt aaaagaaatt ttggagtatc ctggcttata    55980
cacaagacca taaagcaaga catttgaaga ggatactaaa gttgtggatt atttcctaag    56040
ctctgactcc ctgtgattac cctcactatg tataaagaaa agaagtttgg cattacagag    56100
cttacttata aaaaggaacc caaactcggg catttcatag cagcatgatt ctgagcacac    56160
gtgggtaaga cctttcttct ctggttagat atcatatgct ggtgtataat tagcttaaat    56220
gattgtgatt tagacaccta ggaaataatc aatagggcaa ttgctttcca taatacttta    56280
tcttcttgtg ctttatttct gaagcagagt agaatgctaa agatgtatcc tagtgacagc    56340
ataaacccta gaggtgacag tctgtattat tgcttttcgc ttctcttttc tgcttctgtt    56400
gggagccagt tttcttctta cgccgcatta cagagagaac gtcaaattta gcagccatat    56460
ctgccatagg gtccaaataa agagacaata aaaacattat tctctctttt ttggatggaa    56520
tactgcgtga atggttatc catacaaaga tactttatgt agaatagaaa aaggaggccg    56580
ggtgcagtgg ctcacacatg taatcctagt gctttgggag gctaagccgg gagcactgat    56640
tgaggccagg agttcatgat cagcctgggc aatgaagtga acccccgtct ctacaaaaaa    56700
atatgaaaaa attagccgagg tgtggtgaca catgcctgta gtcccagcta ctcaagaggc    56760
tgaggtagag gatcacttga gcctacgagt tcaaggctgc agtgagctat gataactcca    56820
ctgcactgcc gcctggatga cacagagaga ccgtttctaa attaattaat taacaatttt    56880
aagaaagaaa aagggccatt gcttattttt ccatacaaaa gtaaaataaa tcataatggc    56940
caataagcca atgtaacttt ttttttttaag ggaaagcaaa acttgtaaaa cctaaaatct    57000
cttagagttt tggcatttac ccaaatgttt tcagtgattc tgagaattgg tggatataaa    57060
acacatttct cagcaaacac tttcttcatt ttgcatccct tactgtacgt actttcttgt    57120
actgaatctt tgcttgacca gggaacccac ctagcccaac aagaacaatc cattctactt    57180
cttggaactc actttatttt ccttttcccc catttcctat aagataacct ctaaccaatg    57240
acaatctcga cagctattcc tgcaccaact gacctgaagt tcactcaggt cacacccaca    57300
agcctgagcg cccagtggac accacccaat gttcagctca ctggatatcg agtgcgggtg    57360 accccccaagg agaagaccgg accaatgaaa gaaatcaacc ttgctcctga cagctcatcc    57420
gtggttgtat caggacttat ggtaagacat gaccgttgtt cattggaata aagatggaga    57480
tcatctctaa cacagtttct aaggtggtga aatataata tcataataaa tctaactgtt    57540
cttttcctct gcatcaaata atcttattgt aattttatat caacggaatt cctttatgtt    57600
gacctaagtt ttccagatga ctattgggac agaattttat aaatagcttt ggattttgtg    57660
cagctctttt agatgtattg tgcttatttt aaaaggttgt gggggggcaat ttacatatcc    57720 attggttgaa tgcataaatc gacttagtta tgcattttct gagctctgtt accttggtaa    57780
agaatatttt acagtttgta ccagtctacc ttgagcctac cctcattaaa acattttaaa    57840
atccttccag acatacatgc agaaaactgc taggaaccta ggggactgat gtacctctta    57900
acataaggcc aatttcaggg gaaactacag aaagagggtt cagagacaaa atggaacatt    57960
```

```
ctctttgcct ctctatgata aggaaaaaat tatgatttac acctgtcaga tcataaaaaa   58020
gaaaaatacg ctaataccca cttttctcat ttttttacc agcttagttt aagtatataa     58080
tctatggctt acttaagctt aaccgctaag agcattttaa aattgataaa tacatttatc   58140
acctgcactg taggaatgaa attaatctag gaattttcaa ggttgtgggt tttgctggtt   58200
tgtttatttt ttattttcta accattgcat ttacctaatg ctgtagtgaa actccttggg   58260
tttcagttga ggacgttgct aaagctcacc atgcccttat ttctctaggt ggccaccaaa   58320
tatgaagtga gtgtctatgc tcttaaggac actttgacaa gcagaccagc tcagggagtt   58380
gtcaccactc tggagagtaa gtaacaaaat gtcttcatat ggacaaacct tctgtataga   58440
caaaaattaa agaatggtaa atcagtgggg ttcagtggct catgtctaaa atccaagcac   58500
tttgggaagc tgaggcggga gcgtcacttg aggccaggag tttgagacct acccgggcaa   58560
atagcaaggc cctgtctctt aaaaaaaata aaataaataa aataaataat tttttagatt   58620
tatatgttaa cagtggaatg agtcctaatt tgaaaatcaa tttgattgcc ttttttgacgc  58680 atgactgtca tcttttatac tccttcagaa aggggtctac tgacccataa aatggaatca   58740
cttcataagc ttataatgtt gatattatgg actatgactg acatctagtt tatgctctac   58800
ttgttagaat ttgttttcat agagctaagc ttggggagac cccactggct tctgctatat   58860
cttaacaatg catattaggc cattcttgca ttactataaa gaaataccgg agactgggta   58920
atttctaaag aaaagaggct taattggccc acaggccagc aggctttaca ggaagcatgg   58980
tgctggtatc ttcttggctt ctagggaggc cttgggaagc ttactcatgg tggaaggcca   59040 aggggagca ggcacatcac atggctgtgg caaaagcaag accgagagag agagagagtt    59100
ggggggggag gaccttatac atttaaatga cccagtctct tgagaactca ctgtcataaa   59160
gagggcacca agccacaagg gatctgcccc catgatccaa acacctctca ccaggcccca   59220
cctccagcat tggagattac aactcaacag agatttggac agggacaaat atccaaatta   59280
tatcacagca cagtaaccat tggaccaaat caggcttaga ttctagtctt ctgttatatc   59340
aataccttga tgtatgcctt ttcaaaagtc aggtaaagtg tcaaagtttt atcatttata   59400
aaagagggat ggcattgtac ctgttgagag aaaatacaaa atacttgccg taatattaga   59460
cacacacaca cacacacaca cacacacact ctctctctct ctcacacaca catacacaca   59520
cacacacaca aaattgttag ctggccatgt tattgtaact cctaccacac atattttac    59580 attataatac attaataatt ttaatatta ttgaagtatt tgtagatact ataaagccag     59640
ccctgggaac cactggtagt atctataaag cttttcagct cttcaaaata aaatgtctga   59700
gaggtagata ttttcctatt ttctaattac agttgacctt tctctctgaa tgccaaagga   59760
gataatctac acattactag ttatatattt cttgaaatgg atgaatttga tatataccaa   59820
ggaaacgttt taaaatacca aaactttaca tggatgagcc aagcaggcac taatctctag   59880
ctatgctcct gtgcagatgt cagcccacca agaagggctc gtgtgacaga tgctactgag   59940
accaccatca ccattagctg gagaaccaag actgagacga tcactggctt ccaagttgat   60000
gccgttccag ccaatggcca gactccaatc cagagaacca tcaagccaga tgtcagaagc   60060
tacaccatca caggtcaggg aactcattgc actaaccaca tttgttaaca aatacccaca   60120
atgtaaacgg gcttattaac tgttctacga ctgacactga taaaatttat tttcagtgtt   60180
atcatcataa cccagttta gaacgttatt ttcatgctat gatcagaaat agttttgtcc     60240
tttgaatgcc tgattttgtg taatatttgt catggaaatt gcgtaagtgt caatcaacaa   60300
```

```
gtttgatctt ccatcattgt gcccttctt atttaaaaaa ttgtaacata aggtttaaaa    60360
ctaaaagaaa taaaaaacag tgatgtatag atcttagcat taaaaagcat agttaatata    60420
aaagtaaaca ataccactta ataaaggcca aaattgtaac cgaagaatat tcaatatctg    60480
aggtcttttt tagcttttta aaattgtgat tccaaggctc aactattgac catctgatta    60540
cggtaaagag aaaacctcaa taagtggctg acccccattc tgcaagaggg cctcttccaa    60600
catagcattt ttgcattcca gaatttactt taccagtgtc cttgtctgta tcagtgattc    60660
actttcgaga tatgtttctt gttaacagtt aacatccata gcatgctcta ctttactgtt    60720
caaatgtgga ccactttggt agtctatata aatatgggat gatagaagaa cccagaaaaa    60780
ttgcaggcta gcttgagaat tctcctagta aaaagcaaga actgttaaaa atcatctctt    60840
ctcaaatccc aggtttacaa ccaggcactg actacaagat ctacctgtac accttgaatg    60900
acaatgctcg gagctcccct gtggtcatcg acgcctccac tggtaactat accttctact    60960
gaggaaatgc cattgacttg tatgcaatca gtttcatgaa ctcaaaaaac aaatgtgagg    61020
cgtatatttt tgtattatag attccagaga atcttgtttc cggtttacag tattctcaga    61080
ttcttttaag tgtgtttaga acggctcggg agaaaagtgt gggagtaatt ttcttggtta    61140
tttgccttct tagagactta attttgtttt cttcagcca ttgatgcacc atccaacctg     61200
cgtttcctgg ccaccacacc caattccttg ctggtatcat ggcagccgcc acgtgccagg    61260
attaccggct acatcatcaa gtatgagaag cctgggtctc ctcccagaga agtggtccct    61320
cggccccgcc ctggtgtcac agaggctact attactggta ttgctgcttc catgctgtca    61380
ttttccttct tactacctag gacacatgaa gtccttagca aactcccaca cgtctttga    61440 tactgtgtca tgagaatgcg aaactctgtt cctgataacc tcaaaaagca ttctctgtgt    61500
aggagtggta gagcctaata catcccaaaa ggcatgagtg aaggaaaatg caatttcaag    61560
actgtactaa tggcatgact agactcatgt tttcctttcg ctgcaagttt gccagatacc    61620
tgtcaattca gtcctggaga aagatatttt tcaaagcata ctagctgatt gtgattctgt    61680
cattacactc agctctctat agatatggca atcttgcagg acttgccagt gcaccacctg    61740
ccattgacct tgttgaccac tatcacagga taggtcttga ggcagagcag tcccaaccac    61800
ccacattgga agaatgcctg gaatggggaa taagagttgt ctaccttggt gggaaagact    61860
ataagcctct agtattattt ttgcccaaga gatgaaatat ttaaactatc tgtattagtc    61920
tgttttcata ctgctataaa gaggtttaat tgactcacag ttccgcatgg ctggggaggc    61980
ctcagaaaat gtacaatcat ggtggaagga aaagcaggca tgtcttacat ggcagcagga    62040
gagagaagca cacaggagga acttccagat acttacaaaa ctatcagatc ttgtgagaac    62100
tcactatcat gagaacagcc tgggggaacc accccatgat ccaatcacct cctctcctca    62160
atacatgggg attacaattc cagatgagat ttggatgcag acacagagcc aaaccatatc    62220
agtctgtata gagtatcacc tggacttta aattcccaca gaacatacag acattagaag    62280
gagacactgg ctttttagaa ttgggggaa caggaaaata gaagcagaca tgagaggaat    62340
tgaactagac acttcccaca gaggctgcac aaacactggc caatctctcc tacccttcac    62400
ttgcctttag tttcacttt cattgatctg ccactgagga ctgcttggtt attaggccta    62460
agtagattca tgtatataat ctgcaggact ctctttcaaa tttatattcc agtggtggta    62520
tatgatgctg atagattttc ttaaattcaa aaaggcaaat aagaccacgt taaaagaata    62580
ccctggaaag gccaggcgcg gtggctcacg cctgtaatcc cagcactttg ggaggccgag    62640
gcaggcagat cacaaggtca ggagatcgag accatcctgg ctaacacggt gaaaccccat    62700
```

```
ctctactaaa aatacaaaaa caaaattagc caggcgtggt gatgggtgcc tgtagtccca   62760
gctactcggg tggctgaggc aggagaatgg ctgaacctgg gaagcggagc ttgcagtgag   62820
ccgagatagc accactgcac tccagcctgg gtgacagagc cagactccat ctcaaaaaaa   62880
aaaaaaaaaa aaaaaaaaag aatacccctgg aaaagttagc caaaaaatgt ctattcaggc   62940
gtcagatatg atagtaagat aattagtttg cgatgcggac tttatatgca ggatatttgg   63000
gtgtttatgg aggaaaagtg aagtcgattt taccttcaag aggccaacag ccagctggag   63060
aggaagtgcc tgctcccagt agcgtctgct ggtgagaccg acttccactt gactagctga   63120
gcccattgac ataatgtgat ggttctattc tcccttcagg cctggaaccg ggaaccgaat   63180
atacaattta tgtcattgcc ctgaagaata atcagaagag cgagcccctg attggaagga   63240
aaaagacagg taagagtatc ttgcaggtaa caaggagaaa gataggacaa aactaataac   63300
aaatgagcaa tcttgcaata tgaaaaggtt ctccatgttt tgatgcattt cttgtgattt   63360
tttttatcta acagcatagt gtatatattg tattctttaa taggagaaat aatttaacat   63420
gcactgcaga gtttggtttt attttttttc tttactacag ccactcaata taaagccttg   63480
ttattcacct tttaaaaatt caaacaagat gttaaaatgt aaaagaagag ctatcattgc   63540
tcttctttta taccttctgt tgaattttaa aatgtttcct tttttaaagg agggagagaa   63600
acctctcaca tttatctttta tttggtttct acaacttaga gctaaataat gtcttacttt   63660
tgcatccagt ttcagttaat ttcaagaaaa tgtgtattcc tgatataaga aaatttcaaa   63720
aatgaacatg tgtgttttat ctattttttac catttcaaac catgaaaaac tgttgagcca   63780
aacctctgta attctcatac ttatgacact gatatgatta gtctggattc tacttcctac   63840
aacttgcttc tcaaatttaa aaaagaaaga gagaaagaga aagactgcac atttcagttc   63900
cattaggtct aatttgagca gaggcagctt ctacggggct cagcggttta aagctgtgtg   63960
tatgataaat tcatactaac actttttttct ttctaaacta taaagaaacc tttgagaaaa   64020
atcctaaaga tttctttctg gaaaaagtgt tttgtgatct cagaactgct cattttctgg   64080
tggcttttat caaattgatg aacagtcatt gttgcctgaa tcgattatta tcattgctgc   64140
tacttcctgg agcttaatgc gctttgcttt tttggctcta acctctctcg gctagacgag   64200
cttccccaac tggtaaccct tccacacccc aatcttcatg gaccagagat cttggatgtt   64260
ccttccacag ttcaaaagac ccctttcgtc acccaccctg ggtatgacac tggaaatggt   64320
attcagcttc ctggcacttc tggtcagcaa cccagtgttg ggcaacaaat gatctttgag   64380
gaacatggtt ttaggcggac cacaccgccc acaacggcca cccccataag gcataggcca   64440
agaccatacc cgccgaatgt aggtgaggaa atccaaattg gtcacatccc cagggaagat   64500
gtagactatc acctgtaccc acacggtccg ggactcaatc caaatgcctc tacaggacaa   64560
gaagctctct ctcagacaac catctcatgg gccccattcc aggacacttc tgagtacatc   64620
atttcatgtc atcctgttgg cactgatgaa gaacccttac aggtaattaa ttgttctctt   64680
cacttctcat ggggcagcac agaaaggaat aagttaggta actgaagtga ccagccctcg   64740
aataaaaagt ggcttcatgg ccgggtgtga tggctcacgc ctgtaatccc agcactttgg   64800
gaggccgagg caggtggatc atttgaggtt aggagttcaa gaccagcctg ccaacatgg   64860 tgaaaccctcg tctcttgaaa aaaaaaaaaa aaaaaagtg gctccacttt tagaacctct   64920
tagaagatgg cacatttaag ccctgctttt tttttttttt aaatcccaat atggctctac   64980
tttggaggac ataccagaga gtcactagct tttatttcat agagaaaatg aaactatttc   65040
```

```
tcttattctc acacatttga ggttccttt  tgagtaagat agatgattct agaaaagaaa   65100
gatattctac ctgaatttcc atttgtgtgc agaagtctaa aacactacct ttacgatttg   65160
tccttgaaga accccactat ctacaacata tctaaagaaa aaaaaaaaca ggcgaagctg   65220
tgcatagcag ctgataagtg attgattctc taaaacgtat attatttaat ttgtgttgac   65280
agtatccatt ttttttttc  cccgagatgg agtcttgctc tatggccctg gctggagtgc   65340
agtggcgtga tctcggctca ctgcaacctc tgcctccag  gttcaagcaa ttctcctgcc   65400
tcagcctccc aaatagctgg gattacaggc atgtgccacc gcacccagct aattttgta    65460
tttttagtag agacggggtt tcacgatgtt ggccaggatg gtctcgatct cctgacctcg   65520
tgatccgccc gccttggcct cccaaagtgc tgggactaca agcatgagcc acccactaca   65580
cccggcccac tgacagtatc aattttatt  gtgttgttac ttttagaaag tggcagaatt   65640
taaaaactga caacactgta ggaaatttat gagcttagaa acatgagttt gaggatttgc   65700
ccaactgttt taaggactcc acactggggt cagatgtcac ctggaggagc atgaccgtgt   65760
ctcccatata gcgcagtgtc caggttttat gtgaagcaaa catggccagg gcttccagag   65820
ggcttatgca gacctgcgac tgaagcaaga tcaatggcag gccgtctcta gtattgtcga   65880
gggctcctgt taactacgga gcacgtaggt agattgttgg caggaaaatc tggcaggaac   65940
gatggcccct atccttgttc catttctctc ctcagctggt taggaccact ataccctccc   66000
tcttttttt  tttttgttt  tttgttttt  gtcttccttt gctttgttta aacagtgagg   66060
gttattggta agaggagagc ccgtgtcatt cctcactata atgctttctc tctgctttgg   66120
atgtaccgat aattgcagtt cagggttcct ggaacttcta ccagtgccac tctgacaggc   66180
ctcaccagag gtgccaccta caacgtcata gtggaggcac tgaaagacca gcagaggcat   66240
aaggttcggg aagaggttgt taccgtgggc aactctggta tgtaaacacg tactatttag   66300
acacaggctc ccctctgctg tacaccagag atgggctttt ctgttgactg tacctttgtt   66360
gccattgtct tttatctttt gggatttaat gcaacacatc aacatgaaat aaatgagcaa   66420
ctttatatta aattaatctc tcccccacct cctgccatat cctgttgtct tcacaaaatg   66480
catacgtaat tgacagactc tcaaatggtg atatgattat agatctggaa gggatttcaa   66540
atattattta gtacaacact ctgagtcctt acttctgagt atctgagttg atatagggca   66600
caggtttcct gatgtctttt cccagaccct ctccatctca ccatgctgct gtcctcttga   66660
gtgattaaat actgaaacga ttacctataa agaaaatacc ccttctgcag acatggggac   66720
agttggcttt tgctcctgat ataaaatgct accaacattg tgcatttctg tctgcagaga   66780
atgttattcc aatgttattt ccattttttt ccaatgttat ttccattttt ttttctgact   66840
atacaggtta aaagcttcta tagaggttaa aagatcatta actcttcttt gtagcacctg   66900
ggaaatcctt ttaaatcaat agcgtgccac ctggctgctc aatttgcagc agctgaaaat   66960
tcaccaaggc acatgagata gggataatc  aaaaccgtga atccccaatc ttccaacagg   67020
agagttctct actccacacc aacagagagt gctaagtcct gtctatgcca agtgacagat   67080
tttattccta aggccagttg tttaatttta gcccctccc  tcatctgata gaagactgtg   67140
ctactttaca tgtataaatt cctgtgaatt aagcagttga gcatttggct ggagagaggt   67200
tgggaggaga ttattttgtg tttgttgtat tacatatcca cagtaatgct tatctttgcc   67260
ttttgtggtt ttactagtag aatgccacgt gaacagaatt ttcaagagca aaaaggtctt   67320
tgtgcttttc taagtcattt tttttttttt ttttaaaga  ttccatctct ttaacttag   67380
ttaggatgga atttgaactc ctggctcttt tgagtataga aacccctagt aacaatttaa   67440
```

```
gttccttcca ttttctttt aaactcctta ttcccagcag cagtattcta cattctaacc   67500
aggttctccc agctttgaga cgtctcagac ttaccagttc tccaaaacgc tattttcttt   67560
aagggtgaca ccttttaaaa attaggcacc tcaaatatct actgcttttg agcttttgag   67620
ttttgcactg taaaaagaaa aatacacagt gggattttaa gtcaaattag tttatctaat   67680
ttttagggaa taatttgaag catgctttgt ttgcatagat ttttttaaaa taagcttttc   67740
caaatcataa agagataaga tcttaggtaa catgaagaga ctcccttact tattcctaaa   67800
tcatctatat tccaagggca ttttcttatt tggaacagtt gacctcactg ataaagctgt   67860
ctcaccacta taataacaat gtccaaaatc taggctttct gcactattat gcaaaaatta   67920
caataataaa agtgaaaatt acattataat ggtatattaa aatgctaaga cttttgcatt   67980
ataagcaaaa gacagccttt aataattatt ctttatttag tgaacatttt ctaagtcttg   68040
gaaaagggtc aatgttttga attcatggcc ttatataatc ttcacaagat tccccaggag   68100
gtatagatat ttttattatt acgctagtat tgcagatgag ggaagcaagg cagagtggta   68160
ttaaatagct ggcccaaggt cactcaggta ccaatggaga ggcatcatta gtctttgcat   68220
cccactaaag ttctccacta gcttcaattg cctcaagatc tgttccatgt tctatgaagt   68280
agtttcaaca gaaatggcaa ttatcttaga agcaagggaa aaataaaaga tgggcttcct   68340
gtcgggtgcc tgtgacaggt gtcacatcta accatggttt tttagagcag ttaatgcctt   68400
gatagaacag atgaatgcct cttaatcctc ctggaattct tgttttagat taagtcattg   68460
tatacagtca ttcgattttc ttcttatggt ccaaatcgat taataagatg tctcttttg    68520 cttttcttc cttttcttca tagtcaacga aggcttgaac caacctacgg atgactcgtg   68580
ctttgacccc tacacagttt cccattatgc cgttggagat gagtgggaac gaatgtctga   68640
atcaggcttt aaactgttgt gccagtgctt aggctttgga agtggtcatt tcagatgtga   68700
ttcatctagt gagtagttgc tttgtccatc cacttccgtg tttgtctcct caagttccat   68760
gcatgcactc atgtgccaag gaagcatgtt tggaagacac aggttcttcc aaacatgaag   68820
caaacaagag aatactgttt gactcgaagt aatattttgc atcatagaaa aatgatggga   68880
aattttactt gttggacatt gcttcatttc aagggttgta tgccaataca actattaatt   68940
acacataaga ttatggtgct aatttgattt ttgaaatttt ctgtgaaaac aaatggataa   69000
agacttttgg aaccaggtct atttaagagt attagagaca cagaaaaacc tcaaatctct   69060
tttaatcttc agtgttgaat gagatcagag gtgaacattt agactcaaaa acagcctcct   69120
tcaacataaa ccaaacatgc acatatcata gtacccatgc acacactttt gcgtcacaca   69180
catagcccag gtagcttgaa cgttgctaga aatatgaaag aaaaaacaga taatctgctt   69240
ttagatcatt aaaaatcaac ttgaattgat aaatgtttga ttttcaaatt ctaatacgtt   69300
ttaattttca aattttttaa gttaaaatgt gcctaggaaa tatctattat gctttgagat   69360
taggattaga atttataaac cttttcattta ttctttgtgt ttaggagatg tgatgattat   69420
tgacaattgg ttcattttta taggtgttga ccgttatgcc tataaataag cctcctatag   69480
acatacagaa atcatatcct gtggaattag aatataagac ttggtaaaag agattttcaa   69540 agtatttac ttaacttgta tacttgaaat catttaatcc agactgaagt tgtaaaagcc   69600
agccagtgtt ttcaatatag acttccatgt tgaccatct gaaaatgaaa aacactaaaa   69660
acatcacatg ctgtttagga gctggaaatt ttaaatatttg acttcaagta gatggttttt   69720
aactcctgaa atcgaactac gtttaagttt gtatgtttat tacctgtttg agcacttagg   69780
```

-continued

```
tgcaattgtg ggagcgggga tgtcaagttc atttatgtga ctctttggct caacttacat      69840
aatctttgtt ttgatatcac agttgtctaa ttattttact ttgtagctta aggcaggctg      69900
aattgttgat aaaatggaaa aagtagtata ttgttatata agcttctgag gtgtgttttg      69960
ttgtataagc cctggaggtt aaaaagtcat cccttatgta tagtagttaa aggcataaaa      70020
ctgtgacttt tagatattcc acagaaccag acttatttga tgtggataat aaccaatgat      70080
ttagcatttt gtttgctttt gttttatttt atccgggttc attttttact cttcccatgt      70140
acatgaaaca ggtggtggcg tgtagagatc agctgatcct tgttttatgg ttaattgaac      70200
tactttgtat ccagggtttc tgcaaatcca aaagtgattt ttcatctagg atctattcct      70260
aacagtctac tccaatccca ctttagtttt ccacaatttt aaatcttaat agtgagaatt      70320
caaatgaaag tcatttcatt tgactattct gatgacatga ttgtggcaga ataaattggg      70380
tcttaaaatg ccctagaaaa tggtaaatga taaaaaataa tattttaaaa ttcaaccaaa      70440
gaaatggccc attggccagg tgtggtggct cacacctgta atcccagcac ttttggaggc      70500
tgaggcgggt ggatcacctg agctcacgag tttgagacca gcctacccaa catggtaaaa      70560
ccccatctct acaaaaaata caaaaaaaaa aaaaaaaaaa aaaatagcac tgtggggagt      70620
gcctgtaatc ccagctactc aggaggctga ggcaggataa ctgcatgaac ccaggagatg      70680
gaggttacag tgagccgaga ttgcaccact tcactccagt ctgggcgaca gagaaagact      70740
ttgtctcaaa aaaaaaaaaa aaaataaaaa gtaaataaat aaataaaata aatgcccat       70800
tataggggtt tttatcttta acttgctatt tttccagatc atggttctga agaccctgtg      70860
acacgtccca gttcacctac tgtcttgtga gtcagaatat acaaataact ttttggtcct      70920
gactttcccc acccctacag gatggtgcca tgacaatggt gtgaactaca agattggaga      70980
gaagtgggac cgtcagggag aaaatggcca gatgatgagc tgcacatgtc ttgggaacgg      71040
aaaaggagaa ttcaagtgtg accctcgtat gtcatcacag atcattttta gtgccttatt      71100
aagcattctc actttcatta tcaggctgta actctcattc acagaaatga ttggagactt      71160
taggtctcct tgaggagtga acagtgggtt tcttaatctt ttgatttggg aaagtggaga      71220
caagcttcaa aaatgagtca tgatttaatg ttattacagg cactttagc acttgtccaa       71280
cctgagtatt ttgaccatta tctgcagtaa aatgctacaa agaagcttta ttggtctgta      71340
gattcaactt ttaaaatatg atttccatct tcccgttgga ccctttccag tgtattaggt      71400
ctaatttttg gaagtgccac cctaagatct gtatagcagt actgctctta gggatgattc      71460
acataaatat gtggtgtttg cgctgtgatg atacaaattt aggacagaaa tagaacccac      71520
ccctagatca agtctgcagt attgttctca gcttatgcgt gcatctgtct tgtgtctata      71580
tgcagatgag gcaacgtgtt atgatgatgg gaagacatac cacgtaggag aacagtggca      71640
gaaggaatat ctcggtgcca tttgctcctg cacatgcttt ggaggccagc gggtaagact      71700
ggatgtgcca ggctccctac aagttagata agataaaggg tgggctcctg caaggatgtg      71760
tcgtacacac aggaggggca gagacccttc ggaagtatta aaataccaca tttcctgttg      71820
gcatacaact gctgacatag agctctagag cagctctatg tctaccttac atgccattca      71880
ttctttctat tactccttagt agaaagaatg aatgaatggc atgtagagta ccaaaaacac     71940
aagtcttgag tcattcttaa tagcaacacc tgtcatttat atgatgttag aatcattttc     72000
ctaagctccc tagcatgtca gagatactat ttacactgaa aaatagtgaa gcagagatac     72060
tattcaaatt aattagtggt aaatagaatg tgtttcattt cagccggttc tccccatcct     72120
gggcagcctg agaccctccc ctcccctact attctcaggc tgcttctatt tttcagcaaa     72180
```

| | | | | | |
|---|---|---|---|---|---|
| gtgttaagtg | cagtgtagct | ctaggcctcc | aactccattc | tgatggacag | gtgtcccatg | 72240 |
| gcaacgttgt | taaatatttt | gaataatatc | tcagatgtaa | gaaaatgcca | cttcttttaa | 72300 |
| cctctctctt | gattcagaac | agatgcttgt | tataggtcta | gcactgtgct | aagtagtata | 72360 |
| ggaaaaacag | aggaaatgag | aaatggcttg | gctcttaatg | atatagttga | agatgttaaa | 72420 |
| ttagcataca | tttcaaagtc | aagctaatta | agttctaagt | gggtctgaca | aatacagttc | 72480 |
| tgggtaggct | ggaattagca | agaaagagaa | gcatgaactg | gctgaggttt | acgatgacta | 72540 |
| aggtttagtt | gggaggggag | aaagcagaga | gacacacccc | ctgggataga | aaggagctgg | 72600 |
| cccaggtggg | ctttggtgag | ccaaccctct | gcctgctgtc | ttctggtaag | aaaatagatg | 72660 |
| ggaagaagtg | gcttatggag | ggccttggca | acccattatt | taagccagta | cttctcaacc | 72720 |
| atttctaaaa | tatgcccagt | ataacaaaaa | ataataagcc | tttctctaat | atgatttcaa | 72780 |
| atttcaaaat | gaattatgt | gtaactcaaa | agcaatggaa | tgtgacagcc | ctttgttttc | 72840 |
| aacgaagaca | tgccctccca | gcaactcccc | aaatcctggt | gggtgagggg | catgcttcac | 72900 |
| actcaagggt | gagactcatt | ggttaatgcc | aaatgcatta | accaattaca | ggtatccaag | 72960 |
| atgcaaagaa | acatgatgga | aaatagtctt | tgggaaaatt | aatctggcag | cagggggtgtt | 73020 |
| caggggcctg | tcttggctcc | accaggggca | gcccatggaa | actactatga | tcttgtttca | 73080 |
| cccccagtga | ttcatggggg | agggaggtgc | tcccaattct | gatggaggag | aattggagat | 73140 |
| tggaatttag | attgaattca | gtatctctct | ctgtctctct | ctctctctct | ctcccattaa | 73200 |
| cacttacaac | gactgtgatt | gtatgaccttt | agaactcagt | cattctggta | tgaaattgtg | 73260 |
| tgatggagaa | tgaatttgct | gggaagttga | ttttggtctc | acttcagcat | cttctcatta | 73320 |
| tttatgcaca | tgaaaccttt | catgtgcgac | acttattcta | ttctcaagtg | ctaaatgaaa | 73380 |
| catttaagac | aggagtggaa | actgttcact | ttctcatatg | aaagcaagat | tcagtgattc | 73440 |
| tgtaaggagg | tagtcactgg | tattgtgtta | ggtattaagg | ggcatatgtg | cttaaacaga | 73500 |
| gaaatatgtc | taaaatatttt | aaattctaat | ataaaaaaga | aagtgactgt | attatttagg | 73560 |
| gctgcatttt | agttgtaaga | aaaaagtcca | actcaagcaa | aaatggccca | cacaatggaa | 73620 |
| cagtcccagg | acccaccggc | ttcaggggct | gctccagcaa | tggcgcccgg | actccctctt | 73680 |
| gctccgcgtg | ccttcccatg | cactggcttc | gtgcttcagc | ggggtctctg | ctgatggtgc | 73740 |
| cattgatgac | tgacctccat | gagccttgctt | tacccctgc | cagcttaaga | acagtagtga | 73800 |
| aagagaacat | gtgtgtcctc | ccatttccag | taaaaacttc | aggcaggagc | ctcactggct | 73860 |
| cagcttggtc | ccgtttccat | ctcccatgcc | atctccggcc | aggtgacagg | ctaccatgtc | 73920 |
| actgcctagg | gaagtttagg | aagagagtgg | caaagtggtg | cattagaaag | aacatggcca | 73980 |
| ggtcaccccca | cctcctgggc | ggcaggccca | actccaccag | tggtccactg | tgtgacttcc | 74040 |
| ctgctcccctc | taagcaagtc | actcctctcc | tctgggtctc | tgtttccttaa | cctataaaat | 74100 |
| gagaacgttt | cttcatgtga | tctcaagtcc | cttttaaaat | cgctaggatt | ctttgaaaac | 74160 |
| cttttctatc | atctagtgca | gagaacttgt | tgaggaagtt | gggattggaa | tgagcctcag | 74220 |
| cagatgggca | aggtttgaat | aggaagagaa | gagacatttc | aggagaaaga | aacaacatag | 74280 |
| agagacagat | gtaggtataa | gatatggtaa | taagccaaaa | tgtattaaga | gttataaatg | 74340 |
| catgaaatca | tcatcaaagc | ttgcttagtg | attaactgct | tatattttgc | cagtgcatat | 74400 |
| gatgtgacat | ttttctttaa | ctcaaacact | aaattacgat | gtcctcaggt | tatcataaac | 74460 |
| cccatttgac | ttcatgcctc | tactctctca | gggctggcgc | tgtgacaact | gccgcagacc | 74520 |

```
tgggggtgaa cccagtcccg aaggcactac tggccagtcc tacaaccagt attctcagag    74580
ataccatcag agaacaaaca ctgtaagtgc attagcagca caagtgtgtt ccctcatact    74640
agacagtctc tttctacagg tatctttctt cagaatgaac caagtgtttt aattaattaa    74700
aaaaaaaaac aactcataaa tgacttaagt gaaacactgt attccataat atagtttaag    74760
ttataattta tgtaactctt gaacatctcc tattgcccag tatgctgcta ggttcttgaa    74820
actaggaaga aatattatcc tatctataag cagctgtcat gagtccccac ctccccgcat    74880 tttttttct gtacacttta cagtatttgc cactaatttt ttttccttc ttccttttta     74940 acagaatgtt aattgcccaa ttgagtgctt catgccttta gatgtacagg ctgacagaga    75000
agattcccga gagtaaatca tctttccaat ccagaggaac aagcatgtct ctctgccaag    75060
atccatctaa actggagtga tgttagcaga cccagcttag agttcttctt tctttcttaa    75120
gccctttgct ctggaggaag ttctccagct tcagctcaac tcacagcttc tccaagcatc    75180
accctgggag tttcctgagg gttttctcat aaatgagggc tgcacattgc ctgttctgct    75240
tcgaagtatt caataccgct cagtatttta atgaagtga ttctaagatt tggtttggga     75300
tcaataggaa agcatatgca gccaaccaag atgcaaatgt tttgaaatga tatgaccaaa    75360
attttaagta ggaaagtcac ccaaacactt ctgctttcac ttaagtgtct ggcccgcaat    75420
actgtaggaa caagcatgat cttgttactg tgatatttta aatatccaca gtactcactt    75480
tttccaaatg atcctagtaa ttgcctagaa atatctttct cttacctgtt atttatcaat    75540
ttttcccagt attttatac ggaaaaaatt gtattgaaaa cacttagtat gcagttgata     75600
agaggaattt ggtataatta tggtgggtga ttatttttta tactgtatgt gccaaagctt    75660
tactactgtg gaaagacaac tgttttaata aaagatttac attccacaac ttgaagttca    75720
tctatttgat ataagacacc ttcggggaa ataattcctg tgaatattct ttttcaattc     75780
agcaaacatt tgaaaatcta tgatgtgcaa gtctaattgt tgatttcagt acaagatttt    75840
ctaaatcagt tgctacaaaa actgattggt ttttgtcact tcatctcttc actaatggag    75900
atagctttac actttctgct ttaatagatt taagtggacc ccaatattta ttaaaattgc    75960
tagtttaccg ttcagaagta taatagaaat aatcttagt tgctctttc taaccattgt      76020 aattcttccc ttcttccctc ccctttcct tcattgaata aacctctgtt caaagagatt     76080
gcctgcaagg gaaataaaaa tgactaagat attaaaagta tttgaatagt ataatatgga    76140
ggagttttat cttagggaaa ccccatggta tgataacccc catctaacat gtcttacttt    76200
gggtcagc                                                             76208
```

```
<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
ggagagagtc agcctctggt tcag                                           24

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
```
tgtcaactgg gcgctcaggc ttgtg                                            25

<210> SEQ ID NO 4

<400> SEQUENCE: 4

000

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 5
gcaaattaat ggtaa                                                       15

<210> SEQ ID NO 6
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 6
ttaggcaaat taatg                                                       15

<210> SEQ ID NO 7
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 7
tctgttaggc aaatt                                                       15

<210> SEQ ID NO 8
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 8
atgtctgtta ggcaa                                                       15

<210> SEQ ID NO 9
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 9
tcaatgtctg ttagg                                                       15

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
cgatcaatgt ctgtt                                          15

<210> SEQ ID NO 11
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 11
gggcgatcaa tgtct                                          15

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
tttagggcga tcaat                                          15

<210> SEQ ID NO 13
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 13
gtcctttagg gcgat                                          15

<210> SEQ ID NO 14
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 14
ccaatcaggg gctgg                                          15

<210> SEQ ID NO 15
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 15
ggttccaatc agggg                                          15

<210> SEQ ID NO 16
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 16
actgggttcc aatca                                          15

<210> SEQ ID NO 17
<211> LENGTH: 15
<212> TYPE: DNA

```
<213> ORGANISM: Artificial sequence
<220> FEATURE:
<223> OTHER INFORMATION: Synthetic oligonucleotide

<400> SEQUENCE: 17
tggactgggt tccaa                                                    15

<210> SEQ ID NO 18
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 18
ctgtggactg ggttc                                                    15

<210> SEQ ID NO 19
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 19
tacctgtgga ctggg                                                    15

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
atatacctgt ggact                                                    15

<210> SEQ ID NO 21
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 21
aaccatatac ctgtg                                                    15

<210> SEQ ID NO 22
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 22
aattaaccat atacc                                                    15

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 23
gatcaatgtc tgttaggc                                                 18
```

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
cctgtggact gggttcca                                                  18

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ccttccctga aggttcctcc                                                20

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
gtaacccgtt gaaccccatt                                                20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
ccatccaatc ggtagtagcg                                                20

<210> SEQ ID NO 28

<400> SEQUENCE: 28

000

<210> SEQ ID NO 29
<211> LENGTH: 68651
<212> TYPE: DNA
<213> ORGANISM: Mus musculus
<220> FEATURE:
<221> NAME/KEY: misc_feature
<222> LOCATION: (45900)..(45900)
<223> OTHER INFORMATION: n is a, c, g, or t
<220> FEATURE:
<221> NAME/KEY: misc_feature
<222> LOCATION: (45905)..(45905)
<223> OTHER INFORMATION: n is a, c, g, or t

<400> SEQUENCE: 29
tttcccttcc cacaaaatac actctggtgt gcacagactt ttctcagagg tgacgcaatg     60
ttctcaaaca ccaccacagc caccaattta aaaaaaaaaa agttaagaga tgagggggt    120 aagccttacc accccaggct tccttaggct ccagcccctc cctcccttc cttcgagtct    180 acatcacttt acagccgttt cccatcccta cccccaatcc tcctcccaaa agtttgacga   240

```
ccgcaaagga aaccagaaag gggaaaaaag ttctctagtc ccagacctgg cgggagatca    300
gcatctcttt tgttcggggc gaacccaccg taccccgtga cgtcacccgg actctgggcc    360
aataggcgcg cggtcggcgg cggctgcggc ggcaggaggg gcgggaggag tcggaccgga    420
ccctcctccc cggcgcgcag ggcctcgtgg ggggcgggaa ggtactgtcc catataagcc    480
tctgctcttg gggctcaacc gctcgcaccc gctgcgctgc acaggggag aaaaggagcc     540
cagggtgtga gccggacaac ttctggtcct ctccttccat ctccttaccg gcgtccccac    600
ctcaggactt ttcccgcagg ctgcgagggg acccacagtt cgtggccact tgcctcctgg    660
ggagggcgac tctcctccca tccactcaag atgctcaggg gtccgggacc cgggcggctg    720
ctgctgctgg cagtcctgtg cctggggacc tcggtgcgct gcaccgaagc cgggaagagc    780
aagaggcagg ctcagcaaat cgtgcagcct caatccccgg tggctgtcag tcagagcaag    840
cgtgagtacc gacagtctgg ttcaaaccgg ccggcggcag ggatgggttg gtcctcaagc    900
gcccgctcaa gttgtggcta aagttttgc gcgcgtgcgt ggctgtgcga acgtgtgtga     960
gtgcgcgctt tatcgaggga aaccagctgt ggacacaaaa ggcttaggtc tgaacaggct   1020
ggttgctggt gaagtggagg tagggaccgt ctgttcttcc cctcaagtgc gctaacaaat   1080
tctacacctt cagttcgccc ttccaggaac caaaacgtgt gaaagagaaa agagacacga   1140
acttacaaat tttacatcag agattattgt ggttcccctg atccttattt tctttatcag   1200
caaatagctg gttaaatatt taacacgggg aggaggtgag actatctaaa taggtagttt   1260
cttaccaact tgaaagagat gttagttggc tcagtgcttt ggggggggg gggtagccta   1320
ggattctttc cccaagagca aggatagcca tttctcttcc agttttcag agacacactc   1380
ttcctttatc ttgggctaga ggaaaattta aagttctcc ctccttttt tcttttctt    1440
ttcttttctt ttctttttctt tttttttct ttttttttt ttttttttt ttttgccatg    1500
atctcacact gtagcctaag ctagcctgg attctcctgt gttgtccagg cttgtgtgtt   1560
caacttggga gcaattcttc tgcctcagtt tctacagagc tggggttatt ggcatagtca   1620
tcaagacacc caacttaagt tttctttctt gtcttttgt tgttgttgtt aagagtattg    1680
aagccctcag gatttaaaag taatttctat ttctggcctc tcagagtgtt tcaagtctgc   1740
tgaggtagtt cccctgccca taaggacatg acgtcattgt ataactttta cccaagttaa   1800
aagataagaa ggaaaaaacc cctaaacatc catctacata aacaatgctt aaatctttga   1860
ttagctagtt tccacatctg aactttagtg gaatattgct tttaagagtt tttttgtttg   1920
tgcaggctca ccaagtcagt tggcaaaatt cagtagtttt gtaggggaaa aaagagaggg   1980
agggatggaa ctgttaataa ctttcccccat caattcttcg cagctggctg ttttgacaat   2040
gggaagcact atcagataaa tcagcagtgg gaacggacct acctaggcaa cgccctggtt   2100
tgtacctgct atggaggaag ccggggtttt aactgcgaga gcaagcctga gcgtaagtgg   2160
aaggcagtct gggccctggc agagatgatg ctctaagtaa aaccacattt gcttctcct    2220
cctccctgct ccagtcgctt gtaattccct cttattagac ttcttgcact ggcttttcac   2280
atgctcttac ctctaaaaca aatgtaatcc acacgagtct ccaaagccgc cttttattc    2340
tcttggagct tttgattaga aaatgagagg ttttgcgtgt ctcccttcaa aaagaaaact   2400
tataaaagtt tgcttataaa agtttaattt attagaaagt gatctcggat cttttggctc   2460
ccaattatgg gccagaagtt gctttgaggc actgggttgt aaagtgattt gttagctgca   2520
gttccgtgaa aaaacaaaa acaacaaccc actaccactt cggagactcc tgaagcccct   2580
```

```
tgatacgctt ccggtgagct acagcagtcc cttcagagag gctgctgagg gagggtacag    2640
gacaaatgtt tcagtgggc  tgacaaaggc cagccactgc tgggaggccg gcaaccttca    2700
aactgtttgt gtcccttgtg acccttgaat tgatttccct ggtttgagac tggaatttgg    2760 aatcttttcct ctgcaactca gctggtcaca gggtgtggct ttttcctggg aactcttttac   2820 attataaata agggaaccgc tgagagctgg ccaaaggtca agagctctgg ttttattaaa    2880
gcctaactta aaaacttgtc tctcttaagt ttcagagtcg ccatgtatgt gtgtgagact    2940
cacatggact ttttttttt   cccctttcca cagctgaaga gacttgcttt gacaaataca    3000
ctgggaacac ttacaaagtg ggtgacactt atgagcgccc taaagattcc atgatctggg    3060
actgtacctg catcggggct gggagaggca ggatcagctg taccattgca agtaagagag    3120
gccttctgtg gagttattga ggtcacatat acacacttcc ctctggcctg tccttgcctt    3180
ttcctgttat ccctgactga atagtgaata ctttttactt caatgaccaa accccatgtc    3240
gtcacccacc tagctcctct acatctggaa gatggatcta agcagagatg gaatctctct    3300
gtctctctct ctgtatgtgt gtgtgtgtgt gtgtgtgtgt gtggacagtg gaagatctct    3360
tggttctttt caataagata tgcccaaggg acctacctat tttaaattat ctgggcctct    3420
ttaagccaga ttgatcattt tatcctctgc agctatgagc cagaagggtt tttgctcttt    3480
gtcatggagt ctggttcttt tgatgagta  gattagattt ggggagaaaa ccttgcggtt    3540
ctcaaattca acacaggctg atgagcacag tgcatctcca aggaactta   ggtcctgggc    3600 tttctctcag gaagtctaca gctgcggcag tcttttctcgt gtgactcatt gggttgccag    3660
tacgttctat taataagact ttctctctaa aaaccaactt ttaaatataa gtcctctgtc    3720
caaaagaacc aattagtccc ttctgaatag accaaatcaa tatttccaac atttaacatg    3780 agggttttt  ccaagtttcc tgcaaagcc  caagagtcga tggtacactt gtgaccctgc    3840
gtacaattca gccattggat ttcacagcct aagaaagtat cagggtttcc aaccctcatg    3900
agtgtgtctg cttgctttct gccagagtgc tatttccacc ctggagtaga atgcaggctc    3960
tccgtcctcc aggagatcgg aatgctatgc ccaagtagct caccttgctg tctaggagga    4020
cagttccccc agctcttctc tgtctaggga acagattgcc tgtgatgtct ccggggaacc    4080
acaatttatg acttcttgcc attcagagtt ctccatggct ttccttttttg tgctttaacg    4140 attgacccaa agtgggctga tatggtgtta gccttctttc tgctttttttt ttttttttg    4200 gcaggagagc tgcctgccaa aaaaatccct caggattagg gattgcattt tggccaacat    4260
acatacttat ttatctcagg cagaaactga gatgagcacc ccctgaattc tctcaatccc    4320
ctaacgtttg cctttgatct gtaacagatc gctgccatga agggggtcag tcctacaaga    4380
ttggcgacaa gtgaggagg  ccacatgaga ctggtggcta catgttagag tgtctgtgtc    4440
tgggaaatgg aaaaggggaa tggacctgca aacctatagg taagtggctc gtgtgtgtga    4500
tcgaggggaa cggagccaca agcagatagc ctaagcaaac cagtggccgg gatagctgaa    4560
tcacagcata aaaaccagtg aaatgtgctg cgagtcacca gccttaagga aatcagatcc    4620
tgaactatgg aacataaagg aatcttaatt ttgtttgaaa agcacaaggt ggagttaaaa    4680
tctttaggaa gaagtgattt cttttgttta tatactatgc tgtccccttg gtgaagaaga    4740
catgttattt aaaggaggaa aaattacact attgacacat ttcttgttgg aacacagttt    4800
gttaaagcac aaaatgccac gtggctccgg tcacaccttg gcaatttcct taaaacaaa    4860 cattaaaggt tgtgggggat ttttgttggt ttgttttatt tattttttct gttttttttgt   4920 cttagccttg gttgtactct gaagcccaaa gttttgggtt ctctttctta gatctccaag    4980
```

```
tcagacgtgt gtttttttcaa atttgttttg tttttgtttt ttacattagt ctaaaattta    5040
aagagcgctc ctctcattct ttgtaagtcg ttcatatttt atagtggttt agtttaggga    5100
cacacagatc agtggtagag agcacttgct gaggctaaca taaggttctg ggttcaattc    5160
ccaggactga attaatgagt taaaagagaa aggttgggat tttgcatagg gtcgtctccc    5220
acagggtaaa gacttgcatt tctttccact tgaaatgtta gtgggaagct tgggacaggc    5280
agaaaaatcc ggtctgtgta ctcattagga caacagaatt tacttgcagc aaggctgggg    5340
cttcctcttg ctccggcttc ttgctccgtg cttagctgca gggcgtgcct gctcatctga    5400
acagagtgcc actttaagaa atgtggctgg ggttttgatt ccatgctaca ctgtaaatta    5460
tagggagacg ctatcatttt aaatcgctct tcctcctttc tttttgcttt cccatttctt    5520
ctccagctga gaagtgtttt gatcatgctg ctgggacgtc ctacgtcgtg ggggagacct    5580
gggaaaagcc ctaccaaggc tggatgatgg tggactgtac ttgtctaggc gaaggcaatg    5640
gacgcatcac ctgtacctcc agaagtaggt ttagctcttt tctgttgaca atgcagccca    5700
ctgttgcttc tggatcccta gagagagttg tgatgccttg gtgactctgt ggtatcataa    5760
gatgtccaga aaaactgtat aaccatcacc ttctgcttct tcagaggaca ctcaataact    5820
aggaaaggca gttctcagtt caaccctgcc ttaggcagtc agctagtaaa aatgaaaaga    5880
gccttagtgg tattcgcttg ctggatgggt cttccttgat ctgggaatta tctcagagat    5940
acctttctgg taccgaggac aattaaatcc ctaaagtagc atgtaaatga atcctttgac    6000
ctgggggagc gattggaaat aaaaggctct accccatgtt cggatttcct tctatgtttg    6060
aagtttaaat aaggtttact gactctaaac aagaacctag tggaaatgag tccgtgccca    6120
gtattatcct tcaaatagga aagtggaatg aatttctgtg tgttgtttgt tcatcgattg    6180
ggcagagaga ctgttaaatt ataacccatc cttgctctta cgctacaatg tgggcagtaa    6240
gggtctaact ttgtgactta aatattgctg catttgcagt gtcaggaaaa aaaaatcaac    6300
cattgattca ggcaaatgca tagacacaca agaacagagg tccaagaccc cagctaacag    6360
tgttgtcaaa cctgaacctg ttttcagtat ctttgaatca gtatctcttg aaactcctaa    6420
tgctgagctt tgtaagtgat taatacatga gccttcctca tctttgacct actaagtgtt    6480
ctctgaaggc tgatgcccag ttcgtatttc cctccccata ttgccacata caaagtaagt    6540
acttataaaa ttttgttgat cacatgctat ttgtttgaga aactttgcat gctgtcagaa    6600
gggttttaaa tgataggtaa gagtctgaat tagatttctt tctacatgtg tttattttgt    6660
gtgtggaggt gggaggcaca cacgccacag tgtgcatgtg gagggcaaag gacagtttgg    6720
accgcgcagg gtgcagtgac ctcaggttgt caggtttggt ggcaaggttc tttactcact    6780
aagccagctc agtggctcag aattagatgt ctaatttgtc ttcaatgaaa atactgccac    6840
aaacgacttg gaagactgaa gctcatcaca gttttaaatc aaaagatcta aggatcctat    6900
aagtttgggg gaaacatttg atcttttttcc atgacttatt tttgtgtggc aaagaatttg    6960
aacttgggtg gtatttttaa ttactagttt aagctggata acaaaacac attcaagata    7020
tctagatttg acttttttttt tttttgcatg cgttttaaaa ttcatgcttc agcaaattcc    7080
aaggctgttg ttagtttgaa attctaaatg gaacttgaa ggcagaagca gcaattaaga    7140
cttcaagaca atcttagaag cgggagggaa gaaggatgcc tggggccagc ttttttacaag    7200
gataataaga gacagcatcc ttaactccag aagagacctt ttaaccgtgg gataagccat    7260
tttgtcgttg ctattggtta ttgtcactgt tattattaca attactatta tacagggagg    7320
```

```
attctcataa gcccaggctg gcctagaact tactgtgttg ctgagagaga ccttgggctc    7380
ttaacactcc tgctcctacc tcccagacgc tggggttaac cacgtgggtg actttgtaat    7440
tgtaaaacag gtggttttgg gtggggcaag aaaagagaac cttctagcca gagaagttgt    7500
ttttccacag gaatactttt acataacaag tggagagatt ggtgtggtta acttttttagc   7560 ttccctgggg cagtcggaag agacctgcct cctattgtt tattgaaagg agggccatgg     7620
gctgtaatta cagaaaaagg tctggaagac actgaggagt aaagagtaga ttgccagata    7680
attaattgag tcaaagaacc aatgtagaaa atcttaattt tttttaatca ataaaagaca    7740
ctgaatagta tttttttcttt ttttcctttg gcaaatggag aggtagggct gtactgtaac   7800
gaaccgggta tctgaatttt aatatatgca tcaccagcac tgggtaggat gtactaacac    7860
caacaacagc cactcagaag cattcaactg cagcattccc atcttagtgt ggatggctgc    7920
gtgtcggtta ctagataact tctatattca atgcttctct cctgaaacag acagatgcaa    7980
cgatcaggac acccggacat cctataggat tggagacacg tggagcaaga aggacaaccg    8040
aggaaacctg cttcagtgtg tctgcacagg caatggcaga ggggagtgga agtgtgagcg    8100
acatgctcta caaagtgctt cagccggtga ggcgctggga ccggggacag ctccacgcca    8160
gggtgattta tagcgtttca gctaagaagc tggaatcgtt cacataactg tttaaaaata    8220
ttcattctat attgtgaaca aagttgagtg gaatgaagtt gagacgtgcc tttagcacag    8280
agggctgggt tggaaagcat agtgtactct ggtcatggct ctattagtat aggctttggc    8340
ttatgagcat gagactcaga gttcagtcta gaaccaaagt aaatatccaa gtgtgatggt    8400
gttatcccag caccaagaag gtggaggcag gaggatacct ggggattaca gaccagccag    8460
cttacactac tttggaagtg tgggggtggt tccaggttag tgagatggtg tggctggcca    8520
gcccactttt cttggggag ttgggggaag ttgtgttcta ggtttgtgaa agatggtgtc     8580
atagaaaaca agatggctct gggcataatc cctgccttct acatgcacaa gctctccaca    8640
cgcatgcgca catagataat gtgcatgcac cctccctcac atggacaagc aatagtgagt    8700
gaatgtgtgg tatgtacttg gaatcctcaa gccctgggtt cagttcccag caccctccca    8760
aaacacccca ataattatta tataaattta aaagaataac taaaacaaag aaaggtattt    8820
gtatgtatct tggatgcttg gtcagagtct gaggaagggg tcggagcact tgccaaccat    8880
gcgcaaagcc ctggttctgg ttccccatca ctaaataaaa ggagggtgtg ttgtgcctgc    8940
gattccaggg atcaggaagt agagggacgg aggatcagaa gtccagagtc agccttggct    9000
acgtagtgag ttctagtcaa acctgctcaa tgtggctcag tgggtaagag cacccaactg    9060
ctcttccgaa ggtccagagt tcaaatccca gcaaccacat ggtggctcac aaccacccgt    9120
aacgagatct gacgccctct tctggtgtgt ctgaagacag ctatggtgta cttacatgta    9180
ataaataaat aaatctttaa aaaaaaataa aaaaaaaaa agatgctgtc tctcatgcac     9240
acacacatcg gaagaaggaa gtgcagctct tgtgggtggt accttcccgc tattgcgctc    9300
tgggtttcca tctagctttt actgtgtgat agtccagcct tgttacttag cctcttagca    9360
gtcagtcatt caggcaatag taattagatt ttttccct tttgacgagt ttatctggac      9420
ctaattaatc cttgtgaaag caaacaaggt tacatttgat gatctctaca ttatccaatt    9480
atcatcgata aaaacagcta ttggccataa ggcagaggaa gaacagttac gaatgtcagt    9540
cgactgaact acatgaagga ttaactgagc taactgggat taaacaatac gtgttaacta    9600
tttttatggc atcactaata taccgagtg tttcactatt aaagggtttg agaaacactg      9660
ttaaacgaaa caacctcttc taggagggcc ttgccgtcct tctgtatggt gggccttgac    9720
```

```
accattggcg tcctctgtct gagttctctt tgggtatttg tgctcgtcag cgctggggga   9780
agaggctaga ttcattctag aagctcttcc gctgccatac ggactctgac cttcaaaagc   9840
cagatttcta aaagagaagc tagcacaatc tgttgtgtta actatccgag gaaacttgtg   9900
aggattggtt gcttctagga aaacaaacag acatcctaag gaattctgct gagcaccgac   9960
acccaggaag agggataact taggaaatcc gtagctctcc agggtgtcct cctgagagcc  10020
aagttttaga gaaggcagga tatcccctgt gggtcttcag gggtctctca ggaagaggaa  10080
aggccacaca cagagcatat gagagctatg agggaagaca ggcaaggcag accatttcag  10140
atgagtgggg agccataggg agaaggcagg agcatggtac ccaggaatga tgagcagctc  10200
agtgggttga agcttagaac agggcaggga aggctagcag ccaggcggga ggggagagtg  10260
gtagagggg gtggagctca cagatggatc gcttcctagc gtgactgaag gtttgtgaaa  10320
gataacctgt tgtgttgtgc ggcaggataa tgttgtcgct tagatgtgct gttcaggtgt  10380
ggctccgatg aggattatat gaggagtctt gtgaaccact tcttgggctg agtgcggaag  10440
ttccgggtca agccaagaag actctggact cattgacttc tcccttccag ttttataact  10500
ttttcattct cctgccctta ggatctggct ccttcactga tgtccgaaca gctatttacc  10560
aaccgcagac tcaccccag cccgctccct acggccactg tgtcaccgac agtggtgtgg  10620
tctactctgt gggaatgcag tggctgaagt cgcaaggaaa caagcaaatg ctgtgcacgt  10680
gcctgggcaa tggcgtcagc tgccaggaga caggtaggca ccatctgccc acggatgcca  10740
gaggacctac attcagtgtc tgcagtatct tagctgttcg taaaaaaaaa tgtaaaacca  10800
taaatccaga aaagtttata atcctgtgat aaaaatcata gtagctgaca ttttcttctc  10860
tggtcttttt ttttttttt ggttttttga dacagggttt ctctgtgtat ccctggctgt  10920
ggccttgaac tcagaaatcc ccctgcctct gcttcctgaa tgctgggatt aaaggcgtgt  10980
gccaccacgc ccggctcttc tctagtatta aacttgtat attttcttcc tatcatgagg  11040
atcaaactgc tttgtagtat ctgtatttgc cgaaagggat gctgcaagaa caccattttt  11100
ttcctgtttg ttttgtttt ttctcaacta gccaataatc tgtactctga gttcaatttg  11160
gaattataga tgtctttag cagcacatgg cctcttctgg gtcaaacatg ctctctttta  11220
taattgtttt tctagagcag ccatatatac tgtttcttct gagaatgtaa gcaagcatgt  11280
atcgctctgt gccgtcttca aatcataata atttgtatta ataaagcttt acaagtgggg  11340
aaactgagtc acggtagcag aagtgtctcc caaagacatt aaaaggagaa ctctggctca  11400
cccttaacca gctgactaga cttttcatct tggcccttta gtagcacagt ttccatttaa  11460
attagaaatt tgtcaccact ggggtcagag gtgagggtgg gaaacaactg tactgactga  11520
gactcttggt tatgcttgta gccgtgaccc agacttatgg tggcaattca aacggggagc  11580
cctgtgtcct cccgttcacc tacaacggta ggaccttcta ttcctgcacc accgaagggc  11640
ggcaagacgg acatctgtgg tgtagcacaa cttccaatta cgaacaagac cagaagtatt  11700
ccttctgcac agaccatgcg ggtgagtgtc ctgggaggaa ccagagaggg cggtcgtctg  11760
tctgtccttg ccgtgcacac ccttctgtgt gccagcagtc agtcagtcat tccgaggctg  11820
cacgggaact atagctttga tctatttgaa cccacagcta atcccttagc agaggcaggc  11880
agtttccatg tcccttagcg ccactgggga aatgtcactg agggaaaagc cctatggttt  11940
gattatttcg acacatgggg attatgatgt gattaaagac actcaagtat tgaaatcagt  12000
ggatgatccc acagagccga tgaacacaca ggataaatgt caagggtgcc ggtacttatc  12060
```

```
ttctgtgtag agtcgaattt tacacaaagc tatcatttaa tcttttttt  ccccccttgg  12120 ctgggaaaat gagaaaacat gagatttaaa tctattttga aagtgaagat gaaaatccac  12180
taagaagctt agggctgtat tatcagatat cttttattt  gtggataggc cctctgggac  12240
ttaacagccg gaacctggct ctgtctaagc ctgcggtagt ctctccttgt cgtacacaac  12300
acagctcagc tgtaatcttc gggtttgtgt gttgtcttgg gcagttttgg ttcagactcg  12360
aggcggaaat tccaatggtg ctctgtgcca cttcccttc  ctgtacaaca accggaatta  12420
caccgactgt acttctgagg gtcgcaggga caacatgaaa tggtgcggca ccacccagaa  12480
ctacgatgcc gatcagaagt ttggattctg cccaatggct ggtaagagga agccctgtga  12540
gttatgggtg tggacccgct agcagcctgt tgatggtctg ggagagtacg atgtgcatct  12600
atgtattata tcttcatttt gcaaattgag aaaactgtca atggcaatgt attctggcaa  12660
atacagagct gtcctcattt tacctggata cagaaagagg aatcagggat tgcttattgt  12720
ttttaagttt cgagagtccg gtagaagaca tcttttccag ttgtagaacc aatagcctga  12780
gggtcatgga gagtcatgtg ctcagacgca aggaaactac acttttgtt  ttctcatttt  12840 caacagaaga tgacattggg tttaagaggg acagtcactt ttacctggga ttttatgctc  12900
acagtttccc tttgaacttg agtgaaccag gtgaagtcac aaggctatag ttaaatccag  12960
tcctctagac aacgagaatc aatgagtata tgagattttc ctagtctaat cttcttcagc  13020
ccttttggta tttctctcca atctcctctg gaccggttct ttcctggaga gttcaaaact  13080
ccaccttcat ccagctacat gcatgcaagt cttcttccca aaggagagag aattgtcagg  13140
attatcaaac aagactgcta tcttcacata actatccatt tgtattccat ggctgtttac  13200
caagtgtttc tcctccattt ccaaccagcc cacgaggaga tctgcacaac caatgaaggg  13260
gtcatgtatc gcattgggga tcagtgggat aagcagcatg acctgggcca catgatgagg  13320
tgcacgtgtg tggggaacgg tcgtggagaa tgggcctgca tccctactc  ccagctccga  13380 ggtatgctgt tgtgttgacc agagagtttg tgtgaaagcc tgtagttgca aaagcagaga  13440
gggaagcatg cagtgtgtag ctatccactc acccgctgtg ctgaagaggt ctcttgattc  13500
caggagcccg ctgagaaaag ctggcgagtg agttgaatag ttctagggct ctggaaatat  13560
tctcaggatg taagcatta  ggttgagcca aaaggatggc tttcccaaag agagatcaat  13620
atttgaaatc ctttagctc  aaggttctgc ccgtgtttat gtctagagaa gatggtatca  13680
tttctccaag ccggggtgg  ggggggtggg ggggtggga  gggcgggaa  tggatggata  13740 ttttctattt gtcaaattta aggtgatgaa tacatcacat cctcagacta atttctttt   13800 ttcaaatcag cttttttcc  cctttggact cagatgtgtg ataggaggag ctgttaatgt  13860
attaaagcaa tttcagcttc tttgattgga aaagtaacat ttaggtggaa ctcagtgggt  13920
aaacagttcc catagccagt ccataaacag tgcgccctac attgattcct ttaatggtgt  13980
ccaatggcta gagatatctg ggagtcctct ttgttactta gaacattcca gagcaggagg  14040
aaaactaata agacatgcaa aacagccctt agtttgacag atgagaaaat ggggtcccaa  14100
agatagaatg taacttattc gggatttctc attgagtgag gaacagcatt gatttacatt  14160
ctaaaacttt ctgaacatca cagatgtcat tgtatttccc agatccaatt accttctgtc  14220
ttaggcttct attgctgtgg aacaccatga gcaaaaccaa accaaaccca accaaaccaa  14280
accatcttgg ggaggaaaag gttaatttta gcttacacct ttcaggccac agtccatcac  14340
tggggagagt cagggcagga agtcaaggca ggcatctgga ggtaggaact gaagcagcag  14400
aggcccacca gaccgaggag cccagcttac aggcttgctc tcccctgact tgttcaacct  14460
```

```
cctttgttat atagctcagg actacctgcc caggggtaac actacctgcc tgccatggac   14520
tgggtcctcc tccagttaac cactcatcaa atcagttcct cccagactgg cctgcaggcc   14580
agtgttgtgc agacagtttt ctcaatcgag attctctcat ctcagatctg tgtagattat   14640
gtcaagttgg taaaacccaa ccagcgcaca ctgctctcca tcccagaaag gagactacca   14700
catggtggtg tatgctatgt aaatttctct cttcgtctta gggtaacaac caaaaattta   14760
actaaaatca tcaactaaat gaggatgtta gaggaactaa ggcatgcctt tgttgagaaa   14820
ttagtttctc cacaggaaac tatattttac catggctttt agtttaatgg actgtaatcc   14880
ctgacaatta caagtctatt agtcagaata agagggagt aaaaattaat attattaagc   14940
tttgaaaaaa agattattct gtgccagtag aaaatgtatt ttagcaggtg ttaaatccag   15000
cagtagaact gactgccttg aaaaaatgca gtttcttttg atttcattag tcaaagctta   15060
tcactcaccc aactgttccc tggacagacc agtgcatcgt tgatgacatt acttacaatg   15120
tgaacgacac gttccacaag cgtcacgagg agggacatat gctgaactgt acctgctttg   15180
gtcagggccg gggcagatgg aagtgtgacc ccattggtaa gtggccgcct ctgcttggtt   15240
ggttttcacc gaggacgttg gctggttggt tggttggttg gttggccact tgcagataag   15300
gaaagctatt tggtatcgcc agacttcctt ctctccaaac ctgcctcatc catcagtctg   15360
cagagagcct tgcaaatgtg ttggtaacaa gggtggcttt actgcagtga gtgagtgggg   15420
ttagctttgt tggttctgag tcatgacaaa ggaagtttcg ttactgactg cagaaaagaa   15480
acatgggtat aggactcagc cagtagatgc ctgcctccgg ccaaaacact tcagcttttg   15540
cctctctgta caataagtag ataaatagat agggctgggc catcactgag cgatcaacat   15600
taaaaggagc ctattcccca aatccaaagt ttaagataat cagttcttac tcctttactg   15660
aaggaggcag actgcttact gagacagcaa attgatccca gcagtttgtt cggcctgcga   15720
ttgtaaagcc gagaggtccc gggaggcttg cttagaaagc tgttcatgct ttaaatttag   15780
ctcattaatg taaagctacc tactgaattc cgaagaagta cacaaaatga aatcattgca   15840
aagttctttt cttatttac agatggcaag ttttaaaact tttaattggt atctagtttc   15900
ctaaaattaa ttttcagatt ttggctatat gctgaaattt taatctttac attttttta   15960 aatttagcaa tgtttcccct gtaggacacc aaatatcctt cccaaaaggt acattttaat   16020
tttaacgact aattttccca taaggtaaat gacttgaata aaatattact ttaggactgg   16080
ggaaatggtt tcacacaaca tatgcacgta tctcacacac aagcacatat cacacacaca   16140
aacacataca cttataactt actttaacta tatttgtaag aactggaatt tttatattca   16200
tactttaaga atacacttca tcacactaca gtgatgtgtt tgaggctgtt ttaatctttt   16260
ctttgtgttt gttttagacc agtgccaaga ttcagagacc cggacatttt accagattgg   16320
tgactcctgg gagaagtttg tgcatggtgt ccgataccag tgttactgct acggccgtgg   16380
catcggggag tggcactgtc aacctctgca gacctaccca ggtaagtagc tctgagacag   16440
aagcagaccc atggatgcca gtctatgcta ctatttggaa tcccagtggg ggccttgctc   16500
tgtcccatcc cttttcatat tactgtctaa tagttaattg cattttttgtc ttaaattgtt   16560 ttatttcacc cttcatcagg gaaaaatcac caaagactat gaaaaagtgc atgctacaat   16620
tttgcatttt acacagttga ggactccatt aggtgaaaac atttcagttc attttatctc   16680
agtcctgtgt gtgtgtgtgt gtgtatctgt gcttgtgcaa acacatgtgt ggatgtgtgt   16740
atgtatgtgc acatgcatgc gtgtgcatgt gtgtacatgt gtgagtgagt gtgtgtgcct   16800
```

```
gtgtttgtga gtgtacatgt gtgtgcacat gcgcatacat gggcatgcat gcttgcattc   16860
gtgcatgtgt atgtgtgtgt gttcaagtag agccataaag taactcagac tggaagtgaa   16920
agagttttac attctgtttc ttaaagagaa gtcacatcga cagaaggcaa gaagtacagt   16980
atgaggcata aatttgtttc ctgccatctt aagcccttct ttgtgtcaga tttcatttgt   17040
ttagtgagat gtaatgtgga acaaaatctg gagccaagaa acttggtcaa ctccacccac   17100
accgttcgaa taccttaaaa tatttattgt ggttttgttg ttgatattta ttgctaggtt   17160
ctcattgttt tgtttggttg ttgtttgttc tcccatagag acatcatgcc tagccatagg   17220
cattaattca ttttggggaa aacatttaaa attcacacgt tgattatgag tgccatttca   17280
gcagactcct agatttccgt taatgattta tttatttatc tgtatgtgtg tgggagagggc   17340 actgggtcac agcacatacg tgaaggtcag agtggacttt gaagttcttt cttcacacac   17400
gattctttat gtggggatca gactcaggtc tacaggcttg tgggaggcga gcaccttacc   17460
ctgagccatc ttgctggccc aaatttaaga catgaaatac cacctgtatt cagaaacaaa   17520
aagatttggg gtgggggag ataatccaca agaatacaaa atattataat aataaattaa   17580
ctccataagt attaagatta aatactaaga ttaaactaat cttcctaaga gtgtcccaaa   17640
gtgaacgatg agagcccaag gcagtgtgag tcctcgctct gactgtgctg tgagagagat   17700
actagttaac ttctcctgtg gacaaaggga gacttgctaa ccacctttaa aattgcttcc   17760
agtccttcac taacagtcag agacccagag cacccgtcca ccactcatgc aatcatgttt   17820
tgtttgtttt tcaatgacag ggtttcactg tgtaactctg gctactttgt ggaccaggct   17880
ggcctcagac tcatagagat ccacctgcct cttcctccca agtgctggga ttagagttgc   17940
atgcctccca tatccagaat acgctcattg ttttatgtg ctggggacat cctcctccgc   18000 tcagcccttta gacattgtca gggtaggata ggtgattgct tccgcaacta tgtagctcag   18060
agcagcctgc attttgctg gactttggtt taagagtgag ttacttgccg ggcgtggtgg   18120
cgcatgcctt taattccagc acttaggagg cagaggcagg cggatttctg agttcaaggc   18180
cagcctagtc tacaaagtga gttccaggac agccagggct ataacaaagg aaccctgtct   18240
cgaaaaacaa aacaaaacaa aacaaaacaa aacaaaacca agagtgagtt acttaacatt   18300
tttaaaaatt gaatccagtt gctttgtttt gcttttgag tctcatctag ccctgggtgg   18360
cctcaaactt actatgtagc caatgatgac cttgaacttc tgaccatgcc tcctgtctct   18420
tgtttccaaa aggctggggt cacaggtgtg cacattacac ctggtcaact taatatagtt   18480
taaaaatctg attacaaatg agccataaat tcagaaaaca catatttagg aggattggat   18540
tttccaatga tacaagccaa gaatagaagt ttatttttgt gttcacagtc agttttttgca   18600 gggcaatttt tgaaatttat tttcttttaa gaccttttct tttaaaaata agtctattca   18660
catatatctt gctgcaagca ttgagggtag atctgctgat ggacaggaag agtcacctag   18720
cgggagtttt acctgttgac tttgttccct gtttctaaaa agggcaatgt caaaaaccca   18780
ttgaacacag aagagatttc agggcaagcg gatgagtgtt tgaccctaga tagcaggctc   18840
agtgtttatc tcaatggagg ctttgctcaa gggctcatgc ctagcctttg aggctccgat   18900
ggctgaaaga ccgtgtctga gccttgccct gtttgttctt cctactaggt tggtagagat   18960
gttcaaacta acaaaaggta gcaggaattt ggtttgtcaa taagcaacca ggaaagcaca   19020
gctctcagca aattaggtag agaaagaacc tttcgggtca aaaaaaatca tgaatgttta   19080
acttctccag ggtcactatt atcggaaatc actcttctg accttactgt caactgattt   19140
tgaaagtgta taatgtggca ccctacaagt gaagatctca cagtgggcat tgctattaga   19200
```

```
agtgtaaaag gtccagggag gtggatggtc gggatcacac aactagccag catcaaaggg    19260
gatataaaaa cacttcaatt taagtagtgt aaatgatagc tagcctttt ttaacttc      19320 ccatctttaa atcatgtgtt gtagtgtaga gtatagtgga gagctggaat ttaattgacc    19380
tagaaaacag atgaggggtt ttccttcttc cttccttcct tccttccttc cttcttcct    19440 tccttccttc cttccttcct tccttccttc ccattcctgc acagaaatgc tttaaatccc    19500
ctttgccatt cagggcagtc acttgaaggt ggaccctgtc atcatcttag gggcctggag    19560
agctgagagc tcagaggttg tagtccctac gcagtttaat tcccatccct cccattagac    19620
agcacaattg ctgaaccttc agctcagggg acccatgcct ctgtctcctg ccggcacccg    19680
tactctctca tatgtaggca ttttaaaaat taaaattaaa aataatggga tttcagatct    19740
gcgctgaaag gctgagaaag gaaatgaagt tctgagtcac ttgggttaac cattgcgagc    19800
atctttccct ccctcccttt cccgcgtctt ctgtcaccct tgtgaacaca gggtttgatg    19860
actggacaga cagtaaatgt catttatatt ctcttaataa tagatttatc aaggagattt    19920
agttatcaca agttttccag cctcaaattc agtaaataag atgcatgaga catgtctatc    19980
tacctgagag attatactag gatttttcta aaacagcaat atttaacagc ttatgcaga     20040 ttgtcactaa taacataagg tctgttttta ctgattcata tgaaacctct ttaaatagtg    20100
tttgaaagaa atgttttaa tgtatttgta tttgtgaggc tcttcatcta tggaaggagc    20160
tattccagag ggctgtgcaa tggacttgag ttgattaatg ggacaaccaa cctgtgtggc    20220
gcgtgggtcc tatgcccctt aggatgcaaa gatgagaatt ttgacatttc agcttgtagc    20280
attaagtgaa atcaagactc aatgaatatg tgttagtctt caacaagctg agttattccc    20340
aatgaagaag ttgagttcaa aatcttttga ggtcacataa atatgtaagt tacatattta    20400
ttctgctaaa gaagattttg ctttaaaga atttagaagc ttaagaccat aattaaatct    20460
gaaagtcaat atatttttc caagagcact cagaaatcgc aggtagtgta gagaactcct    20520
ttatcagcat gcagaattt cttctgtctc acagagcatc agtgagaact ttgtgtctta    20580 ggttttgta aggactttgt acaaatggat tttgactgac aaagaattag agagaagata    20640
aatttccatt ctgtaaacag agttttgat aaaatttcat tattatccta aatggaatct    20700
actatattaa aaaattgatt cccttctctt atttgcctt ttttttcccc ccaaggaaaa    20760
aacctgaatc tatcttaaat tttgttaata acagtcatat caagatctga aaatactgaa    20820
ttttaaatat atgctttcaa atgtcatttc aattgatgat tgcttaaaaa gatttttt    20880 ttgaacaatt cgctcacagt ggctttaaga gtgtacttaa gtaaatgtaa aacgaacaaa    20940
caaacaaaaa cactaaagga gagaaggctt agactgatgg ggaaataaac cttgggcttt    21000
aattattacc tctgtctgtt tgtccggatt cagccccatt tagaaatgtt tgttttgtgt    21060
cacgccgtaa ggccttggga tcattgcttc tgagcagagt cctctgtccc gaaagcctcc    21120
atgattcgga atttgtctta caagagcctt catgtaatta gcacatgagg tctgtattct    21180
gagctacatt cttcgtgtta aggaaattc acagttgtcc cacgtcttac tttgaaagcc    21240
agagaagaag gcaagctatg agacactgga gtggtttctc tcgtatttat tagaaaaaga    21300
attctaattg cttttcttat gggaaaggca atgattacca ggtcaaatca gactgtgctt    21360
tttcttcagc taatgtcaca atgtagaagg tttaactaga ctctttgccc acatttcccg    21420
agaagcgaaa agtctttaag gatggacatc catgttttgt aaaactttaa gaccacacaa    21480
gctaaagaga tggcatgttt tcattttcag gcacaactgg acctgtccaa gtaattatca    21540
```

```
cggagacccc cagccagccc aattcccacc ccatccagtg gaatgccccg gagccttcac   21600
acatcaccaa gtacattctc agatggagac ctgtgagtaa tagctccgca gccttggact   21660
ctgacccctg acctgatggg actaggatgt gttgccctct gggtttgtta ctgcttttga   21720
gtcgacagat ctgatgccat gtcgaacagt gctgacattt attttcttag tgtctagcca   21780
atatgtagtt agtcgaatca acatgtagat tcagggtttt ttgattgttt ttggtttttt   21840
tgttttgata tgtagaagaa attaaattag gcctttggct taggaaaatc ttagaagcca   21900
taatgctaac aactattctc atccaatgtg gaaagaaaat ttgaaatttt ggtatccatt   21960
tgcaatgtca ttaaaattaa aatcacattt tcaagttatt tccagagttt aaaaccagct   22020
aaatgaacat cgttcttttg actcaactca gttgtcctgt agtcctcttg agttgtgtag   22080
acagaaggga atgaggtatt gagagaagga ggagcgggga agggtttata tttggtttct   22140
aaaaggaccc ccaaacccta gcgttttcta accatccaga tgccaaaacc atagcaagga   22200
gtctctcata ttagtctatt aacccttgat gtctcgtccc ttctcagact tgccctcttc   22260
catctccaaa gtttatgaca gaatttaaaa ccactacttc agaaggaga aatgcacttt   22320 taaaaatcaa atctactcaa ttgaactatt attaatccta gactacaaca acctgtctga   22380
cttaggacgt caactcactc ggtcgaattt aaactcttgg ggaattccat tctgctgagc   22440
tcactctttt ccttcagccg tcccatgttg tcactacaaa tgaggcattt ataaataggt   22500
ttcgaaatac acatttgagtt gaggcgtctt cacatttgat taaactctca gcaaacattt   22560
tagcttcggt tttgttgtgt ttcgttttga gatgatgacc ccattaggcc aagactgact   22620
tcatattctt acgtagctca cgttgatctc cctgctgagt gcttgattat aggttcagct   22680
cccccttggt atgtgatgct agggactgaa ctcaggactt tggccacctt taggcaagtg   22740
ctctgccaac cgagccgcat ccatggctct gaaaatttaa aaagaatttc tgttgtttcg   22800
tttttttaaa tgtaggccat ctgagagttt atattctcat attttcttct gatggccaat   22860
tgctaatttt taagctaaca aaatggctaa cttcaatttc tttcagcata tttgagctaa   22920
aactaaagat taaagagaac ttgcttggat сактттtatt tatctccaaa ataaaaaacc   22980
gggcattaga acatttgaag tatgtacaaa cttgattaga taacattaaa aaaaaaaatc   23040
actgggcatt aaccatgtat ttgatattta aaccgcttta gaatatttac acttaaaagg   23100
atttcttgtt tgaagtctgg gtgtttcttt tccacacaat ctattgcaat gagttctgtg   23160
gtccatgaca tattaatgaa gctggacagg atataaaaat gtaaactgga ggggggaagat   23220 taaacaaacc gaaccctatt cttctgcagt ctttcccaga gttggctaac gactcttgat   23280
gggtcgttca tttccaagga tgagtcacgc caccagacac gttgaacctt gtttgtgatg   23340
gccccaggat ctgagtccag gcaatgttat tatacttttc agtgtctcgc gaggcaagaa   23400
gcttgaaatg tatcccacca agttgaaaga tagagcgtga ggccttttct cacttcagaa   23460
gagagacgtg cctctgttta ccacaaaagt ctagaggctg aattgatggc gctggtctta   23520
aatgattcga ggcctcaagt gtgtaacttt gaaaacctca tttctccacc tgtaaagtgc   23580
agtgaggcac ttcacttccg gcaggaaggt gaagatcagg gggagaaaca aacaagcaaa   23640
acagccctga gtgcttggtc aaccacttgg acgaataatt aattaacatc gacaaactgt   23700
agaggccctg ttcccagtca ggttttccac catctttctt ccaaaacaga gcctcgagaa   23760
tcctatctat cctccattct tctttgaaga tgactaacca ccgcttttt tttcctttta   23820 catattcaga aaacctctac gggtcgctgg aaggaagcta ccattcctgg ccaccttaac   23880
tcctatacca tcaaaggcct gaccccaggt gtgatctatg agggacagct catcagcatc   23940
```

```
cagcagtatg gccacagaga agtgacacgc ttcgacttca ccaccagcgc cagcacccct   24000
gtgaccagta cgtagccagc atctgttggg gctgtgcctg cactgctcag acgtgggttc   24060
cccagagaag gttctgtcct tagctgcttc tttgctcgga tggtgaacat cctctgaaca   24120
cagagagcgt gggtattcca gataatcaaa ggctcttgtc ccctgctccc attcctctag   24180
gcaacacggt gaccggagag actgcgccct actctcctgt tgtggccact tctgaatctg   24240
taactgaaat cacagccagc agctttgtgg tctcatgggt ctcagcctcc gacaccgtgt   24300
caggcttccg ggtggagtat gagctgagcg aggagggaga tgaaccacag taccttggta   24360
agtagaatgt ctggcttcct cggctcgtgt ttctagatac ttacttggct cgcaggagtt   24420
ttgattccgg aacgcctcca cagttcaaac ggaagacggt ccctttcatc agagccagga   24480
gagaggtgac tcctctctgg ccaggctggg attccctggg caccttttgtg gcctctggtg   24540 ctgtgtattt ctcatagcca tggaaggggg accaggatga ggcctatggc tgacaatgtt   24600
atcctttagg ggtgcggagt taccttcttg tttactttta aaatagccca gtgatgaggg   24660
ggtctttaaa aatatttgct ggtgccagtg aggcggctca gtgagtaaag gccctcaccc   24720
ctaagcctta taacccaagt tcaccctcca gtctgacctc catcacgtgt gtacgccccc   24780 ccccaccaa tgtaataatg agaagatact gaacatacat gtgaatagga cccagatcat   24840 aaaatgaat ctccttccaa cccctgccct gtcatccttc cttccaccat ggctactact   24900
ctgatatcta atgacagctc tgtttttaaaa aacaaaaaaa cagagagatg ttattaaaaa   24960
ttatacatct tcgggggtgg gggaaagtgg aaaatgaaag aacttactta cattggaaat   25020
tgcaggctat tcactagaac atttctcgtg ggctttcacc ctctgagtat agcgctctta   25080
gaagccgtgg aagattggtt tgctcaggcc actaaccttt gccctgtatt ttaaagatct   25140
cccaagcacg gccacttccg tgaacattcc tgacctgctc ccgggcagaa agtacattgt   25200
caatgtctat cagatatctg aggagggaaa acagagcttg atcctgtcta cctcacagac   25260
tacaggtatg tgggcaccca gccatgataa aagcaacttt aggtatgggg tatggtggta   25320
tggtgggtga tacgatacat acatacatca taatcacaca tacttacact catacataca   25380
gctttgggat gctgagggta gagatccagg ctagcctgca gtaagaacca ctgttttaaa   25440
aaacaaattt ttgaagactc tttttgtttt tctgtaacgc gtgggcttgt agcaacactg   25500
actgatttcc tttcttcttc tttcagcacc tgacgctcct ccagaccta ccgtggacca   25560 ggttgatgat acttccattg ttgttcggtg gagtagaccc caggcaccta tcacaggtca   25620
tccttggctt ctgtgtttct tttgatgtat agatgtggaa ggggaaaatt ctgatcacac   25680
tggtaccacc ttaaatcttc cattttaagt ggttggaggt gtgtgtgcat gtgtgtgcat   25740
gtgtgagtgc gtgcgtgggt gtgtccactt caaatcttcc agggattctt cgttttgat   25800 tcgttttcct tcaagtctgt tcacacgccc ccattcctaa tacctgcatc tgcaacctat   25860
aaggccagcc ccgctgttca ctgcagtggg cagttcccgg gctgtacagg tgggtgattc   25920
ctgcagagct gctgctcact gctgaagagg gagctgagtc gccgctctag cttcaccagt   25980
gaagttccca aaggtgcaaa cactgctcag gctgattcca ttcctctgct ccgagaaggg   26040
aaagccgcta gtactatgaa tgtctcacgt catggcatca cttactgaca ttcattaagg   26100
atctctgggt tcaaggatgc tatttgatta ttaaaagctt cctatcaact tattcttatt   26160
tctgtgcccg tcaggcatta tcagaggaag tggtaacatt gaaagacccg gaaagaatct   26220
tgctgattct tagccatgag aaaggagagt tataatttgt ctagcctccg cttctgaaga   26280
```

```
ccatgtgtct aaacgctgtt ctcctaaacc tgcagggtat agaattgtct attcaccttc   26340
agtagaaggc agtagcacag agctcaacct ccctgaaacg gccaactccg tcaccctcag   26400
cgacctgcag cccggtgttc agtacaacat cactatctat gctgtggagg agaaccagga   26460
gagcacaccc gttttcatcc aacaagagac cactggcacc ccaagatctg gtaacttaaa   26520
aacagcccat tccctgatgt ctgatctctt aggactagac cagagagccg ctctaacctt   26580
ccaggggaag ataaagccca cgtggattag actcattctt tagccttcag ggaggactga   26640
ggtgcaggtc acgtgggtga cagatccctg agagggagct gtttttgtct ttgccagctc   26700
tttctatgtc ccccatcacc caaatcaatg gctctcaccc ttcctaatgc tgtggtgacc   26760
cccaactata aaattagtgt catgctgctc tatagccaca ctgtcgtgaa tcataatgta   26820
agtatctgtg tagaattctg atggtcttag gtgacccctg tgaaagggtc atctgccacc   26880
aaagggtct caactcacag gttgagaact accgagttaa atgctaaaat gtcagcactt    26940
ggaaggaatt tatttatcca aggcaactat tgggttttct ggttaaaaac tcacagcatc   27000
tcctctttct tttcctggga ggcttaagaa ttactgttct cttaactacc attttcttaa   27060
gaaaatctgt tctcttaact accataaaat gagtcagtta acaaacaca ccagctgtct    27120
tgtaaagtga aaacatttat ttttgtatat tattttaact tggttttatg ttataacatg   27180
cctatctata gatactaaat agagattcca atatcagttt gactaaccat gagtatacac   27240
acacacacac acacacacac acacacacac acacacacac atttattttt tgattaagag   27300
gcaaagccca gtattggcct agaatgagtg ggtctaagag atggcggaat tgttcaggga   27360
gctaacttct agcatcaacc ttcagtggga attgtgactg actgactcat cgctcttgtc   27420
tgctagataa cgtcccccct ccgacggacc tacagtttgt ggaactgact gatgtgaaag   27480
tcaccatcat gtgaccccct cctgatagtg tggtgtctgg ataccgtgtg gaggtcctgc   27540
ctgtcagcct gcccggggaa catgggcaga ggctgcctgt caacagaaat acctttgctg   27600
aaatcactgg gctgtcccct ggggtcacgt acctcttcaa agtctttgct gtgcaccagg   27660
gcagggaaag caatcctctg acggcacaac agaccaccag tacgttccag gcctgcctgc   27720
ctgtcttgtg gcccctcct tccagctctg aaccctcagc tctacctggg ataactccat    27780
agcatgctgc tcactcccag gttcacagct cagcagttag ggaacatcga gttgaaagga   27840
atgttgaagg tggaatgaaa ctagcgttct gagaatgctg actccaacat acatgcttcc   27900
aacacgcatg tcatgtccaa catgctcact gctggagtta gagttttctt tgctaatgga   27960
gatgcaattt cagtgctttt gtctctctgt ttcccctccc ttcttccctc ctccttccct   28020
cttttttctt ccttccctcc ctccctttct ccctcccttc ccttccctta accttccttt   28080
ctttaagctg tgaatcaaaa aatgctctac cactatacaa catccccagc ccttaagtgc   28140
attttttaaaa aatatatggc cgggcgtggt ggtgcacgcc tttaatccca gcactcggga   28200
ggcagaggca ggcggatttc tgagttggag gccagcctgg tctacaaagt gagttccagg   28260
acagccaggg ctacacagag aaaccctgtc tcgaaaaacc aaagggaaaa aaaaatatat   28320
gtagttagat atagtagaat tcatttgagg ctagcagttg ccaggcagca gggtgtgtaa   28380
atgtatgtct gggatgtgtg aggccctggg ttctctctct agcaccacac aacgagttga   28440
taccttaagt aattcatcct aaacatttag tggccctggg cagcgaggta tcatctattt   28500
agctctttat cagcagaacc tggctggctc ttaagtcttt agctgacatg tgcaagggaa   28560
aatgctactt ctgttggatg tgggaagaga cctaaggtct tccctgagga agtgacagtg   28620
gtttggattc caaagctcat gtatgttctc aattacactc gaccacctct ggaaggttct   28680
```

```
ttctatcaaa gatgttctaa cttcctatgg gaggcccagt tatcatcctt agaaagaaga    28740
aaaatggtga tctatgtgat tctttctgat actccatggg actggggttc tgcccatctg    28800
ttttagttat tgtaattaga tccatgtgag gcagctttta tttctccagc agaggttagg    28860
tcagccaatg aacatacacg ttagcatatt gcctgcagga cccatggagc ttttcttgcc    28920
ctaactctgt tggacttagc cccctccctt aacctttctg gcccaaaaca aattgtgggg    28980
tttgcaaaat gtttgttttg ctttagaaaa aaaaaagtaa tactgttatt ataatgtgac    29040
tataatttcc aagggtggtg ggtaaatctt tactgggaaa agtagccttt ccaaaggatg    29100
atagacaagt gaaaagggtc aacgaatttt cataactgat aaagtttcgg caaaattcta    29160
cactatcctg agtctcccag agccccacgg tatccagggc tgtggctctg actttagttc    29220
caaccttgag taagggagct tgggatgctt aatcaagcgg gaggatttcc gcatggctgt    29280
tactgatcta aacgtttctt gacacatttc atcttatttt ttccccagaa ctcgacgctc    29340
ccactaacct ccagtttgtc aatgaaactg acagaacagt tctggtaacg tggactccac    29400
ctcgagcccg tatagcaggc taccgactga ccgcgggcct gacccgagga ggccagccca    29460
agcagtacaa tgtgggaccc ttggcctcca agtatcccct gagaaatctg cagcctgggt    29520
ctgagtacac cgtgaccttg gtgctgtgaa agggaaccag gcagagtccc aaagccaccg    29580
gagtctttac tacccgtaag ctaaaattca aatgccttgc tttcgtgaag ctagagttct    29640
caattaactc ttggctttt ctgtccttt gcttttcaaa agtgaaccta aaaagccctg    29700
gtgcaccatt taaagccgcc ccattgaagg tgtgccccat ggacaggctg gtgttctctg    29760
agtatttctt gctggtctgc tgtaacatac acagctttgc cagcgtgggc agcacagttc    29820
gtggcctttg cccgggctga taagtgcttg atgaagataa cagtgtgtta atttgcaggt    29880
atttccaggt tctttctatc tttctgggct aacactatga gtcaggagga cttgggaggt    29940
agctcagtgg ataaaacaag tgcggctaac acatgagggc cagagttcgg atccctggca    30000
tggacataaa aggccaggtg ctttggtgga taattgtaat cctagcactg agagacagag    30060
acaagaggat ctggaggctc acagccagtg ttgctgatca gtagctccag gttctccaaa    30120
aatccaccgc cgaggctggt gtggcggcgt acgctttat tcattcatcc cagcaagtgg    30180
gaggcaaaag caggcggatc tctgagtttg agaccagcct ggtctacata gcgagttcca    30240
gaacagtcag gactatatag aaagacccta tctcaaacaa acaaacaaac aaacaaaat    30300
acacaaacaa gaaacaaaaa agaaagaaag aaggaaaagg aaatatggtg gagactggtt    30360
aaggaagtca cacgaatcca tgggcgcata gactgaatac aaagtagaaa aggctgagta    30420
aatactagta gacagaatct aacccatatg catagctcca tcacatcact ctctagacat    30480
caactgagag tcatatatgt ttaaaaaaaa tccacccatg gactgaacag acatcagcaa    30540
atggaaagag aggttaagta tgtgacttcc ttgagagcct ggaccgcccg ccgaaggcta    30600
ccgtccttca cagcagagcc tggtttcctc ttccttaact ttctcttcca catcttccac    30660
acagaggaaa aagacaaggg ttttgggtat gactagcctt tgactcaata ttttagagga    30720
aatggcctta actctcttat ttatccacat tcccataaac tcctgtcttc acaagctgct    30780
ttcctcctac gtacactcca tttacatgac agagagctct gagacttatt tcttgctgag    30840
tacttgttat ttttttgact tgcgggtttg aattatagga ggacctaaca ataagcatgc    30900
tttgggcatt tatggccgtc tacctctggt tcccagcttt ccaggagctt tcagcaagtc    30960
ttgtttgcat taaaaagtaa tctaagccct gcatggtagc acatacctgc ctttagtgct    31020
```

```
atcacttggt aggtagactc aggtggatct ctctgagttc aaggccactc tggtcattag    31080
tgaggtctag aacagctagg gctaagcaaa gaggccctgt ctcaaaaaca aacaaataaa    31140
taaataagca acaatttaga aaaactgtca actgttcccc acaggaatct attgtttacc    31200
acaaacttct ttgcatgcac atttggtaat gtgaggttga acaccgaagg cctgtttttt    31260
cctacgaaac tgttcaccag caaatgaagt ctgctttcta gtttgcagac ttcttttta a   31320 atgtttggta tttgacattg cccagttttg agaaagtcta agatccactc ttacagaact    31380
agtatccttg tttttcttgc aaaacccatt tcttggagct gtcccttaaa ttaatgagca    31440
tggagtttct gtgcacacag cctcttactt ggcctcgtac ccgaggcttc tgggtgtaac    31500
agtaaaactg tatttgctga ccattaatta acataccgaa ttgcgtggag tatcctttcc    31560
aacacggtag ggtaggtgac tgaaagacaa atgagcagct caccgtggct cagatttaaa    31620
taaaccagtg gaaccaagga gttaagcaaa tccatttgga cctcagatag tcttggtata    31680
aacatgagca gggcctagga actttggttt ctgatgcttt accaaaatta agttttggaa    31740
acaaccagtt ttctgacttt tatatctcat gctaaattct taagagcaac tgtgagaaaa    31800 gtgggggga a taagttattt atagaggagg aatccagcct ccttctgttt gggggcgtat    31860
gtcatttctc aacagccagg ttgttcctta cctaacaagc cctgccagag cccataattc    31920
atacttacag gcacatcctt tgtttgacaa cactttgtgg gtttgtggct tggtgatttt    31980
cctgtaatgg tcttgtctag gcaagagaat attgtctcaa acatgggca agatttagct     32040 gcttggctga cgcaatagaa aatgcctagg tgtgaaaatg gacagttctg aattgcagga    32100
gcagtatttg gtcctaattg ctgaacattc tctccaggct gttaaaaagt tagaattttc    32160 agcccggca t tggtggcgca cgcctttaat cccagcactc gggaggcaga ggcaggcgga    32220
tttctgagtt cgaggccagc ctggtctata gagtgagttc caggacagcc agggctaca    32280 cagagaaact ctgtctcgaa aaacaaaaa caaacaaaa caaaaaagt tagaattttc       32340 agtagaagaa atgatggtgg tgtcaggata ctagaatacc aagcatacta gttataattt    32400
ctatgtctag tggtcaggta ttaagtgtct gtagcatttt tgtttgaatg atcaaccaca    32460
tgttggagga atggatcttt gatgttgatg ataagatccc caaatcatga aaagatacag    32520
atcataaggc ccaagaaatt aaaaggagct tccattgagg tgagcgagcc cctcttttcta   32580 ctacctgtga gtgacaggtc tctgccagaa attcaagccc cagcccaaac aaagctggac    32640
ctgcagaatc accaccctcg gccccctt cc cgggtctcac caggtcctgg gtgccttgaa    32700
gcagttcaac ttcttagccg atgaatgcac cttagctaca ttctctgtgt acttactggt    32760
tagaccaaag ctctgtttac aatgctcgtt aatctgcagt cctggcctac acctatgcgc    32820
ctaacgttga acctcatgtt ggttaatttg cagtgcagcc tctgcgctcc attccacctt    32880
acaacaccga ggtgacagag accacaattg tgatcacctg gaccccgct caaggattg     32940 gcttcaaggt gagtttcaga tgcacctctc atgatccagc ccaggggtgt ctttccattc    33000
ccactacact ttacagacct gggttttta a agttctatgc tcatactcca ggaccttctg    33060
agagcaaagc ctgcattgag gcttctctgt gttgcaaggg aagaaaacca tgagccatgg    33120
aactgtagtg ttgttctgtt ttctgtcctt ctccccaggg aactccattt taaaataaaa    33180
gtatagccaa acctcatttg atgtgttgct ctaaatgggt gtcgagaagc ttatgaaaac    33240
caatttggga agaccaatta aactgagagt cacttaaaaa tcacattttt atccaatcag    33300
tttcatctca acttgttcaa agccctgtgg gtgaatttct taatagaagt taaaattgag    33360
gtcttcgctt tagatatcca gagtcatgtt cctttaaagca gtgataccag ggacgtgatg    33420
```

```
gatacaaatg aatatgtttt ttaaaaagaa tcccatcctt aggcatccag aggataaaaa    33480
aaaaagagac acttattatg tctggaatca aagcctgatt gtttaaaaga gagaaaaaag    33540
aaatagaccg agggtcactc tgcttttag tatgcaaata gccatcttga tgagtgggct     33600
gctcaggtac agaggggacc tttatgaaga ccgccacggc accttttag tttcccttaa     33660 taatgtcgtt cagagtttta gaagccacag agaatctgaa gggtttctct ggagctgagt    33720
actgtttgat aatgtcacct aagcttttgt agttaggaac acacggacgt cttcgtggga    33780
atgtgttttt catttccgtg tgtcaaagtg gctgcagata acttattaaa gagagagcct    33840
agagcatttc ttccctgtgt actgctggta tgcaccagaa gggtttgtgt caaacagtta    33900
tactgacatt tctctagaac ctttctatta taaaggaccc tagtaccaaa ggaagatacc    33960
tccagctaat tgcaagatca ctaaagtgag ccctcaatgt gttatccacc cagtaaatgc    34020
agtgtggagt tgtaacggac ttccccctgt gtaaatctac aacctctcgg gatctctgga   34080
atattcatcc ttcatgctga ttttgctgtc ttccttccag ctgggtgtac gaccgagcca    34140
gggaggtgag gcaccccgag aagtgacttc agactctggg agcattgttg tgtctggctt    34200
gactccaggc gtggaataca cttacaccat ccaagtcctg cgagatggcc aggagagaga   34260
tgcaccgatt gtcaacagag tagtgacacg tgaggagagc cttccttctt cttttaactt    34320
gtaaactatt ttaaagatt gccaaagcca ggtgtggtag ggtgtgcctt taatcctagt     34380
gcttgggaaa gttaagaatg atgatgggag ttcaagacca gccaaaaact ggaggcggag    34440
ctgggtttta taatacacac ctctagtccc agtacttagg aagcagagag aggcagatat    34500
tggagaattt atggctagcc tggtctacat agtaagttct aggccaacca acagtgagag    34560 cctgtcccc caaaaagaa acatattcct ctaattattt gaatgttagc gtcccagctt      34620
tcttttgaga cagaacaagg gaagaacctc tctcttattt atatcagcag agtcttcaga    34680
actggatgta gtttagctgg tgtcatgcag gccacagaat tagaagtgtt ccttccatgt    34740
caaaagtctt ccaaactggc aagatgaaac aatttcagta gtgaattaca atagcgttaa    34800
tcctagagac cacctatcgg ggttactgtc gcctgtattt ttatagaata ctttatttc     34860 ccagtcctag agggaaggga taagaaagg caaaaaagga gggaggtgcg aggaaagaag     34920
ggtggagaga gggcgtagag gaaacatttc acaggccacg tgttctgtgt tcagtttaac    34980
ttttaagttt tcttttctgt tgtgtagcgc tgtctccacc gaccaacttg catctggagg    35040
caaaccctga cactggagtg cttactgtct cctgggagag gagcactacc ccaggtaaca    35100
aaggggagca ccaccctagg gaagcgtggg gcggatctga gagccgcgta cacataaggc    35160
tttcccaaga cagatttgga ttccattcag agaaagagag aaagcaagtg ctctgctctc    35220
catgagtgac agaggagaat gagagagttc atgaactacg tgtaaacacg gctgcatctt    35280
ttcttaactc gcaggaaaga gaacaatcaa atgctaggct gtggggcgg gggagactaa     35340 cgtttatact acagggaatt ttgagaggat tagatgaaa gaagattttg ttcagctcgt     35400
taaaaatgcc caaactgggg ctggagggat ggctcagcag ttcagagccc cagctgcctt    35460
tttcagagaa ccctggttca attcccagca cccacatggc agctcacaac tgtctgtaac    35520
tccagtttcc aggggatctg aaaccctcac acatgtaggc acaacacgca tgcacataat    35580
aaataaacaa acaagcaaat aacaaataaa taacaagtaa ataaatgaca aataaataaa    35640
taaatttaaa gccaattttt aaaggctgaa atcatagtct atagtccata aatcttaagt    35700
tgactgttta ctgaagtttg acagatcgct tggtatctgg gtggggctgg cttcagggtt    35760
```

```
cccattgatt ccaaactctg tagctgctca gccaattgca taaaatggtg ttgtgcttgc    35820
gtataaccta tacattgctt gcatacttca actatctgta ggttacttgt agcctaatag    35880
attgcaaatg ctgtggaagt cattgtccca ctggattgtt ttggggacag taacaagaaa    35940
gagtgcatgc atagcataga tccaaattat cttcaaccag tattttcttt taatccatgt    36000
tggttcagta tgcacatctg taacctatga atatgtaatg aattgaacca taagatgtat    36060
gagagacagg gatgggcaga ggctcacatg gggaagaaca tttgatgtgc atgcagaagg    36120
acatagttca tccccagcca ctaggcaaaa agctgggcgt ggctacacga gcagctatga    36180
ttcccctggg agacccgctg ccacaccttg ctacttgaga acatggtcaa tgggagccaa    36240
ctagttggag caatatttt agttcattat ttgattgttg ctaattttac tcattgatca    36300
tttttttttt tgagacaggg tttctctgta tagccctggc tgtcctggaa ctcactctat    36360
agaccaggct ggcctcaaac tcagaaatcc accttcctct gcctcccaag tgctgggatt    36420
aaaggcgtga gccaccatcg cccggtgata atggttttct aaaagtaacg tcaccccaac    36480
actaaggctg aggcaggagg attagcctgg tatatacagc aagtcttaat gctagcctgg    36540
agtcatagtg tgggctatgt cttgacaaaa ctatataaac tatatctgca tctatctcta    36600
tatattatat acatacacat atataatatc atcttaaagt acctttgtat gatggatgca    36660
tgcctacatg cattttcatg tgtctaagtt caggtggtac agtgtgtgta tggaggtcag    36720
aggataacct tcagtatacg tgactgcctt ccatcttctt taagacagtg agaccaatag    36780
cttctgggaa ctctcctgtc ttcacttccc aatgctctct agcaacattg gggatttcag    36840
acacgctctc gtgtctggct ttatgtggat tctggagata ggaactcagt caggtcctca    36900
tgagtacgtg gccaacagct tatccaccga gccaaatctt tagtctataa tttgtagcta    36960
taatctctta cactgttctt acccttgctc gggcgtaggt gtcaagcagt tatctataaa    37020
tgtgtgtgat tatagtcaca caaaataaaa ctagtttaaa atactccttt taatctcctt    37080
ttgaaataga cagactgagt gatgtttcct tctctgtggc aatgtattgt ataatgtgac    37140
agctacagtg tttccagata agtttctctg ggtttgaaac ttgaagctga caagttcttg    37200
cttctgggca gctggatcat caatctttgg tttcagtggc ctgcccattc aatggtcagg    37260
cgtaaagcaa atgaccgaaa tgttattgac ttcccatccc actgggtttc ctagcacata    37320
acacgttaat gttcacctc tccccactga caggatatac cctcattccc tgttctcagt    37380
gggtcagtct tgttctgtct tcttccagcc tggccctgca gagctctggc cactactaga    37440
tttattgata tctcctttcc tttaatgcct tcactgccca ttttcatga ttctgaagtc     37500 ttctatgatt aatatttgtt ttcgagaatg agcatctaca cttctgtgtt ctgtgccctc    37560
cagcccctac cccccccccc cccgttccc atagttcaaa cttttacact cttcggagaa    37620
tgtttaagtg gaaagcaacc tcagagcatt caaaaaaaaa aatgtagatt tcctagctct    37680
cccacaggtc gcccattaag gaaaacagg ataaatagt aaaagaggc tggaatttgt      37740 agacaggaaa ctctcaggtc ttctctaaga tttccttatc tttgttaaag gtcccatgat    37800
tttactttgt agttaacaca tttatatggg ttgtaagatc gcccaatgga tgcaatgtag    37860
aatgatcgag ttagcatttc catctaaaac attcatgtct aagtgctgga cactctcaga    37920
ctctagttat tatgaaatta tcataagttg ctgtggacta gtcacccggc agagtaattc    37980
ctactttctg actgttggta cattacagcc ctgcccttg gtcccacctt ttcctctcta     38040
ggtccatcat tggtgtacag tttaatatac cctgagtcac attggttctg tatggtaact    38100
tcctctctgc atttactcca gatatcactg gctacagaat aactactacc cccacgaacg    38160
```

```
ggcagcaggg gacctctctg gaagaagtgg tccatgctga tcagagttcc tgcacttttg    38220
agaacctgaa tcctggcctg gagtacaacg tcagtgttta cactgtcaaa gatgacaagg    38280
aaagtgcccc tatctctgat accgttgtcc caggtaatag aaaaataagc tgttatcctt    38340
agagtggcag ttttgagtag cgatggggat aagcatctta atccgagata gctgagtgtg    38400
tcagatacag ttgggattta atgccaacct cccagggcgc tctccaaaac cacaaagcca    38460
aaaagcaact gtttggatga aggctttcct gtttcctctg cttcactatc tgtgcttccc    38520
tgggatgctg tttgttgcca tgggtacctg atgagtgcgg ccacggcatt aactctgtac    38580
tgtttgctca cacggaaaga ttactaaaca gtgtcgcgtg tctgtaccca gtgctgacag    38640
gctaaaagta atgtggtaaa tgcatccctt tggggctttt gtgcccgggt tttacagtcc    38700
atctccacct ccaactgtta tctagaaaac agcctttgtc tccatatgtg agcactgaaa    38760
cacacttggt tgacaatcca atctttatc ttgcagcttc aaatccttt taaaattgca     38820 agtggggtga aaaccacag aaaggaaaga agtaaaggcc aggcccccca tggcttgctt    38880
tcttctgaat tgaaagacag cgtcacaaag gcctgtctag ggataggttc attgtttgtc    38940
cccagtcttc tgtagattga aagccctggt cagactctct taccctctgc agtattttgc    39000
tatgcattta tgaatactaa ttaaattaca tgaattaaaa tgttggcagt ggagtgggct    39060
cagggctctg tgctggctgg ccttggcctg actgtgcatt tgagtggcac attcacaaca    39120
tagattaata ccatggtcat gatgccatca tggcttttga acatggaaaa taagtcaatt    39180
agccagccaa tttttttta aaaaaccttt ggaagatttt attttcttac taaaggtttt    39240
gtgttctccc cactcccaac cccccacccc gccaacattg ctagtgtctt ttatagatca    39300
gttcaggctc tgagaatgat tttgacattg taaatgggtt tatgattaat ttttttaac    39360 acttgagaag ttaaaactgt accattcagg gacatttct aaatgggagg aagcccctga    39420
aagaatgtgg taacctgcat tagtctccca ggggagcaaa ttactcatga tgcttgggac    39480
gtcttttcag ataatttggg atacattgca tataccatca ttgcttgagc attccgtcaa    39540
tttcactacc ggtcacctga tgtacactgc tttattttt cctttgtttt ttgcctctac    39600
ttttcttttg cctcctcttt gcttcgtaac tcaatagagg tgcccagct cactgaccta    39660 agctttgttg atataactga ttcaagcatc ggcctgaggt ggaccccgct aaactcttcc    39720
accattatcg ggtaccgaat cacagtagtt gcggcaggaa aagggatccc tatttttgaa    39780
gattttgtgg actcctcagt aggatactac acagttacag ggctggagcc tggcattgac    39840
tatgacatca gcgttatcac tctcattaat ggcggagaga gtgcccctac tacactgaca    39900
cagcaaacgg gtgaatcttg aagtcttctg tgtttgagac atggatggtg ttgcatgctg    39960
ctcagtcgct gtggttaaat ctggatgttt ccaagccagt gattggctac ggagatgaag    40020
acggggcccg ctcagagata agggatacat tagtctggtt gcatgaaagt atgcgtaaat    40080
agtctcaagc actttcagtc aaagcacaaa cagatgtgaa gggaagagc tctagatctc     40140 tgatttatga aatgcaaagg agattacatt tgcagatctt gagggtgttt gttttttttt    40200
aaagtatgac tatcaaactg aacaatgagc actcatttac actaagacag gcctccaaag    40260
tgtgccactg cgtgcttcct cttaccttga taagctcctt ttgtagctaa taaacaccct    40320
accaaaaatg agtgtggaac agaaggggag atctcagggt aggatgacga cgagccgtag    40380
ggctttctgg atagtgctgc tctacagggt aaagaaactc ctctttaacc acagtctaga    40440
gacgagcatg caacatctta aaggttctct gccctgcatg gtaagaaaca ttgctgagaa    40500
```

```
ccactgtgca tgaatccctc acttgtaagt agagttcact gaatggaatt atggcaatgc   40560
agtagtgtgt agatatctca ctccggggaa actgaggacc ccttgtctt tttgtcttcg    40620 tgcatgtgtt tcttcggaaa gtactgctat gtgtctttgc tgtgtggcaa cttaagcctc   40680
ttcagcctgg gagaaacatc ttccgtggta tcgatgtact aaaacggcaa tagcagccac   40740
caaaaaaaaa gcctacctat ttgaaaagta gactaaaatt cttttaaaat gcattgatca   40800
tggcagaaag gttaaagggg cctaacagtg ttctctatag tgttttgttt attttttaa    40860 cagtagcgtg tcatgattta gattagatta gattagactg tttgcatggt tgtaactgtt   40920
tcttttctgc atgaaatact ggttttacc ttttcagcta ttttttttt ttagctttga     40980 ctttaaaatc gcattaactc aatcctcctt atttgatatc agctgtccct cctcccacgg   41040
atctgcgatt caccaatatc ggtccagaca cgatgcgggt cacttgggcc ccgcctccgt   41100
ccatcgagct gaccaacctc ttggtgcgct actcacccgt gaagaatgaa gaggacgttg   41160
cagagctatc catttcacct tcagacaatg ccgtggtcct aacaagtaag ccctcaaaca   41220
tagcttgtcc cgtagatacg cagatcccta gatctggagc acaaggcatg gatcctgagt   41280
tttcctggag gaccacctaa gagaaaggag aactgtgacc gagagacacg ctctccaagt   41340
tcagtaggcg gctctgtaaa ctgtgaaaga tgtaatgatt ctgccggagt ggcagacctt   41400
tgatcgctac aaatcgtagt cgaaggcacg gtctgtgaag caccaaggtg tcagacattc   41460
tctaatcagt gcacaaaaga tacgtgactc ccaagtgaat tctgtaacta aggcaagagt   41520
gagaaacatg gagatcagcg catctggttt attgtccttt cttgtgtgag atctaccacc   41580 accagggggat ctatttagca ctagaaaact tagaatggct tttgcgtgga acaggcagaa   41640
cgtttagttc atatttcaga aagcacgtgt ttgcaccatt tccctgaagc tgggagagtt   41700
tagaaagcaa ctgacatgta ttagacaagt tatagaaatt gtttcttccc gagtcctact   41760
ggaagaggat actttgaatt aaagagaaca agagcttgca acattgtagg aaattgtata   41820
agtacagggg ttctacagga gaggaaagta gttacattca ggcccatttc caaatagggt   41880
cagaaaacat cctctgctct tcagatacgg ctcagaaagc taactacaaa gaggcagcag   41940
cagcagctct cacttggtgg ctaaagacca gaggacccag atacttaacc cgagtgtgga   42000
aatgtctgtc cagtcagtag gaaccacatt gtccaatata ctagacccat cgccacctgt   42060
tggcaccggt ttagccaaac cgtgtcacat gttaattatg tatcttaaag agtcctaatg   42120
ctagaagaaa ctcccccttta gagaagtcat tattacccta ttttaaaaat taagcagttt   42180
gagggcagtg gagtgagtcc aggggcacta ggtatgttca ttgtcttgaa tacattcatg   42240
gccccaacaa ggacacatgt caaatttgt ccaactgtac atcttgacat tgcatagcat    42300
ggaagctgct gaccacctca tgtggttgtt gtgatgggta gatggtaatg tagactccca   42360
caaaagttac atcagtggcc ctcacagatg ccctttcaaa tggacgggag agatagtaac   42420
atcccgtgtt tacacttgac tgagttccat ttatacctgt ggagctgggg cttacagaca   42480
ggacagagcg gcccttattt acagattatg tccagacaga catactcact tagccacagg   42540
taggctatgg gactgaacgc ttggatgttt tatcagatga cggagtcccg gggagcgtta   42600
tgctttctca aagtctcaat caagtttaaa gcaaatccca ctttgcctct tcagatctcc   42660
tgcctgggac agaatactta gtcagtgtct ccagtgtcta cgaacaacat gagagcatcc   42720
ctctccgggg aaggcagaaa acaggtgagc cacgttagct accaacgtta agcaacaaaa   42780
tgataggttg agtctatagt tgcatctcca cctttgtgg cattgataca ttacttttaa     42840
tttattaatt aatttatgat gacaataatt aattacaact aattaataat taattttagt   42900
```

-continued

```
tattgtagag tagtggtttt gccatggtat tttcacatgc tctgttgatg ttcctcttcc    42960
gttcctctcc ttgcccctg tcatccttcc tggtcccctt tctccctgta gtaatgtaca    43020
gccccgtttt cactctcgtc atcttgtcac ctctatccta tgacccttt cactttctac     43080 cctctccgcc ttaaagcacc ttctcttctc cccacattcc tttttctagt ttcaggacct    43140
ttgctctgca catacatgta gatgctctat acacacatat gaaaaattaa agctaggatc    43200
caggtaccag aaaactccac ttgtctttct gagactggat tgctttgttt aacataataa    43260
tgttactttg tttaacataa caatagagtt ccctggtttc cttgtgaatt tcactggttt    43320
cttgtcttag ttaaggttgt tgtgatattt gtgaggaaac accatgatca atagcaaact    43380
ggggagggaa gggtttattc gacttacact tccacactgt agtccatcac tgcagggaaa    43440
ccaggacagg aactcaagca gggcaggaac ttggaggcag gagctgatac ccggggccat    43500
ggaggagtgc tgcttactga ctggcttcta ccatgacctg ctcagcctgg tttcttatag    43560
aatccaggac catgagccca gagaaggcac tgtcccgccc acagtgggca gggccctgcc    43620
ctgtcaatca ctgataaaga gaaagcccta caagcttgcc tagatcttac agaggcattt    43680
tcttaattaa cgactccttc ctcttagata actttagctt ggtcaagttt atgatataaa    43740
gctacccaga acaacgctga agccctcaga agtatcagtg tttcggtata atgtagaaat    43800
cggctataat tttacatatt gtttcaatta cttttaaaag gaaaaaaaga aagaaatgct    43860
tgtgtaagct gattgcggtc agctatcagt cccgtataac agtgtcagtt gcgttcccca    43920
catcctccat cctcgatgtc taagctcgtg gttgttgtct tttgctcccc tccttgggtg    43980
ggaaaaacag gtctcgattc cccaactggt tttgattctt ctgatatcac cgccaactca    44040
ttcactgtcc actgggtggc tcctcgggcc cccatcaccg gctacatcat ccgccatcac    44100
gccgagcatt ctgtcggaag acccaggcag gatcgagtgc cgccctcgcg gaattccatc    44160
accctcacca accttaatcc gggcaccgag tacgttgtca gcatcattgc tgttaatggc    44220
agagaggaga gcccgccact gattggccag caagccacag gtaattttgt tttttttaatc    44280 cgcaaagaaa tcccttggtg tggactttgt ataggtttgg tgtagactgt gaaaaagctt    44340
catgttagac acaaagagca gtggtggagc caggcgcagc tgtgcgcgct catgcacgca    44400
ggcacgcgcg cacacacgcg cacacacaca cacgcacg cgtacgcaca cacgcacg     44460 cacgcctttg atcccagcgc ttggaggcag gtggatttct ggattggagg tcagcttggt    44520
ctacagagtg agttccagac tagccagagc tacacaacaa gatcttatct caataaaaag    44580
ggaaagagga cagtgataga ctgtgtggta aacatttctc cctctaaaaa catatttatt    44640
tctctgagag attgtcacct ggttcagcta tgttctggtg ttttgctgg tcagtcttta    44700 tttatgatgg tttgagagag cgtcatagcc cagactgact cagaagctgg ctctgtagcc    44760
caagcttatc taagatactt cgccttgact tgtgagtgct ggagttacag gcatgagcta    44820
ctactactca tggatattta ctggttttta agaaggtttc atacaaaacc ataatatggt    44880
accaaagtta ctgtaaacct atgattttg tttcgttagc tgggcttggt agcacagatg     44940
tgtaatccca ggtacttggg aggctggagc aagaaggcca tcctgggcta ctgtgagttc    45000
aaagttagcc tgtgcaattc agtgaggctc atctcaaagt aaataaagt tttttaaagg     45060 ggtgcagtgg atgtagtgta gtggtggagt gctctgtgtg gcgtgagtca agccctagat    45120
tttggcttta agcacagata gatatatttt cagtgacaat gactgggaga cctgttatca    45180
gaacaatctg tagcttagct gtgaataggg gcgtgtgtga ccactatttc caaataacac    45240
```

```
atagttaagg gtgcatgggg tgggatctct gtgagttcca ggccagcctg gtctacaaag    45300
cgagttccag gacagacagg gctgttataa cacacagaga aaccctgtct tcaaaaacca    45360
aaagaaaaaa gaaaagtgca tggtgagtgc tgctgtagtt tttataactt ctgtgattta    45420
aattatttcc caaagagact gttgaggaaa aaaggaattc acaattggga tggtctccat    45480
agccccttcc cttgacctcg ccatagaatt taactctgct aattcagtgt tgcatttaga    45540
tttttgtttg aagaggatgt gtgtaatcgt tatctgggaa aggacaaagt gaacctgagc    45600
tttctttgga agttatacat gtgaagtttt cctgtgattt ttttttttct agtttctgat    45660
attccgagag atctggaggt cattgcctcc accccacca gcctgctcat cagttgggaa    45720 cccctgccg tctctgtgcg ctattacaga atcacctacg gagagacagg tctgttcatt    45780
ttgggccatt tcacccttag aggatcaggg ttcgggtggg taacttggaa atctgacagt    45840
gggaacagga ttaaatgcaa acaggcccat ttagaaaacc ccctccttc cctccctccn    45900 tcccnctccc ctcccctccc cctctttctt tctttctttc tttctttctt tctttctttc    45960
tttctttctt tctttctttc ttttctgtc caaaaatgca tgggagctac atttaattga    46020
ttgtaatgaa gttcaaaggt ggtttataca ctacagcaag ggtgggaagc agagctgaga    46080
aaaaaaagtt tatatattta caaatattac cattggtaat tcttactatt cttttctttc    46140
agtgttctct aaatttaaca aatattctgt taacccttt gtaaagactt cattccattt    46200
taggttgagt gagccacatt cttgtcccct ttttctattt aatttaaaca attaattaaa    46260
tataattaca tgatttcctc cttcccttc ctcttccaaa ctatcccaca ccctctcgc    46320 tccacttcct ctcagttct tggcttcttt gtcttactgt tacacacaca cacacacaca    46380
cacacacaca cacacacaca cacagagtgc atgtgcatcc aacaaataag tataaataca    46440
acccaccgag tctgcttact gttgcttata tggacatggt ttcagggctg actgcttggt    46500
atttattatc aaccagggag ctcatttctg gggatttctt cacctttgc ctgttaatct    46560 gcaactcagt gacattttaa cccagggatg ttaatatggc attagcttga gagttctcct    46620 ggttttata tacttctcag ggcttactac acacataaat acacttgtct gtcaggttgg    46680
gttaaagcag ccactcctta tgatggaacc agcaagctgc agtgacttac ataccgcttt    46740
cgatgtgtta ataatattgg agtaactcct agctcctcaa attctatgct aactcctttc    46800
gtacaggagg aaatagccct gtccaggagt tcactgtgcc cggaagcaag tccacagcca    46860
ccatcaacaa cattaaacca ggagcagact acaccatcac cctgtatgct gtcactggcc    46920
gtggggacag tccagcaagc agcaagccag tttccatcaa ttataaaaca ggtacaaatt    46980
tctcttgggg taacacgggg ttatttatga agatggttat ccctgtattc gtccaaggta    47040
ttgtcttcac tacacagttg atttcctt agtttgtgt ggtgctgggg accaaaccca    47100
gcatctcata aatatata tgctgtacca ctgaactaca cccttgaccc tgatttattt    47160 ttctttttt ttttccgaga cagggtttct ctgtgtacaa aagcctgtag ctaacaacac    47220
cttcaagtaa tagagtcttg agacaaatgt acaaagaaga ccccaagagc agacattttt    47280
gtctgtgttt ttaactgcta ccgctatgta tctacattag acacaagcca gagagtgttt    47340
ataaatacct gtagaaaatg actggatggg ttgactatta ggagacaaag gcctacctga    47400
gatgtaatgc tttgtttgtg gaatgaaaga atcaggttgt aaatagttgt aatagtgact    47460
ggatgcatgg ctttccttct tcaagctaac acccttatt cttgtcaaaa gaaacatttg    47520
caatacatta atagaagcaa gagaacattc gcatacacac tggaactaaa ggccagggct    47580
tgtccagccc tcccccaca ctgggacatc actgctttct tttgtactta cagaaattga    47640
```

```
caagccgtcc cagatgcagg tgacagatgt ccaggacaac agcatcagtg tcaggtggct   47700
gccttcaact tctcctgtga caggctacag agtgaccacc actcccaaaa atggcctagg   47760
accatcaaaa actaaaactg ccagtccagg taaggataac cacaaggcca cacctagcaa   47820
gagaaacact gtaggagctc agaagttgcc atttgaagtg agtgtcctat gtggtgtgtg   47880
tatgctactc ccattcatag gcttggcacc agctcagtat tggtatccgt gtatctcggg   47940 ttttatttt ttttaatact gtcttgtgta gtaggaagag aaggatatac tgatgttata   48000
gatccttcta gatctgatgt tcttatatga aatggcttgc aaggtctcaa gccagtttct   48060
taagatcaat tttcatttct ttcttgaaat tttcaagaa tagcctcatt aattttgggg   48120 gatgggcat catgttaagt tagttgtaaa gcttattctt gaatatgatt ttacttcagt   48180
atgctagatt ttgttttgag atgggggtct catgaagtct gtgctggcct tcactgcact   48240
acgtaggcaa ggatggcgtt aaacttctga tcttgttgtc agtatctcct gagtgctaga   48300
actatagata cgcacacagt ttactgtgcc gcttggttat ctaagcctgg gtttgttcat   48360
gggaacagca ttctaccaac taagccgagc tccccagccc cagttttggt accagtgaac   48420
aagttgtcct gagaggaaac aggcatctga cttccccaag tggaatgggt gtttcatggt   48480
tattctgcaa atgaaaatta taggctcagc atctgcttct cattgagtcc ttaggagtgg   48540
cttgggtggc tctatagacc tgcaattaat tgcttctccc tccttttcag atcaaacaga   48600
aatgaccatt gaaggtttgc aacccactgt ggagtacgtg gttagtgttt atgctcagaa   48660
ccggaacgga gaaagccagc ccctggttca aactgcagtg accagtacgt aaccaatgct   48720
cggtttccta cttccaaagt catattgtcc tcaggtgtct ctcgatgccc accgcacatc   48780
ttgtgccatt gtatacacac agggaaaggc aatgtgtcag ctggttcata tcttgagatg   48840
agcccttggc ctacatttct tggcgccaaa gcgagcttgc aggaaaaatc actgtagtgt   48900
tgccatcaat ggctgctgtg ctttgaatct cctttgctta aacagcctca gcaaaatctt   48960
atttgctttt agcaaatcta tgaaagatct ctccaggacc tactttttct atgactggat   49020
ggtaatgttg actgtagtgt gccccaagaa gtggttatgg ttgaaggact gtggctgggt   49080
cagccttgtt ttttttcct ttttaaagat tttattttt tcatctatat gagtacactg   49140
tcactgtctt cagacacacc agaagagggc atcggatccc attacagatg gttgtgagcc   49200
accatgtggt tgctaggaat tgaactcagg acctctggaa gagcagtcag tgctcctaac   49260
ctctgagcca tctctccagc ccagggtcag cctttttaaa tataaagact aagagaggg   49320 gaaaaagaa gaacctaaga caaattatga cttgaggaaa aaaaaaatca actttaccat   49380
ttccaagata tagaaaatcc aggtccttga gactaacatc acattgcaga atcaaatcta   49440
gaatatcttt aaattgatat aaataaattt ccttggtgga gattttttc ttcagggtgt   49500 ctacatacct tacacacact tgtgtcttaa taagcaacgt gacactgcat atgctaaatc   49560
tcaaaaaaaa aaaaaaagcc ttttaagcag atgtcaagca actttctgtt ttaatagtgt   49620
gataattgga acttaattca tcaaagacaa gagttatctg cagaactgct ttgcatggta   49680
tggaaatatg cttgtttcac aacttgcttt tcacataacc tcttaccatt aatttgccta   49740
acagacattg atcgccctaa aggactggca ttcactgatg tggatgtcga ttccatcaaa   49800
attgcttggg aaagcccaca ggggcaagtt tccaggtaca gggtgaccta ctcgagccct   49860
gaggatggaa tccgggagct tttccctgca cctgatggtg aagacgacac tgcagagctg   49920
cagggcctca ggccggggtc tgagtacaca gtcagtgtgg ttgccttgca cgatgatatg   49980
```

```
gagagccagc ccctgattgg aatccagtcc acaggtatat cgttaaccgc acccaccacc    50040
cgggtgcttc tgggaacagt ggctttatgc cttgctggcg ttatacttta ctgggctatt    50100
gagtcccatg taagggagag tagaaaaatg ccttcaaact cttagtaaag aaaggccctc    50160
tttaatgagg aatggttgtg aacaatgaaa gtcaggtgat gtttaggtaa ctaagtctag    50220
gaaagagaaa tttaaagtag ctaagcacag acgtgcaaac atatgaaata tataaatatt    50280
taaagattat gaagcaagac atttgaaggt actaaattac ggattgtttc ctaagtgaga    50340
cacctcggtg gtgaccctcc ctctccacac atggaggaaa gaagtctaga atcatagagc    50400
ttactctgag aattgaccct cttaagccag gcattttctt gcaacatgat caaagaatac    50460
atgggtaaga cctcccctgg ctagctctcc tgtgctgggc cttcatttgc ttaaaggatg    50520
atgatgcaga tgcacaggac agcgtcatta ggaccagtgc ttcttaccag cctcttatgc    50580
ttttaccgct ggagcaagat tggaatgctc aaagcataca gaggtgacag tctgtggaac    50640
tgctctctgc ttctctctcc tgcctctatt gtaaaccaat tttcttctta tgctacgccg    50700
cagagaatac ttcaaattta gcagtgctat ctgccgtggg gtccaaataa aagagacaaa    50760
taaaaacaat tctatctcta ggatggaata gtctgtgaaa ttgtttcctg tacaaagata    50820
atttatatag aaaaagggc cattgctcat cttttttcata caaatggaaa aaaaatcaat    50880
tctaatgact aataagggaa ttcaactctt ggcttctaaa ggcgtagggt agggagataa    50940
gacccaaagt ctctcggaac cctggtgttt atgcagatgt ttgcagtggt tctgagagtt    51000
gctggtataa atactcctct cgttttatt atctgtttgt gcagactctc ctgggagtct    51060
ccagggagtc caccagtccc tacgaggacc atccattctc cttcttcaag tttgcttttct    51120 ttccccgttc ctcgttccct ataagataac cttttaacca atgaccatcc tgacagccat    51180
tcctgcgccc accaatctga agttcagtca ggtgacaccc accagcttta ctgcccagtg    51240
gatagcaccc agtgttcagc tcactggcta ccgggtgcgg gtgaacccga agagaagac     51300 aggaccaatg aaagaaatca acctttctcc agacagctca tcggtgattg tgtcaggact    51360
catggtaaga agtgagcttc cctctgcaga gtaaggcagg aggtcatttc atagagttca    51420
taggtgcaat ctcataataa acctagtgtt ctttgcttct accatcaaat agggttgtca    51480
caaatgtgta caatagaatt cttttatgta gacctaggat tttctagata ccctaagatg    51540
actattggat tagaatggtg taaatagctt tggatttcgt gcaggtcttt gacagaagta    51600
ttccacttat ttaaaagaag tggtattcgg tagggagcaa tttatataca cacacacaca    51660
cacacacaca cacacactct ggctgagttt atggctttta tgagtgatgt ttccctggca    51720
agacgcattc tccagttagt accagcctaa cttgacacta cccccattaa aacatttgac    51780
aatcagccag ctgtgcttta atcttgggag gcagaataag caggtggatt tctgagttcg    51840
agcccagctt ggtctacaag aatgagttcc aggacagcca gagatacaca aagagaccct    51900
gccgcaaaca agcaagcaag tagtatttaa aacttttttct agccatgcag aaattagcta    51960
ggatcctata agggcttaat gcacatctta acacaaggcc aattcttaga gaagtagcag    52020
tagaatagaa gctttctctt gctttttttg tgatcaggaa aaaagcaaaa cctgatttat    52080
atctgtcata tcataaaggc aaaaaaaaaa aaaggctaag actgatttct ttcttattct    52140
ttttttgctg ctccttgtgg attgtggact taaccctga gaacatttta aaattcactt     52200
aatttaaatg taaatgtatt gtcactcata ggtaacagtg aagttgctct gggaacctgg    52260
gggtttgggg tttgctgggc tatgcagatg gtcttttata atcaccgcat ttctctaatg    52320
ctttggtaag aactccgggc atcatgcaac accattgcca aagtttctgg tacctctgct    52380
```

```
tccaggtggc cactaaatac gaagtcagtg tctatgctct caaggacaca ctgacaagca    52440
gaccagccca gggagtcatc actactctgg agagtgagta atccgatgag tgacatgttt    52500
taatcctgac acaccctgag tggaagtcaa aagaaaagat ctttacattt aagccactga    52560
cttagcaata gaatttggaa gttgatagaa cagcttgtcg tttcgggaat ccatccagga    52620
aatgacctgc cgaaacaaaa tggaatcact tcactgtgtt gtgttggtgc tggtgggtta    52680
aaactcacag ctggcttatg cggtactggt gagggtctgt attcgtaggg ttcaatgtgg    52740
ggaagatgaa ctggcttcca ccatagggaa tgtgggcta aattagatct gtggtctagt    52800
ctgttgatgt ttcatcacct atggaatgat taacacgtga agccttatag aaatgaccga    52860
agattcgcca cccagacaga cgttattact aattgtctgt gttataattc ctaccataca    52920
tccttacata ttagtaaagt aatcattgtc acacttgttt gacatagctc tagacactag    52980
agagtcaacc ctgggcacca ctgatagtat ttagaaagct tttctgttta gtgaacattt    53040
ccatatttcc tcaataccgt taacccatct ttctgtaacc tccacattac tttttagtgt    53100
atttcctgaa gtggatgtat ttgcataatg aggactcttt ttaaaatatc caaaccttac    53160
atgtatgagc caagcgtgct ttaatctctg gctctgctcc tacacagatg ttagccctcc    53220
aagaagggcc cgtgtgacgg acgctacaga gaccaccatc actattagct ggagaacaaa    53280
gacagagaca atcactggct tccaagtcga tgccatccca gccaatggcc agaccccagt    53340
tcagaggagc atcagcccgg atgttagaag ctacaccatt acaggtcagt gtactcgtgg    53400
tctgcctgtg tgcgcccgca ggagaccctg gctcggtaga tagtctggtc tggtattgag    53460
aatgtgggca ccattccacg atctgttggc ttcctgatgt ttgcttgacc tataaatctc    53520
attcattgaa tttgttgttt tataaatgct cattcattat tgtctaatga aaatctgcac    53580
actgtagtca taggcaggag tctgaggcag gaggatgtga gtttgagact agacatagtg    53640
aaaccctact tttttttaaag ttaatataga gaacataaag atacaaaata gtaaaattag    53700
catgcctaga ttttaaaagg cataatgaaa tttatgatta caaacagcat tatgtataat    53760
aaaaccggaa actgtaatca gagacgattc agtattggga cataagtgag gtgcttttga    53820
gatgagtttt tcattagtag tgacctgtcc accccgtgaa gcccttact cttccctgta    53880 actgcttctg ccagtatagg agtcaaggaa actgtaggca agcatgagaa ctcgcctagt    53940
aaagtaggag tggattaaac aggcgtcttt ttaacttcca ggtttacagc caggcactga    54000
ctacaagatc cacctgtaca ctctgaacga caatgcccgg agctcgcccg tgatcatcga    54060
tgcctccacc ggtaactatg ctttctatgg aggaaatgtc agctgctgca tattgtaatc    54120
agccgcgtca agtttagaaa cagttaggga gctggaattt ccatgttctg gctcccggga    54180
ctctctgatt ctctctctcc tcctctgttc gctagggctg ggctcaactg tgagaatgga    54240
cattcatttt tctaaggtgt cactttgctt gcctttcagc catcgacgca ccatccaacc    54300
tgcggttcct gaccaccaca cccaactcct tgctggtgtc atggcaggcg cccgtgcca    54360 ggattactgg ctacattatc aagtatgaga agcctggatc ccctcccaga gaagtggtcc    54420
ctcggccccg ccctggtgtc acggaggcca ccattactgg tattgcttcc acactgtgat    54480
tttttttccc ccttaatcat agatgcccca agtccataat actccccaat tgtgtctttg    54540
atgctatttc atgagaatga ggtgcccagc actctagatg ttctgtttag ggacagtagt    54600
tttctcaaga gatatgagca actgagcatg caatttcagt gccgtcctat gacacagctg    54660
tgatgtatta cactctggtg taaattcttc attattcccc cctcccccat aggataaatt    54720
```

```
gtgtgtatag attctcctgg atgttgaagt ctctaaaaca cacagatata aggagatcac    54780
agcttctttg ttgcatttat tgaagaagaa aataagagtc tgatatggga agacttaagc    54840
agaagacatc ctaattttg ctctgtcact gacagctgtc tgagattaga cctaaataga    54900
agtctgaagt ctctgatggc ctctcccaaa tacatatttc attgtcggcc cacagtatag    54960
atagtttatc tacaggctga aagaatcctc taggaaggtt gccatgaaac tgctcattca    55020
agtatcagct gtggttgtga aatgactaac tagccaaggg gctttggggt tcgcagagta    55080
gataaacaag gagtgaagct gaaagacttc acaggcagct ggcaggaatg cctgctcccc    55140
agtcgcctct gctgagccaa tcactggccg tgcccgccaa cgtgagtgaa acggccgcgt    55200
ttcccatcag gtctggagcc aggaaccgag tacaccatct acgtcattgc cctgaagaac    55260
aatcagaaga gtgagcccct gattgggagg aagaagacag gtaaagactc ataaccagtg    55320
gttgctttgc agggtgaagt ctctacattt ccacacatca cacatctctc acggattttt    55380
tttatttccc tagcagagtg gcttatatat tttactcttt gacaggaatc acctaacatg    55440
ctctaaaaat gtctgattta tttcttttc tacaacctta agcttcgttt accttgcaga    55500
gattcaaact agatagtttg aattggaagg gggggaagc tttataatgg tgggagtaaa    55560
acctttctga tttgggtcga tttatttatt atttgatttc tgaacttcaa acacttcagt    55620
tcgttgcaaa gccttaattg gagcagagat ggctttctgt ggggctcagc ggttcaaagc    55680
tttgtctgta tgagaattca tactaacttt ttttttttc tgtctgaact ataaagaaat    55740
ctgtgagaaa aaaaaaatca cgatttcttt ctctaagagt gttttgtgat ctgagaaccg    55800
ctggttgtgt gggagctctg atcgggttga taaacagttg ttgcctgggt tgacagtgat    55860
tggttgcttc ttcttcgagc ttaacttttg cgctttgctt ttttggctct aacctctctt    55920
ggctagatga gcttccccaa ctggttaccc ttccacaccc caatcttcat ggaccagaga    55980
tcttggatgt tccctccaca gttcaaaaga cccccttcat caccaaccct gggtatgaca    56040
ccgaaaatgg tattcagctt cctggcacaa cccaccagca acccagtgtt gggcaacaaa    56100
tgatctttga ggaacatggc tttaggcgga caacgccacc cactgcggcc accccgtca    56160 ggcttaggcc aagaccatac ctgccgaatg tagatgagga ggtccaaatc ggtcatgttc    56220 ccagggaga cgtagactac cacctctatc ctcatgttcc gggcctcaat ccaaatgcct    56280
ctacaggaca ggaagctctc tctcagacaa ccatctcttg gacgccgttc caggagagtt    56340
ctgagtacat catttcatgc caaccagttg gcaccgacga agagccctta caggtacatg    56400
acagcccttg caaagtgtct ctctatgtaa ctgtgtcttc agaaacaacc acagcttcat    56460
gtctgatgcc cactgtctta gtcagggttt ctattcctgc acaaatatca tgaccaagaa    56520
gcaagttggg gaggaaaggg tttattcggc ttacacttcc atactgctgt tcatcaccaa    56580
aggaagtcag gactgcaatt caagcaggtc aggaagcagg agctgatgca gaagccatgg    56640
agggatgttc cttactggct tgcttcccct ggcttgctca gcctgctctc ttatagaacc    56700
caagtctacc agcccagaga tggtcccacc cacaaggggc ctttgcccct tgatcactaa    56760
ttgagaaaat accccatagc tggatctcat ggaggcattt cccccaacta agctcctttt    56820
ctttgtgata accccagcct gtgtcaagtt gacacataac accagccagt atacccaccc    56880
tcccagggca gaggctacga ctctgactgg aggttgtttg actcagagag catcactgag    56940
cgtcacgcag tagagaaaac gaaattcttt ttattattct catacactgg agactactta    57000
gtgagatgga tgaaacaatt atcttaggaa gtagaggaaa agtaatttat atgaagtttg    57060
aaatgccacc tttggcgtct gtccttgaag aggcacgctg ttacgtgtct aggaagacga    57120
```

```
ggtgaaccgt tggggaccag ctgttatgag agatcgattc tccaaaactc tcttctttaa    57180
tttgtcccac aggtgctaga atcaattttt attgtgttat ttttagaaag tggcagaaat    57240
tttaaaattg actgtaccct aggacattta ttagcttaga aactttagtc tggggatgtg    57300
ccggtatttt aggaaaaccc aagttctact gtgttggcac cttacatggc acatgttgtc    57360
tgtctgtggc actcatgttt atgaaggggc ttttttcca ggagttctag tggccacagg     57420
attcagagga agctggtata gctgagggtt tctgggaatt gtggaacacc taggtagaaa    57480
aatctagcag aaatgatttt tttttaagtt actcttttaa taattttta tgtaccttgg     57540 tgttttgtct gcatgtatgt cagggtgagg atgtcagaag ctctggaact ggagttacag    57600
atggttgtga gccaccatgt ggctgctggg aattgaaccc aggtcctctg gaagagcatt    57660
tagtgctctt aaccactgag ccatctcccc aatcttaaaa cgatggtttt ttgcactcat    57720
ttaatatctc atcttgacta ggtgggagtc ctatacagcc ctgttctctc ccttcgtctg    57780
tttttaaatg ggagtggggg attgctcata gactaaggaa gctcatgccg attcatcatt    57840
gaaatgcttt ctccctgctt tggatgtata gttccaagtt cctggaactt ctaccagtgc    57900
gactctgact ggccttacca gagggtcac ctacaacatc atagtggagg cactgcagaa     57960
ccagaggagg cacaaggttc gggaagaggt tgtgactgtg ggcaacgctg gtaggtacac    58020
tgctggcctg ttgaggcaca cgcttcttgc tggatcagcc cagagaagac ttggtctgtc    58080
gttctttgtt ggctttaaac ttaggaaaat gagattgcac aacagtcaga gatgtcccct    58140
tatgtaaccc atatgttcac caacacatat tgacaggatg ccaggcctgg gagggacatg    58200
aatattattt actctaatac attttccccc tcctgttgag gatccagttg acagaggcaa    58260
tggttttttg tacctttac tattctctca tcccatactg tggtccactt aagcgttcct     58320
aacccgaacc gaacacctat aaacagtcct ccttggcaat cttaagtgat gacttaggtt    58380
ttgtacctaa tgtaaaatgt taccaatatt gcccttgct ttcctaagag cttcccattc     58440
caaatttcaa ctttatatac ttctttgttt tcttcttctt tagatttacg tattttaatg    58500
ttatgtgtac gggtgttttg cctgcatgta tgtgtgcaac atgcattcag cacccatgga    58560
ggccagaaga ggacaccggg tcctctggaa ctggacttat agagggttgt tagtgactat    58620
gtgggtgcta gaacctatgt aatgtcctgt ggaagaggag ccagtgacat aactcctgag    58680
ccatctctcc agccccttta tatgtgtctt aatacataaa ttatatatgt catgttatat    58740
acatgcaagc tcttaaaggt taaatggcca tcatacaaac gtaataaaga tgaaacgacc    58800
cccatgcagc cttttaataa aggttaaatg accagcatgc aacatcttaa taaggttaa     58860 ataaatttaa tcctgaaaat ttttgataaa ggttgaatga ccctgactct gagaagcctt    58920
ttgaagccag tgatgtgtca tttggcttaa gttgcaatag ctaaagattc accaaggagc    58980
atgagttaag ggctaactga gactggatcc cgagtcctct taccctggaa gggctaactc    59040
ccactttttc cagggagcag gacttctggg taggaccact gccttctttt cagccttctt    59100
cctcttagcg aagactgcta ttatttgact cttcagttaa gcagttgcat gtctggcaat    59160
gcagaagtgg gcagatcttc tgtgttccat ccacagtaat tagcatttgc cttttgtggt    59220
ttcactagta aaatgccact tgaaagggat ttttttcaaa agcataggg ttttgtggtt      59280 ttccacatca ttttcttgaa ggtgtgtgtg tggtgtgttt cagacagtcc tactgtattg    59340
tatgctgttt gtatatagtg tgctagactg aactgctatg tagcccaggc tcctaatgtt    59400
agggcagacc tcctagatat tttaaaatag tgaaccccca tgagagtttt agccccttg     59460
```

| | | | | |
|---|---|---|---|---|
| ttttctttcc | gactcctgtc | tttaccaggt | cctcttggtt | tcaaaacatt ttggatagac | 59520 |
| tttttagttc | ttccagaatg | atggcttttg | aaatattagg | catttcaaat attgatttca | 59580 |
| tttgcacttt | tgattttac | actattaaaa | gaagctatcc | acaagtagga tttttttttt | 59640 |
| cctgagacag | ggtttctctg | tatatagccc | tggctgtcct | ggaactcact ctgtagacta | 59700 |
| ggctggcttc | gaactcagaa | atccgcctgc | ctctgcctcc | caagtacggg gatgaaatct | 59760 |
| tgggaaaccc | actgcagctt | ttctacttat | tcctaactgc | acggtggtga tttctcttac | 59820 |
| ttgaaaatca | ggtcttatct | agttttacag | taaccataag | catctaggtt ttcaaactat | 59880 |
| ttagcaaaag | aaaagctaca | atgtaagtaa | agattgtgtt | ataatgctat ataaagatgc | 59940 |
| taagacattg | actacagcaa | agacgtatct | aacaataatt | gttaattatt gagtaacagt | 60000 |
| agttagtaag | tcatctctgc | atagtgatac | tggtccagag | ctttgattcc tcagtttcat | 60060 |
| gtagccttta | caagatccaa | aaagtgggg | ctagttatat | tattatcccg taatagatga | 60120 |
| gagaagagag | acagacaaat | gttaattggc | tccatgtact | caggtgtctt ggggaagcac | 60180 |
| cactgcccat | attctcagct | agttaaaatg | cctgacgatc | tgcttcatgt catgagaaac | 60240 |
| agaagacggg | aatgaaggaa | gacgtccttt | gaccctgctg | tgacaagtgc ctactgactg | 60300 |
| catcaaagtg | ttgccgatga | aacgtctgt | gttgttagtg | ctgattaggt cacaatatac | 60360 |
| agtatggccg | tttccccatc | aataaccgtc | aataaaatgt | cttctccttt ttttcctttc | 60420 |
| tccttctttt | cttcatagtc | agcgaaggcc | tgaaccagcc | tacagatgac tcatgctttg | 60480 |
| acccttacac | ggtttcccat | tacgccattg | gagaggagtg | ggagcggttg tctgacgctg | 60540 |
| gctttaagct | cacatgccag | tgcttgggct | ttggcagtgg | tcatttcaga tgcgattcat | 60600 |
| ctagtgagta | gcttgcgttc | cccaccctct | cactcctcca tctcttctgg | tctcatgcgt | 60660 |
| tcgcactagg | tggccacgga | aacatgtttg | gcagactcgg | gctcttccaa acatgatgca | 60720 |
| aacagaagta | gactgtttga | ctccaagtaa | cattttgcat | catagaagga tgatgggaaa | 60780 |
| ttttacttgt | gcaatatgac | tgcatttcaa | gagttgtgta | ctaatctaac tattccttac | 60840 |
| aaatatatct | gtagtgttga | tatgctcctt | gtagtgttta | gctctatgta aattgaagtt | 60900 |
| aaaaaatatc | tcattagagt | ttggtttaat | tgagacaggc | aggcagagac tccaaattct | 60960 |
| tttcagtctt | tagtattgag | taaggacaga | ggtgaacatt | tatactcaca aacaccactt | 61020 |
| tttcagcata | accagatata | catgcacaca | tcacacacac | atatacacac acacacatct | 61080 |
| cacaacccag | atatcccaaa | cattgctcgt | ataaggaaa | atgtctctct gtatagccct | 61140 |
| ggctgtcctg | gaagtcactt | tgtagaccag | gtcggcctca | aactcagaaa tctgcctgcc | 61200 |
| tctgccttct | gagtgctggg | attaaaggcg | tgtgccacca | cgcctagttt gcattctaca | 61260 |
| tttaaggatc | aagttcaggg | ctggtgagct | aggctaggca | tcccatccct ggaacccagg | 61320 |
| tggtgccagt | ccccacaaat | tgtcccttga | ccttcacata | ttcctggggg gacactaagg | 61380 |
| cccatatgta | catacatatg | tacacacaca | tgcaaatcaa | taaatctaat aaatgttaag | 61440 |
| atcaactttg | actgaaaaat | aatttgattt | tcaaatctta | aagaggttaa aatttcaaat | 61500 |
| tattagtgaa | aatgatccta | tgagttatct | atgtttctag | agatttagta ttggagtata | 61560 |
| taaccattca | ttctttgttt | ttagagctat | aattattatt | agcttttttaa tgtgcttttt | 61620 |
| ttatgtgttc | atcatatatc | atagatatcc | acaggcctat | ggacaattat aggtcccata | 61680 |
| ttccatggaa | tgacatttaa | tagatctcta | aagttttttg | tgtaacattt tccttttcctt | 61740 |
| tacatgaaat | agcaaaatcc | agactggttt | caatgtgtgt | tgttgggtag agcccagtgg | 61800 |
| gcaatatacc | atgctgggga | caggagggac | accatttggc | cttgaccagg tgcttttttca | 61860 |

```
gagagtgaac tgcactgaag tttgcatgtt tttcataact cagtacaaat gtggacgtat   61920
acaatgattt ttatccgtga gcctctgact caccagtctt tgctggatat gtcataactg   61980
ccttatacat ttgctcatcg tttaaggaag gctgaattgt taaagtggaa gaatcactgc   62040
cctggatgag ggtcgtaagt gaactctgtt tagtataaat cttagaggtt aaagggcatt   62100
tttacatctg ccattagaca cagctcgtgg tgacttctta ggacttgtct atttgtacaa   62160
caagcctgat tcatttcatt tgtctttatt ttgttggctg ttatattcgt tcgttcttca   62220
cttatatgaa tcaggtgaca ccagctgttt ttctctttaa tcttcttgtt tgttttgtt    62280 tgtttgcttt tgtcgttgtt tcatgagaca gggtttctct gtgtgtccct ggatgtggta   62340
cactcagtct gtagacaggg ctgtcctcaa actcagagat ctgcctgcct ctgcctccct   62400
aatgctggga gcaaattcgt gcacgacgac gcctgccctc tctttaatgt ttaattaaac   62460
tattttgtat ctaggatctc tgcgaaccta aaatatatat tttttaattc tccaatccca   62520
ttttaatttt ccatatttgt aaaatttaaa aggagctgaa tgaatcactg gttggtcctc   62580
tgaaatgatc ttggtggtag tgttaagtct taacactggc ctggaagata ttaaatgtta   62640
tgatgaagaa atgcttcatc attagaaatg tgatcttgga cttcctgctc tgtatggatt   62700
ttcgtcctgt tccagtgttc tgcccatcct gtgagtcaga acacagagta actctctgcc   62760
tgcgatgtcc ctaccttcca gaatggtgcc atgacaacgg tgtcaactac aagatcggag   62820
agaagtggga tcggcaggga gaaaatggcc agcggatgag ctgcacatgc ctcgggaatg   62880
gaaagggaga attcaagtgt gatccccgta cgtcatccta aaaatgcttt ctagactttt   62940
taagtactcc catgttccta actgagccga aacacccatt tacaggctgg gctggacgtg   63000
gtgggcttgt cagtctgtgg ttggtaagtc agtagcttgc ttcagaaagt gaatcatgac   63060
tgaatggcac gtctaagcac tttagcactt tcacaacttg agcactttgg tcatctgcag   63120
tgaagtgcta tgtagactca gttttttaaaa cataacttca aagccaagca gtggtggcac   63180
atgtctttaa tcccagcact tgggaggcag aggcaggagg atttctgagt tggaggacag   63240
cttggtctac acagagagaa cctgtctcaa aaaaccaaaa aaaaaaaaag acttcaatcg   63300
ttccatctgg cctagtctac caaggctttg gaacatctcc ttgtgattca cctaagttga   63360
tgagatttgg cccgtgctca ttcaggtcga gggcagatgc atcaacttga gtgtacctga   63420
ttgtccttgg tcttacaact gttcctttct gctctgtgcc cacgtgcaga tgaagcaacg   63480
tgctatgacg atgggaagac ctaccatgta ggagaacagt ggcagaaaga atatctcgga   63540
gccatttgct cctgcacgtg tttcggaggc cagcgggtaa gctggttgg cgtttagata    63600 aagcacttag gaggttgcag catggatatg ctttgtgcac aggagccttg ccttttagga   63660
agagtctcta agatgggtgt ctcagttagg gtttgcgttg ctttgaagag acaccatgac   63720
caaggtaact tttataaggg acaatattta attgggctg gcttacagtt tcagaggttc     63780
agtccattat catcatggca ggaagcttgg cagtgtgcag gcagacatgg tactctgaaa   63840
agagctgagt gttctgcatc ttgaactgac aaagacagct agaagaaagc tttcttcttc   63900
attgggtaga gcttgaacat aggacctcaa agcccacccc cacagtgact cacttcctct   63960
aacaaagagt gccacttccc atggaccaag catattcaaa ccaccacaat gggtctgtcc   64020
ctcccagttg ataatagctt cagcaccttc tcccatgact aaaattctca ggctgccctg   64080
tttgtcctcg cctggagtgt agcactaagg ccccagctct gagctgatgg actagcatct   64140
gagtattgtt cacatttta ataatactgt gatctaagaa aatttaacta tttttgagcc    64200
```

-continued

```
tttgttcaat ctaaaaatta ttatcactct aatactgagc taagtaacaa tagacacaca    64260
gggaagggtg gccgttgctc ttgaggatat acttggaggc agcaaattag catacectge    64320 caagccaagc taatcacagg agattttgac gaatacagtt ctggatggcc tgcaatcagc    64380
aagaaggctt cctagaaaag agaaacataa accagccgcc tggggtttag gatagctatc    64440
attaagtggg gagggaagga agcagagact acatacttcc tggcctaggg agagctggcc    64500
cagcgaggca gtccttccgc tggaatcttt tggtaagaaa ttagatttga ggaggagact    64560
catggaaagc tgggaaagcc atcatttaag acagtaattc tcagtcatgt ctaacgtggg    64620
cccttcttca atataacaac aacttccact ccatctttta ataagtgaaa tatcaaaatg    64680
acttttaact taaatgtaat aggggctggg agatggtggc acatcccttt aatcccagca    64740
ctcagagtag tcagaggcag gtagatctct tgagtacgag ggcagcctgg tccacaaagc    64800
aagttccagg acagccaggg ctacacagag aaaccctgat tcataaaaac gaaacaaaca    64860 aaaaagaaa atgatcgggc aggtcccaca agtttccctt tgacctccac acattttggg    64920
cacatgtgta tacatacaca tatgtaaata aatgtgctta attttttagg aattaaattg    64980
ttatgtaaag ggcttgacct taaagggtcc cagaaatctg gggcacaagg aataatgccc    65040
ctcaccccca cagtgaagtt cacccattaa tgctattggc attcatcaat gattaaaagt    65100
agcataatgg acaataacct tttaaaaaaa tgaatctggg agctggagaa atggctcagt    65160
gcttaatggg actcactgtt ctcctgggga cctggacttg gttctctcc tcacatggtc    65220 cataaccacc attcccagaa gaactgacgt cctcatctgg cttccttgag catcatgcac    65280
acatggtgca cagacataca cacaggcaag cacttatcac ataaaataaa aacatatgat    65340 aaatccttt taaaagaaga agggcagtta atgtggccac aagaaagact ctatgtatca    65400
tcacaacctt cttaggtctg ggcagccggc aggattgaca atctcgtttt atctgttatt    65460
catggagtgg actgtctgtc cctctgtctc tctgtctctt tctcagacac acagaagcag    65520
atcatatgac tcagtcatca tggtctgaat gagtggcttt gttgggaggc agattttagt    65580 cttttcttcac tccattcttg ttccctatga acgggaatct cttgggtaa tgcctgtctc    65640 taaagttctg aaacatggtg gcggttgcta tggtctttga gaatcgttat tgattctgca    65700 agcaggcct ctgggaaata ggctcctaaa tggagaaata cgtcaaagat gtttaaatga    65760
ttctataaga aagtgattgt aggatttatt tattttgag acagagtcta gtagccctga    65820
ctatcctgga acttgctatg tagagcaggc tggccttcag ctcacagaga tctacctgcc    65880
tctgggtgtg tgccaccact ctccagcctg gccttatttc ttcattttgt tgttgttgtt    65940
gttgttgttt tcaaccctaa atgtaaagtc ttgctagtta ggcaaaagat ggctaccaac    66000
atgaactccc ccattctgtg aacttcaagg actactttgc cccaagagtg cgcctctctc    66060
tgtgtccccc tagtgtccat ttctgtgtcc cctgggcctt ctgctaatgg tgccatcgtt    66120
caccacatca gctccagatc ttcctcctcc cagctcagga gtgatgagaa agcaaatgtg    66180
tgccagcaaa actcaggaag aagcacaggc ccgctgtggt gtcttcctgt acccagcccc    66240
acctctggcc agagctaagg ctatatagta taggttaggg aggttttaga agggactgga    66300
aagagaatgt ggccaggtac ccagttctac ctgggaccca cggcgtcctt tctgttcct    66360 tccaagtcat tcctctcctt caccagaaag tgatggcatt tgtccccaca ctctcaagtc    66420
actgtgactg atttcgcagc cctaggggtc tgtgagaaat cttccaccta gagcagaaag    66480
cctaccaagg aggaaggtag gaccaaagat gagaagagca aaagaagtga ggaggatatt    66540
tcagcggaaa ggaaagcata tgtagacaga tgaataagcc aagatctatt gtaagagtta    66600
```

```
cgactgtaca caggcatcat tgcagtctcc tgattaactg cttgtactgc tgatgggcaa    66660
gagctgaaac tcagtcatga taccctcagg ttatcctaaa ccccatttaa cttcgtgtct    66720
ttcctctcag ggctggcgct gtgacaactg ccgtagacct ggggctgctg aacccagtcc    66780
cgatggcacc accggccaca cctacaacca gtatacacag agatacaatc agagaacaaa    66840
cactgtaagt gtacacatat ccccacccac ccccaccacc gtgactctcc ctgcatgcag    66900
ccaggggcag gtggatagat gcttttcttg aatgaaccaa atgagtttta tttggagata    66960
agtcttttgc tcatgagtcc agtcctcagg acccatccat gtaaagagc taggcgctac     67020 agcaagtgct tataatctcc tcactgagga ggtagaaata gggtgtgggt ggtgtccctg    67080
gggctgtctg gccagccact gtagccttgt taatgaactt caggctcatg aacaaagcag    67140
acagcatttg cttgattaaa gttaactctt ggctccttat acacacaaag tcatgaatta    67200
attataactc gttataattt actaaatccc taagcattgt ctattgctca gtacattgct    67260
agtcttttga aactatttat ccttcctata aaacacctgt gacacaaatc tccactcaac    67320
cctccccgaa acacacacac ttttggtttt ccgagtattt gctactaatg tttgtcttct    67380
attttgacag aacgtaaatt gccccattga gtgcttcatg ccgctagatg tgcaagctga    67440
cagagacgat tctcgagagt aatctttcca gccccaccct acaagtgtct ctctaccaag    67500
gtcaatccac accccagtga tgttagcaga ccctccatct ttgagtggtc ctttcaccct    67560
taagcctttt gctctggagc catgttctca gcttcagcac aatttacagc ttctccaagc    67620
atcgccccgt gggatgtttt gagacttctc tcctcaatgg tgacagttgg tcaccctgtt    67680
ctgcttcagg gtttcagtac tgctcagtgt tgtttaagag aatcaaaagt tcttatggtt    67740
tggtctggga tcaataggga aacacaggta gccaactagg aggaaatgta ctgaatgcta    67800
gtacccaaga ccttgagcag gaaagtcacc cagacacctc tgctttcttt tgccatctga    67860
cctgcagcac tgtcaggaca tggcctgtgg ctgtgtgttc aaacacccct cccacaggac    67920
tcactttgtc ccaacaattc agattgccta gaaataccct tctcttacct gtttgttatt    67980
tatcaatttt tcccagtatt tttatacgga aaaaattgta ttgaagcac tttgtatgca     68040 gttgataaga ggaattcagt ataattatgg ttggtgatta tttttataag cacatgccaa    68100
cgctttacta ctgtggaaag acaagtgttt taataaaaag atttacattc catgatgtgg    68160
acgtcatttc ttttttttttt taacatcatg tgtttggaga gaaaaattgt cttcatgcat    68220 gtccttttc ttttcgatgc tacaagcatg tgaagaggca ctgtgttggg ctggggtggt     68280
ttctgcacat gagcgcctgc ctggcctac agaagcactg atactttgcg tcattttgtg     68340
tcctcacttg tggttctgcc ttatcagatt taaatggatt caaatgtggg ctaagcttgc    68400
tagctagcac gttaggagta taaggaaat aagattcgtg tgtgtgtgtg tgtgtgtgtg     68460
tacatacata caagtgtgtg tgtagctgct catgaaaatc aggaggccag aagggatgc     68520 tgggtcccctt agagctggat acaagtgttt gtgagataga tactgggatt tgaactcata    68580
acagagcggc aaatgccctc acctctccag ccctatagtt ctgtttaatc atcacaggcc    68640
tttgcttctt t                                                          68651
```

<210> SEQ ID NO 30
<211> LENGTH: 15
<212> TYPE: DNA
<213> ORGANISM: Artificial sequence
<220> FEATURE:
<223> OTHER INFORMATION: Synthetic oligonucleotide

```
<400> SEQUENCE: 30
gtaagaggtt atgtg                                                15

<210> SEQ ID NO 31
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 31
ttaatggtaa gaggt                                                15

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
aatgtctgtt aggcaaat                                             18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
caatgtctgt taggcaaa                                             18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
tcaatgtctg ttaggcaa                                             18

<210> SEQ ID NO 35
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 35
aatgtctgtt aggca                                                15

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
atcaatgtct gttaggca                                             18

<210> SEQ ID NO 37
<211> LENGTH: 15
```

```
<212> TYPE: DNA
<213> ORGANISM: Artificial sequence
<220> FEATURE:
<223> OTHER INFORMATION: Synthetic oligonucleotide

<400> SEQUENCE: 37
caatgtctgt taggc                                                          15

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
cgatcaatgt ctgttagg                                                       18

<210> SEQ ID NO 39
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 39
atcaatgtct gttag                                                          15

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
gcgatcaatg tctgttag                                                       18

<210> SEQ ID NO 41
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 41
gatcaatgtc tgtta                                                          15

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
ggcgatcaat gtctgtta                                                       18

<210> SEQ ID NO 43
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 43
```

```
gccagtcctt taggg                                                    15

<210> SEQ ID NO 44
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 44
gtgaatgcca gtcct                                                    15

<210> SEQ ID NO 45
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 45
acatcagtga atgcc                                                    15

<210> SEQ ID NO 46
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 46
acatccacat cagtg                                                    15

<210> SEQ ID NO 47
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 47
gaatcgacat ccaca                                                    15

<210> SEQ ID NO 48
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 48
ttgatggaat cgaca                                                    15

<210> SEQ ID NO 49
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 49
gcaattttga tggaa                                                    15

<210> SEQ ID NO 50
<211> LENGTH: 15
<212> TYPE: DNA
<213> ORGANISM: Artificial sequence
```

```
<220> FEATURE:
<223> OTHER INFORMATION: Synthetic oligonucleotide

<400> SEQUENCE: 50
tcccaagcaa ttttg                                                      15

<210> SEQ ID NO 51
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 51
gggctttccc aagca                                                      15

<210> SEQ ID NO 52
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 52
ccctgtgggc tttcc                                                      15

<210> SEQ ID NO 53
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 53
acttgcccct gtggg                                                      15

<210> SEQ ID NO 54
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 54
ctggaaactt gcccc                                                      15

<210> SEQ ID NO 55
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 55
ctgtacctgg aaact                                                      15

<210> SEQ ID NO 56
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 56
gtcaccctgt acctg                                                      15
```

<210> SEQ ID NO 57
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 57
gagtaggtca ccctg                                                    15

<210> SEQ ID NO 58
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 58
gggctcgagt aggtc                                                    15

<210> SEQ ID NO 59
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 59
tcctcagggc tcgag                                                    15

<210> SEQ ID NO 60
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 60
attccatcct caggg                                                    15

<210> SEQ ID NO 61
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 61
tcatggattc catcc                                                    15

<210> SEQ ID NO 62
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 62
aatagctcat ggatt                                                    15

<210> SEQ ID NO 63
<211> LENGTH: 15
<212> TYPE: DNA
<213> ORGANISM: Artificial sequence
<220> FEATURE:
<223> OTHER INFORMATION: Synthetic oligonucleotide

```
<400> SEQUENCE: 63
gcagggaata gctca                                                    15

<210> SEQ ID NO 64
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 64
tcaggtgcag ggaat                                                    15

<210> SEQ ID NO 65
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 65
tcaccatcag gtgca                                                    15

<210> SEQ ID NO 66
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 66
tcttcttcac catca                                                    15

<210> SEQ ID NO 67
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 67
gcagtgtctt cttca                                                    15

<210> SEQ ID NO 68
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 68
agctctgcag tgtct                                                    15

<210> SEQ ID NO 69
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 69
ccttgcagct ctgca                                                    15

<210> SEQ ID NO 70
```

```
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 70
ctgaggcctt gcagc                                                    15

<210> SEQ ID NO 71
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 71
cccggtctga ggcct                                                    15

<210> SEQ ID NO 72
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 72
tcagaacccg gtctg                                                    15

<210> SEQ ID NO 73
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 73
gtgtactcag aaccc                                                    15

<210> SEQ ID NO 74
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 74
ctgactgtgt actca                                                    15

<210> SEQ ID NO 75
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 75
accacactga ctgtg                                                    15

<210> SEQ ID NO 76
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 76
```
aaggcaacca cactg                                                     15

<210> SEQ ID NO 77
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 77
tcgtgcaagg caacc                                                     15

<210> SEQ ID NO 78
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 78
atatcatcgt gcaag                                                     15

<210> SEQ ID NO 79
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 79
ctctccatat catcg                                                     15

<210> SEQ ID NO 80
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 80
ggctggctct ccata                                                     15

<210> SEQ ID NO 81
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 81
gattccaatc agggg                                                     15

<210> SEQ ID NO 82
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 82
actggattcc aatca                                                     15

<210> SEQ ID NO 83
<211> LENGTH: 15
<212> TYPE: DNA

```
<213> ORGANISM: Artificial sequence
<220> FEATURE:
<223> OTHER INFORMATION: Synthetic oligonucleotide

<400> SEQUENCE: 83
tggactggat tccaa                                                    15

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 84
cctgtggact ggattcca                                                 18

<210> SEQ ID NO 85
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 85
ctgtggactg gattc                                                    15

<210> SEQ ID NO 86
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 86
tacctgtgga ctgga                                                    15

<210> SEQ ID NO 87
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 87
aacgatatac ctgtg                                                    15

<210> SEQ ID NO 88
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 88
aattaatcat aaacc                                                    15

<210> SEQ ID NO 89
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 89
ggtgcaatta accat                                                    15
```

<210> SEQ ID NO 90
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 90
cctggtggtg caatt                                                      15

<210> SEQ ID NO 91
<211> LENGTH: 20
<212> TYPE: DNA
<213> ORGANISM: Artificial sequence
<220> FEATURE:
<223> OTHER INFORMATION: Primer

<400> SEQUENCE: 91
gccttgcacg atgatatgga                                                 20

<210> SEQ ID NO 92
<211> LENGTH: 21
<212> TYPE: DNA
<213> ORGANISM: Artificial sequence
<220> FEATURE:
<223> OTHER INFORMATION: Primer

<400> SEQUENCE: 92
tgtgggtgtg acctgagtga a                                               21

<210> SEQ ID NO 93
<211> LENGTH: 17
<212> TYPE: DNA
<213> ORGANISM: Artificial sequence
<220> FEATURE:
<223> OTHER INFORMATION: Probe

<400> SEQUENCE: 93
attggaaccc agtccac                                                    17

<210> SEQ ID NO 94
<211> LENGTH: 21
<212> TYPE: DNA
<213> ORGANISM: Artificial sequence
<220> FEATURE:
<223> OTHER INFORMATION: Primer

<400> SEQUENCE: 94
gaatccaagc ggagagagtc a                                               21

<210> SEQ ID NO 95
<211> LENGTH: 23
<212> TYPE: DNA
<213> ORGANISM: Artificial sequence
<220> FEATURE:
<223> OTHER INFORMATION: Primer

<400> SEQUENCE: 95
acatcagtga atgccagtcc ttt                                             23

<210> SEQ ID NO 96
<211> LENGTH: 30
<212> TYPE: DNA
<213> ORGANISM: Artificial sequence
<220> FEATURE:

<223> OTHER INFORMATION: Probe

<400> SEQUENCE: 96
ttcagactgc agtaaccaac attgatcgcc　　　　　　　　　　　　　　　30

<210> SEQ ID NO 97
<211> LENGTH: 8374
<212> TYPE: DNA
<213> ORGANISM: Homo sapiens

<400> SEQUENCE: 97

| | |
|---|---|
| gcccgcgccg gctgtgctgc acaggggag gagagggaac cccaggcgcg agcgggaaga | 60 |
| ggggacctgc agccacaact tctctggtcc tctgcatccc ttctgtccct ccacccgtcc | 120 |
| ccttccccac cctctggccc ccaccttctt ggaggcgaca accccgggga ggcattagaa | 180 |
| gggatttttc ccgcaggttg cgaagggaag caaacttggt ggcaacttgc ctcccggtgc | 240 |
| gggcgtctct cccccaccgt ctcaacatgc ttaggggtcc ggggcccggg ctgctgctgc | 300 |
| tggccgtcca gtgcctgggg acagcggtgc cctccacggg agcctcgaag agcaagaggc | 360 |
| aggctcagca aatggttcag ccccagtccc cggtggctgt cagtcaaagc aagcccggtt | 420 |
| gttatgacaa tggaaaacac tatcagataa atcaacagtg ggagcggacc tacctaggca | 480 |
| atgcgttggt ttgtacttgt tatggaggaa gccgaggttt aactgcgag agtaaacctg | 540 |
| aagctgaaga gacttgcttt gacaagtaca ctggaacac ttaccgagtg ggtgacactt | 600 |
| atgagcgtcc taaagactcc atgatctggg actgtacctg catcggggct gggcgaggga | 660 |
| gaataagctg taccatcgca aaccgctgcc atgaagggg tcagtcctac aagattggtg | 720 |
| acacctggag gagaccacat gagactggtg gttacatgtt agagtgtgtg tgtcttggta | 780 |
| atggaaaagg agaatggacc tgcaagccca tagctgagaa gtgttttgat catgctgctg | 840 |
| ggacttccta tgtggtcgga gaaacgtggg agaagcccta ccaaggctgg atgatggtag | 900 |
| attgtacttg cctgggagaa ggcagcggac gcatcacttg cacttctaga aatagatgca | 960 |
| acgatcagga cacaaggaca tcctatagaa ttggagacac ctggagcaag aaggataatc | 1020 |
| gaggaaacct gctccagtgc atctgcacag gcaacggccg aggagagtgg aagtgtgaga | 1080 |
| ggcacacctc tgtgcagacc acatcgagcg gatctggccc cttcaccgat gttcgtgcag | 1140 |
| ctgtttacca accgcagcct caccccagc ctcctcccta tggccactgt gtcacagaca | 1200 |
| gtggtgtggt ctactctgtg gggatgcagt ggctgaagac acaaggaaat aagcaaatgc | 1260 |
| tttgcacgtg cctgggcaac ggagtcagct gccaagagac agctgtaacc cagacttacg | 1320 |
| gtggcaactc aaatggagag ccatgtgtct taccattcac ctacaatggc aggacgttct | 1380 |
| actcctgcac cacagaaggg cgacaggacg gacatctttg gtgcagcaca acttcgaatt | 1440 |
| atgagcagga ccagaaatac tcttctctgca cagaccacac tgttttggtt cagactcgag | 1500 |
| gaggaaattc caatggtgcc ttgtgccact tcccttcct atacaacaac cacaattaca | 1560 |
| ctgattgcac ttctgagggc agaagagaca acatgaagtg gtgtgggacc acacagaact | 1620 |
| atgatgccga ccagaagttt gggttctgcc ccatggctgc ccacgaggaa atctgcacaa | 1680 |
| ccaatgaagg ggtcatgtac cgcattgag atcagtggga taagcagcat gacatgggtc | 1740 |
| acatgatgag gtgcacgtgt gttgggaatg gtcgtgggga atggacatgc attgcctact | 1800 |
| cgcagcttcg agatcagtgc attgttgatg acatcactta caatgtgaac gacacattcc | 1860 |
| acaagcgtca tgaagagggg cacatgctga actgtacatg cttcggtcag gtcgggggca | 1920 |
| ggtggaagtg tgatccccgtc gaccaatgcc aggattcaga gactgggacg ttttatcaaa | 1980 |

```
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatgggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cggctgtcc cctggggtca   3180 cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccagggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccacccccat   4140
ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
```

```
gaagacagaa aacaggtctt gattccccaa ctggcattga ctttctgat attactgcca    4380
actcttttac tgtgcactgg attgctcctc gagccaccat cactggctac aggatccgcc    4440
atcatcccga gcacttcagt gggagacctc gagaagatcg ggtgccccac tctcggaatt    4500
ccatcaccct caccaacctc actccaggca cagagtatgt ggtcagcatc gttgctctta    4560
atggcagaga ggaaagtccc ttattgattg ccaacaatc aacagtttct gatgttccga    4620
gggacctgga agttgttgct gcgaccccca ccagcctact gatcagctgg gatgctcctg    4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct tgcagcccac agtggagtat gtggttagtg    5100
tctatgctca gaatccaagc ggagagagtc agcctctggt tcagactgca gtaaccaaca    5160
ttgatcgccc taaaggactg gcattcactg atgtggatgc cgattccatc aaaattgctt    5220
gggaaagccc acaggggcaa gtttccaggt acagggtgac ctactcgagc cctgaggatg    5280
gaatccatga gctattccct gcacctgatg gtgaagaaga cactgcagag ctgcaaggcc    5340
tcagaccggg ttctgagtac acagtcagtg tggttgcctt gcacgatgat atggagagcc    5400
agccctgat tggaacccag tccacagcta ttcctgcacc aactgacctg aagttcactc    5460
aggtcacacc cacaagcctg agcgcccagt ggacaccacc caatgttcag ctcactggat    5520
atcgagtgcg ggtgacccc aaggagaaga ccggaccaat gaaagaaatc aaccttgctc    5580
ctgacagctc atccgtggtt gtatcaggac ttatggtggc caccaaatat gaagtgagtg    5640
tctatgctct taaggacact ttgacaagca gaccagctca gggagttgtc accactctgg    5700
agaatgtcag cccaccaaga agggctcgtg tgacagatgc tactgagacc accatcacca    5760
ttagctggag aaccaagact gagacgatca ctggcttcca agttgatgcc gttccagcca    5820
atggccagac tccaatccag agaaccatca gccagatgt cagaagctac accatcacag    5880
gtttacaacc aggcactgac tacaagatct acctgtacac cttgaatgac aatgctcgga    5940
gctcccctgt ggtcatcgac gcctccactg ccattgatgc accatccaac ctgcgtttcc    6000
tggccaccac acccaattcc ttgctggtat catggcagcc gccacgtgcc aggattaccg    6060
gctacatcat caagtatgag aagcctgggt ctcctcccag agaagtggtc cctcggcccc    6120
gccctggtgt cacagaggct actattactg gcctggaacc gggaaccgaa tatacaattt    6180
atgtcattgc cctgaagaat aatcagaaga gcgagcccct gattggaagg aaaaagacag    6240
ttcaaaagac cccttttcgtc acccacccctg ggtatgacac tggaaatggt attcagcttc    6300
ctggcacttc tggtcagcaa cccagtgttg ggcaacaaat gatctttgag aacatggtt    6360
ttaggcggac cacaccgccc acaacggcca ccccataag gcataggcca agaccatacc    6420
cgccgaatgt aggacaagaa gctctctctc agacaaccat ctcatgggcc ccattccagg    6480
acacttctga gtacatcatt tcatgtcatc ctgttggcac tgatgaagaa cccttacagt    6540
tcagggttcc tggaacttct accagtgcca ctctgacagg cctcaccaga ggtgccacct    6600
acaacatcat agtggaggca ctgaaagacc agcagaggca taaggttcgg gaagaggttg    6660
ttaccgtggg caactctgtc aacgaaggct tgaaccaacc tacggatgac tcgtgctttg    6720
```

```
accctacac agtttcccat tatgccgttg gagatgagtg ggaacgaatg tctgaatcag      6780
gctttaaact gttgtgccag tgcttaggct ttggaagtgg tcatttcaga tgtgattcat      6840
ctagatggtg ccatgacaat ggtgtgaact acaagattgg agagaagtgg gaccgtcagg      6900
gagaaaatgg ccagatgatg agctgcacat gtcttgggaa cggaaaagga gaattcaagt      6960
gtgaccctca tgaggcaacg tgttatgatg atgggaagac ataccacgta ggagaacagt      7020
ggcagaagga atatctcggt gccatttgct cctgcacatg ctttggaggc cagcggggct      7080
ggcgctgtga caactgccgc agacctgggg gtgaacccag tcccgaaggc actactggcc      7140
agtcctacaa ccagtattct cagagatacc atcagagaac aaacactaat gttaattgcc      7200
caattgagtg cttcatgcct ttagatgtac aggctgacag agaagattcc cgagagtaaa      7260
tcatctttcc aatccagagg aacaagcatg tctctctgcc aagatccatc taaactggag      7320
tgatgttagc agacccagct tagagttctt cttttcttct taagcccttt gctctggagg      7380
aagttctcca gcttcagctc aactcacagc ttctccaagc atcaccctgg gagtttcctg      7440
agggttttct cataaatgag ggctgcacat tgcctgttct gcttcgaagt attcaatacc      7500
gctcagtatt ttaaatgaag tgattctaag atttggtttg ggatcaatag gaaagcatat      7560
gcagccaacc aagatgcaaa tgttttgaaa tgatatgacc aaaattttaa gtaggaaagt      7620
cacccaaaca cttctgcttt cacttaagtg tctggcccgc aatactgtag gaacaagcat      7680
gatcttgtta ctgtgatatt ttaaatatcc acagtactca cttttccaa atgatcctag       7740
taattgccta gaaatatctt tctcttacct gttatttatc aattttttccc agtattttta     7800
tacggaaaaa attgtattga aaacacttag tatgcagttg ataagaggaa tttggtataa      7860
ttatggtggg tgattatttt ttatactgta tgtgccaaag ctttactact gtggaaagac      7920
aactgtttta ataaaagatt tacattccac aacttgaagt tcatctattt gatataagac      7980
accttcgggg gaaataattc ctgtgaatat tctttttcaa ttcagcaaac atttgaaaat      8040
ctatgatgtg caagtctaat tgttgatttc agtacaagat tttctaaatc agttgctaca      8100
aaaactgatt ggttttgtc acttcatctc ttcactaatg gagatagctt tacactttct      8160
gctttaatag atttaagtgg accccaatat ttattaaaat tgctagttta ccgttcagaa      8220
gtataataga aataatcttt agttgctctt ttctaaccat tgtaattctt cccttcttcc      8280
ctccaccttt ccttcattga ataaacctct gttcaaagag attgcctgca agggaaataa      8340
aaatgactaa gatattaaaa aaaaaaaaa aaaa                                    8374
```

<210> SEQ ID NO 98
<211> LENGTH: 24
<212> TYPE: DNA
<213> ORGANISM: Artificial sequence
<220> FEATURE:
<223> OTHER INFORMATION: Primer

<400> SEQUENCE: 98
aaactgcagt gaccaacatt gatc                                              24

<210> SEQ ID NO 99
<211> LENGTH: 18
<212> TYPE: DNA
<213> ORGANISM: Artificial sequence
<220> FEATURE:
<223> OTHER INFORMATION: Primer

<400> SEQUENCE: 99
cttgcccctg tgggcttt                                    18

<210> SEQ ID NO 100
<211> LENGTH: 18
<212> TYPE: DNA
<213> ORGANISM: Artificial sequence
<220> FEATURE:
<223> OTHER INFORMATION: Probe

<400> SEQUENCE: 100
ctgatgtgga tgtcgatt                                    18

<210> SEQ ID NO 101
<211> LENGTH: 17
<212> TYPE: DNA
<213> ORGANISM: Artificial sequence
<220> FEATURE:
<223> OTHER INFORMATION: Primer

<400> SEQUENCE: 101
gccagcccct gattgga                                     17

<210> SEQ ID NO 102
<211> LENGTH: 20
<212> TYPE: DNA
<213> ORGANISM: Artificial sequence
<220> FEATURE:
<223> OTHER INFORMATION: Primer

<400> SEQUENCE: 102
ccggtagcca gtgagctgaa                                  20

<210> SEQ ID NO 103
<211> LENGTH: 16
<212> TYPE: DNA
<213> ORGANISM: Artificial sequence
<220> FEATURE:
<223> OTHER INFORMATION: Probe

<400> SEQUENCE: 103
caccaatctg aagttc                                      16

<210> SEQ ID NO 104
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 104
gcaaattaat ggtaa                                       15

<210> SEQ ID NO 105
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 105
cgatcaatgt ctgtt                                       15

<210> SEQ ID NO 106
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 106
tccataccat gcaaa                                                    15

<210> SEQ ID NO 107
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 107
atatttccat accat                                                    15

<210> SEQ ID NO 108
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 108
caagcatatt tccat                                                    15

<210> SEQ ID NO 109
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 109
tgaaacaagc atatt                                                    15

<210> SEQ ID NO 110
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 110
agttgtgaaa caagc                                                    15

<210> SEQ ID NO 111
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 111
aagcaagttg tgaaa                                                    15

<210> SEQ ID NO 112
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 112
gtgaaaagca agttg                                                    15

<210> SEQ ID NO 113
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 113
gttatgtgaa aagca                                                    15

<210> SEQ ID NO 114
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 114
aagaggttat gtgaa                                                    15

<210> SEQ ID NO 115
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 115
atggtaagag gttat                                                    15

<210> SEQ ID NO 116
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 116
aattaatggt aagag                                                    15

<210> SEQ ID NO 117
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 117
aggcaaatta atggt                                                    15

<210> SEQ ID NO 118
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 118
ctgttaggca aatta                                                    15

<210> SEQ ID NO 119
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 119
tagggcgatc aatgt                                                        15

<210> SEQ ID NO 120
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 120
tcctttaggg cgatc                                                        15

<210> SEQ ID NO 121
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 121
tgaatgccag tcctt                                                        15

<210> SEQ ID NO 122
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 122
atcagtgaat gccag                                                        15

<210> SEQ ID NO 123
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 123
tccacatcag tgaat                                                        15

<210> SEQ ID NO 124
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 124
cgacatccac atcag                                                        15

<210> SEQ ID NO 125
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 125
ggaatcgaca tccac                                                        15

<210> SEQ ID NO 126

```
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 126
caattttgat ggaat                                              15

<210> SEQ ID NO 127
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 127
ccaagcaatt ttgat                                              15

<210> SEQ ID NO 128
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 128
ctttcccaag caatt                                              15

<210> SEQ ID NO 129
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 129
gtgggctttc ccaag                                              15

<210> SEQ ID NO 130
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 130
cccctgtggg ctttc                                              15

<210> SEQ ID NO 131
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 131
tggaaacttg cccct                                              15

<210> SEQ ID NO 132
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 132
```
gtacctggaa acttg    15

<210> SEQ ID NO 133
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 133
accctgtacc tggaa    15

<210> SEQ ID NO 134
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 134
aggtcaccct gtacc    15

<210> SEQ ID NO 135
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 135
cgagtaggtc accct    15

<210> SEQ ID NO 136
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 136
cctcagggct cgagt    15

<210> SEQ ID NO 137
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 137
tccatcctca gggct    15

<210> SEQ ID NO 138
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 138
cggattccat cctca    15

<210> SEQ ID NO 139
<211> LENGTH: 15
<212> TYPE: DNA

<213> ORGANISM: Artificial sequence
<220> FEATURE:
<223> OTHER INFORMATION: Synthetic oligonucleotide

<400> SEQUENCE: 139
gctcccggat tccat                                                        15

<210> SEQ ID NO 140
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 140
gaaaagctcc cggat                                                        15

<210> SEQ ID NO 141
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 141
gcagggaaaa gctcc                                                        15

<210> SEQ ID NO 142
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 142
caggtgcagg gaaaa                                                        15

<210> SEQ ID NO 143
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 143
accatcaggt gcagg                                                        15

<210> SEQ ID NO 144
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 144
tcttcaccat caggt                                                        15

<210> SEQ ID NO 145
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 145
tgtcgtcttc accat                                                        15

<210> SEQ ID NO 146
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 146
tgcagtgtcg tcttc                                              15

<210> SEQ ID NO 147
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 147
agctctgcag tgtcg                                              15

<210> SEQ ID NO 148
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 148
cctgcagctc tgcag                                              15

<210> SEQ ID NO 149
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 149
gaggccctgc agctc                                              15

<210> SEQ ID NO 150
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 150
ggcctgaggc cctgc                                              15

<210> SEQ ID NO 151
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 151
accccggcct gaggc                                              15

<210> SEQ ID NO 152
<211> LENGTH: 15
<212> TYPE: DNA
<213> ORGANISM: Artificial sequence
<220> FEATURE:

<223> OTHER INFORMATION: Synthetic oligonucleotide

<400> SEQUENCE: 152
ctcagacccc ggcct                                                          15

<210> SEQ ID NO 153
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 153
gtgtactcag acccc                                                          15

<210> SEQ ID NO 154
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 154
tgactgtgta ctcag                                                          15

<210> SEQ ID NO 155
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 155
cacactgact gtgta                                                          15

<210> SEQ ID NO 156
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 156
gcaaccacac tgact                                                          15

<210> SEQ ID NO 157
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 157
gcaaggcaac cacac                                                          15

<210> SEQ ID NO 158
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 158
atcgtgcaag gcaac                                                          15

```
<210> SEQ ID NO 159
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 159
tctccatatc atcgt                                                       15

<210> SEQ ID NO 160
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 160
ctggctctcc atatc                                                       15

<210> SEQ ID NO 161
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 161
gactggattc caatc                                                       15

<210> SEQ ID NO 162
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 162
tatacctgtg gactg                                                       15

<210> SEQ ID NO 163
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 163
cggttaacga tatac                                                       15

<210> SEQ ID NO 164
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 164
gggtgcggtt aacga                                                       15

<210> SEQ ID NO 165
<211> LENGTH: 15
<212> TYPE: DNA
<213> ORGANISM: Artificial sequence
<220> FEATURE:
<223> OTHER INFORMATION: Synthetic oligonucleotide
```

```
<400> SEQUENCE: 165
gtggtgggtg cggtt                                                  15

<210> SEQ ID NO 166
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 166
cccgggtggt gggtg                                                  15

<210> SEQ ID NO 167
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 167
aagcacccgg gtggt                                                  15

<210> SEQ ID NO 168
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 168
cccagaagca cccgg                                                  15

<210> SEQ ID NO 169
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 169
ctgttcccag aagca                                                  15

<210> SEQ ID NO 170
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 170
agccactgtt cccag                                                  15

<210> SEQ ID NO 171
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 171
cataaagcca ctgtt                                                  15

<210> SEQ ID NO 172
<211> LENGTH: 15
```

```
<212> TYPE: DNA
<213> ORGANISM: Artificial sequence
<220> FEATURE:
<223> OTHER INFORMATION: Synthetic oligonucleotide

<400> SEQUENCE: 172
caaggcataa agcca                                                    15

<210> SEQ ID NO 173
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 173
gccagcaagg cataa                                                    15

<210> SEQ ID NO 174
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 174
ataacgccag caagg                                                    15

<210> SEQ ID NO 175
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 175
aaagtataac gccag                                                    15

<210> SEQ ID NO 176
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 176
ccagtaaagt ataac                                                    15

<210> SEQ ID NO 177
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 177
gttaggcaaa ttaatggt                                                 18

<210> SEQ ID NO 178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 178
```

```
tgttaggcaa attaatgg                                                    18

<210> SEQ ID NO 179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 179
ctgttaggca aattaatg                                                    18

<210> SEQ ID NO 180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 180
tctgttaggc aaattaat                                                    18

<210> SEQ ID NO 181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 181
gtctgttagg caaattaa                                                    18

<210> SEQ ID NO 182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 182
tgtctgttag gcaaatta                                                    18

<210> SEQ ID NO 183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 183
atgtctgtta ggcaaatt                                                    18

<210> SEQ ID NO 184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 184
gatcaatgtc tgttaggc                                                    18

<210> SEQ ID NO 185
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 185
gggcgatcaa tgtctgtt                                                 18

<210> SEQ ID NO 186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 186
agggcgatca atgtctgt                                                 18

<210> SEQ ID NO 187
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 187
tagggcgatc aatgtctg                                                 18

<210> SEQ ID NO 188
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 188
ttagggcgat caatgtct                                                 18

<210> SEQ ID NO 189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 189
tttagggcga tcaatgtc                                                 18

<210> SEQ ID NO 190
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 190
ctttagggcg atcaatgt                                                 18

<210> SEQ ID NO 191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 191
cctttagggc gatcaatg                                                 18
```

<210> SEQ ID NO 192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 192
tcctttaggg cgatcaat                                                 18

<210> SEQ ID NO 193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 193
gtcctttagg gcgatcaa                                                 18

<210> SEQ ID NO 194
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 194
agtcctttag ggcgatca                                                 18

<210> SEQ ID NO 195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
cagtccttta gggcgatc                                                 18

<210> SEQ ID NO 196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 196
ggaatcgaca tccacatc                                                 18

<210> SEQ ID NO 197
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 197
tggaatcgac atccacat                                                 18

<210> SEQ ID NO 198
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 198
atggaatcga catccaca                                                 18

<210> SEQ ID NO 199
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 199
gatggaatcg acatccac                                                 18

<210> SEQ ID NO 200
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 200
tgatggaatc gacatcca                                                 18

<210> SEQ ID NO 201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 201
ttgatggaat cgacatcc                                                 18

<210> SEQ ID NO 202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 202
tttgatggaa tcgacatc                                                 18

<210> SEQ ID NO 203
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 203
caattttgat ggaatcga                                                 18

<210> SEQ ID NO 204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 204
gcaattttga tggaatcg                                                 18

<210> SEQ ID NO 205
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 205
agcaattttg atggaatc                                                 18

<210> SEQ ID NO 206
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 206 aagcaattttt gatggaat                                                18
```

```
aagcaatttt gatggaat                                                 18

<210> SEQ ID NO 207
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 207
caagcaattt tgatggaa                                                 18

<210> SEQ ID NO 208
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 208
ccaagcaatt ttgatgga                                                 18

<210> SEQ ID NO 209
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 209
cccaagcaat tttgatgg                                                 18

<210> SEQ ID NO 210
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 210
gtcaccctgt acctggaa                                                 18

<210> SEQ ID NO 211
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 211
```
ggtcaccctg tacctgga                                               18

<210> SEQ ID NO 212
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 212
aggtcaccct gtacctgg                                               18

<210> SEQ ID NO 213
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 213
taggtcaccc tgtacctg                                               18

<210> SEQ ID NO 214
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 214
gtaggtcacc ctgtacct                                               18

<210> SEQ ID NO 215
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 215
agtaggtcac cctgtacc                                               18

<210> SEQ ID NO 216
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 216
gagtaggtca ccctgtac                                               18

<210> SEQ ID NO 217
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 217
cgagtaggtc accctgta                                               18

<210> SEQ ID NO 218
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 218
tcgagtaggt caccctgt                                                    18

<210> SEQ ID NO 219
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 219
ctcgagtagg tcaccctg                                                    18

<210> SEQ ID NO 220
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 220
gctcgagtag gtcaccct                                                    18

<210> SEQ ID NO 221
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 221
ggctcgagta ggtcaccc                                                    18

<210> SEQ ID NO 222
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 222
gggctcgagt aggtcacc                                                    18

<210> SEQ ID NO 223
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 223
agggctcgag taggtcac                                                    18

<210> SEQ ID NO 224
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 224
cagggctcga gtaggtca                                                    18
```

<210> SEQ ID NO 225
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 225
tcagggctcg agtaggtc                                           18

<210> SEQ ID NO 226
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 226
ctcagggctc gagtaggt                                           18

<210> SEQ ID NO 227
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 227
cctcagggct cgagtagg                                           18

<210> SEQ ID NO 228
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 228
tcctcagggc tcgagtag                                           18

<210> SEQ ID NO 229
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 229
atcctcaggg ctcgagta                                           18

<210> SEQ ID NO 230
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 230
catcctcagg gctcgagt                                           18

<210> SEQ ID NO 231
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 231
ccatcctcag ggctcgag                                        18

<210> SEQ ID NO 232
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 232
tccatcctca gggctcga                                        18

<210> SEQ ID NO 233
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 233
ttccatcctc agggctcg                                        18

<210> SEQ ID NO 234
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 234
attccatcct cagggctc                                        18

<210> SEQ ID NO 235
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 235
gattccatcc tcagggct                                        18

<210> SEQ ID NO 236
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 236
ggattccatc ctcagggc                                        18

<210> SEQ ID NO 237
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 237
cggattccat cctcaggg                                        18

```
<210> SEQ ID NO 238
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 238
ccggattcca tcctcagg                                                 18

<210> SEQ ID NO 239
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 239
cccggattcc atcctcag                                                 18

<210> SEQ ID NO 240
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 240
tcccggattc catcctca                                                 18

<210> SEQ ID NO 241
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 241
ctcccggatt ccatcctc                                                 18

<210> SEQ ID NO 242
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 242
gctcccggat tccatcct                                                 18

<210> SEQ ID NO 243
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 243
agctcccgga ttccatcc                                                 18

<210> SEQ ID NO 244
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 244
aagctcccgg attccatc                                                  18

<210> SEQ ID NO 245
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 245
aaagctcccg gattccat                                                  18

<210> SEQ ID NO 246
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 246
aaaagctccc ggattcca                                                  18

<210> SEQ ID NO 247
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 247
gaaaagctcc cggattcc                                                  18

<210> SEQ ID NO 248
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 248
ggaaaagctc ccggattc                                                  18

<210> SEQ ID NO 249
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 249
gggaaaagct cccggatt                                                  18

<210> SEQ ID NO 250
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 250
agggaaaagc tcccggat                                                  18

<210> SEQ ID NO 251
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 251
cagggaaaag ctcccgga                                                    18

<210> SEQ ID NO 252
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 252
gcagggaaaa gctcccgg                                                    18

<210> SEQ ID NO 253
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 253
tgcagggaaa agctcccg                                                    18

<210> SEQ ID NO 254
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 254
gtgcagggaa aagctccc                                                    18

<210> SEQ ID NO 255
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 255
ggtgcaggga aaagctcc                                                    18

<210> SEQ ID NO 256
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 256
aggtgcaggg aaaagctc                                                    18

<210> SEQ ID NO 257
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 257
```
caggtgcagg gaaaagct                                           18

<210> SEQ ID NO 258
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 258
tcaggtgcag ggaaaagc                                           18

<210> SEQ ID NO 259
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 259
atcaggtgca gggaaaag                                           18

<210> SEQ ID NO 260
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 260
catcaggtgc agggaaaa                                           18

<210> SEQ ID NO 261
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 261
ccatcaggtg cagggaaa                                           18

<210> SEQ ID NO 262
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 262
accatcaggt gcagggaa                                           18

<210> SEQ ID NO 263
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 263
caccatcagg tgcaggga                                           18

<210> SEQ ID NO 264
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 264
tcaccatcag gtgcaggg                                                 18

<210> SEQ ID NO 265
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 265
ttcaccatca ggtgcagg                                                 18

<210> SEQ ID NO 266
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 266
cttcaccatc aggtgcag                                                 18

<210> SEQ ID NO 267
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 267
tcttcaccat caggtgca                                                 18

<210> SEQ ID NO 268
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 268
gtcttcacca tcaggtgc                                                 18

<210> SEQ ID NO 269
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 269
cgtcttcacc atcaggtg                                                 18

<210> SEQ ID NO 270
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 270
tcgtcttcac catcaggt                                                 18
```

```
<210> SEQ ID NO 271
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 271
gtcgtcttca ccatcagg                                              18

<210> SEQ ID NO 272
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 272
tgtcgtcttc accatcag                                              18

<210> SEQ ID NO 273
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 273
gtgtcgtctt caccatca                                              18

<210> SEQ ID NO 274
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 274
agtgtcgtct tcaccatc                                              18

<210> SEQ ID NO 275
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 275
cagtgtcgtc ttcaccat                                              18

<210> SEQ ID NO 276
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 276
gcagtgtcgt cttcacca                                              18

<210> SEQ ID NO 277
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 277
tgcagtgtcg tcttcacc                                                 18

<210> SEQ ID NO 278
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 278
ctgcagtgtc gtcttcac                                                 18

<210> SEQ ID NO 279
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 279
tctgcagtgt cgtcttca                                                 18

<210> SEQ ID NO 280
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 280
ctctgcagtg tcgtcttc                                                 18

<210> SEQ ID NO 281
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 281
gctctgcagt gtcgtctt                                                 18

<210> SEQ ID NO 282
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 282
agctctgcag tgtcgtct                                                 18

<210> SEQ ID NO 283
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 283
cagctctgca gtgtcgtc                                                 18

<210> SEQ ID NO 284
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 284
gcagctctgc agtgtcgt                                                    18

<210> SEQ ID NO 285
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 285
tgcagctctg cagtgtcg                                                    18

<210> SEQ ID NO 286
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 286
ctgcagctct gcagtgtc                                                    18

<210> SEQ ID NO 287
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 287
cctgcagctc tgcagtgt                                                    18

<210> SEQ ID NO 288
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 288
ccctgcagct ctgcagtg                                                    18

<210> SEQ ID NO 289
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 289
gccctgcagc tctgcagt                                                    18

<210> SEQ ID NO 290
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 290
```
ggccctgcag ctctgcag                                             18

<210> SEQ ID NO 291
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 291
aggccctgca gctctgca                                             18

<210> SEQ ID NO 292
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 292
gaggccctgc agctctgc                                             18

<210> SEQ ID NO 293
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 293
tgaggccctg cagctctg                                             18

<210> SEQ ID NO 294
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 294
ctgaggccct gcagctct                                             18

<210> SEQ ID NO 295
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 295
cctgaggccc tgcagctc                                             18

<210> SEQ ID NO 296
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 296
gcaaggcaac cacactga                                             18

<210> SEQ ID NO 297
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 297
tgcaaggcaa ccacactg                                                 18

<210> SEQ ID NO 298
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 298
gtgcaaggca accacact                                                 18

<210> SEQ ID NO 299
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 299
cgtgcaaggc aaccacac                                                 18

<210> SEQ ID NO 300
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 300
tcgtgcaagg caaccaca                                                 18

<210> SEQ ID NO 301
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 301
atcgtgcaag gcaaccac                                                 18

<210> SEQ ID NO 302
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 302
catcgtgcaa ggcaacca                                                 18

<210> SEQ ID NO 303
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 303
atatcatcgt gcaaggca                                                 18
```

<210> SEQ ID NO 304
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 304
catatcatcg tgcaaggc                                                 18

<210> SEQ ID NO 305
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 305
ccatatcatc gtgcaagg                                                 18

<210> SEQ ID NO 306
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 306
tccatatcat cgtgcaag                                                 18

<210> SEQ ID NO 307
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 307
ctccatatca tcgtgcaa                                                 18

<210> SEQ ID NO 308
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 308
tctccatatc atcgtgca                                                 18

<210> SEQ ID NO 309
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 309
ctctccatat catcgtgc                                                 18

<210> SEQ ID NO 310
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 310
gctctccata tcatcgtg                                                       18

<210> SEQ ID NO 311
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 311
ggctctccat atcatcgt                                                       18

<210> SEQ ID NO 312
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 312
tggctctcca tatcatcg                                                       18

<210> SEQ ID NO 313
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 313
ctggctctcc atatcatc                                                       18

<210> SEQ ID NO 314
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 314
gctggctctc catatcat                                                       18

<210> SEQ ID NO 315
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 315
atatacctgt ggactgga                                                       18

<210> SEQ ID NO 316
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 316
gatatacctg tggactgg                                                       18

```
<210> SEQ ID NO 317
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 317
cgatatacct gtggactg                                                 18

<210> SEQ ID NO 318
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 318
acgatatacc tgtggact                                                 18

<210> SEQ ID NO 319
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 319
aacgatatac ctgtggac                                                 18

<210> SEQ ID NO 320
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 320
taacgatata cctgtgga                                                 18

<210> SEQ ID NO 321
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 321
ttaacgatat acctgtgg                                                 18

<210> SEQ ID NO 322
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 322
gttaacgata tacctgtg                                                 18

<210> SEQ ID NO 323
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 323
ggttaacgat atacctgt                                          18

<210> SEQ ID NO 324
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 324
cggttaacga tatacctg                                          18

<210> SEQ ID NO 325
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 325
gcggttaacg atatacct                                          18

<210> SEQ ID NO 326
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 326
tgcggttaac gatatacc                                          18

<210> SEQ ID NO 327
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 327
gtgcggttaa cgatatac                                          18

<210> SEQ ID NO 328
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 328
ggtgcggtta acgatata                                          18

<210> SEQ ID NO 329
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 329
gggtgcggtt aacgatat                                          18

<210> SEQ ID NO 330
<211> LENGTH: 16

-continued

<212> TYPE: DNA
<213> ORGANISM: Artificial sequence
<220> FEATURE:
<223> OTHER INFORMATION: Synthetic oligonucleotide

<400> SEQUENCE: 330
agggaaaagc tcccgg                                                   16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
gtcaccctgt acctgg                                                   16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
gtaggtcacc ctgtac                                                   16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
tcgagtaggt caccct                                                   16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
gggctcgagt aggtca                                                   16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
ctcagggctc gagtag                                                   16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336

```
catcctcagg gctcga                                                      16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
attccatcct cagggc                                                      16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 338
ccggattcca tcctca                                                      16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
gctcccggat tccatc                                                      16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
aaaagctccc ggattc                                                      16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
gtgcagggaa aagctc                                                      16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
tcaggtgcag ggaaaa                                                      16

<210> SEQ ID NO 343
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 343
accatcaggt gcaggg                                                         16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
cttcaccatc aggtgc                                                         16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
tcgtcttcac catcag                                                         16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
agtgtcgtct tcacca                                                         16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
ctgcagtgtc gtcttc                                                         16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
agctctgcag tgtcgt                                                         16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
ctgcagctct gcagtg                                                         16
```

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
ggccctgcag ctctgc                                                             16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
ctgaggccct gcagct                                                             16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
cggcctgagg ccctgc                                                             16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
accccggcct gaggcc                                                             16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
tcagaccccg gcctga                                                             16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
gtactcagac cccggc                                                             16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
ctgtgtactc agaccc                                                      16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
ctgactgtgt actcag                                                      16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
cacactgact gtgtac                                                      16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
caaccacact gactgt                                                      16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
aaggcaacca cactga                                                      16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
gtgcaaggca accaca                                                      16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
catcgtgcaa ggcaac                                                      16

<210> SEQ ID NO 363

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
atatcatcgt gcaagg                                                   16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
ctccatatca tcgtgc                                                   16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
ggctctccat atcatc                                                   16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
ggctggctct ccatat                                                   16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
ctggattcca atcagg                                                   16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
tggactggat tccaat                                                   16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
```
cctgtggact ggattc                                                    16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
tatacctgtg gactgg                                                    16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
acgatatacc tgtgga                                                    16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
gttaacgata tacctg                                                    16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
tgcggttaac gatata                                                    16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
tgggtgcggt taacga                                                    16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
aaattaatgg taagag                                                    16

<210> SEQ ID NO 376
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 376
aggcaaatta atggta                                                       16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
tgttaggcaa attaat                                                       16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
tgtctgttag gcaaat                                                       16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
tcaatgtctg ttaggc                                                       16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
gcgatcaatg tctgtt                                                       16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
tagggcgatc aatgtc                                                       16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
cctttagggc gatcaa                                                       16
```

-continued

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
cagtccttta gggcga                                                   16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
atgccagtcc tttagg                                                   16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
gtgaatgcca gtcctt                                                   16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
atcagtgaat gccagt                                                   16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
ccacatcagt gaatgc                                                   16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
acatccacat cagtga                                                   16

<210> SEQ ID NO 389
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 389
atcgacatcc acatca                                           16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
tggaatcgac atccac                                           16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
ttgatggaat cgacat                                           16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
aattttgatg gaatcg                                           16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
aagcaatttt gatgga                                           16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
tcccaagcaa ttttga                                           16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
gctttcccaa gcaatt                                           16

```
<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
gtgggctttc ccaagc                                                   16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
ccctgtgggc tttccc                                                   16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
ttgcccctgt gggctt                                                   16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
aaacttgccc ctgtgg                                                   16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
ctggaaactt gcccct                                                   16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
gtacctggaa acttgc                                                   16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 402
ccctgtacct ggaaac                                                    16

<210> SEQ ID NO 403
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 403
gcctgaggcc ctgcagct                                                  18

<210> SEQ ID NO 404
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 404
cccggcctga ggccctgc                                                  18

<210> SEQ ID NO 405
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 405
agaccccggc ctgaggcc                                                  18

<210> SEQ ID NO 406
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 406
actcagaccc cggcctga                                                  18

<210> SEQ ID NO 407
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 407
gtgtactcag accccggc                                                  18

<210> SEQ ID NO 408
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 408
gactgtgtac tcagaccc                                                  18

<210> SEQ ID NO 409
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 409
cactgactgt gtactcag                                           18

<210> SEQ ID NO 410
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 410
accacactga ctgtgtac                                           18

<210> SEQ ID NO 411
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 411
ggcaaccaca ctgactgt                                           18

<210> SEQ ID NO 412
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 412
atcatcgtgc aaggcaac                                           18

<210> SEQ ID NO 413
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 413
gactggattc caatcagg                                           18

<210> SEQ ID NO 414
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 414
tgtggactgg attccaat                                           18

<210> SEQ ID NO 415
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 415
```

```
tacctgtgga ctggattc                                                 18

<210> SEQ ID NO 416
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 416
ggtgggtgcg gttaacga                                                 18

<210> SEQ ID NO 417
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 417
gcaaattaat ggtaagag                                                 18

<210> SEQ ID NO 418
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 418
ttaggcaaat taatggta                                                 18

<210> SEQ ID NO 419
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 419
gccagtcctt tagggcga                                                 18

<210> SEQ ID NO 420
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 420
gaatgccagt cctttagg                                                 18

<210> SEQ ID NO 421
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 421
cagtgaatgc cagtcctt                                                 18

<210> SEQ ID NO 422
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 422
acatcagtga atgccagt                                                   18

<210> SEQ ID NO 423
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 423
atccacatca gtgaatgc                                                   18

<210> SEQ ID NO 424
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 424
cgacatccac atcagtga                                                   18

<210> SEQ ID NO 425
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 425
gaatcgacat ccacatca                                                   18

<210> SEQ ID NO 426
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 426
ttttgatgga atcgacat                                                   18

<210> SEQ ID NO 427
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 427
tttcccaagc aattttga                                                   18

<210> SEQ ID NO 428
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 428
gggctttccc aagcaatt                                                   18
```

<210> SEQ ID NO 429
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 429
ctgtgggctt tcccaagc                                                 18

<210> SEQ ID NO 430
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 430 gccctgtgg gctttccc                                                  18

<210> SEQ ID NO 431
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 431
acttgcccct gtgggctt                                                 18

<210> SEQ ID NO 432
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 432
ggaaacttgc ccctgtgg                                                 18

<210> SEQ ID NO 433
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 433
acctggaaac ttgcccct                                                 18

<210> SEQ ID NO 434
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 434
ctgtacctgg aaacttgc                                                 18

<210> SEQ ID NO 435
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 435
caccctgtac ctggaaac                                                    18
```